US012479928B2

(12) United States Patent
Bamdad et al.

(10) Patent No.: US 12,479,928 B2
(45) Date of Patent: *Nov. 25, 2025

(54) ANTI-CANCER PEPTIDE

(71) Applicant: Minerva Biotechnologies Corporation, Waltham, MA (US)

(72) Inventors: Cynthia Bamdad, Waltham, MA (US); Benoit Smagghe, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/719,302

(22) Filed: Apr. 12, 2022

(65) Prior Publication Data

US 2022/0289865 A1 Sep. 15, 2022
US 2025/0011469 A9 Jan. 9, 2025

Related U.S. Application Data

(60) Continuation of application No. 16/111,894, filed on Aug. 24, 2018, now Pat. No. 11,702,483, which is a division of application No. 15/302,461, filed as application No. PCT/US2015/024764 on Apr. 7, 2015, now abandoned.

(60) Provisional application No. 62/127,746, filed on Mar. 3, 2015, provisional application No. 62/114,526, filed on Feb. 10, 2015, provisional application No. 61/976,390, filed on Apr. 7, 2014.

(51) Int. Cl.

| | |
|---|---|
| ***C07K 16/40*** | (2006.01) |
| ***A61K 39/00*** | (2006.01) |
| ***C07K 16/30*** | (2006.01) |
| ***C07K 16/32*** | (2006.01) |

(52) U.S. Cl.

CPC .......... *C07K 16/40* (2013.01); *A61K 39/0011* (2013.01); *C07K 16/30* (2013.01); *C07K 16/3092* (2013.01); *C07K 16/32* (2013.01); *A61K 2039/505* (2013.01); *C07K 2317/33* (2013.01); *C07K 2317/622* (2013.01); *C07K 2317/73* (2013.01); *C07K 2317/76* (2013.01); *C12N 2800/22* (2013.01)

(58) Field of Classification Search

CPC .... C07K 16/40; C07K 16/30; C07K 16/3092; C07K 16/32; C07K 2317/33; C07K 2317/622; C07K 2317/73; C07K 2317/76; C07K 14/7051; C07K 2319/00; A61K 39/0011; A61K 2039/505; A61K 39/395; A61K 48/00; C12N 2800/22; C12N 5/0693; A61P 35/00; A61P 35/04; A61P 37/04; A61P 43/00; C12Q 1/6883; G01N 33/574

See application file for complete search history.

(56) References Cited

U.S. PATENT DOCUMENTS

| | | | | |
|---|---|---|---|---|
| 5,631,271 | A | 5/1997 | Serfontein | |
| 6,331,415 | B1 | 12/2001 | Cabilly et al. | |
| 6,818,749 | B1 | 11/2004 | Kashmiri et al. | |
| 9,814,782 | B2 | 11/2017 | Park et al. | |
| 12,037,413 | B2 | 7/2024 | Bamdad et al. | |
| 12,049,514 | B2 | 7/2024 | Bamdad et al. | |
| 2003/0022306 | A1 | 1/2003 | Bandman et al. | |
| 2003/0109690 | A1 * | 6/2003 | Ruben .................... | C07K 14/47 536/23.1 |
| 2004/0057952 | A1 | 3/2004 | Payne et al. | |
| 2005/0163784 | A1 | 7/2005 | Valentijn et al. | |
| 2010/0316688 | A1 | 12/2010 | Bamdad | |
| 2013/0287748 | A1 | 10/2013 | June et al. | |
| 2014/0010861 | A1 | 1/2014 | Bancel et al. | |
| 2015/0037371 | A1 | 2/2015 | Landry | |
| 2015/0252430 | A1 | 9/2015 | Bryant et al. | |
| 2016/0326263 | A1 | 11/2016 | Bamdad et al. | |
| 2017/0119903 | A1 | 5/2017 | Park et al. | |
| 2017/0204196 | A1 | 7/2017 | Bamdad et al. | |
| 2018/0230225 | A1 | 8/2018 | Fan et al. | |
| 2018/0258186 | A1 | 9/2018 | Bamdad et al. | |
| 2019/0031778 | A1 | 1/2019 | Bamdad et al. | |
| 2019/0031779 | A1 | 1/2019 | Bamdad et al. | |
| 2019/0290692 | A1 | 9/2019 | Bamdad et al. | |
| 2019/0389956 | A1 | 12/2019 | Zhang et al. | |
| 2020/0165354 | A1 | 5/2020 | Liu et al. | |
| 2022/0259324 | A1 | 8/2022 | Bamdad et al. | |
| 2023/0242678 | A1 | 8/2023 | Bamdad et al. | |
| 2023/0279141 | A1 | 9/2023 | Bamdad et al. | |
| 2024/0392038 | A1 | 11/2024 | Bamdad et al. | |
| 2025/0011469 | A9 | 1/2025 | Bamdad et al. | |

FOREIGN PATENT DOCUMENTS

| | | | | |
|---|---|---|---|---|
| CN | 101918844 | A | 12/2010 | |
| CN | 104220458 | A | 12/2014 | |
| WO | WO-0222164 | A1 | 3/2002 | |
| WO | WO-2004050860 | A2 * | 6/2004 | ............. C07K 14/47 |
| WO | WO-2007072221 | A2 | 6/2007 | |
| WO | WO-2008157490 | A1 | 12/2008 | |

(Continued)

OTHER PUBLICATIONS

U.S. Appl. No. 16/111,894 Office Action dated Sep. 1, 2022.

(Continued)

*Primary Examiner* — Alana Harris Dent

(74) *Attorney, Agent, or Firm* — WILSON SONSINI GOODRICH & ROSATI

(57) ABSTRACT

The present application discloses anti-NME antibodies and their use in treating or preventing diseases.

20 Claims, 47 Drawing Sheets
(36 of 47 Drawing Sheet(s) Filed in Color)
Specification includes a Sequence Listing.

(56) References Cited

FOREIGN PATENT DOCUMENTS

| | | | |
|---|---|---|---|
| WO | WO-2010031749 | A1 | 3/2010 |
| WO | WO-2010042562 | A2 | 4/2010 |
| WO | WO-2013059373 | A2 | 4/2013 |
| WO | WO-2014018679 | A2 | 1/2014 |
| WO | WO-2014028668 | A2 | 2/2014 |
| WO | WO-2014052693 | A2 | 4/2014 |
| WO | WO-2014130741 | A2 | 8/2014 |
| WO | WO-2015157322 | A2 | 10/2015 |
| WO | WO-2016130726 | A1 | 8/2016 |
| WO | WO-2018071583 | A2 | 4/2018 |
| WO | WO-2019104306 | A1 | 5/2019 |
| WO | WO-2020163325 | A1 | 8/2020 |
| WO | WO-2021252551 | A2 | 12/2021 |
| WO | WO-2021263227 | A2 | 12/2021 |

OTHER PUBLICATIONS

Adams et al. The c-myc oncogene driven by immunoglobulin enhancers induces lymphoid malignancy in transgenic mice. Nature 318:533-538 (1985).
Alexander et al. Expression of the c-myc oncogene under control of an immunoglobulin enhancer in E mu-myc transgenic mice. Mol. Cell. Biol. 7:1436-1444 (1987).
Benoist et al. In vivo sequence requirements of the SV40 early promoter region. Nature 290:304-310 (1981).
Brinster et al. Regulation of metallothionein-thymidine kinase fusion plasmids injected into mouse eggs. Nature 296:39-42 (1982).
Chen et al., Understanding and targeting cancer stern cells: therapeutic implications and challenges. Acta Pharmacologica Sinica 34:732-740 (2013).
Clarke et al. Cancer stem cells—perspectives on current status and future directions: AACR Workshop on Cancer stem cells. Cancer Res 66(19):9339-9344 (2006).
Darash-Yahana et al., Role of high expression levels of CXCR4 in tumor growth, vascularization, and metastasis. FASEB J 18(11):1240-1242 (2004).
Deboer et al. The tac promoter: a functional hybrid derived from the trp and lac promoters. PNAS USA 80:21-25 (1983).
Desvignes et al., Nme protein family evolutionary history, a vertebrate perspective. BMC Evol Biol. 9:256 [1-25] (2009).
Expression of NME7 in cancer—Summary—The Human Protein Atlas, printed Mar. 2018.
Faber et al., SDF-1-CXCR4 axis: cell trafficking in the cancer stem cell niche of head and neck squamous cell carcinoma. Oncol. Rep. 29(6):2325-2331 (2013).
Fessler et al. MUC1 is a determinant of trastuzumab (Herceptin) resistance in breast cancer cells. Breast Cancer Res Treat 118:113-134 (2009).
Fingl et al. Chapter 1: General Principles. In: The Pharmacological basis of therapeutics (pp. 1-46) (1975).
Gafni et al. Derivation of novel human ground state naive pluripotent stem cells. Nature 504:282-286 (2013).
Gilbert et al. Useful proteins from recombinant bacteria. Scientific American 242:74-94 (1980).
Goldspiel et al. Human gene therapy. Clin Pharm 12:488-505 (1993).
Grosschedl et al. Introduction of a mu immunoglobulin gene into the mouse germ line: specific expression in lymphoid cells and synthesis of functional antibody. Cell 38:647-658 (1984).
Hammer et al. Diversity of alpha-fetoprotein gene expression in mice is generated by a combination of separate enhancer elements. Science 235:53-58 (1987).
Hanahan. Heritable formation of pancreatic beta-cell tumours in transgenic mice expressing recombinant insulin/simian virus 40 oncogenes. Nature 315:115-122 (1985).
Hanna et al. Human embryonic stem cells with biological and epigenetic characteristics similar to those of mouse ESCs. PNAS USA 107(20):9222-9227 (2010).
Herreros-Villanueva et al., SOX2 promotes dedifferentiation and imparts stem cell-like features to pancreatic cancer cells. Oncogenesis 2:e61 (2013).
Hikita et al. MUC1 Mediates the Growth of Human Pluripotent Stem Cells. PLoS One 3(10):1-13 (2008).
Human Protein Atlas (2 pp.) printed Oct. 2, 2020.
Jeter et al., NANOG promotes cancer stem cell characteristics and prostate cancer resistance to androgen deprivation. Oncogene 30(36):3833-3845 (2011).
Kelsey et al. Species- and tissue-specific expression of human alpha 1-antitrypsin in transgenic mice. Genes and Dev 1:161-171 (1987).
Koller et al. Inactivating the beta 2-microglobulin locus in mouse embryonic stem cells by homologous recombination. PNAS USA 86:8932-8935 (1989).
Kollias et al. Regulated expression of human A gamma-, beta-, and hybrid gamma beta-globin genes in transgenic mice: manipulation of the developmental expression patterns. Cell 46:89-94 (1986).
Krumlauf et al. Developmental regulation of alpha-fetoprotein genes in transgenic mice. Mol. Cell. Biol. 5:1639-1648 (1985).
Kumar et al., Acquired cancer stem cell phenotypes through Oct4-inediated dedifferentiation. Oncogene 31(47):4898-4911 (2012).
Leder et al. Consequences of widespread deregulation of the c-myc gene in transgenic mice: multiple neoplasms and normal development. Cell 45:485-495 (1986).
Liu et al., Brd4 and JMJD6-associated anti-pause enhancers in regulation of transcriptional pause release. Cell 155(7):1581-1595 (2013).
Liu et al. The multiple roles for Sox2 in stem cell maintenance and tumorigenesis. Cellular Signaling 25(5):1264-1271 (2013).
Lombardi et al. nm23: Unraveling its Biological Function in Cell Differentiation. J Cell Physiol 182:144-149 (2000).
Macdonald. Expression of the pancreatic elastase I gene in transgenic mice. Hepatology 7:42S-51S (1987).
Magram et al. Developmental regulation of a cloned adult beta-globin gene in transgenic mice. Nature 315:338-340 (1985).
Mahanta et al. A Minimal Fragment of MUCI Mediates Growth of Cancer Cells. PLoS One 3(4):e2054 (2008).
Mason et al. The hypogonadal mouse: reproductive functions restored by gene therapy. Science 234:1372-1378 (1986).
Miki et al. Identification of putative stem cell markers, CD133 and CXCR4, in hTERT-immortalized primary nonmalignant and malignant tumor-derived human prostate epithelial cell lines and in prostate cancer specimen. Cancer Res., 67(7):3153-3161 (2007).
Min et al., Crystal structure of human nucleoside diphosphate kinase A, a metastasis suppressor. Proteins 46:340-342 (2002).
Morgan et al. Human gene therapy. Ann Rev Biochem 62:191-217 (1993).
Mukherjee et al., The Role of chemokine receptor CXCR4 in breast cancer metastasis. Am J Cancer Res. 3(1):46-57 (2013).
Mulligan. The basic science of gene therapy. Science 260(5110):926-932 (1993).
Nm23-H7 (C-15): sc-82256 datasheet by Santa Cruz Biotechnology https://datasheets.scbt.com/sc-82256.pdf (ret. 2014).
Okabe-Kado et al., A New Function of Nrn231NDP Kinase as a Differentiation Inhibitory Factor, Which Does Not Require it's Kinase Activity. FEES Letters 363:311-315 (1995).
Ornitz et al. Elastase I promoter directs expression of human growth hormone and SV40 T antigen genes to pancreatic acinar cells in transgenic mice. Cold Spring Harbor Symp. Quant. Biol. 50:399-409 (1986).
PCT/US2015/024764 International Search Report and Written Opinion dated Oct. 28, 2015.
Pinkert et al. An albumin enhancer located 10 kb upstream functions along with its promoter to direct efficient, liver-specific expression in transgenic mice. Genes and Dev 1:268-276 (1987).
Porter et al., Chimeric antigen receptor-modified T cells in chronic lymphoid leukemia. N Engl J Med 365:725-733 (2011).
Rais et al., Deterministic direct reprogramming of somatic cells to pluripotency. Nature 502(7469):65-70 (2013).
Rath et al., Rho-associated kinases in tumorigenesis: re-considering ROCK inhibition for cancer therapy. EMBO Rep. 13(10):900-908 (2012).

(56) References Cited

OTHER PUBLICATIONS

Readhead et al. Expression of a myelin basic protein gene in transgenic shiverer mice: correction of the dysmyelinating phenotype. Cell 48:703-712 (1987).
Shani. Tissue-specific expression of rat myosin light-chain 2 gene in transgenic mice. Nature 314:283-286 (1985).
Silva et al., Promotion of reprogramming to ground state pluripotency by signal inhibition. PLoS Biol. 6(10):e253 (2008).
Smagghe et al. MUCI ligand, NM23-H1, is a novel growth factor that maintains human stem cells in a more naive state. PLoS One 8(3):E58601 (2013).
Squinto et al., TrkB encodes a functional receptor for brain-derived neurotrophic factor and neurotrophin-3 but not nerve growth factor. Cell 65(5):885-893 (1991).
Swift et al. Tissue-specific expression of the rat pancreatic elastase I gene in transgenic mice. Cell 38:639-646 (1984).
Takahashi et al. Induction of pluripotent stem cells from mouse embryonic and adult fibroblast cultures by defined factors. Cell 126(4):663-676 (2006).
Theunissen et al., Systematic identification of culture conditions for induction and maintenance of naive human pluripotency. Cell Stem Cell. 15(4):524-526 (2014).
Tiller et al. A fully synthetic human Fab antibody library based on fixed VH/VL framework pairings with favorable biophysical properties. mAbs 5(3):445-470 (May/Jun. 2013).
Tolstoshev. Gene Therapy, Concepts, Current Trials and Future Directions. Ann. Rev. Pharmacol. Toxicol. 32:573-596 (1993).
U.S. Appl. No. 15/302,461 Office Action dated Mar. 26, 2018.
U.S. Appl. No. 15/302,461 Restriction Requirement dated Aug. 10, 2017.
U.S. Appl. No. 16/111,862 Office Action dated Mar. 18, 2021.
U.S. Appl. No. 16/111,862 Office Action dated Oct. 13, 2020.
U.S. Appl. No. 16/111,862 Office Action dated Sep. 30, 2021.
U.S. Appl. No. 16/111,894 Office Action dated Mar. 23, 2021.
U.S. Appl. No. 16/111,894 Office Action dated Oct. 13, 2020.
Valamehr et al., Platform for induction and maintenance of transgene-free hiPSCs resembling ground state pluripotent stem cells. Stem Cell Reports 2(3):366-381 (2014).
Villa-Kamaroff et al. A bacterial clone synthesizing proinsulin. PNAS USA 75:3727-3731 (1978).
Wagner et al. Nucleotide sequence of the thymidine kinase gene of herpes simplex virus type 1. PNAS USA 78:1441-1445 (1981).
Wang et al., Targeting cancer stem cells: emerging role of Nanog transcription factor. Oncotargets and Therapy 6:1207-1220 (2013).
Ware et al. Derivation of naive human embryonic stem cells. PNAS USA 111:4484-4489 (2014).
Webb et al., The crystal structure of a human nucleoside diphosphate kinase, NM23-H2. J Mol Biol. 251:574-587 (1995).
Wu et al. Receptor-mediated in vitro gene transformation by a soluble DNA carrier system. J Biol Chem 262(10):4429-4432 (1987).
Wu et al. Delivery systems for gene therapy. Biotherapy 3:87-95 (1991).
Xu et al., Basic FGF and suppression of BMP signaling sustain undifferentiated proliferation of human ES cells. Nature Methods 2(3):185-90 (2005).
Xu et al. Basic Fibroblast Growth Factor Supports Undifferentiated Human Basic Fibroblast Growth Factor Supports Undifferentiated Human. Stem Cells 23(3):315-23 (2005).
Yamamoto et al. Identification of a functional promoter in the long terminal repeat of Rous sarcoma virus. Cell 22:787-797 (1980).
Zijlstra et al. Germ-line transmission of a disrupted β2-microglobulin gene produced by homologous recombination in embryonic stem cells. Nature 342:435-438 (1989).
Al-Hajj et al. Prospective identification of tumorigenic breast cancer cells. PNAS 100(7):3983-3988 (2003).
PCT/US2020/016570 International Search Report and Written Opinion dated May 21, 2020.
U.S. Appl. No. 16/111,894 Office Action dated Jan. 20, 2023.
Apantaku. Breast cancer diagnosis and screening,. An Fam Physician 62(3):596-606 (2000).
Martin et al. Genetic and hormonal risk factors in breast cancer. J Natl Cancer Inst 92(14):1126-1135 (2000).
U.S. Appl. No. 18/000,249 Office Action dated Sep. 12, 2023.
Harrell et al., Estrogen receptor positive breast cancer metastasis: altered hormonal sensitivity and tumor aggressiveness in lymphatic vessels and lymph nodes. Cancer Res 66(18):9308-15 (2006).
PCT/US2021/036500 International Search Report and Written Opinion dated Aug. 3, 2022.
PCT/US2021/039291 International Invitation to Pay Additional Fees dated Oct. 18, 2021.
PCT/US2021/039291 International Search Report and Written Opinion dated Dec. 30, 2021.
Suzuki et al., Combined effect of dehydroxymethylepoxyquinomicin and gemcitabine in a mouse model of liver metastasis of pancreatic cancer. Clin Exp Metastasis 30:381-392 (2013).
Bendig. Humanization of rodent monoclonal antibodies by CDR grafting. Methods: A Companion to Methods in Enzymology 8:83-93 (1995).
Bonsignori et al. Maturation Pathway from Germline to Broad HIV-1 Neutralizer of a CD4-Mimic Antibody. Cell 165(2):449-463 (2016).
Panka et al. Variable region framework differences result in decreased or increased affinity of variant anti-digoxin antibodies. PNAS USA 85:3080-3084 (1988).
Paul. Fundamental Immunology, 3rd Edition, Chapter 9, pp. 292-295 (1993).
Rudikoff, Stuart et al. Single Amino Acid Substitution Altering Antigen-binding Specificity. PNAS USA 79(6):1979-1983 (1982).
U.S. Appl. No. 17/392,981 Office Action dated Nov. 16, 2023.
U.S. Appl. No. 18/002,832 Office Action dated Mar. 21, 2024.
U.S. Appl. No. 18/002,832 Office Action dated Nov. 6, 2023.
Cuzick, J. et al. Overview of the Main Outcomes in Breast-cancer Prevention Trials. Lancet 361(9354):296-300 (2003).
Evans, T R J. et al. Vaccine Therapy for Cancer—Fact or Fiction ?. QJM: An International Journal of Medicine 92(6):299-307 (1999).
Hernandez-Ledesma, Blanca et al. Lunasin, a Novel Seed Peptide for Cancer Prevention. Peptides 30(2):426-430 (2009). Published Online Nov. 13, 2008.
Komenaka, Ian et al. Immunotherapy for Melanoma. Clinics in Dermatology 22(3):251-265 (2004).
Schiffman, Mark. et al. The Promise of Global Cervical-cancer Prevention. The New England Journal of Medicine 353(20):2101-2104 (2005).
U.S. Appl. No. 18/002,832 Office Action dated Jul. 22, 2024.
Queen, Cary et al. A Humanized Antibody That Binds to the Interleukin 2 Receptor. PNAS USA 86(24):10029-10033 (1989).
Riechmann, Lutz et al. Reshaping Human Antibodies for Therapy. Nature 332(6162):323-327 (1988).
U.S. Appl. No. 18/002,832 Office Action dated Jan. 6, 2025.
U.S. Appl. No. 18/892,093 Office Action dated Dec. 13, 2024.
U.S. Appl. No. 18/892,093 Office Action dated Jan. 28, 2025.

* cited by examiner

NME1 (~17 KDa)

NME7 (~42KDa)

C) NME1 (~17KDa)

D) NME7 (~42KDa)
I. Cell Lystae
II. MUC1* pull down
1 2 3 4
50 KDa
37
25
20
15

Western Blot Analysis of Cancer and Stem Cells, Probing for Presence of NME1, NME6 and NME7 in the Cell Lysates

Fig. 3A

Detection of NME7 in cell lysate by western blot

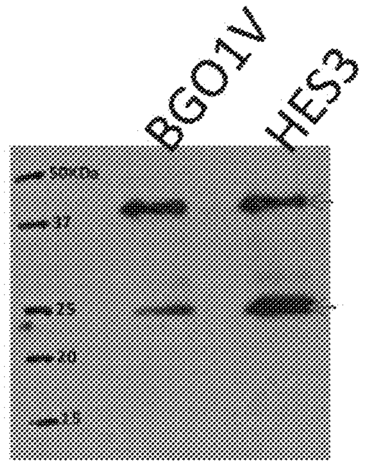

Reducing western blot 1- lyse cells with RIPA buffer
2- run reducing SDS-PAGE (20ul per lane)
3- transfer protein to PVDF membrane
4- probe membrane with anti NM23-H7 (B-9, Santa Cruz Biotechnology)
5- use goat anti mouse-HRP as secondary
6- detect protein by chemiluminescence

Fig. 3B

Detection of NME7 in conditioned media of iPS cells (SC101-A1) by western blot

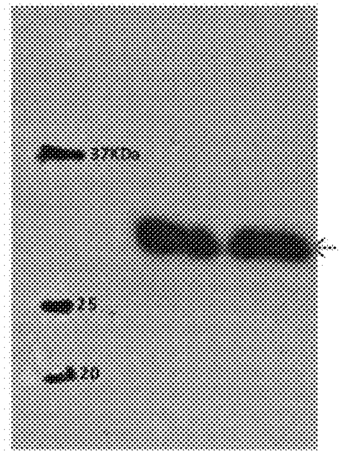

Reducing western blot 1- run reducing SDS PAGE (20ul of CM per lane)
2- transfer protein to PVDF membrane
3- probe membrane with anti NM23-H7 (B-9, Santa Cruz Biotechnology)
4- use goat anti mouse-HRP as secondary
5- detect protein by chemiluminescence

Fig. 3C

Detection of NME7 in lysate of iPS cells (SC101-A1) by western blot

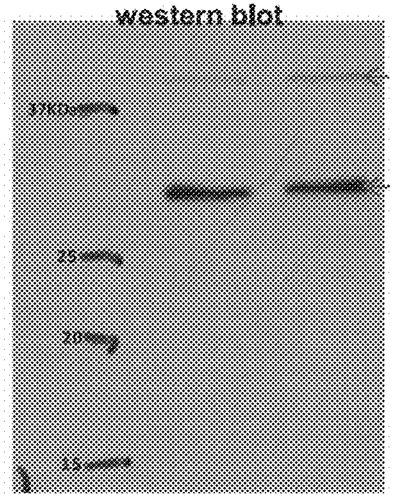

Reducing western blot 1- lyse cells with RIPA buffer
2- run reducing SDS-PAGE (20ul per lane)
3- transfer protein to PVDF membrane
4- probe membrane with anti NM23-H7 (B-9, Santa Cruz Biotechnology)
5- use goat anti mouse-HRP as secondary
6- detect protein by chemiluminescence

**Recombinant NME7 novel variant containing NDPK domains A and B, "NME7-AB", expresses well with high yield in E. *coli* and as the soluble protein**

FPLC purification of NME7-AB

SDS-PAGE of NME7-AB

12% non-reducing SDS-PAGE

NME7-AB is purified

ELISA shows NME7 Dimerizes MUC1*

MUC1* extra cellular domain peptide immobilized on plate was bound by NME7 to saturation; a second MUC1* peptide with a C-terminal His-tag or Biotin tag was added and visualized by HRP labeled antibody to either His-tag or HRP labeled streptavidin

T47D + anti-NM23-H7 rabbit polyclonal – t=48h

T47D + anti-NM23-H7 rabbit polyclonal - t=48h
Fig. 7A Fig. 7B Fig. 7C Fig. 7D Fig. 7E
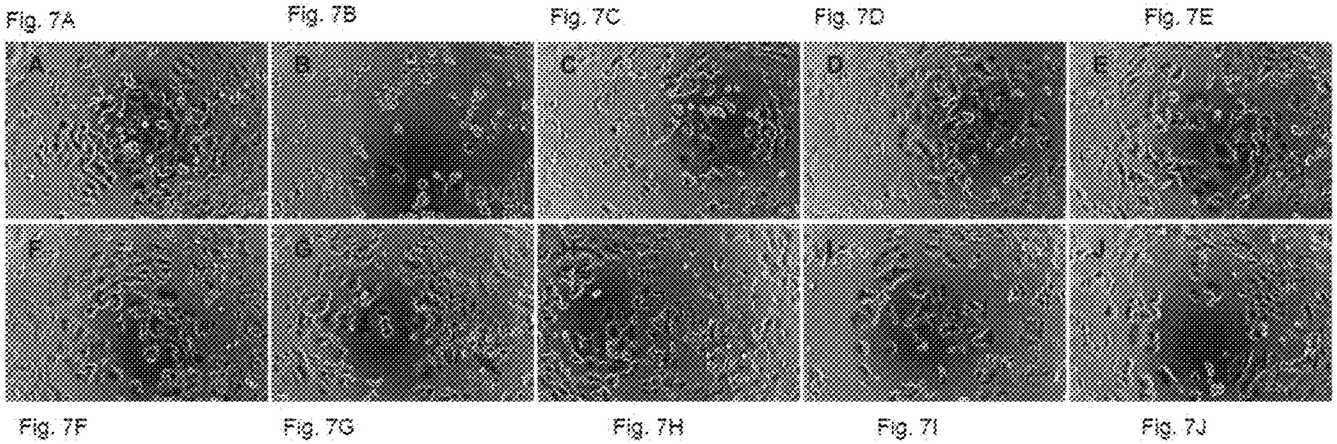
Fig. 7F Fig. 7G Fig. 7H Fig. 7I Fig. 7J
Fig. 7K
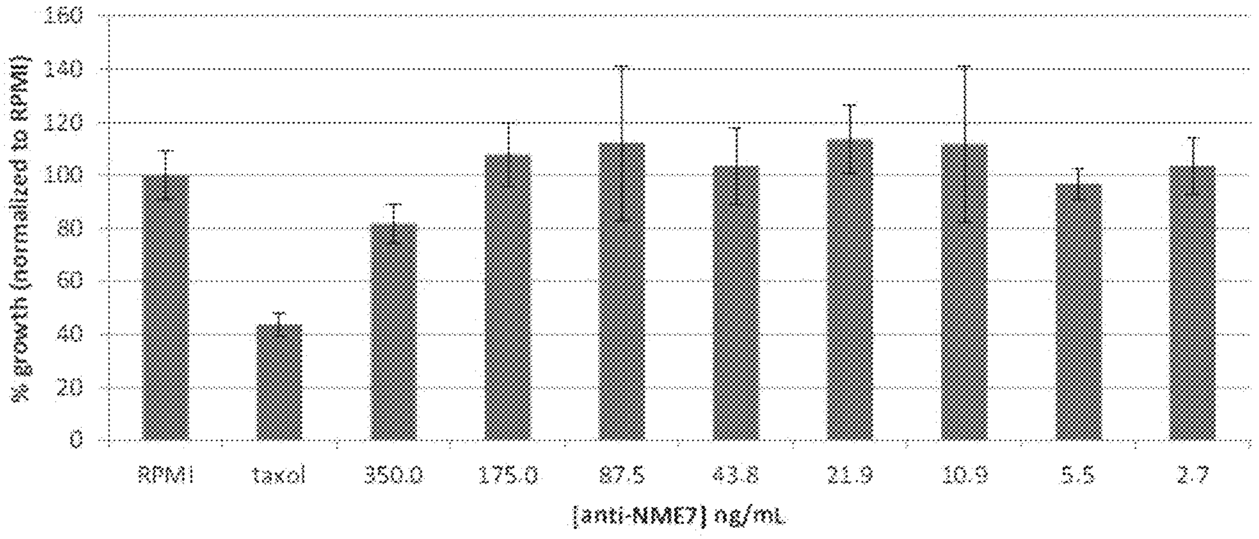

T47D + anti-NM23-H7 rabbit polyclonal - t=96h
Fig. 8A Fig. 8B Fig. 8C Fig. 8D Fig. 8E
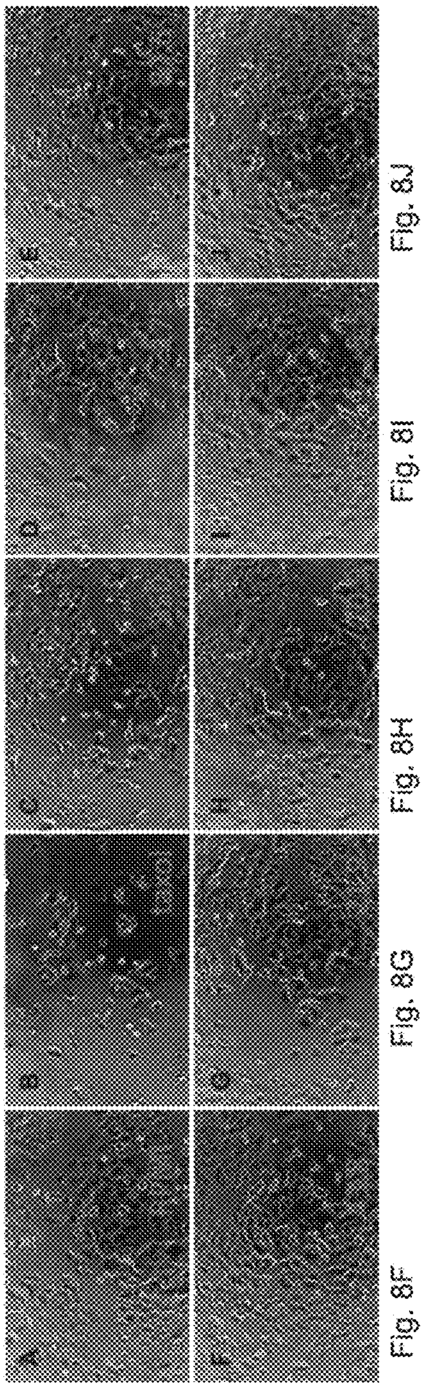
Fig. 8F Fig. 8G Fig. 8H Fig. 8I Fig. 8J
Fig. 8K
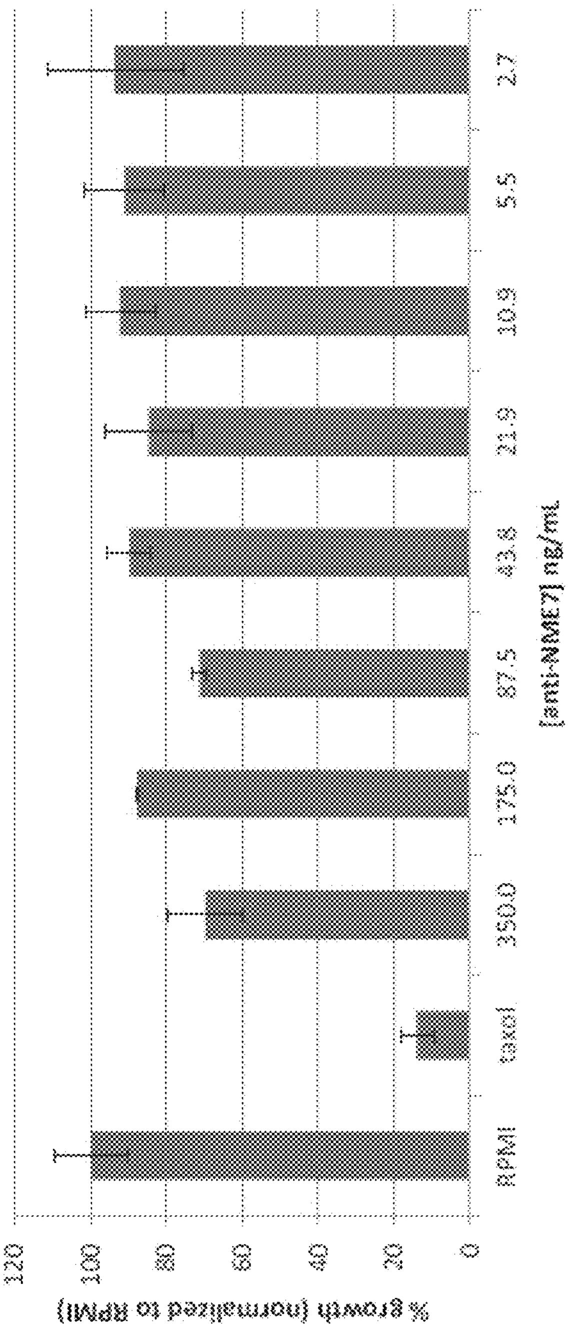

Stem Cell Lysates + Corresponding Conditioned Media Probed for Presence of NME-7

Breast cancer cells are progressed to a more metastatic state by culturing in the presence of 2i inhibitors or in NME7-AB Breast cancer cells are progressed to a more metastatic state by culturing in the presence of a bacterial NME that has high sequence homology to human NME1 or NME7-AB

Fig. 15

Sequence alignment of human NME1 to human NME7-A and -B domains

Fig. 16

NME7 specific peptides for generating antibodies to inhibit NME7 for the treatment or prevention of cancers.

The following peptide sequences are identified as being immunogenic peptides giving rise to antibodies that target human NME7 but not human NME1. The sequences were chosen for their lack of sequence homology to human NME1.

1. LALIKPDA
2. MMMLSRKEALDFHVDHQS
3. ALDFHVDHQS
4. EILRDDAICEWKRL
5. FNELIQFITTGP
6. RDDAICEW
7. SGVARTDASESIRALFGTDGIRNAA
8. ELFFPSSGG
9. KFTNCTCCIVKPHAVSEGLLGKILMA
10. LMAIRDAGFEISAMQMFNMDRVNVEEFYEVYKGVVT
11. EFYEVYKGVVTEYHD
12. EIQQNNATKTFREFCGPADPEIARHLRPGTLRAIFGKTKIQNA
13. YSGPCVAM
14. FREFCGP
15. VHCTDLPEDGLLEVQYFFKILDN
16. IQNAVHCTD
17. TDLPEDGLLEVQYFFKILDN
18. PEDGLLEVQYFFK
19. EIINKAGFTITK
20. MLSRKEALDFHVDHQS
21. NELIQFITT
22. EILRDDAICEWKRL
23. SGVARTDASESIRALFGTDGI
24. SGVARTDASES

Fig. 16 (Continued)

25. ALFGTDGI

26. NCTCCIVKPHAVSE

27. LGKILMAIRDA

28. EISAMQMFNMDRVNVE

29. EVYKGVVT

30. EYHDMVTE

31. EFCGPADPEIARHLR

G T N

Fig. 17

NME7 specific peptides for generating antibodies to inhibit NME7 for the treatment or prevention of cancers.

The following are preferred as they are likely areas that are important for structural integrity or for binding to the MUC1* peptide. Bivalent antibodies wherein each variable region would bind to each one of a pair are preferred.

35. ICEWKRL
36. LGKILMAIRDA

37. HAVSEGLLGK
38. VTEMYSGP

39. NATKTFREF
40. AIRDAGFEI

41. AICEWKRLLGPAN
42. DHQSRPFF

43. AICEWKRLLGPAN
44. VDHQSRPF
45. PDSFAS
46. KAGEIIEIINKAGFTITK

Fig. 18

The following peptide sequences are from human NME1 and were selected for their high homology to human NME7 as well as for their homology to other bacterial NME proteins that are able to mimic its function.

47. MANCERTFIAIKPDGVQRGLVGEIIKRFE
48. VDLKDRPF
49. HGSDSVESAEKEIGLWF

Especially preferred for their high homology to human NME7-A or -B and also to HSP 593 are:

50. ERTFIAIKPDGVQRGLVGEIIKRFE
51. VDLKDRPFFAGLVKYMHSGPVVAMVWEGLN
52. NIIHGSDSVESAEKEIGLWFHPEELV
53. KPDGVQRGLVGEII

Fig. 19

NME7-AB specific peptides preferred for generating antibodies for the treatment or prevention of cancer.

<u>NME7A peptide 1</u>
MLSRKEALDFHVDHQSC

<u>NME7A peptide 2</u>
SGVARTDASESC

<u>NME7B peptide 1</u>
DAGFEISAMQMFNMDRVNVEC

<u>NME7B peptide 2</u>
EVYKGVVTEYHDMVTEC

<u>NME7B peptide 3</u>
AIFGKTKIQNAVHCTDLPEDGLLEVQYFFC

The Test of Whether or not a Cancer Cell is Metastatic or a 'Cancer Stem Cell' is if 200 or less are able to Form a Tumor in a test Animal; Regular Cancer Cells Require 6M or more.
As Few as 50 NME-p-Induced Metastatic Cancer Cells are Sufficient to Form Tumors in test Animals. Animals that were also injected Daily with Human NME-p Developed Metastatic Cancer rather than just Localized Tumors

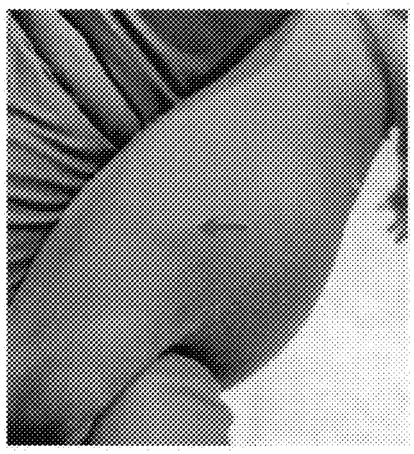

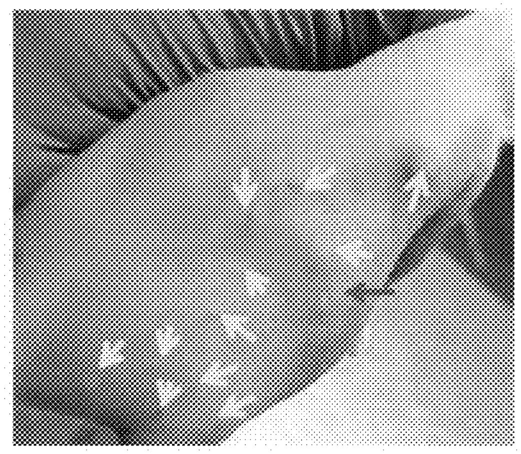

Figure 20

| MOUSE # | # CELLS IMPLANTED | + NME7 | TUMOR | METS | SIZE |
|---|---|---|---|---|---|
| 1 | 50 | Y | Y | Y | M |
| 2 | 50 | N | Y | Y | S |
| 3 | 50 | Y | Y | Y | M |
| 4 | 50 | N | Y | N | M |
| 5 | 50 | Y | Y | Y | M |
| 6 | 50 | N | N | N | No visible tumor |
| 7 | 100 | Y | Y | Y | S |
| 8 | 100 | N | N | N | N |
| 9 | 100 | Y | Y | Y | S |
| 10 | 100 | N | N | N | No visible tumor |
| 11 | 100 | Y | Y | Y | S |
| 12 | 1,000 | Y | Y | Y | S/M |
| 13 | 1,000 | N | Y | N | S/M |
| 14 | 1,000 | Y | N | N | No visible tumor |
| 15 | 1,000 | N | Y | N | L |
| 16 | 1,000 | Y | Y | N | No visible tumor |
| 17 | 1,000 | N | N | N | No visible tumor |
| 18 | 10,000 | Y | Y | Y | S |
| 19 | 10,000 | N | Y | N | S |
| 20 | 10,000 | Y | Y | Y | L |
| 21 | 10,000 | N | Y | N | L |
| 22 | 10,000 | Y | Y | N | L |

Figure 21

KEY MOUSE # AND NUMBER OF CANCER CELLS ENGRAFTED
50 cells: MICE # 1-6
100 cells: MICE # 7-11
1,000 cells: MICE # 12-17
10,000 cells: MICE # 18-22

KEY
Number is Mouse #
' = primary tumor
r = remote tumor
RED = injected daily with NME7-AB Anti-NME7 antibodies generated with peptides A1, A2, B1,B2 & B3 bind to NME7 (left) but not to NME1 (right); C20 is an anti-NME1 antibody ELISA assay tests NME7 antibodies for ability to block binding of NME7-AB to MUC1* peptide on surface, but not human NME1 dimers Antibodies generated from NME7-specific peptides inhibit cancer cell growth; peptides themselves also inhibit cancer cell growth T47D cancer cells. antibody combo 52 (A1), 55 (A2), 56 (B1), 57 (B1), 58 (B2), 59 (B2) at 5ug/mL each 30 ug total. All five peptides were combined and added at 1uM each or 10uM each

Treating cancer cells with anti-NME7 antibodies inhibits transition to "floater" cells, which PCR shows have greatly increased expression of metastatic markers such as CXCR4; xenograft experiments show that the floater cells form a tumor at extremely low copy number – 50 – and thus fulfill the requirement for being classified cancer stem cells or metastatic cancer cells.

| Antibodies | Floater observation |
|---|---|
| Control IgG | 100% |
| 53,55,57 (A1,A2,B1) | 70% |
| 53,57 (A1,B1) | 50% |
| 61 (B3) | 5% |

JR observations

| Antibodies | Floater observation |
|---|---|
| Control IgG | 100% |
| 53,55,57 (A1,A2,B1) | 65% |
| 53,57 (A1,B1) | 40% |
| 61 (B3) | 5% |

VH observations

The number of "Floater" cells, which are the ones that have higher expression of metastatic markers and that form tumors in animals at extremely low copy number is typically 20% of the amount of plated cells by Day 7. Here, we define 100% as the number of floater cells that results when a control antibody is added. Other percentages of floater cells is relative to the control in which a control IgG antibody was added.

Fig. 30

Fig. 31A

Treating cancer cells with anti-NME7 antibodies inhibits transition to metastatic cancer cells; CXCR4 is metastasis marker for cancers

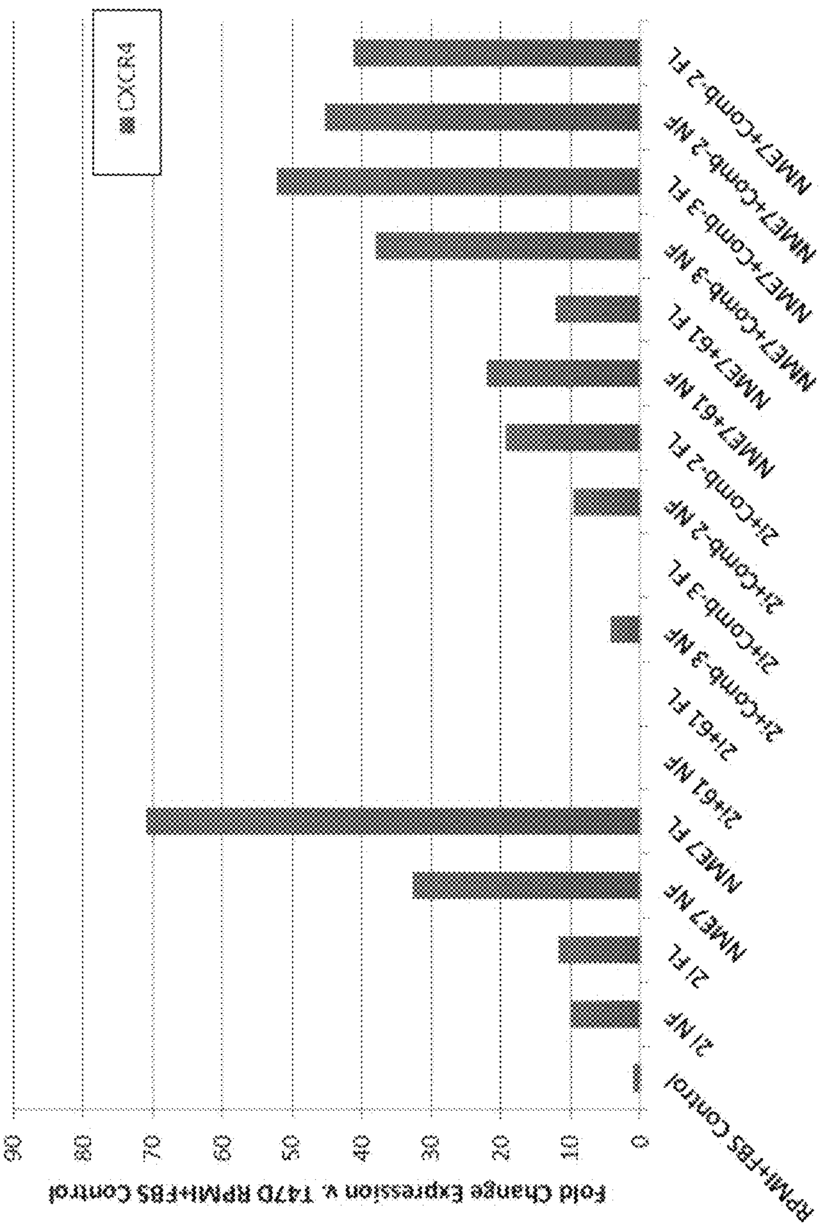

T47D breast cancer cells. 2i are MEK and GSK3-beta inhibitors. NF=non-floaters; FL=floaters. 61= rabbit #61 immunized with B3 peptide derived from NME7. Comb-2 = combination of antibodies from rabbits immunized with A1 and A2. Comb-3 = combination of antibodies from rabbits immunized with peptides A1, A2 and B1.

Treating cancer cells with NME7-AB peptides inhibits transition to metastatic cancer cells; CXCR4 and SOX2 are metastasis marker for cancers

| Cell Line T47D | Medium | Total RNA ng/µL | Yield (µg) | EEF1A1 Threshold Cycle |
|---|---|---|---|---|
| Control | RPMI + 10% FBS | 395.8 | 47.49 | 15.2 |
| 2i attached | MM + 2i | 387.8 | 11.64 | 14.5 |
| 2i Floaters | MM + 2i | 234.6 | 7.04 | 14.9 |
| NME7 attached | MM+NME7 4nM | 334.8 | 10.04 | 14.7 |
| NME7 Floaters | MM+NME7 4nM | 259.3 | 7.78 | 16.0 |
| 2i+ Antibody B3 rabbit 61 attached | MM + 2i | 2.7 | 0.08 | 25.9 |
| 2i+ Antibody B3 rabbit 61 Floaters | MM + 2i | 3.6 | 0.11 | 25.0 |
| 2i + Antibody Combination 3 attached | MM + 2i | 44.7 | 1.34 | 17.0 |
| 2i+ Antibody Combination 3 Floaters | MM + 2i | 39.0 | 1.17 | 15.9 |
| 2i+ Antibody Combination 2 attached | MM + 2i | 46.0 | 1.38 | 15.6 |
| 2i+ Antibody Combination 2 Floaters | MM + 2i | 77.8 | 2.33 | 16.3 |
| NME7+ Antibody B3 rabbit 61 attached | MM+NME7 4nM | 65.7 | 1.97 | 17.0 |
| NME7+ Antibody B3 rabbit 61 Floaters | MM+NME7 4nM | 15.8 | 0.47 | 19.9 |
| NME7+ Antibody Combination 3 attached | MM+NME7 4nM | 32.1 | 0.96 | 17.0 |
| NME7+ Antibody Combination 3 Floaters | MM+NME7 4nM | 109.3 | 3.28 | 16.1 |
| NME7+ Antibody Combination 2 attached | MM+NME7 4nM | 134.5 | 4.03 | 16.1 |
| NME7+ Antibody Combination 2 Floaters | MM+NME7 4nM | 139.5 | 4.19 | 18.6 |

CONTROLS

Figure 32

**BT-474 HER2 positive breast cancer cells express almost no MUC1 or MUC1* until they become Metastatic, which is resistant to Herceptin and other chemotherapy drugs. Blocking MUC1* with siRNA or anti-MUC1* Fab reversed the metastatic transition**

Fessler et al 2009, MUC1* is a Determinant of Herceptin Resistance in Breast Cancer Cells, 2009 Breast Cancer Res Treat Co-Immunoprecipitation of MUC1* and NME7 in serum grown T47D breast cancer cells
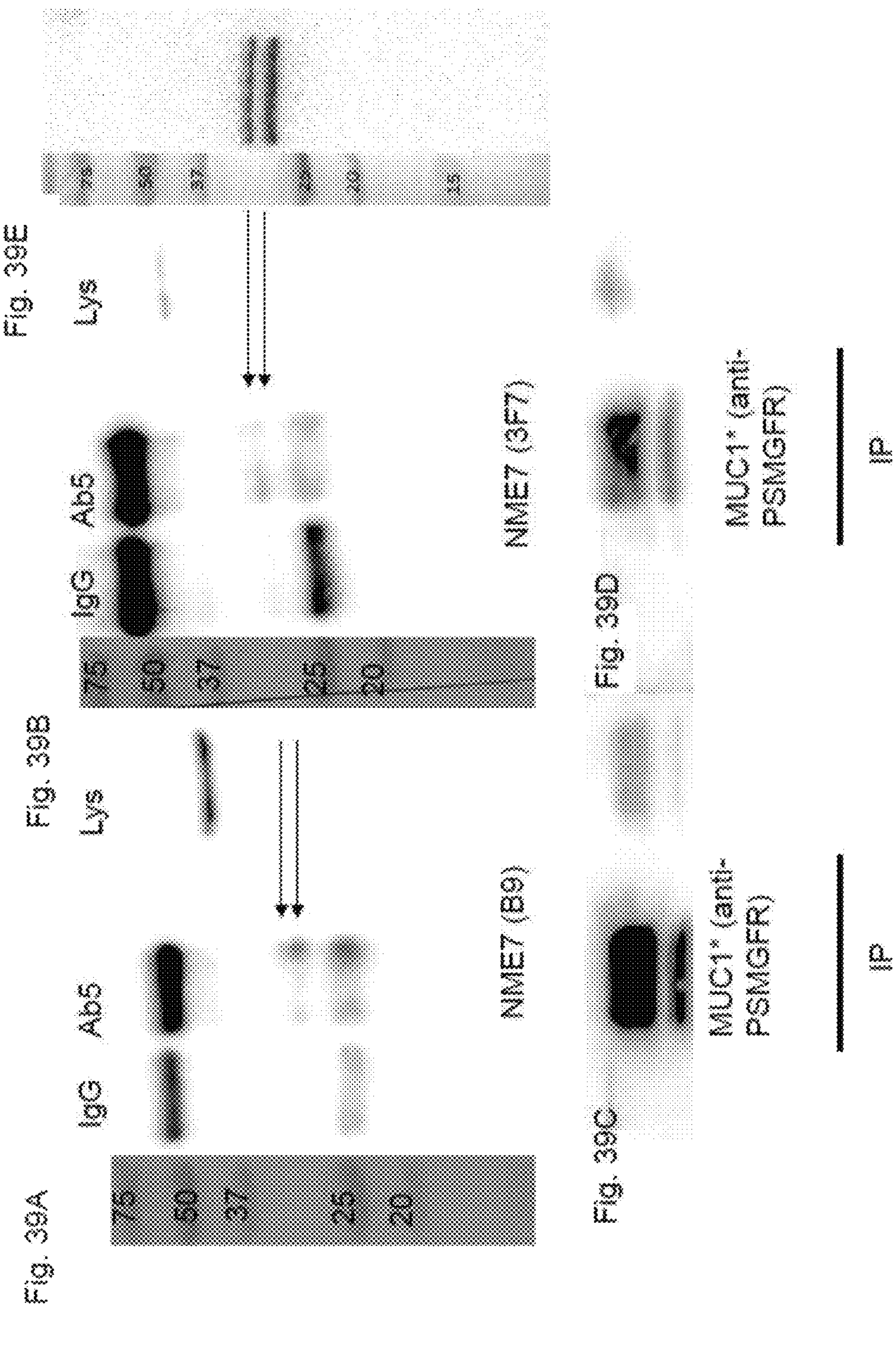

Co-Immunoprecipitation of MUC1* and NME7 from human embryonic stem cells & iPS cells NME7 (B9)
iPS7
HES3
IgG
Ab5
IgG
Ab5
iPS7
HES3
50
37
25
20
Immunoprecipitation
Lysate MUC1*
(anti-PSMGFR)
37
25
20
Immunoprecipitation
Lysate

SEQUENCE LISTING

```
<160> NUMBER OF SEQ ID NOS: 162

<210> SEQ ID NO 1
<211> LENGTH: 1255
<212> TYPE: PRT
<213> ORGANISM: Artificial Sequence
<220> FEATURE:
<223> OTHER INFORMATION: full-length MUC1 Receptor

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
```

```
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655
```

```
Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
    770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
    850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
    930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp  Thr Pro Thr Thr Leu  Ala Ser His
        995                 1000                1005

Ser Thr  Lys Thr Asp Ala Ser  Ser Thr His His Ser  Ser Val Pro
    1010                1015                1020

Pro Leu  Thr Ser Ser Asn His  Ser Thr Ser Pro Gln  Leu Ser Thr
    1025                1030                1035

Gly Val  Ser Phe Phe Phe Leu  Ser Phe His Ile Ser  Asn Leu Gln
    1040                1045                1050

Phe Asn  Ser Ser Leu Glu Asp  Pro Ser Thr Asp Tyr  Tyr Gln Glu
    1055                1060                1065
```

```
Leu Gln  Arg Asp Ile Ser Glu  Met Phe Leu Gln Ile  Tyr Lys Gln
    1070                 1075                 1080

Gly Gly  Phe Leu Gly Leu Ser  Asn Ile Lys Phe Arg  Pro Gly Ser
    1085                 1090                 1095

Val Val  Val Gln Leu Thr Leu  Ala Phe Arg Glu Gly  Thr Ile Asn
    1100                 1105                 1110

Val His  Asp Val Glu Thr Gln  Phe Asn Gln Tyr Lys  Thr Glu Ala
    1115                 1120                 1125

Ala Ser  Arg Tyr Asn Leu Thr  Ile Ser Asp Val Ser  Val Ser Asp
    1130                 1135                 1140

Val Pro  Phe Pro Phe Ser Ala  Gln Ser Gly Ala Gly  Val Pro Gly
    1145                 1150                 1155

Trp Gly  Ile Ala Leu Leu Val  Leu Val Cys Val Leu  Val Ala Leu
    1160                 1165                 1170

Ala Ile  Val Tyr Leu Ile Ala  Leu Ala Val Cys Gln  Cys Arg Arg
    1175                 1180                 1185

Lys Asn  Tyr Gly Gln Leu Asp  Ile Phe Pro Ala Arg  Asp Thr Tyr
    1190                 1195                 1200

His Pro  Met Ser Glu Tyr Pro  Thr Tyr His Thr His  Gly Arg Tyr
    1205                 1210                 1215

Val Pro  Pro Ser Ser Thr Asp  Arg Ser Pro Tyr Glu  Lys Val Ser
    1220                 1225                 1230

Ala Gly  Asn Gly Gly Ser Ser  Leu Ser Tyr Thr Asn  Pro Ala Val
    1235                 1240                 1245

Ala Ala  Ala Ser Ala Asn Leu
    1250                 1255


<210> SEQ ID NO 2
<211> LENGTH: 19
<212> TYPE: PRT
<213> ORGANISM: Artificial Sequence
<220> FEATURE:
<223> OTHER INFORMATION: N-terminal MUC-1 signaling sequence

<400> SEQUENCE: 2

Met Thr Pro Gly Thr Gln Ser Pro Phe Phe Leu Leu Leu Leu Leu Thr
1               5                   10                  15

Val Leu Thr


<210> SEQ ID NO 3
<211> LENGTH: 23
<212> TYPE: PRT
<213> ORGANISM: Artificial Sequence
<220> FEATURE:
<223> OTHER INFORMATION: N-terminal MUC-1 signaling sequence

<400> SEQUENCE: 3

Met Thr Pro Gly Thr Gln Ser Pro Phe Phe Leu Leu Leu Leu Leu Thr
1               5                   10                  15

Val Leu Thr Val Val Thr Ala
            20


<210> SEQ ID NO 4
<211> LENGTH: 23
<212> TYPE: PRT
<213> ORGANISM: Artificial Sequence
<220> FEATURE:
<223> OTHER INFORMATION: N-terminal MUC-1 signaling sequence

<400> SEQUENCE: 4
```

Met Thr Pro Gly Thr Gln Ser Pro Phe Phe Leu Leu Leu Leu Leu Thr
1 5 10 15

Val Leu Thr Val Val Thr Gly
20

<210> SEQ ID NO 5
<211> LENGTH: 146
<212> TYPE: PRT
<213> ORGANISM: Artificial Sequence
<220> FEATURE:
<223> OTHER INFORMATION: truncated MUC1 receptor isoform having nat-PSMGFR at its N-terminus

<400> SEQUENCE: 5

Gly Thr Ile Asn Val His Asp Val Glu Thr Gln Phe Asn Gln Tyr Lys
1 5 10 15

Thr Glu Ala Ala Ser Arg Tyr Asn Leu Thr Ile Ser Asp Val Ser Val
20 25 30

Ser Asp Val Pro Phe Pro Phe Ser Ala Gln Ser Gly Ala Gly Val Pro
35 40 45

Gly Trp Gly Ile Ala Leu Leu Val Leu Val Cys Val Leu Val Ala Leu
50 55 60

Ala Ile Val Tyr Leu Ile Ala Leu Ala Val Cys Gln Cys Arg Arg Lys
65 70 75 80

Asn Tyr Gly Gln Leu Asp Ile Phe Pro Ala Arg Asp Thr Tyr His Pro
85 90 95

Met Ser Glu Tyr Pro Thr Tyr His Thr His Gly Arg Tyr Val Pro Pro
100 105 110

Ser Ser Thr Asp Arg Ser Pro Tyr Glu Lys Val Ser Ala Gly Asn Gly
115 120 125

Gly Ser Ser Leu Ser Tyr Thr Asn Pro Ala Val Ala Ala Ala Ser Ala
130 135 140

Asn Leu
145

<210> SEQ ID NO 6
<211> LENGTH: 45
<212> TYPE: PRT
<213> ORGANISM: Artificial Sequence
<220> FEATURE:
<223> OTHER INFORMATION: Native Primary Sequence of the MUC1 Growth Factor Receptor

<400> SEQUENCE: 6

Gly Thr Ile Asn Val His Asp Val Glu Thr Gln Phe Asn Gln Tyr Lys
1 5 10 15

Thr Glu Ala Ala Ser Arg Tyr Asn Leu Thr Ile Ser Asp Val Ser Val
20 25 30

Ser Asp Val Pro Phe Pro Phe Ser Ala Gln Ser Gly Ala
35 40 45

<210> SEQ ID NO 7
<211> LENGTH: 44
<212> TYPE: PRT
<213> ORGANISM: Artificial Sequence
<220> FEATURE:
<223> OTHER INFORMATION: Native Primary Sequence of the MUC1 Growth Factor Receptor

<400> SEQUENCE: 7

```
Thr Ile Asn Val His Asp Val Glu Thr Gln Phe Asn Gln Tyr Lys Thr
1               5                   10                  15

Glu Ala Ala Ser Arg Tyr Asn Leu Thr Ile Ser Asp Val Ser Val Ser
            20                  25                  30

Asp Val Pro Phe Pro Phe Ser Ala Gln Ser Gly Ala
        35                  40


<210> SEQ ID NO 8
<211> LENGTH: 45
<212> TYPE: PRT
<213> ORGANISM: Artificial Sequence
<220> FEATURE:
<223> OTHER INFORMATION: "SPY" functional variant of the native Primary
      Sequence of the MUC1 Growth Factor Receptor

<400> SEQUENCE: 8

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45


<210> SEQ ID NO 9
<211> LENGTH: 44
<212> TYPE: PRT
<213> ORGANISM: Artificial Sequence
<220> FEATURE:
<223> OTHER INFORMATION: SPY" functional variant of the native Primary
      Sequence of the MUC1 Growth Factor Receptor

<400> SEQUENCE: 9

Thr Ile Asn Val His Asp Val Glu Thr Gln Phe Asn Gln Tyr Lys Thr
1               5                   10                  15

Glu Ala Ala Ser Pro Tyr Asn Leu Thr Ile Ser Asp Val Ser Val Ser
            20                  25                  30

Asp Val Pro Phe Pro Phe Ser Ala Gln Ser Gly Ala
        35                  40


<210> SEQ ID NO 10
<211> LENGTH: 216
<212> TYPE: DNA
<213> ORGANISM: Artificial Sequence
<220> FEATURE:
<223> OTHER INFORMATION: MUC1 cytoplasmic domain nucleotide sequence

<400> SEQUENCE: 10

tgtcagtgcc gccgaaagaa ctacgggcag ctggacatct ttccagcccg ggatacctac      60

catcctatga gcgagtaccc cacctaccac acccatgggc gctatgtgcc ccctagcagt     120

accgatcgta gcccctatga gaaggtttct gcaggtaacg gtggcagcag cctctcttac     180

acaaacccag cagtggcagc cgcttctgcc aacttg                               216


<210> SEQ ID NO 11
<211> LENGTH: 72
<212> TYPE: PRT
<213> ORGANISM: Artificial Sequence
<220> FEATURE:
<223> OTHER INFORMATION: MUC1 cytoplasmic domain amino acid sequence

<400> SEQUENCE: 11

Cys Gln Cys Arg Arg Lys Asn Tyr Gly Gln Leu Asp Ile Phe Pro Ala
1               5                   10                  15
```

```
Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Ala Ser Ala Asn Leu
65                  70


<210> SEQ ID NO 12
<211> LENGTH: 854
<212> TYPE: DNA
<213> ORGANISM: Artificial Sequence
<220> FEATURE:
<223> OTHER INFORMATION: NME7 nucleotide sequence

<400> SEQUENCE: 12

gagatcctga gacaatgaat catagtgaaa gattcgtttt cattgcagag tggtatgatc     60

caaatgcttc acttcttcga cgttatgagc ttttatttta cccaggggat ggatctgttg    120

aaatgcatga tgtaaagaat catcgcacct ttttaaagcg gaccaaatat gataacctgc    180

acttggaaga tttatttata ggcaacaaag tgaatgtctt ttctcgacaa ctggtattaa    240

ttgactatgg ggatcaatat acagctcgcc agctgggcag taggaaagaa aaaacgctag    300

ccctaattaa accagatgca atatcaaagg ctggagaaat aattgaaata ataaacaaag    360

ctggatttac tataaccaaa ctcaaaatga tgatgctttc aaggaaagaa gcattggatt    420

ttcatgtaga tcaccagtca agaccctttt tcaatgagct gatccagttt attacaactg    480

gtcctattat tgccatggag attttaagag atgatgctat atgtgaatgg aaaagactgc    540

tgggacctgc aaactctgga gtggcacgca cagatgcttc tgaaagcatt agagccctct    600

ttggaacaga tggcataaga aatgcagcgc atggccctga ttcttttgct tctgcggcca    660

gagaaatgga gttgtttttt ccttcaagtg gaggttgtgg gccggcaaac actgctaaat    720

ttactaattg tacctgttgc attgttaaac cccatgctgt cagtgaaggt atgttgaata    780

cactatattc agtacatttt gttaatagga gagcaatgtt tattttcttg atgtacttta    840

tgtatagaaa ataa                                                      854


<210> SEQ ID NO 13
<211> LENGTH: 283
<212> TYPE: PRT
<213> ORGANISM: Artificial Sequence
<220> FEATURE:
<223> OTHER INFORMATION: NME7 amino acid sequence

<400> SEQUENCE: 13

Asp Pro Glu Thr Met Asn His Ser Glu Arg Phe Val Phe Ile Ala Glu
1               5                   10                  15

Trp Tyr Asp Pro Asn Ala Ser Leu Leu Arg Arg Tyr Glu Leu Leu Phe
            20                  25                  30

Tyr Pro Gly Asp Gly Ser Val Glu Met His Asp Val Lys Asn His Arg
        35                  40                  45

Thr Phe Leu Lys Arg Thr Lys Tyr Asp Asn Leu His Leu Glu Asp Leu
    50                  55                  60

Phe Ile Gly Asn Lys Val Asn Val Phe Ser Arg Gln Leu Val Leu Ile
65                  70                  75                  80

Asp Tyr Gly Asp Gln Tyr Thr Ala Arg Gln Leu Gly Ser Arg Lys Glu
```

```
                85                  90                  95

Lys Thr Leu Ala Leu Ile Lys Pro Asp Ala Ile Ser Lys Ala Gly Glu
            100                 105                 110

Ile Ile Glu Ile Ile Asn Lys Ala Gly Phe Thr Ile Thr Lys Leu Lys
        115                 120                 125

Met Met Met Leu Ser Arg Lys Glu Ala Leu Asp Phe His Val Asp His
    130                 135                 140

Gln Ser Arg Pro Phe Phe Asn Glu Leu Ile Gln Phe Ile Thr Thr Gly
145                 150                 155                 160

Pro Ile Ile Ala Met Glu Ile Leu Arg Asp Asp Ala Ile Cys Glu Trp
                165                 170                 175

Lys Arg Leu Leu Gly Pro Ala Asn Ser Gly Val Ala Arg Thr Asp Ala
            180                 185                 190

Ser Glu Ser Ile Arg Ala Leu Phe Gly Thr Asp Gly Ile Arg Asn Ala
        195                 200                 205

Ala His Gly Pro Asp Ser Phe Ala Ser Ala Ala Arg Glu Met Glu Leu
    210                 215                 220

Phe Phe Pro Ser Ser Gly Gly Cys Gly Pro Ala Asn Thr Ala Lys Phe
225                 230                 235                 240

Thr Asn Cys Thr Cys Cys Ile Val Lys Pro His Ala Val Ser Glu Gly
                245                 250                 255

Met Leu Asn Thr Leu Tyr Ser Val His Phe Val Asn Arg Arg Ala Met
            260                 265                 270

Phe Ile Phe Leu Met Tyr Phe Met Tyr Arg Lys
        275                 280
```

<210> SEQ ID NO 14
<211> LENGTH: 534
<212> TYPE: DNA
<213> ORGANISM: Artificial Sequence
<220> FEATURE:
<223> OTHER INFORMATION: NM23-H1 nucleotide sequence

<400> SEQUENCE: 14

```
atggtgctac tgtctacttt agggatcgtc tttcaaggcg aggggcctcc tatctcaagc      60

tgtgatacag gaaccatggc caactgtgag cgtaccttca ttgcgatcaa accagatggg     120

gtccagcggg gtcttgtggg agagattatc aagcgttttg agcagaaagg attccgcctt     180

gttggtctga aattcatgca agcttccgaa gatcttctca aggaacacta cgttgacctg     240

aaggaccgtc cattctttgc cggcctggtg aaatacatgc actcagggcc ggtagttgcc     300

atggtctggg aggggctgaa tgtggtgaag acgggccgag tcatgctcgg ggagaccaac     360

cctgcagact ccaagcctgg gaccatccgt ggagacttct gcatacaagt tggcaggaac     420

attatacatg gcagtgattc tgtggagagt gcagagaagg agatcggctt gtggtttcac     480

cctgaggaac tggtagatta cacgagctgt gctcagaact ggatctatga atga           534
```

<210> SEQ ID NO 15
<211> LENGTH: 177
<212> TYPE: PRT
<213> ORGANISM: Artificial Sequence
<220> FEATURE:
<223> OTHER INFORMATION: NM23-H1 describes amino acid sequence

<400> SEQUENCE: 15

```
Met Val Leu Leu Ser Thr Leu Gly Ile Val Phe Gln Gly Glu Gly Pro
1               5                   10                  15
```

```
Pro Ile Ser Ser Cys Asp Thr Gly Thr Met Ala Asn Cys Glu Arg Thr
            20                  25                  30

Phe Ile Ala Ile Lys Pro Asp Gly Val Gln Arg Gly Leu Val Gly Glu
        35                  40                  45

Ile Ile Lys Arg Phe Glu Gln Lys Gly Phe Arg Leu Val Gly Leu Lys
    50                  55                  60

Phe Met Gln Ala Ser Glu Asp Leu Leu Lys Glu His Tyr Val Asp Leu
65                  70                  75                  80

Lys Asp Arg Pro Phe Phe Ala Gly Leu Val Lys Tyr Met His Ser Gly
                85                  90                  95

Pro Val Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
        115                 120                 125

Ile Arg Gly Asp Phe Cys Ile Gln Val Gly Arg Asn Ile Ile His Gly
    130                 135                 140

Ser Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
                165                 170                 175

Glu


<210> SEQ ID NO 16
<211> LENGTH: 534
<212> TYPE: DNA
<213> ORGANISM: Artificial Sequence
<220> FEATURE:
<223> OTHER INFORMATION: NM23-H1 S120G mutant nucleotide sequence

<400> SEQUENCE: 16

atggtgctac tgtctacttt agggatcgtc tttcaaggcg aggggcctcc tatctcaagc      60

tgtgatacag gaaccatggc caactgtgag cgtaccttca ttgcgatcaa accagatggg     120

gtccagcggg gtcttgtggg agagattatc aagcgttttg agcagaaagg attccgcctt     180

gttggtctga aattcatgca agcttccgaa gatcttctca aggaacacta cgttgacctg     240

aaggaccgtc cattctttgc cggcctggtg aaatacatgc actcagggcc ggtagttgcc     300

atggtctggg aggggctgaa tgtggtgaag acgggccgag tcatgctcgg ggagaccaac     360

cctgcagact ccaagcctgg gaccatccgt ggagacttct gcatacaagt tggcaggaac     420

attatacatg gcggtgattc tgtggagagt gcagagaagg agatcggctt gtggtttcac     480

cctgaggaac tggtagatta cacgagctgt gctcagaact ggatctatga atga           534


<210> SEQ ID NO 17
<211> LENGTH: 177
<212> TYPE: PRT
<213> ORGANISM: Artificial Sequence
<220> FEATURE:
<223> OTHER INFORMATION: NM23-H1 S120G mutant amino acid sequence

<400> SEQUENCE: 17

Met Val Leu Leu Ser Thr Leu Gly Ile Val Phe Gln Gly Glu Gly Pro
1               5                   10                  15

Pro Ile Ser Ser Cys Asp Thr Gly Thr Met Ala Asn Cys Glu Arg Thr
            20                  25                  30

Phe Ile Ala Ile Lys Pro Asp Gly Val Gln Arg Gly Leu Val Gly Glu
        35                  40                  45
```

```
Ile Ile Lys Arg Phe Glu Gln Lys Gly Phe Arg Leu Val Gly Leu Lys
    50                  55                  60

Phe Met Gln Ala Ser Glu Asp Leu Leu Lys Glu His Tyr Val Asp Leu
65                  70                  75                  80

Lys Asp Arg Pro Phe Phe Ala Gly Leu Val Lys Tyr Met His Ser Gly
                85                  90                  95

Pro Val Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
        115                 120                 125

Ile Arg Gly Asp Phe Cys Ile Gln Val Gly Arg Asn Ile Ile His Gly
    130                 135                 140

Gly Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
                165                 170                 175

Glu
```

<210> SEQ ID NO 18
<211> LENGTH: 459
<212> TYPE: DNA
<213> ORGANISM: Artificial Sequence
<220> FEATURE:
<223> OTHER INFORMATION: NM23-H2 nucleotide sequence

<400> SEQUENCE: 18

```
atggccaacc tggagcgcac cttcatcgcc atcaagccgg acggcgtgca gcgcggcctg     60

gtgggcgaga tcatcaagcg cttcgagcag aagggattcc gcctcgtggc catgaagttc    120

ctccgggcct ctgaagaaca cctgaagcag cactacattg acctgaaaga ccgaccattc    180

ttccctgggc tggtgaagta catgaactca gggccggttg tggccatggt ctgggagggg    240

ctgaacgtgg tgaagacagg ccgagtgatg cttggggaga ccaatccagc agattcaaag    300

ccaggcacca ttcgtgggga cttctgcatt caggttggca ggaacatcat tcatggcagt    360

gattcagtaa aaagtgctga aaaagaaatc agcctatggt ttaagcctga agaactggtt    420

gactacaagt cttgtgctca tgactgggtc tatgaataa                           459
```

<210> SEQ ID NO 19
<211> LENGTH: 152
<212> TYPE: PRT
<213> ORGANISM: Artificial Sequence
<220> FEATURE:
<223> OTHER INFORMATION: NM23-H2 amino acid sequence

<400> SEQUENCE: 19

```
Met Ala Asn Leu Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
    50                  55                  60

Val Lys Tyr Met Asn Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95
```

```
Ala Asp Ser Lys Pro Gly Thr Ile Arg Gly Asp Phe Cys Ile Gln Val
            100                 105                 110

Gly Arg Asn Ile Ile His Gly Ser Asp Ser Val Lys Ser Ala Glu Lys
        115                 120                 125

Glu Ile Ser Leu Trp Phe Lys Pro Glu Glu Leu Val Asp Tyr Lys Ser
    130                 135                 140

Cys Ala His Asp Trp Val Tyr Glu
145                 150
```

```
<210> SEQ ID NO 20
<211> LENGTH: 1023
<212> TYPE: DNA
<213> ORGANISM: Artificial Sequence
<220> FEATURE:
<223> OTHER INFORMATION: Human NM23-H7-2 sequence optimized for E. coli
      expression

<400> SEQUENCE: 20

atgcatgacg ttaaaaatca ccgtaccttt ctgaaacgca cgaaatatga taatctgcat     60

ctggaagacc tgtttattgg caacaaagtc aatgtgttct ctcgtcagct ggtgctgatc    120

gattatggcg accagtacac cgcgcgtcaa ctgggtagtc gcaaagaaaa aacgctggcc    180

ctgattaaac cggatgcaat ctccaaagct ggcgaaatta tcgaaattat caacaaagcg    240

ggtttcacca tcacgaaact gaaaatgatg atgctgagcc gtaaagaagc cctggatttt    300

catgtcgacc accagtctcg cccgtttttc aatgaactga ttcaattcat caccacgggt    360

ccgattatcg caatggaaat tctgcgtgat gacgctatct gcgaatggaa acgcctgctg    420

ggcccggcaa actcaggtgt tgcgcgtacc gatgccagtg aatccattcg cgctctgttt    480

ggcaccgatg gtatccgtaa tgcagcacat ggtccggact cattcgcatc ggcagctcgt    540

gaaatggaac tgtttttccc gagctctggc ggttgcggtc cggcaaacac cgccaaattt    600

accaattgta cgtgctgtat tgtcaaaccg cacgcagtgt cagaaggcct gctgggtaaa    660

attctgatgg caatccgtga tgctggcttt gaaatctcgg ccatgcagat gttcaacatg    720

gaccgcgtta acgtcgaaga attctacgaa gtttacaaag gcgtggttac cgaatatcac    780

gatatggtta cggaaatgta ctccggtccg tgcgtcgcga tggaaattca gcaaaacaat    840

gccaccaaaa cgtttcgtga attctgtggt ccggcagatc cggaaatcgc acgtcatctg    900

cgtccgggta ccctgcgcgc aatttttggt aaaacgaaaa tccagaacgc tgtgcactgt    960

accgatctgc cggaagacgg tctgctggaa gttcaatact tttcaaaat tctggataat   1020

tga                                                                 1023
```

```
<210> SEQ ID NO 21
<211> LENGTH: 340
<212> TYPE: PRT
<213> ORGANISM: Artificial Sequence
<220> FEATURE:
<223> OTHER INFORMATION: Human NM23-H7-2 sequence optimized for E. coli
      expression

<400> SEQUENCE: 21

Met His Asp Val Lys Asn His Arg Thr Phe Leu Lys Arg Thr Lys Tyr
1               5                   10                  15

Asp Asn Leu His Leu Glu Asp Leu Phe Ile Gly Asn Lys Val Asn Val
            20                  25                  30

Phe Ser Arg Gln Leu Val Leu Ile Asp Tyr Gly Asp Gln Tyr Thr Ala
        35                  40                  45
```

```
Arg Gln Leu Gly Ser Arg Lys Glu Lys Thr Leu Ala Leu Ile Lys Pro
    50                  55                  60

Asp Ala Ile Ser Lys Ala Gly Glu Ile Ile Glu Ile Ile Asn Lys Ala
65                  70                  75                  80

Gly Phe Thr Ile Thr Lys Leu Lys Met Met Met Leu Ser Arg Lys Glu
                85                  90                  95

Ala Leu Asp Phe His Val Asp His Gln Ser Arg Pro Phe Phe Asn Glu
            100                 105                 110

Leu Ile Gln Phe Ile Thr Thr Gly Pro Ile Ile Ala Met Glu Ile Leu
        115                 120                 125

Arg Asp Asp Ala Ile Cys Glu Trp Lys Arg Leu Leu Gly Pro Ala Asn
    130                 135                 140

Ser Gly Val Ala Arg Thr Asp Ala Ser Glu Ser Ile Arg Ala Leu Phe
145                 150                 155                 160

Gly Thr Asp Gly Ile Arg Asn Ala Ala His Gly Pro Asp Ser Phe Ala
                165                 170                 175

Ser Ala Ala Arg Glu Met Glu Leu Phe Phe Pro Ser Ser Gly Gly Cys
            180                 185                 190

Gly Pro Ala Asn Thr Ala Lys Phe Thr Asn Cys Thr Cys Cys Ile Val
        195                 200                 205

Lys Pro His Ala Val Ser Glu Gly Leu Leu Gly Lys Ile Leu Met Ala
    210                 215                 220

Ile Arg Asp Ala Gly Phe Glu Ile Ser Ala Met Gln Met Phe Asn Met
225                 230                 235                 240

Asp Arg Val Asn Val Glu Glu Phe Tyr Glu Val Tyr Lys Gly Val Val
                245                 250                 255

Thr Glu Tyr His Asp Met Val Thr Glu Met Tyr Ser Gly Pro Cys Val
            260                 265                 270

Ala Met Glu Ile Gln Gln Asn Asn Ala Thr Lys Thr Phe Arg Glu Phe
        275                 280                 285

Cys Gly Pro Ala Asp Pro Glu Ile Ala Arg His Leu Arg Pro Gly Thr
    290                 295                 300

Leu Arg Ala Ile Phe Gly Lys Thr Lys Ile Gln Asn Ala Val His Cys
305                 310                 315                 320

Thr Asp Leu Pro Glu Asp Gly Leu Leu Glu Val Gln Tyr Phe Phe Lys
                325                 330                 335

Ile Leu Asp Asn
            340
```

<210> SEQ ID NO 22
<211> LENGTH: 399
<212> TYPE: DNA
<213> ORGANISM: Artificial Sequence
<220> FEATURE:
<223> OTHER INFORMATION: Human NME7-A

<400> SEQUENCE: 22

```
atggaaaaaa cgctagccct aattaaacca gatgcaatat caaaggctgg agaaataatt      60

gaaataataa acaaagctgg atttactata accaaactca aaatgatgat gctttcaagg     120

aaagaagcat tggattttca tgtagatcac cagtcaagac cctttttcaa tgagctgatc     180

cagtttatta caactggtcc tattattgcc atggagattt taagagatga tgctatatgt     240

gaatggaaaa gactgctggg acctgcaaac tctggagtgg cacgcacaga tgcttctgaa     300

agcattagag ccctctttgg aacagatggc ataagaaatg cagcgcatgg ccctgattct     360
```

```
tttgcttctg cggccagaga aatggagttg tttttttga                     399


<210> SEQ ID NO 23
<211> LENGTH: 132
<212> TYPE: PRT
<213> ORGANISM: Artificial Sequence
<220> FEATURE:
<223> OTHER INFORMATION: Human NME7-A

<400> SEQUENCE: 23

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe
    130


<210> SEQ ID NO 24
<211> LENGTH: 444
<212> TYPE: DNA
<213> ORGANISM: Artificial Sequence
<220> FEATURE:
<223> OTHER INFORMATION: Human NME7-A1

<400> SEQUENCE: 24

atggaaaaaa cgctagccct aattaaacca gatgcaatat caaaggctgg agaaataatt      60

gaaataataa acaaagctgg atttactata accaaactca aaatgatgat gctttcaagg     120

aaagaagcat tggattttca tgtagatcac cagtcaagac cctttttcaa tgagctgatc     180

cagtttatta caactggtcc tattattgcc atggagattt taagagatga tgctatatgt     240

gaatggaaaa gactgctggg acctgcaaac tctggagtgg cacgcacaga tgcttctgaa     300

agcattagag ccctctttgg aacagatggc ataagaaatg cagcgcatgg ccctgattct     360

tttgcttctg cggccagaga aatggagttg ttttttcctt caagtggagg ttgtgggccg     420

gcaaacactg ctaaatttac ttga                                            444


<210> SEQ ID NO 25
<211> LENGTH: 147
<212> TYPE: PRT
<213> ORGANISM: Artificial Sequence
<220> FEATURE:
<223> OTHER INFORMATION: Human NME7-A1

<400> SEQUENCE: 25

Met Glu Lys Thr Leu Ala Leu Ile Lys Pro Asp Ala Ile Ser Lys Ala
1               5                   10                  15
```

```
Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr
145
```

<210> SEQ ID NO 26
<211> LENGTH: 669
<212> TYPE: DNA
<213> ORGANISM: Artificial Sequence
<220> FEATURE:
<223> OTHER INFORMATION: Human NME7-A2

<400> SEQUENCE: 26

```
atgaatcata gtgaaagatt cgttttcatt gcagagtggt atgatccaaa tgcttcactt      60

cttcgacgtt atgagctttt attttaccca ggggatggat ctgttgaaat gcatgatgta     120

aagaatcatc gcaccttttt aaagcggacc aaatatgata acctgcactt ggaagattta     180

tttataggca acaaagtgaa tgtcttttct cgacaactgg tattaattga ctatggggat     240

caatatacag ctcgccagct gggcagtagg aaagaaaaaa cgctagccct aattaaacca     300

gatgcaatat caaaggctgg agaaataatt gaaataataa acaaagctgg atttactata     360

accaaactca aaatgatgat gctttcaagg aaagaagcat tggattttca tgtagatcac     420

cagtcaagac cctttttcaa tgagctgatc cagtttatta caactggtcc tattattgcc     480

atggagattt taagagatga tgctatatgt gaatggaaaa gactgctggg acctgcaaac     540

tctggagtgg cacgcacaga tgcttctgaa agcattagag ccctctttgg aacagatggc     600

ataagaaatg cagcgcatgg ccctgattct tttgcttctg cggccagaga aatggagttg     660

ttttttga                                                              669
```

<210> SEQ ID NO 27
<211> LENGTH: 222
<212> TYPE: PRT
<213> ORGANISM: Artificial Sequence
<220> FEATURE:
<223> OTHER INFORMATION: Human NME7-A2

<400> SEQUENCE: 27

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45
```

```
Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe
    210                 215                 220
```

<210> SEQ ID NO 28
<211> LENGTH: 714
<212> TYPE: DNA
<213> ORGANISM: Artificial Sequence
<220> FEATURE:
<223> OTHER INFORMATION: Human NME7-A3

<400> SEQUENCE: 28

```
atgaatcata gtgaaagatt cgttttcatt gcagagtggt atgatccaaa tgcttcactt      60

cttcgacgtt atgagctttt attttaccca ggggatggat ctgttgaaat gcatgatgta     120

aagaatcatc gcaccttttt aaagcggacc aaatatgata acctgcactt ggaagattta     180

tttataggca acaaagtgaa tgtcttttct cgacaactgg tattaattga ctatggggat     240

caatatacag ctcgccagct gggcagtagg aaagaaaaaa cgctagccct aattaaacca     300

gatgcaatat caaaggctgg agaaataatt gaaataataa acaaagctgg atttactata     360

accaaactca aaatgatgat gctttcaagg aaagaagcat tggattttca tgtagatcac     420

cagtcaagac cctttttcaa tgagctgatc cagtttatta caactggtcc tattattgcc     480

atggagattt taagagatga tgctatatgt gaatggaaaa gactgctggg acctgcaaac     540

tctggagtgg cacgcacaga tgcttctgaa agcattagag ccctctttgg aacagatggc     600

ataagaaatg cagcgcatgg ccctgattct tttgcttctg cggccagaga aatggagttg     660

ttttttcctt caagtggagg ttgtgggccg gcaaacactg ctaaatttac ttga           714
```

<210> SEQ ID NO 29
<211> LENGTH: 237
<212> TYPE: PRT
<213> ORGANISM: Artificial Sequence
<220> FEATURE:
<223> OTHER INFORMATION: Human NME7-A3

<400> SEQUENCE: 29

```
Met Asn His Ser Glu Arg Phe Val Phe Ile Ala Glu Trp Tyr Asp Pro
```

```
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr
225                 230                 235
```

<210> SEQ ID NO 30
<211> LENGTH: 408
<212> TYPE: DNA
<213> ORGANISM: Artificial Sequence
<220> FEATURE:
<223> OTHER INFORMATION: Human NME7-B

<400> SEQUENCE: 30

```
atgaattgta cctgttgcat tgttaaaccc catgctgtca gtgaaggact gttgggaaag      60

atcctgatgg ctatccgaga tgcaggtttt gaaatctcag ctatgcagat gttcaatatg     120

gatcgggtta atgttgagga attctatgaa gtttataaag gagtagtgac cgaatatcat     180

gacatggtga cagaaatgta ttctggccct tgtgtagcaa tggagattca acagaataat     240

gctacaaaga catttcgaga attttgtgga cctgctgatc ctgaaattgc ccggcattta     300

cgccctggaa ctctcagagc aatctttggt aaaactaaga tccagaatgc tgttcactgt     360

actgatctgc cagaggatgg cctattagag gttcaatact tcttctga                  408
```

<210> SEQ ID NO 31
<211> LENGTH: 135
<212> TYPE: PRT
<213> ORGANISM: Artificial Sequence
<220> FEATURE:
<223> OTHER INFORMATION: Human NME7-B

<400> SEQUENCE: 31

```
Met Asn Cys Thr Cys Cys Ile Val Lys Pro His Ala Val Ser Glu Gly
```

```
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
        35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe
    130                 135
```

<210> SEQ ID NO 32
<211> LENGTH: 426
<212> TYPE: DNA
<213> ORGANISM: Artificial Sequence
<220> FEATURE:
<223> OTHER INFORMATION: Human NME7-B1

<400> SEQUENCE: 32

```
atgaattgta cctgttgcat tgttaaaccc catgctgtca gtgaaggact gttgggaaag      60

atcctgatgg ctatccgaga tgcaggtttt gaaatctcag ctatgcagat gttcaatatg     120

gatcgggtta atgttgagga attctatgaa gtttataaag gagtagtgac cgaatatcat     180

gacatggtga cagaaatgta ttctggccct tgtgtagcaa tggagattca acagaataat     240

gctacaaaga catttcgaga attttgtgga cctgctgatc ctgaaattgc ccggcattta     300

cgccctggaa ctctcagagc aatctttggt aaaactaaga tccagaatgc tgttcactgt     360

actgatctgc cagaggatgg cctattagag gttcaatact tcttcaagat cttggataat     420

tagtga                                                                426
```

<210> SEQ ID NO 33
<211> LENGTH: 140
<212> TYPE: PRT
<213> ORGANISM: Artificial Sequence
<220> FEATURE:
<223> OTHER INFORMATION: Human NME7-B1

<400> SEQUENCE: 33

```
Met Asn Cys Thr Cys Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
        35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95
```

```
Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe Lys Ile Leu Asp Asn
    130                 135                 140


<210> SEQ ID NO 34
<211> LENGTH: 453
<212> TYPE: DNA
<213> ORGANISM: Artificial Sequence
<220> FEATURE:
<223> OTHER INFORMATION: Human NME7-B2

<400> SEQUENCE: 34

atgccttcaa gtggaggttg tgggccggca aacactgcta aatttactaa ttgtacctgt      60

tgcattgtta aaccccatgc tgtcagtgaa ggactgttgg gaaagatcct gatggctatc     120

cgagatgcag gttttgaaat ctcagctatg cagatgttca atatggatcg ggttaatgtt     180

gaggaattct atgaagttta taaaggagta gtgaccgaat atcatgacat ggtgacagaa     240

atgtattctg gcccttgtgt agcaatggag attcaacaga ataatgctac aaagacattt     300

cgagaatttt gtggacctgc tgatcctgaa attgcccggc atttacgccc tggaactctc     360

agagcaatct ttggtaaaac taagatccag aatgctgttc actgtactga tctgccagag     420

gatggcctat tagaggttca atacttcttc tga                                  453


<210> SEQ ID NO 35
<211> LENGTH: 150
<212> TYPE: PRT
<213> ORGANISM: Artificial Sequence
<220> FEATURE:
<223> OTHER INFORMATION: Human NME7-B2

<400> SEQUENCE: 35

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
    50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe
145                 150


<210> SEQ ID NO 36
<211> LENGTH: 471
```

<212> TYPE: DNA
<213> ORGANISM: Artificial Sequence
<220> FEATURE:
<223> OTHER INFORMATION: Human NME7-B3

<400> SEQUENCE: 36
atgccttcaa gtggaggttg tgggccggca aacactgcta aatttactaa ttgtacctgt 60
tgcattgtta aaccccatgc tgtcagtgaa ggactgttgg gaaagatcct gatggctatc 120
cgagatgcag gttttgaaat ctcagctatg cagatgttca atatggatcg ggttaatgtt 180
gaggaattct atgaagttta taaaggagta gtgaccgaat atcatgacat ggtgacagaa 240
atgtattctg gcccttgtgt agcaatggag attcaacaga ataatgctac aaagacattt 300
cgagaatttt gtggacctgc tgatcctgaa attgcccggc atttacgccc tggaactctc 360
agagcaatct ttggtaaaac taagatccag aatgctgttc actgtactga tctgccagag 420
gatggcctat tagaggttca atacttcttc aagatcttgg ataattagtg a 471

<210> SEQ ID NO 37
<211> LENGTH: 155
<212> TYPE: PRT
<213> ORGANISM: Artificial Sequence
<220> FEATURE:
<223> OTHER INFORMATION: Human NME7-B3

<400> SEQUENCE: 37

Met Pro Ser Ser Gly Gly Cys Gly Pro Ala Asn Thr Ala Lys Phe Thr
1 5 10 15

Asn Cys Thr Cys Cys Ile Val Lys Pro His Ala Val Ser Glu Gly Leu
20 25 30

Leu Gly Lys Ile Leu Met Ala Ile Arg Asp Ala Gly Phe Glu Ile Ser
35 40 45

Ala Met Gln Met Phe Asn Met Asp Arg Val Asn Val Glu Glu Phe Tyr
50 55 60

Glu Val Tyr Lys Gly Val Val Thr Glu Tyr His Asp Met Val Thr Glu
65 70 75 80

Met Tyr Ser Gly Pro Cys Val Ala Met Glu Ile Gln Gln Asn Asn Ala
85 90 95

Thr Lys Thr Phe Arg Glu Phe Cys Gly Pro Ala Asp Pro Glu Ile Ala
100 105 110

Arg His Leu Arg Pro Gly Thr Leu Arg Ala Ile Phe Gly Lys Thr Lys
115 120 125

Ile Gln Asn Ala Val His Cys Thr Asp Leu Pro Glu Asp Gly Leu Leu
130 135 140

Glu Val Gln Tyr Phe Phe Lys Ile Leu Asp Asn
145 150 155

<210> SEQ ID NO 38
<211> LENGTH: 864
<212> TYPE: DNA
<213> ORGANISM: Artificial Sequence
<220> FEATURE:
<223> OTHER INFORMATION: Human NME7-AB

<400> SEQUENCE: 38
atggaaaaaa cgctagccct aattaaacca gatgcaatat caaaggctgg agaaataatt 60
gaaataataa acaaagctgg atttactata accaaactca aaatgatgat gctttcaagg 120
aaagaagcat tggattttca tgtagatcac cagtcaagac cctttttcaa tgagctgatc 180

```
cagtttatta caactggtcc tattattgcc atggagattt taagagatga tgctatatgt    240

gaatggaaaa gactgctggg acctgcaaac tctggagtgg cacgcacaga tgcttctgaa    300

agcattagag ccctctttgg aacagatggc ataagaaatg cagcgcatgg ccctgattct    360

tttgcttctg cggccagaga aatggagttg ttttttcctt caagtggagg ttgtgggccg    420

gcaaacactg ctaaatttac taattgtacc tgttgcattg ttaaacccca tgctgtcagt    480

gaaggactgt tgggaaagat cctgatggct atccgagatg caggttttga aatctcagct    540

atgcagatgt tcaatatgga tcgggttaat gttgaggaat tctatgaagt ttataaagga    600

gtagtgaccg aatatcatga catggtgaca gaaatgtatt ctggcccttg tgtagcaatg    660

gagattcaac agaataatgc tacaaagaca tttcgagaat tttgtggacc tgctgatcct    720

gaaattgccc ggcatttacg ccctggaact ctcagagcaa tctttggtaa aactaagatc    780

cagaatgctg ttcactgtac tgatctgcca gaggatggcc tattagaggt tcaatacttc    840

ttcaagatct tggataatta gtga                                           864
```

<210> SEQ ID NO 39
<211> LENGTH: 286
<212> TYPE: PRT
<213> ORGANISM: Artificial Sequence
<220> FEATURE:
<223> OTHER INFORMATION: Human NME7-AB

<400> SEQUENCE: 39

```
Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240
```

```
Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe Lys Ile Leu Asp Asn
        275                 280                 285
```

<210> SEQ ID NO 40
<211> LENGTH: 846
<212> TYPE: DNA
<213> ORGANISM: Artificial Sequence
<220> FEATURE:
<223> OTHER INFORMATION: Human NME7-AB1

<400> SEQUENCE: 40

```
atggaaaaaa cgctagccct aattaaacca gatgcaatat caaaggctgg agaaataatt      60

gaaataataa acaaagctgg atttactata accaaactca aaatgatgat gctttcaagg     120

aaagaagcat tggattttca tgtagatcac cagtcaagac ccttttcaa tgagctgatc     180

cagtttatta caactggtcc tattattgcc atggagattt taagagatga tgctatatgt     240

gaatggaaaa gactgctggg acctgcaaac tctggagtgg cacgcacaga tgcttctgaa     300

agcattagag ccctctttgg aacagatggc ataagaaatg cagcgcatgg ccctgattct     360

tttgcttctg cggccagaga aatggagttg ttttttcctt caagtggagg ttgtgggccg     420

gcaaacactg ctaaatttac taattgtacc tgttgcattg ttaaacccca tgctgtcagt     480

gaaggactgt tgggaaagat cctgatggct atccgagatg caggttttga aatctcagct     540

atgcagatgt tcaatatgga tcgggttaat gttgaggaat tctatgaagt ttataaagga     600

gtagtgaccg aatatcatga catggtgaca gaaatgtatt ctggcccttg tgtagcaatg     660

gagattcaac agaataatgc tacaaagaca tttcgagaat tttgtggacc tgctgatcct     720

gaaattgccc ggcatttacg ccctggaact ctcagagcaa tctttggtaa aactaagatc     780

cagaatgctg ttcactgtac tgatctgcca gaggatggcc tattagaggt tcaatacttc     840

ttctga                                                                846
```

<210> SEQ ID NO 41
<211> LENGTH: 281
<212> TYPE: PRT
<213> ORGANISM: Artificial Sequence
<220> FEATURE:
<223> OTHER INFORMATION: Human NME7-AB1

<400> SEQUENCE: 41

```
Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110
```

```
Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe
        275                 280


<210> SEQ ID NO 42
<211> LENGTH: 399
<212> TYPE: DNA
<213> ORGANISM: Artificial Sequence
<220> FEATURE:
<223> OTHER INFORMATION: Human NME7-A sequence optimized for E. coli
      expression

<400> SEQUENCE: 42

atggaaaaaa cgctggccct gattaaaccg gatgcaatct ccaaagctgg cgaaattatc      60

gaaattatca acaaagcggg tttcaccatc acgaaactga aaatgatgat gctgagccgt     120

aaagaagccc tggattttca tgtcgaccac cagtctcgcc cgtttttcaa tgaactgatt     180

caattcatca ccacgggtcc gattatcgca atggaaattc tgcgtgatga cgctatctgc     240

gaatggaaac gcctgctggg cccggcaaac tcaggtgttg cgcgtaccga tgccagtgaa     300

tccattcgcg ctctgtttgg caccgatggt atccgtaatg cagcacatgg tccggactca     360

ttcgcatcgg cagctcgtga aatggaactg tttttctga                           399


<210> SEQ ID NO 43
<211> LENGTH: 132
<212> TYPE: PRT
<213> ORGANISM: Artificial Sequence
<220> FEATURE:
<223> OTHER INFORMATION: Human NME7-A sequence optimized for E. coli
      expression

<400> SEQUENCE: 43

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45
```

```
Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe
    130
```

```
<210> SEQ ID NO 44
<211> LENGTH: 444
<212> TYPE: DNA
<213> ORGANISM: Artificial Sequence
<220> FEATURE:
<223> OTHER INFORMATION: Human NME7-A1 sequence optimized for E. coli
      expression

<400> SEQUENCE: 44

atggaaaaaa cgctggccct gattaaaccg gatgcaatct ccaaagctgg cgaaattatc      60

gaaattatca acaaagcggg tttcaccatc acgaaactga aaatgatgat gctgagccgt     120

aaagaagccc tggattttca tgtcgaccac cagtctcgcc cgtttttcaa tgaactgatt     180

caattcatca ccacgggtcc gattatcgca atggaaattc tgcgtgatga cgctatctgc     240

gaatggaaac gcctgctggg cccggcaaac tcaggtgttg cgcgtaccga tgccagtgaa     300

tccattcgcg ctctgtttgg caccgatggt atccgtaatg cagcacatgg tccggactca     360

ttcgcatcgg cagctcgtga aatggaactg tttttcccga gctctggcgg ttgcggtccg     420

gcaaacaccg ccaaatttac ctga                                            444
```

```
<210> SEQ ID NO 45
<211> LENGTH: 147
<212> TYPE: PRT
<213> ORGANISM: Artificial Sequence
<220> FEATURE:
<223> OTHER INFORMATION: Human NME7-A1 sequence optimized for E. coli
      expression

<400> SEQUENCE: 45

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125
```

```
Glu Leu Phe Phe Pro Ser Ser Gly Gly Cys Gly Pro Ala Asn Thr Ala
    130                 135                 140

Lys Phe Thr
145


<210> SEQ ID NO 46
<211> LENGTH: 669
<212> TYPE: DNA
<213> ORGANISM: Artificial Sequence
<220> FEATURE:
<223> OTHER INFORMATION: Human NME7-A2 sequence optimized for E. coli
      expression

<400> SEQUENCE: 46

atgaatcact ccgaacgctt tgtttttatc gccgaatggt atgacccgaa tgcttccctg     60

ctgcgccgct acgaactgct gttttatccg ggcgatggta gcgtggaaat gcatgacgtt    120

aaaaatcacc gtacctttct gaaacgcacg aaatatgata atctgcatct ggaagacctg    180

tttattggca acaaagtcaa tgtgttctct cgtcagctgg tgctgatcga ttatggcgac    240

cagtacaccg cgcgtcaact gggtagtcgc aaagaaaaaa cgctggccct gattaaaccg    300

gatgcaatct ccaaagctgg cgaaattatc gaaattatca acaaagcggg tttcaccatc    360

acgaaactga aaatgatgat gctgagccgt aaagaagccc tggattttca tgtcgaccac    420

cagtctcgcc cgtttttcaa tgaactgatt caattcatca ccacgggtcc gattatcgca    480

atggaaattc tgcgtgatga cgctatctgc gaatggaaac gcctgctggg cccggcaaac    540

tcaggtgttg cgcgtaccga tgccagtgaa tccattcgcg ctctgtttgg caccgatggt    600

atccgtaatg cagcacatgg tccggactca ttcgcatcgg cagctcgtga aatggaactg    660

tttttctga                                                             669


<210> SEQ ID NO 47
<211> LENGTH: 222
<212> TYPE: PRT
<213> ORGANISM: Artificial Sequence
<220> FEATURE:
<223> OTHER INFORMATION: Human NME7-A2 sequence optimized for E. coli
      expression

<400> SEQUENCE: 47

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140
```

```
Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe
    210                 215                 220
```

<210> SEQ ID NO 48
<211> LENGTH: 714
<212> TYPE: DNA
<213> ORGANISM: Artificial Sequence
<220> FEATURE:
<223> OTHER INFORMATION: Human NME7-A3 sequence optimized for E. coli expression

<400> SEQUENCE: 48

```
atgaatcact ccgaacgctt tgtttttatc gccgaatggt atgacccgaa tgcttccctg      60

ctgcgccgct acgaactgct gttttatccg ggcgatggta gcgtggaaat gcatgacgtt     120

aaaaatcacc gtacctttct gaaacgcacg aaatatgata atctgcatct ggaagacctg     180

tttattggca acaaagtcaa tgtgttctct cgtcagctgg tgctgatcga ttatggcgac     240

cagtacaccg cgcgtcaact gggtagtcgc aaagaaaaaa cgctggccct gattaaaccg     300

gatgcaatct ccaaagctgg cgaaattatc gaaattatca acaaagcggg tttcaccatc     360

acgaaactga aaatgatgat gctgagccgt aaagaagccc tggattttca tgtcgaccac     420

cagtctcgcc cgtttttcaa tgaactgatt caattcatca ccacgggtcc gattatcgca     480

atggaaattc tgcgtgatga cgctatctgc gaatggaaac gcctgctggg cccggcaaac     540

tcaggtgttg cgcgtaccga tgccagtgaa tccattcgcg ctctgtttgg caccgatggt     600

atccgtaatg cagcacatgg tccggactca ttcgcatcgg cagctcgtga aatggaactg     660

tttttcccga gctctggcgg ttgcggtccg gcaaacaccg ccaaatttac ctga           714
```

<210> SEQ ID NO 49
<211> LENGTH: 237
<212> TYPE: PRT
<213> ORGANISM: Artificial Sequence
<220> FEATURE:
<223> OTHER INFORMATION: Human NME7-A3 sequence optimized for E. coli expression

<400> SEQUENCE: 49

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95
```

```
Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr
225                 230                 235
```

<210> SEQ ID NO 50
<211> LENGTH: 408
<212> TYPE: DNA
<213> ORGANISM: Artificial Sequence
<220> FEATURE:
<223> OTHER INFORMATION: Human NME7-B sequence optimized for E. coli expression

<400> SEQUENCE: 50

```
atgaattgta cgtgctgtat tgtcaaaccg cacgcagtgt cagaaggcct gctgggtaaa     60

attctgatgg caatccgtga tgctggcttt gaaatctcgg ccatgcagat gttcaacatg    120

gaccgcgtta acgtcgaaga attctacgaa gtttacaaag gcgtggttac cgaatatcac    180

gatatggtta cggaaatgta ctccggtccg tgcgtcgcga tggaaattca gcaaaacaat    240

gccaccaaaa cgtttcgtga attctgtggt ccggcagatc cggaaatcgc acgtcatctg    300

cgtccgggta ccctgcgcgc aatttttggt aaaacgaaaa tccagaacgc tgtgcactgt    360

accgatctgc cggaagacgg tctgctggaa gttcaatact ttttctga                 408
```

<210> SEQ ID NO 51
<211> LENGTH: 135
<212> TYPE: PRT
<213> ORGANISM: Artificial Sequence
<220> FEATURE:
<223> OTHER INFORMATION: Human NME7-B sequence optimized for E. coli expression

<400> SEQUENCE: 51

```
Met Asn Cys Thr Cys Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
        35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80
```

```
Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe
    130                 135
```

<210> SEQ ID NO 52
<211> LENGTH: 423
<212> TYPE: DNA
<213> ORGANISM: Artificial Sequence
<220> FEATURE:
<223> OTHER INFORMATION: Human NME7-B1 sequence optimized for E. coli expression

<400> SEQUENCE: 52

```
atgaattgta cgtgctgtat tgtcaaaccg cacgcagtgt cagaaggcct gctgggtaaa     60

attctgatgg caatccgtga tgctggcttt gaaatctcgg ccatgcagat gttcaacatg    120

gaccgcgtta acgtcgaaga attctacgaa gtttacaaag gcgtggttac cgaatatcac    180

gatatggtta cggaaatgta ctccggtccg tgcgtcgcga tggaaattca gcaaaacaat    240

gccaccaaaa cgtttcgtga attctgtggt ccggcagatc cggaaatcgc acgtcatctg    300

cgtccgggta ccctgcgcgc aatttttggt aaaacgaaaa tccagaacgc tgtgcactgt    360

accgatctgc cggaagacgg tctgctggaa gttcaatact ttttcaaaat tctggataat    420

tga                                                                  423
```

<210> SEQ ID NO 53
<211> LENGTH: 140
<212> TYPE: PRT
<213> ORGANISM: Artificial Sequence
<220> FEATURE:
<223> OTHER INFORMATION: Human NME7-B1 sequence optimized for E. coli expression

<400> SEQUENCE: 53

```
Met Asn Cys Thr Cys Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
        35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe Lys Ile Leu Asp Asn
    130                 135                 140
```

<210> SEQ ID NO 54

<211> LENGTH: 453
<212> TYPE: DNA
<213> ORGANISM: Artificial Sequence
<220> FEATURE:
<223> OTHER INFORMATION: Human NME7-B2 sequence optimized for E. coli expression

<400> SEQUENCE: 54

```
atgccgagct ctggcggttg cggtccggca aacaccgcca aatttaccaa ttgtacgtgc     60

tgtattgtca aaccgcacgc agtgtcagaa ggcctgctgg gtaaaattct gatggcaatc    120

cgtgatgctg gctttgaaat ctcggccatg cagatgttca acatggaccg cgttaacgtc    180

gaagaattct acgaagttta caaaggcgtg gttaccgaat atcacgatat ggttacggaa    240

atgtactccg gtccgtgcgt cgcgatggaa attcagcaaa acaatgccac caaaacgttt    300

cgtgaattct gtggtccggc agatccggaa atcgcacgtc atctgcgtcc gggtaccctg    360

cgcgcaattt ttggtaaaac gaaaatccag aacgctgtgc actgtaccga tctgccggaa    420

gacggtctgc tggaagttca atactttttc tga                                 453
```

<210> SEQ ID NO 55
<211> LENGTH: 150
<212> TYPE: PRT
<213> ORGANISM: Artificial Sequence
<220> FEATURE:
<223> OTHER INFORMATION: Human NME7-B2 sequence optimized for E. coli expression

<400> SEQUENCE: 55

```
Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
    50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe
145                 150
```

<210> SEQ ID NO 56
<211> LENGTH: 468
<212> TYPE: DNA
<213> ORGANISM: Artificial Sequence
<220> FEATURE:
<223> OTHER INFORMATION: Human NME7-B3 sequence optimized for E. coli expression

<400> SEQUENCE: 56

```
atgccgagct ctggcggttg cggtccggca aacaccgcca aatttaccaa ttgtacgtgc     60
```

```
tgtattgtca aaccgcacgc agtgtcagaa ggcctgctgg gtaaaattct gatggcaatc    120

cgtgatgctg gctttgaaat ctcggccatg cagatgttca acatggaccg cgttaacgtc    180

gaagaattct acgaagttta caaaggcgtg gttaccgaat atcacgatat ggttacggaa    240

atgtactccg gtccgtgcgt cgcgatggaa attcagcaaa acaatgccac caaaacgttt    300

cgtgaattct gtggtccggc agatccggaa atcgcacgtc atctgcgtcc gggtaccctg    360

cgcgcaattt ttggtaaaac gaaaatccag aacgctgtgc actgtaccga tctgccggaa    420

gacggtctgc tggaagttca atactttttc aaaattctgg ataattga                468
```

```
<210> SEQ ID NO 57
<211> LENGTH: 155
<212> TYPE: PRT
<213> ORGANISM: Artificial Sequence
<220> FEATURE:
<223> OTHER INFORMATION: Human NME7-B3 sequence optimized for E. coli
      expression

<400> SEQUENCE: 57

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
    50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe Lys Ile Leu Asp Asn
145                 150                 155
```

```
<210> SEQ ID NO 58
<211> LENGTH: 861
<212> TYPE: DNA
<213> ORGANISM: Artificial Sequence
<220> FEATURE:
<223> OTHER INFORMATION: Human NME7-AB sequence optimized for E. coli
      expression

<400> SEQUENCE: 58

atggaaaaaa cgctggccct gattaaaccg gatgcaatct ccaaagctgg cgaaattatc     60

gaaattatca acaaagcggg tttcaccatc acgaaactga aaatgatgat gctgagccgt    120

aaagaagccc tggattttca tgtcgaccac cagtctcgcc cgtttttcaa tgaactgatt    180

caattcatca ccacgggtcc gattatcgca atggaaattc tgcgtgatga cgctatctgc    240

gaatggaaac gcctgctggg cccggcaaac tcaggtgttg cgcgtaccga tgccagtgaa    300

tccattcgcg ctctgtttgg caccgatggt atccgtaatg cagcacatgg tccggactca    360

ttcgcatcgg cagctcgtga aatggaactg tttttcccga gctctggcgg ttgcggtccg    420
```

```
gcaaacaccg ccaaatttac caattgtacg tgctgtattg tcaaaccgca cgcagtgtca    480

gaaggcctgc tgggtaaaat tctgatggca atccgtgatg ctggctttga aatctcggcc    540

atgcagatgt tcaacatgga ccgcgttaac gtcgaagaat tctacgaagt ttacaaaggc    600

gtggttaccg aatatcacga tatggttacg gaaatgtact ccggtccgtg cgtcgcgatg    660

gaaattcagc aaaacaatgc caccaaaacg tttcgtgaat tctgtggtcc ggcagatccg    720

gaaatcgcac gtcatctgcg tccgggtacc ctgcgcgcaa tttttggtaa aacgaaaatc    780

cagaacgctg tgcactgtac cgatctgccg gaagacggtc tgctggaagt tcaatacttt    840

ttcaaaattc tggataattg a                                              861
```

```
<210> SEQ ID NO 59
<211> LENGTH: 286
<212> TYPE: PRT
<213> ORGANISM: Artificial Sequence
<220> FEATURE:
<223> OTHER INFORMATION: Human NME7-AB sequence optimized for E. coli
      expression

<400> SEQUENCE: 59

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270
```

```
Gly Leu Leu Glu Val Gln Tyr Phe Phe Lys Ile Leu Asp Asn
        275                 280                 285


<210> SEQ ID NO 60
<211> LENGTH: 846
<212> TYPE: DNA
<213> ORGANISM: Artificial Sequence
<220> FEATURE:
<223> OTHER INFORMATION: Human NME7-AB1 sequence optimized for E. coli
      expression

<400> SEQUENCE: 60

atggaaaaaa cgctggccct gattaaaccg gatgcaatct ccaaagctgg cgaaattatc      60

gaaattatca acaaagcggg tttcaccatc acgaaactga aaatgatgat gctgagccgt     120

aaagaagccc tggattttca tgtcgaccac cagtctcgcc cgtttttcaa tgaactgatt     180

caattcatca ccacgggtcc gattatcgca atggaaattc tgcgtgatga cgctatctgc     240

gaatggaaac gcctgctggg cccggcaaac tcaggtgttg cgcgtaccga tgccagtgaa     300

tccattcgcg ctctgtttgg caccgatggt atccgtaatg cagcacatgg tccggactca     360

ttcgcatcgg cagctcgtga aatggaactg tttttcccga gctctggcgg ttgcggtccg     420

gcaaacaccg ccaaatttac caattgtacg tgctgtattg tcaaaccgca cgcagtgtca     480

gaaggcctgc tgggtaaaat tctgatggca atccgtgatg ctggctttga aatctcggcc     540

atgcagatgt tcaacatgga ccgcgttaac gtcgaagaat tctacgaagt ttacaaaggc     600

gtggttaccg aatatcacga tatggttacg gaaatgtact ccggtccgtg cgtcgcgatg     660

gaaattcagc aaaacaatgc caccaaaacg tttcgtgaat tctgtggtcc ggcagatccg     720

gaaatcgcac gtcatctgcg tccgggtacc ctgcgcgcaa tttttggtaa aacgaaaatc     780

cagaacgctg tgcactgtac cgatctgccg gaagacggtc tgctggaagt tcaatacttt     840

ttctga                                                                846


<210> SEQ ID NO 61
<211> LENGTH: 281
<212> TYPE: PRT
<213> ORGANISM: Artificial Sequence
<220> FEATURE:
<223> OTHER INFORMATION: Human NME7-AB1 sequence optimized for E. coli
      expression

<400> SEQUENCE: 61

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125
```

```
Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe
        275                 280
```

<210> SEQ ID NO 62
<211> LENGTH: 570
<212> TYPE: DNA
<213> ORGANISM: Artificial Sequence
<220> FEATURE:
<223> OTHER INFORMATION: DNA encoding Mouse NME6

<400> SEQUENCE: 62

```
atgacctcca tcttgcgaag tccccaagct cttcagctca cactagccct gatcaagcct      60

gatgcagttg cccacccact gatcctggag gctgttcatc agcagattct gagcaacaag     120

ttcctcattg tacgaacgag ggaactgcag tggaagctgg aggactgccg gaggttttac     180

cgagagcatg aagggcgttt tttctatcag cggctggtgg agttcatgac aagtgggcca     240

atccgagcct atatccttgc ccacaaagat gccatccaac tttggaggac actgatggga     300

cccaccagag tatttcgagc acgctatata gccccagatt caattcgtgg aagtttgggc     360

ctcactgaca cccgaaatac tacccatggc tcagactccg tggtttccgc cagcagagag     420

attgcagcct tcttccctga cttcagtgaa cagcgctggt atgaggagga ggaaccccag     480

ctgcggtgtg gtcctgtgca ctacagtcca gaggaaggta tccactgtgc agctgaaaca     540

ggaggccaca aacaacctaa caaaacctag                                      570
```

<210> SEQ ID NO 63
<211> LENGTH: 189
<212> TYPE: PRT
<213> ORGANISM: Artificial Sequence
<220> FEATURE:
<223> OTHER INFORMATION: Mouse NME6

<400> SEQUENCE: 63

```
Met Thr Ser Ile Leu Arg Ser Pro Gln Ala Leu Gln Leu Thr Leu Ala
1               5                   10                  15

Leu Ile Lys Pro Asp Ala Val Ala His Pro Leu Ile Leu Glu Ala Val
            20                  25                  30

His Gln Gln Ile Leu Ser Asn Lys Phe Leu Ile Val Arg Thr Arg Glu
        35                  40                  45
```

```
Leu Gln Trp Lys Leu Glu Asp Cys Arg Arg Phe Tyr Arg Glu His Glu
    50                  55                  60

Gly Arg Phe Phe Tyr Gln Arg Leu Val Glu Phe Met Thr Ser Gly Pro
65                  70                  75                  80

Ile Arg Ala Tyr Ile Leu Ala His Lys Asp Ala Ile Gln Leu Trp Arg
                85                  90                  95

Thr Leu Met Gly Pro Thr Arg Val Phe Arg Ala Arg Tyr Ile Ala Pro
            100                 105                 110

Asp Ser Ile Arg Gly Ser Leu Gly Leu Thr Asp Thr Arg Asn Thr Thr
        115                 120                 125

His Gly Ser Asp Ser Val Val Ser Ala Ser Arg Glu Ile Ala Ala Phe
    130                 135                 140

Phe Pro Asp Phe Ser Glu Gln Arg Trp Tyr Glu Glu Glu Glu Pro Gln
145                 150                 155                 160

Leu Arg Cys Gly Pro Val His Tyr Ser Pro Glu Glu Gly Ile His Cys
                165                 170                 175

Ala Ala Glu Thr Gly Gly His Lys Gln Pro Asn Lys Thr
            180                 185
```

<210> SEQ ID NO 64
<211> LENGTH: 585
<212> TYPE: DNA
<213> ORGANISM: Artificial Sequence
<220> FEATURE:
<223> OTHER INFORMATION: DNA encoding Human NME6

<400> SEQUENCE: 64

```
atgacccaga atctggggag tgagatggcc tcaatcttgc gaagccctca ggctctccag      60

ctcactctag ccctgatcaa gcctgacgca gtcgcccatc cactgattct ggaggctgtt     120

catcagcaga ttctaagcaa caagttcctg attgtacgaa tgagagaact actgtggaga     180

aaggaagatt gccagaggtt ttaccgagag catgaagggc gtttttteta tcagaggctg     240

gtggagttca tggccagcgg gccaatccga gcctacatcc ttgcccacaa ggatgccatc     300

cagctctgga ggacgctcat gggacccacc agagtgttcc gagcacgcca tgtggcccca     360

gattctatcc gtgggagttt cggcctcact gacacccgca acaccaccca tggttcggac     420

tctgtggttt cagccagcag agagattgca gccttcttcc ctgacttcag tgaacagcgc     480

tggtatgagg aggaagagcc ccagttgcgc tgtggccctg tgtgctatag cccagaggga     540

ggtgtccact atgtagctgg aacaggaggc ctaggaccag cctga                      585
```

<210> SEQ ID NO 65
<211> LENGTH: 194
<212> TYPE: PRT
<213> ORGANISM: Artificial Sequence
<220> FEATURE:
<223> OTHER INFORMATION: Human NME6

<400> SEQUENCE: 65

```
Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60
```

```
Gln Arg Phe Tyr Arg Glu His Glu Gly Arg Phe Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Glu Pro Gln Leu Arg Cys Gly Pro Val Cys Tyr
                165                 170                 175

Ser Pro Glu Gly Gly Val His Tyr Val Ala Gly Thr Gly Gly Leu Gly
            180                 185                 190

Pro Ala
```

<210> SEQ ID NO 66
<211> LENGTH: 525
<212> TYPE: DNA
<213> ORGANISM: Artificial Sequence
<220> FEATURE:
<223> OTHER INFORMATION: DNA encoding Human NME6 1

<400> SEQUENCE: 66

```
atgacccaga atctggggag tgagatggcc tcaatcttgc gaagccctca ggctctccag      60

ctcactctag ccctgatcaa gcctgacgca gtcgcccatc cactgattct ggaggctgtt     120

catcagcaga ttctaagcaa caagttcctg attgtacgaa tgagagaact actgtggaga     180

aaggaagatt gccagaggtt ttaccgagag catgaagggc gtttttttcta tcagaggctg     240

gtggagttca tggccagcgg gccaatccga gcctacatcc ttgcccacaa ggatgccatc     300

cagctctgga ggacgctcat gggacccacc agagtgttcc gagcacgcca tgtggcccca     360

gattctatcc gtgggagttt cggcctcact gacacccgca acaccaccca tggttcggac     420

tctgtggttt cagccagcag agagattgca gccttcttcc ctgacttcag tgaacagcgc     480

tggtatgagg aggaagagcc ccagttgcgc tgtggccctg tgtga                     525
```

<210> SEQ ID NO 67
<211> LENGTH: 174
<212> TYPE: PRT
<213> ORGANISM: Artificial Sequence
<220> FEATURE:
<223> OTHER INFORMATION: Human NME6 1

<400> SEQUENCE: 67

```
Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Phe Tyr Gln Arg Leu
65                  70                  75                  80
```

```
Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Glu Pro Gln Leu Arg Cys Gly Pro Val
                165                 170


<210> SEQ ID NO 68
<211> LENGTH: 468
<212> TYPE: DNA
<213> ORGANISM: Artificial Sequence
<220> FEATURE:
<223> OTHER INFORMATION: DNA encoding Human NME6 2

<400> SEQUENCE: 68

atgctcactc tagccctgat caagcctgac gcagtcgccc atccactgat tctggaggct      60

gttcatcagc agattctaag caacaagttc ctgattgtac gaatgagaga actactgtgg     120

agaaaggaag attgccagag gttttaccga gagcatgaag ggcgtttttt ctatcagagg     180

ctggtggagt tcatggccag cgggccaatc cgagcctaca tccttgccca caaggatgcc     240

atccagctct ggaggacgct catgggaccc accagagtgt tccgagcacg ccatgtggcc     300

ccagattcta tccgtgggag tttcggcctc actgacaccc gcaacaccac ccatggttcg     360

gactctgtgg tttcagccag cagagagatt gcagccttct tccctgactt cagtgaacag     420

cgctggtatg aggaggaaga gccccagttg cgctgtggcc ctgtgtga                  468


<210> SEQ ID NO 69
<211> LENGTH: 155
<212> TYPE: PRT
<213> ORGANISM: Artificial Sequence
<220> FEATURE:
<223> OTHER INFORMATION: Human NME6 2

<400> SEQUENCE: 69

Met Leu Thr Leu Ala Leu Ile Lys Pro Asp Ala Val Ala His Pro Leu
1               5                   10                  15

Ile Leu Glu Ala Val His Gln Gln Ile Leu Ser Asn Lys Phe Leu Ile
            20                  25                  30

Val Arg Met Arg Glu Leu Leu Trp Arg Lys Glu Asp Cys Gln Arg Phe
        35                  40                  45

Tyr Arg Glu His Glu Gly Arg Phe Phe Tyr Gln Arg Leu Val Glu Phe
    50                  55                  60

Met Ala Ser Gly Pro Ile Arg Ala Tyr Ile Leu Ala His Lys Asp Ala
65                  70                  75                  80

Ile Gln Leu Trp Arg Thr Leu Met Gly Pro Thr Arg Val Phe Arg Ala
                85                  90                  95

Arg His Val Ala Pro Asp Ser Ile Arg Gly Ser Phe Gly Leu Thr Asp
            100                 105                 110

Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
```

130 135 140

Glu Glu Glu Pro Gln Leu Arg Cys Gly Pro Val
145 150 155

<210> SEQ ID NO 70
<211> LENGTH: 528
<212> TYPE: DNA
<213> ORGANISM: Artificial Sequence
<220> FEATURE:
<223> OTHER INFORMATION: DNA encoding Human NME6 3

<400> SEQUENCE: 70
atgctcactc tagccctgat caagcctgac gcagtcgccc atccactgat tctggaggct 60
gttcatcagc agattctaag caacaagttc ctgattgtac gaatgagaga actactgtgg 120
agaaaggaag attgccagag gttttaccga gagcatgaag ggcgtttttt ctatcagagg 180
ctggtggagt tcatggccag cgggccaatc cgagcctaca tccttgccca caaggatgcc 240
atccagctct ggaggacgct catgggaccc accagagtgt tccgagcacg ccatgtggcc 300
ccagattcta tccgtgggag tttcggcctc actgacaccc gcaacaccac ccatggttcg 360
gactctgtgg tttcagccag cagagagatt gcagccttct tccctgactt cagtgaacag 420
cgctggtatg aggaggaaga gccccagttg cgctgtggcc ctgtgtgcta tagcccagag 480
ggaggtgtcc actatgtagc tggaacagga ggcctaggac cagcctga 528

<210> SEQ ID NO 71
<211> LENGTH: 175
<212> TYPE: PRT
<213> ORGANISM: Artificial Sequence
<220> FEATURE:
<223> OTHER INFORMATION: Human NME6 3

<400> SEQUENCE: 71

Met Leu Thr Leu Ala Leu Ile Lys Pro Asp Ala Val Ala His Pro Leu
1 5 10 15

Ile Leu Glu Ala Val His Gln Gln Ile Leu Ser Asn Lys Phe Leu Ile
20 25 30

Val Arg Met Arg Glu Leu Leu Trp Arg Lys Glu Asp Cys Gln Arg Phe
35 40 45

Tyr Arg Glu His Glu Gly Arg Phe Phe Tyr Gln Arg Leu Val Glu Phe
50 55 60

Met Ala Ser Gly Pro Ile Arg Ala Tyr Ile Leu Ala His Lys Asp Ala
65 70 75 80

Ile Gln Leu Trp Arg Thr Leu Met Gly Pro Thr Arg Val Phe Arg Ala
85 90 95

Arg His Val Ala Pro Asp Ser Ile Arg Gly Ser Phe Gly Leu Thr Asp
100 105 110

Thr Arg Asn Thr Thr His Gly Ser Asp Ser Val Val Ser Ala Ser Arg
115 120 125

Glu Ile Ala Ala Phe Phe Pro Asp Phe Ser Glu Gln Arg Trp Tyr Glu
130 135 140

Glu Glu Glu Pro Gln Leu Arg Cys Gly Pro Val Cys Tyr Ser Pro Glu
145 150 155 160

Gly Gly Val His Tyr Val Ala Gly Thr Gly Gly Leu Gly Pro Ala
165 170 175

<210> SEQ ID NO 72
<211> LENGTH: 585

<212> TYPE: DNA
<213> ORGANISM: Artificial Sequence
<220> FEATURE:
<223> OTHER INFORMATION: Human NME6 sequence optimized for E. coli expression

<400> SEQUENCE: 72

```
atgacgcaaa atctgggctc ggaaatggca agtatcctgc gctccccgca agcactgcaa     60

ctgaccctgg ctctgatcaa accggacgct gttgctcatc cgctgattct ggaagcggtc    120

caccagcaaa ttctgagcaa caaatttctg atcgtgcgta tgcgcgaact gctgtggcgt    180

aaagaagatt gccagcgttt ttatcgcgaa catgaaggcc gtttctttta tcaacgcctg    240

gttgaattca tggcctctgg tccgattcgc gcatatatcc tggctcacaa agatgcgatt    300

cagctgtggc gtaccctgat gggtccgacg cgcgtctttc gtgcacgtca tgtggcaccg    360

gactcaatcc gtggctcgtt cggtctgacc gatacgcgca ataccacgca cggtagcgac    420

tctgttgtta gtgcgtcccg tgaaatcgcg gccttttttcc cggacttctc cgaacagcgt    480

tggtacgaag aagaagaacc gcaactgcgc tgtggcccgg tctgttattc tccggaaggt    540

ggtgtccatt atgtggcggg cacgggtggt ctgggtccgg catga                    585
```

<210> SEQ ID NO 73
<211> LENGTH: 194
<212> TYPE: PRT
<213> ORGANISM: Artificial Sequence
<220> FEATURE:
<223> OTHER INFORMATION: Human NME6 sequence optimized for E. coli expression

<400> SEQUENCE: 73

```
Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Glu Pro Gln Leu Arg Cys Gly Pro Val Cys Tyr
                165                 170                 175

Ser Pro Glu Gly Gly Val His Tyr Val Ala Gly Thr Gly Gly Leu Gly
            180                 185                 190

Pro Ala
```

<210> SEQ ID NO 74

<211> LENGTH: 525
<212> TYPE: DNA
<213> ORGANISM: Artificial Sequence
<220> FEATURE:
<223> OTHER INFORMATION: Human NME6 1 sequence optimized for E. coli expression

<400> SEQUENCE: 74
atgacgcaaa atctgggctc ggaaatggca agtatcctgc gctccccgca agcactgcaa 60
ctgaccctgg ctctgatcaa accggacgct gttgctcatc cgctgattct ggaagcggtc 120
caccagcaaa ttctgagcaa caaatttctg atcgtgcgta tgcgcgaact gctgtggcgt 180
aaagaagatt gccagcgttt ttatcgcgaa catgaaggcc gtttctttta tcaacgcctg 240
gttgaattca tggcctctgg tccgattcgc gcatatatcc tggctcacaa agatgcgatt 300
cagctgtggc gtaccctgat gggtccgacg cgcgtctttc gtgcacgtca tgtggcaccg 360
gactcaatcc gtggctcgtt cggtctgacc gatacgcgca ataccacgca cggtagcgac 420
tctgttgtta gtgcgtcccg tgaaatcgcg gcctttttcc cggacttctc cgaacagcgt 480
tggtacgaag aagaagaacc gcaactgcgc tgtggcccgg tctga 525

<210> SEQ ID NO 75
<211> LENGTH: 174
<212> TYPE: PRT
<213> ORGANISM: Artificial Sequence
<220> FEATURE:
<223> OTHER INFORMATION: Human NME6 1 sequence optimized for E. coli expression

<400> SEQUENCE: 75

Met Thr Gln Asn Leu Gly Ser Glu Met Ala Ser Ile Leu Arg Ser Pro
1 5 10 15

Gln Ala Leu Gln Leu Thr Leu Ala Leu Ile Lys Pro Asp Ala Val Ala
20 25 30

His Pro Leu Ile Leu Glu Ala Val His Gln Gln Ile Leu Ser Asn Lys
35 40 45

Phe Leu Ile Val Arg Met Arg Glu Leu Leu Trp Arg Lys Glu Asp Cys
50 55 60

Gln Arg Phe Tyr Arg Glu His Glu Gly Arg Phe Phe Tyr Gln Arg Leu
65 70 75 80

Val Glu Phe Met Ala Ser Gly Pro Ile Arg Ala Tyr Ile Leu Ala His
85 90 95

Lys Asp Ala Ile Gln Leu Trp Arg Thr Leu Met Gly Pro Thr Arg Val
100 105 110

Phe Arg Ala Arg His Val Ala Pro Asp Ser Ile Arg Gly Ser Phe Gly
115 120 125

Leu Thr Asp Thr Arg Asn Thr Thr His Gly Ser Asp Ser Val Val Ser
130 135 140

Ala Ser Arg Glu Ile Ala Ala Phe Phe Pro Asp Phe Ser Glu Gln Arg
145 150 155 160

Trp Tyr Glu Glu Glu Glu Pro Gln Leu Arg Cys Gly Pro Val
165 170

<210> SEQ ID NO 76
<211> LENGTH: 468
<212> TYPE: DNA
<213> ORGANISM: Artificial Sequence
<220> FEATURE:
<223> OTHER INFORMATION: Human NME6 2 sequence optimized for E. coli expression

<400> SEQUENCE: 76
atgctgaccc tggctctgat caaaccggac gctgttgctc atccgctgat tctggaagcg 60
gtccaccagc aaattctgag caacaaattt ctgatcgtgc gtatgcgcga actgctgtgg 120
cgtaaagaag attgccagcg tttttatcgc gaacatgaag gccgtttctt ttatcaacgc 180
ctggttgaat tcatggcctc tggtccgatt cgcgcatata tcctggctca caaagatgcg 240
attcagctgt ggcgtaccct gatgggtccg acgcgcgtct ttcgtgcacg tcatgtggca 300
ccggactcaa tccgtggctc gttcggtctg accgatacgc gcaataccac gcacggtagc 360
gactctgttg ttagtgcgtc ccgtgaaatc gcggcctttt tcccggactt ctccgaacag 420
cgttggtacg aagaagaaga accgcaactg cgctgtggcc cggtctga 468

<210> SEQ ID NO 77
<211> LENGTH: 155
<212> TYPE: PRT
<213> ORGANISM: Artificial Sequence
<220> FEATURE:
<223> OTHER INFORMATION: Human NME6 2 sequence optimized for E. coli
expression

<400> SEQUENCE: 77

Met Leu Thr Leu Ala Leu Ile Lys Pro Asp Ala Val Ala His Pro Leu
1 5 10 15

Ile Leu Glu Ala Val His Gln Gln Ile Leu Ser Asn Lys Phe Leu Ile
20 25 30

Val Arg Met Arg Glu Leu Leu Trp Arg Lys Glu Asp Cys Gln Arg Phe
35 40 45

Tyr Arg Glu His Glu Gly Arg Phe Phe Tyr Gln Arg Leu Val Glu Phe
50 55 60

Met Ala Ser Gly Pro Ile Arg Ala Tyr Ile Leu Ala His Lys Asp Ala
65 70 75 80

Ile Gln Leu Trp Arg Thr Leu Met Gly Pro Thr Arg Val Phe Arg Ala
85 90 95

Arg His Val Ala Pro Asp Ser Ile Arg Gly Ser Phe Gly Leu Thr Asp
100 105 110

Thr Arg Asn Thr Thr His Gly Ser Asp Ser Val Val Ser Ala Ser Arg
115 120 125

Glu Ile Ala Ala Phe Phe Pro Asp Phe Ser Glu Gln Arg Trp Tyr Glu
130 135 140

Glu Glu Glu Pro Gln Leu Arg Cys Gly Pro Val
145 150 155

<210> SEQ ID NO 78
<211> LENGTH: 528
<212> TYPE: DNA
<213> ORGANISM: Artificial Sequence
<220> FEATURE:
<223> OTHER INFORMATION: Human NME6 3 sequence optimized for E. coli
expression

<400> SEQUENCE: 78
atgctgaccc tggctctgat caaaccggac gctgttgctc atccgctgat tctggaagcg 60
gtccaccagc aaattctgag caacaaattt ctgatcgtgc gtatgcgcga actgctgtgg 120
cgtaaagaag attgccagcg tttttatcgc gaacatgaag gccgtttctt ttatcaacgc 180
ctggttgaat tcatggcctc tggtccgatt cgcgcatata tcctggctca caaagatgcg 240

```
attcagctgt ggcgtaccct gatgggtccg acgcgcgtct ttcgtgcacg tcatgtggca    300

ccggactcaa tccgtggctc gttcggtctg accgatacgc gcaataccac gcacggtagc    360

gactctgttg ttagtgcgtc ccgtgaaatc gcggcctttt tcccggactt ctccgaacag    420

cgttggtacg aagaagaaga accgcaactg cgctgtggcc cggtctgtta ttctccggaa    480

ggtggtgtcc attatgtggc gggcacgggt ggtctgggtc cggcatga                 528


<210> SEQ ID NO 79
<211> LENGTH: 175
<212> TYPE: PRT
<213> ORGANISM: Artificial Sequence
<220> FEATURE:
<223> OTHER INFORMATION: Human NME6 3 sequence optimized for E. coli
      expression

<400> SEQUENCE: 79

Met Leu Thr Leu Ala Leu Ile Lys Pro Asp Ala Val Ala His Pro Leu
1               5                   10                  15

Ile Leu Glu Ala Val His Gln Gln Ile Leu Ser Asn Lys Phe Leu Ile
            20                  25                  30

Val Arg Met Arg Glu Leu Leu Trp Arg Lys Glu Asp Cys Gln Arg Phe
        35                  40                  45

Tyr Arg Glu His Glu Gly Arg Phe Phe Tyr Gln Arg Leu Val Glu Phe
    50                  55                  60

Met Ala Ser Gly Pro Ile Arg Ala Tyr Ile Leu Ala His Lys Asp Ala
65                  70                  75                  80

Ile Gln Leu Trp Arg Thr Leu Met Gly Pro Thr Arg Val Phe Arg Ala
                85                  90                  95

Arg His Val Ala Pro Asp Ser Ile Arg Gly Ser Phe Gly Leu Thr Asp
            100                 105                 110

Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
    130                 135                 140

Glu Glu Glu Pro Gln Leu Arg Cys Gly Pro Val Cys Tyr Ser Pro Glu
145                 150                 155                 160

Gly Gly Val His Tyr Val Ala Gly Thr Gly Gly Leu Gly Pro Ala
                165                 170                 175


<210> SEQ ID NO 80
<211> LENGTH: 1306
<212> TYPE: DNA
<213> ORGANISM: Artificial Sequence
<220> FEATURE:
<223> OTHER INFORMATION: OriGene-NME7-1 full length

<400> SEQUENCE: 80

gacgttgtat acgactccta tagggcggcc gggaattcgt cgactggatc cggtaccgag     60

gagatctgcc gccgcgatcg ccatgaatca tagtgaaaga ttcgttttca ttgcagagtg    120

gtatgatcca aatgcttcac ttcttcgacg ttatgagctt ttattttacc caggggatgg    180

atctgttgaa atgcatgatg taaagaatca tcgcaccttt ttaaagcgga ccaaatatga    240

taacctgcac ttggaagatt tatttatagg caacaaagtg aatgtcttct ctcgacaact    300

ggtattaatt gactatgggg atcaatatac agctcgccag ctgggcagta ggaaagaaaa    360

aacgctagcc ctaattaaac cagatgcaat atcaaaggct ggagaaataa ttgaaataat    420

aaacaaagct ggatttacta taaccaaact caaaatgatg atgctttcaa ggaaagaagc    480
```

```
attggatttt catgtagatc accagtcaag accctttttc aatgagctga tccagtttat    540

tacaactggt cctattattg ccatggagat tttaagagat gatgctatat gtgaatggaa    600

aagactgctg ggacctgcaa actctggagt ggcacgcaca gatgcttctg aaagcattag    660

agccctcttt ggaacagatg gcataagaaa tgcagcgcat ggccctgatt cttttgcttc    720

tgcggccaga gaaatggagt tgtttttttcc ttcaagtgga ggttgtgggc cggcaaacac    780

tgctaaattt actaattgta cctgttgcat tgttaaaccc catgctgtca gtgaaggact    840

gttgggaaag atcctgatgg ctatccgaga tgcaggtttt gaaatctcag ctatgcagat    900

gttcaatatg gatcgggtta atgttgagga attctatgaa gtttataaag gagtagtgac    960

cgaatatcat gacatggtga cagaaatgta ttctggccct tgtgtagcaa tggagattca   1020

acagaataat gctacaaaga catttcgaga attttgtgga cctgctgatc ctgaaattgc   1080

ccggcattta cgccctggaa ctctcagagc aatctttggt aaaactaaga tccagaatgc   1140

tgttcactgt actgatctgc cagaggatgg cctattagag gttcaatact tcttcaagat   1200

cttggataat acgcgtacgc ggccgctcga gcagaaactc atctcagaag aggatctggc   1260

agcaaatgat atcctggatt acaaggatga cgacgataag gtttaa                  1306
```

<210> SEQ ID NO 81
<211> LENGTH: 407
<212> TYPE: PRT
<213> ORGANISM: Artificial Sequence
<220> FEATURE:
<223> OTHER INFORMATION: OriGene-NME7-1 full length

<400> SEQUENCE: 81

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
```

```
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Glu Phe Tyr Glu Val Tyr
        275                 280                 285

Lys Gly Val Val Thr Glu Tyr His Asp Met Val Thr Glu Met Tyr Ser
    290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn Thr Arg Thr Arg Arg Leu Glu Gln
    370                 375                 380

Lys Leu Ile Ser Glu Glu Asp Leu Ala Ala Asn Asp Ile Leu Asp Tyr
385                 390                 395                 400

Lys Asp Asp Asp Asp Lys Val
                405


<210> SEQ ID NO 82
<211> LENGTH: 376
<212> TYPE: PRT
<213> ORGANISM: Artificial Sequence
<220> FEATURE:
<223> OTHER INFORMATION: Abnova NME7-1 Full length

<400> SEQUENCE: 82

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
```

```
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Glu Phe Tyr Glu Val Tyr
        275                 280                 285

Lys Gly Val Val Thr Glu Tyr His Asp Met Val Thr Glu Met Tyr Ser
    290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn
    370                 375
```

<210> SEQ ID NO 83
<211> LENGTH: 98
<212> TYPE: PRT
<213> ORGANISM: Artificial Sequence
<220> FEATURE:
<223> OTHER INFORMATION: Abnova Partial NME7-B

<400> SEQUENCE: 83

```
Asp Arg Val Asn Val Glu Glu Phe Tyr Glu Val Tyr Lys Gly Val Val
1               5                   10                  15

Thr Glu Tyr His Asp Met Val Thr Glu Met Tyr Ser Gly Pro Cys Val
            20                  25                  30

Ala Met Glu Ile Gln Gln Asn Asn Ala Thr Lys Thr Phe Arg Glu Phe
        35                  40                  45

Cys Gly Pro Ala Asp Pro Glu Ile Ala Arg His Leu Arg Pro Gly Thr
    50                  55                  60

Leu Arg Ala Ile Phe Gly Lys Thr Lys Ile Gln Asn Ala Val His Cys
65                  70                  75                  80

Thr Asp Leu Pro Glu Asp Gly Leu Leu Glu Val Gln Tyr Phe Phe Lys
                85                  90                  95

Ile Leu
```

<210> SEQ ID NO 84
<211> LENGTH: 27
<212> TYPE: DNA
<213> ORGANISM: Artificial Sequence
<220> FEATURE:
<223> OTHER INFORMATION: DNA encoding Histidine Tag

```
<400> SEQUENCE: 84

ctcgagcacc accaccacca ccactga                                          27


<210> SEQ ID NO 85
<211> LENGTH: 36
<212> TYPE: DNA
<213> ORGANISM: Artificial Sequence
<220> FEATURE:
<223> OTHER INFORMATION: DNA encoding Strept II Tag

<400> SEQUENCE: 85

accggttgga gccatcctca gttcgaaaag taatga                                36


<210> SEQ ID NO 86
<211> LENGTH: 35
<212> TYPE: PRT
<213> ORGANISM: Artificial Sequence
<220> FEATURE:
<223> OTHER INFORMATION: N-10 peptide

<400> SEQUENCE: 86

Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala
        35


<210> SEQ ID NO 87
<211> LENGTH: 35
<212> TYPE: PRT
<213> ORGANISM: Artificial Sequence
<220> FEATURE:
<223> OTHER INFORMATION: C-10 peptide

<400> SEQUENCE: 87

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val
        35


<210> SEQ ID NO 88
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 88

Leu Ala Leu Ile Lys Pro Asp Ala
1               5


<210> SEQ ID NO 89
<211> LENGTH: 18
<212> TYPE: PRT
<213> ORGANISM: Artificial Sequence
<220> FEATURE:
<223> OTHER INFORMATION: Immunizing peptides derived from human NME7

<400> SEQUENCE: 89

Met Met Met Leu Ser Arg Lys Glu Ala Leu Asp Phe His Val Asp His
1               5                   10                  15
```

Gln Ser

<210> SEQ ID NO 90
<211> LENGTH: 10
<212> TYPE: PRT
<213> ORGANISM: Artificial Sequence
<220> FEATURE:
<223> OTHER INFORMATION: Immunizing peptides derived from human NME7

<400> SEQUENCE: 90

```
Ala Leu Asp Phe His Val Asp His Gln Ser
1               5                   10
```

<210> SEQ ID NO 91
<211> LENGTH: 14
<212> TYPE: PRT
<213> ORGANISM: Artificial Sequence
<220> FEATURE:
<223> OTHER INFORMATION: Immunizing peptides derived from human NME7

<400> SEQUENCE: 91

```
Glu Ile Leu Arg Asp Asp Ala Ile Cys Glu Trp Lys Arg Leu
1               5                   10
```

<210> SEQ ID NO 92
<211> LENGTH: 12
<212> TYPE: PRT
<213> ORGANISM: Artificial Sequence
<220> FEATURE:
<223> OTHER INFORMATION: Immunizing peptides derived from human NME7

<400> SEQUENCE: 92

```
Phe Asn Glu Leu Ile Gln Phe Ile Thr Thr Gly Pro
1               5                   10
```

<210> SEQ ID NO 93
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 93

```
Arg Asp Asp Ala Ile Cys Glu Trp
1               5
```

<210> SEQ ID NO 94
<211> LENGTH: 25
<212> TYPE: PRT
<213> ORGANISM: Artificial Sequence
<220> FEATURE:
<223> OTHER INFORMATION: Immunizing peptides derived from human NME7

<400> SEQUENCE: 94

```
Ser Gly Val Ala Arg Thr Asp Ala Ser Glu Ser Ile Arg Ala Leu Phe
1               5                   10                  15

Gly Thr Asp Gly Ile Arg Asn Ala Ala
            20                  25
```

<210> SEQ ID NO 95
<211> LENGTH: 9
<212> TYPE: PRT
<213> ORGANISM: Artificial Sequence
<220> FEATURE:
<223> OTHER INFORMATION: Immunizing peptides derived from human NME7

```
<400> SEQUENCE: 95

Glu Leu Phe Phe Pro Ser Ser Gly Gly
1               5


<210> SEQ ID NO 96
<211> LENGTH: 26
<212> TYPE: PRT
<213> ORGANISM: Artificial Sequence
<220> FEATURE:
<223> OTHER INFORMATION: Immunizing peptides derived from human NME7

<400> SEQUENCE: 96

Lys Phe Thr Asn Cys Thr Cys Cys Ile Val Lys Pro His Ala Val Ser
1               5                   10                  15

Glu Gly Leu Leu Gly Lys Ile Leu Met Ala
            20                  25


<210> SEQ ID NO 97
<211> LENGTH: 36
<212> TYPE: PRT
<213> ORGANISM: Artificial Sequence
<220> FEATURE:
<223> OTHER INFORMATION: Immunizing peptides derived from human NME7

<400> SEQUENCE: 97

Leu Met Ala Ile Arg Asp Ala Gly Phe Glu Ile Ser Ala Met Gln Met
1               5                   10                  15

Phe Asn Met Asp Arg Val Asn Val Glu Glu Phe Tyr Glu Val Tyr Lys
            20                  25                  30

Gly Val Val Thr
        35


<210> SEQ ID NO 98
<211> LENGTH: 15
<212> TYPE: PRT
<213> ORGANISM: Artificial Sequence
<220> FEATURE:
<223> OTHER INFORMATION: Immunizing peptides derived from human NME7

<400> SEQUENCE: 98

Glu Phe Tyr Glu Val Tyr Lys Gly Val Val Thr Glu Tyr His Asp
1               5                   10                  15


<210> SEQ ID NO 99
<211> LENGTH: 43
<212> TYPE: PRT
<213> ORGANISM: Artificial Sequence
<220> FEATURE:
<223> OTHER INFORMATION: Immunizing peptides derived from human NME7

<400> SEQUENCE: 99

Glu Ile Gln Gln Asn Asn Ala Thr Lys Thr Phe Arg Glu Phe Cys Gly
1               5                   10                  15

Pro Ala Asp Pro Glu Ile Ala Arg His Leu Arg Pro Gly Thr Leu Arg
            20                  25                  30

Ala Ile Phe Gly Lys Thr Lys Ile Gln Asn Ala
        35                  40


<210> SEQ ID NO 100
<211> LENGTH: 8
<212> TYPE: PRT
<213> ORGANISM: Artificial Sequence
<220> FEATURE:
<223> OTHER INFORMATION: Immunizing peptides derived from human NME7
```

<400> SEQUENCE: 100

Tyr Ser Gly Pro Cys Val Ala Met
1 5

<210> SEQ ID NO 101
<211> LENGTH: 7
<212> TYPE: PRT
<213> ORGANISM: Artificial Sequence
<220> FEATURE:
<223> OTHER INFORMATION: Immunizing peptides derived from human NME7

<400> SEQUENCE: 101

Phe Arg Glu Phe Cys Gly Pro
1 5

<210> SEQ ID NO 102
<211> LENGTH: 23
<212> TYPE: PRT
<213> ORGANISM: Artificial Sequence
<220> FEATURE:
<223> OTHER INFORMATION: Immunizing peptides derived from human NME7

<400> SEQUENCE: 102

Val His Cys Thr Asp Leu Pro Glu Asp Gly Leu Leu Glu Val Gln Tyr
1 5 10 15

Phe Phe Lys Ile Leu Asp Asn
20

<210> SEQ ID NO 103
<211> LENGTH: 9
<212> TYPE: PRT
<213> ORGANISM: Artificial Sequence
<220> FEATURE:
<223> OTHER INFORMATION: Immunizing peptides derived from human NME7

<400> SEQUENCE: 103

Ile Gln Asn Ala Val His Cys Thr Asp
1 5

<210> SEQ ID NO 104
<211> LENGTH: 20
<212> TYPE: PRT
<213> ORGANISM: Artificial Sequence
<220> FEATURE:
<223> OTHER INFORMATION: Immunizing peptides derived from human NME7

<400> SEQUENCE: 104

Thr Asp Leu Pro Glu Asp Gly Leu Leu Glu Val Gln Tyr Phe Phe Lys
1 5 10 15

Ile Leu Asp Asn
20

<210> SEQ ID NO 105
<211> LENGTH: 13
<212> TYPE: PRT
<213> ORGANISM: Artificial Sequence
<220> FEATURE:
<223> OTHER INFORMATION: Immunizing peptides derived from human NME7

<400> SEQUENCE: 105

Pro Glu Asp Gly Leu Leu Glu Val Gln Tyr Phe Phe Lys
1 5 10

<210> SEQ ID NO 106

<211> LENGTH: 12
<212> TYPE: PRT
<213> ORGANISM: Artificial Sequence
<220> FEATURE:
<223> OTHER INFORMATION: Immunizing peptides derived from human NME7

<400> SEQUENCE: 106

Glu Ile Ile Asn Lys Ala Gly Phe Thr Ile Thr Lys
1 5 10

<210> SEQ ID NO 107
<211> LENGTH: 16
<212> TYPE: PRT
<213> ORGANISM: Artificial Sequence
<220> FEATURE:
<223> OTHER INFORMATION: Immunizing peptides derived from human NME7

<400> SEQUENCE: 107

Met Leu Ser Arg Lys Glu Ala Leu Asp Phe His Val Asp His Gln Ser
1 5 10 15

<210> SEQ ID NO 108
<211> LENGTH: 9
<212> TYPE: PRT
<213> ORGANISM: Artificial Sequence
<220> FEATURE:
<223> OTHER INFORMATION: Immunizing peptides derived from human NME7

<400> SEQUENCE: 108

Asn Glu Leu Ile Gln Phe Ile Thr Thr
1 5

<210> SEQ ID NO 109
<211> LENGTH: 14
<212> TYPE: PRT
<213> ORGANISM: Artificial Sequence
<220> FEATURE:
<223> OTHER INFORMATION: Immunizing peptides derived from human NME7

<400> SEQUENCE: 109

Glu Ile Leu Arg Asp Asp Ala Ile Cys Glu Trp Lys Arg Leu
1 5 10

<210> SEQ ID NO 110
<211> LENGTH: 21
<212> TYPE: PRT
<213> ORGANISM: Artificial Sequence
<220> FEATURE:
<223> OTHER INFORMATION: Immunizing peptides derived from human NME7

<400> SEQUENCE: 110

Ser Gly Val Ala Arg Thr Asp Ala Ser Glu Ser Ile Arg Ala Leu Phe
1 5 10 15

Gly Thr Asp Gly Ile
20

<210> SEQ ID NO 111
<211> LENGTH: 11
<212> TYPE: PRT
<213> ORGANISM: Artificial Sequence
<220> FEATURE:
<223> OTHER INFORMATION: Immunizing peptides derived from human NME7

<400> SEQUENCE: 111

Ser Gly Val Ala Arg Thr Asp Ala Ser Glu Ser
1 5 10

<210> SEQ ID NO 112
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 112

Ala Leu Phe Gly Thr Asp Gly Ile
1 5

<210> SEQ ID NO 113
<211> LENGTH: 14
<212> TYPE: PRT
<213> ORGANISM: Artificial Sequence
<220> FEATURE:
<223> OTHER INFORMATION: Immunizing peptides derived from human NME7

<400> SEQUENCE: 113

Asn Cys Thr Cys Cys Ile Val Lys Pro His Ala Val Ser Glu
1 5 10

<210> SEQ ID NO 114
<211> LENGTH: 11
<212> TYPE: PRT
<213> ORGANISM: Artificial Sequence
<220> FEATURE:
<223> OTHER INFORMATION: Immunizing peptides derived from human NME7

<400> SEQUENCE: 114

Leu Gly Lys Ile Leu Met Ala Ile Arg Asp Ala
1 5 10

<210> SEQ ID NO 115
<211> LENGTH: 16
<212> TYPE: PRT
<213> ORGANISM: Artificial Sequence
<220> FEATURE:
<223> OTHER INFORMATION: Immunizing peptides derived from human NME7

<400> SEQUENCE: 115

Glu Ile Ser Ala Met Gln Met Phe Asn Met Asp Arg Val Asn Val Glu
1 5 10 15

<210> SEQ ID NO 116
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 116

Glu Val Tyr Lys Gly Val Val Thr
1 5

<210> SEQ ID NO 117
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 117

Glu Tyr His Asp Met Val Thr Glu
1 5

<210> SEQ ID NO 118
<211> LENGTH: 15
<212> TYPE: PRT
<213> ORGANISM: Artificial Sequence
<220> FEATURE:
<223> OTHER INFORMATION: Immunizing peptides derived from human NME7

<400> SEQUENCE: 118

Glu Phe Cys Gly Pro Ala Asp Pro Glu Ile Ala Arg His Leu Arg
1 5 10 15

<210> SEQ ID NO 119
<211> LENGTH: 12
<212> TYPE: PRT
<213> ORGANISM: Artificial Sequence
<220> FEATURE:
<223> OTHER INFORMATION: Immunizing peptides derived from human NME7

<400> SEQUENCE: 119

Ala Ile Phe Gly Lys Thr Lys Ile Gln Asn Ala Val
1 5 10

<210> SEQ ID NO 120
<211> LENGTH: 18
<212> TYPE: PRT
<213> ORGANISM: Artificial Sequence
<220> FEATURE:
<223> OTHER INFORMATION: Immunizing peptides derived from human NME7

<400> SEQUENCE: 120

Leu Pro Glu Asp Gly Leu Leu Glu Val Gln Tyr Phe Phe Lys Ile Leu
1 5 10 15

Asp Asn

<210> SEQ ID NO 121
<211> LENGTH: 17
<212> TYPE: PRT
<213> ORGANISM: Artificial Sequence
<220> FEATURE:
<223> OTHER INFORMATION: Immunizing peptides derived from human NME7

<400> SEQUENCE: 121

Gly Pro Asp Ser Phe Ala Ser Ala Ala Arg Glu Met Glu Leu Phe Phe
1 5 10 15

Pro

<210> SEQ ID NO 122
<211> LENGTH: 7
<212> TYPE: PRT
<213> ORGANISM: Artificial Sequence
<220> FEATURE:
<223> OTHER INFORMATION: Immunizing peptides derived from human NME7

<400> SEQUENCE: 122

Ile Cys Glu Trp Lys Arg Leu
1 5

<210> SEQ ID NO 123
<211> LENGTH: 11
<212> TYPE: PRT
<213> ORGANISM: Artificial Sequence
<220> FEATURE:
<223> OTHER INFORMATION: Immunizing peptides derived from human NME7

<400> SEQUENCE: 123

Leu Gly Lys Ile Leu Met Ala Ile Arg Asp Ala 1 5 10

<210> SEQ ID NO 124
<211> LENGTH: 10
<212> TYPE: PRT
<213> ORGANISM: Artificial Sequence
<220> FEATURE:
<223> OTHER INFORMATION: Immunizing peptides derived from human NME7

<400> SEQUENCE: 124

His Ala Val Ser Glu Gly Leu Leu Gly Lys
1 5 10

<210> SEQ ID NO 125
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 125

Val Thr Glu Met Tyr Ser Gly Pro
1 5

<210> SEQ ID NO 126
<211> LENGTH: 9
<212> TYPE: PRT
<213> ORGANISM: Artificial Sequence
<220> FEATURE:
<223> OTHER INFORMATION: Immunizing peptides derived from human NME7

<400> SEQUENCE: 126

Asn Ala Thr Lys Thr Phe Arg Glu Phe
1 5

<210> SEQ ID NO 127
<211> LENGTH: 9
<212> TYPE: PRT
<213> ORGANISM: Artificial Sequence
<220> FEATURE:
<223> OTHER INFORMATION: Immunizing peptides derived from human NME7

<400> SEQUENCE: 127

Ala Ile Arg Asp Ala Gly Phe Glu Ile
1 5

<210> SEQ ID NO 128
<211> LENGTH: 13
<212> TYPE: PRT
<213> ORGANISM: Artificial Sequence
<220> FEATURE:
<223> OTHER INFORMATION: Immunizing peptides derived from human NME7

<400> SEQUENCE: 128

Ala Ile Cys Glu Trp Lys Arg Leu Leu Gly Pro Ala Asn
1 5 10

<210> SEQ ID NO 129
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 129

Asp His Gln Ser Arg Pro Phe Phe
1 5

<210> SEQ ID NO 130
<211> LENGTH: 13
<212> TYPE: PRT
<213> ORGANISM: Artificial Sequence
<220> FEATURE:
<223> OTHER INFORMATION: Immunizing peptides derived from human NME7

<400> SEQUENCE: 130

Ala Ile Cys Glu Trp Lys Arg Leu Leu Gly Pro Ala Asn
1 5 10

<210> SEQ ID NO 131
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 131

Val Asp His Gln Ser Arg Pro Phe
1 5

<210> SEQ ID NO 132
<211> LENGTH: 6
<212> TYPE: PRT
<213> ORGANISM: Artificial Sequence
<220> FEATURE:
<223> OTHER INFORMATION: Immunizing peptides derived from human NME7

<400> SEQUENCE: 132

Pro Asp Ser Phe Ala Ser
1 5

<210> SEQ ID NO 133
<211> LENGTH: 18
<212> TYPE: PRT
<213> ORGANISM: Artificial Sequence
<220> FEATURE:
<223> OTHER INFORMATION: Immunizing peptides derived from human NME7

<400> SEQUENCE: 133

Lys Ala Gly Glu Ile Ile Glu Ile Ile Asn Lys Ala Gly Phe Thr Ile
1 5 10 15

Thr Lys

<210> SEQ ID NO 134
<211> LENGTH: 29
<212> TYPE: PRT
<213> ORGANISM: Artificial Sequence
<220> FEATURE:
<223> OTHER INFORMATION: Immunizing peptides derived from human NME1

<400> SEQUENCE: 134

Met Ala Asn Cys Glu Arg Thr Phe Ile Ala Ile Lys Pro Asp Gly Val
1 5 10 15

Gln Arg Gly Leu Val Gly Glu Ile Ile Lys Arg Phe Glu
20 25

<210> SEQ ID NO 135
<211> LENGTH: 8
<212> TYPE: PRT
<213> ORGANISM: Artificial Sequence
<220> FEATURE:
<223> OTHER INFORMATION: Immunizing peptides derived from human NME1

<400> SEQUENCE: 135

Val Asp Leu Lys Asp Arg Pro Phe
1 5

<210> SEQ ID NO 136
<211> LENGTH: 17
<212> TYPE: PRT
<213> ORGANISM: Artificial Sequence
<220> FEATURE:
<223> OTHER INFORMATION: Immunizing peptides derived from human NME1

<400> SEQUENCE: 136

His Gly Ser Asp Ser Val Glu Ser Ala Glu Lys Glu Ile Gly Leu Trp
1 5 10 15

Phe

<210> SEQ ID NO 137
<211> LENGTH: 25
<212> TYPE: PRT
<213> ORGANISM: Artificial Sequence
<220> FEATURE:
<223> OTHER INFORMATION: Immunizing peptides derived from human NME1

<400> SEQUENCE: 137

Glu Arg Thr Phe Ile Ala Ile Lys Pro Asp Gly Val Gln Arg Gly Leu
1 5 10 15

Val Gly Glu Ile Ile Lys Arg Phe Glu
20 25

<210> SEQ ID NO 138
<211> LENGTH: 30
<212> TYPE: PRT
<213> ORGANISM: Artificial Sequence
<220> FEATURE:
<223> OTHER INFORMATION: Immunizing peptides derived from human NME1

<400> SEQUENCE: 138

Val Asp Leu Lys Asp Arg Pro Phe Phe Ala Gly Leu Val Lys Tyr Met
1 5 10 15

His Ser Gly Pro Val Val Ala Met Val Trp Glu Gly Leu Asn
20 25 30

<210> SEQ ID NO 139
<211> LENGTH: 26
<212> TYPE: PRT
<213> ORGANISM: Artificial Sequence
<220> FEATURE:
<223> OTHER INFORMATION: Immunizing peptides derived from human NME1

<400> SEQUENCE: 139

Asn Ile Ile His Gly Ser Asp Ser Val Glu Ser Ala Glu Lys Glu Ile
1 5 10 15

Gly Leu Trp Phe His Pro Glu Glu Leu Val
20 25

<210> SEQ ID NO 140
<211> LENGTH: 14
<212> TYPE: PRT
<213> ORGANISM: Artificial Sequence
<220> FEATURE:
<223> OTHER INFORMATION: Immunizing peptides derived from human NME1

<400> SEQUENCE: 140

Lys Pro Asp Gly Val Gln Arg Gly Leu Val Gly Glu Ile Ile 1 5 10

<210> SEQ ID NO 141
<211> LENGTH: 16
<212> TYPE: PRT
<213> ORGANISM: Artificial Sequence
<220> FEATURE:
<223> OTHER INFORMATION: peptide A1

<400> SEQUENCE: 141

Met Leu Ser Arg Lys Glu Ala Leu Asp Phe His Val Asp His Gln Ser
1 5 10 15

<210> SEQ ID NO 142
<211> LENGTH: 11
<212> TYPE: PRT
<213> ORGANISM: Artificial Sequence
<220> FEATURE:
<223> OTHER INFORMATION: peptide A2

<400> SEQUENCE: 142

Ser Gly Val Ala Arg Thr Asp Ala Ser Glu Ser
1 5 10

<210> SEQ ID NO 143
<211> LENGTH: 20
<212> TYPE: PRT
<213> ORGANISM: Artificial Sequence
<220> FEATURE:
<223> OTHER INFORMATION: peptide B1

<400> SEQUENCE: 143

Asp Ala Gly Phe Glu Ile Ser Ala Met Gln Met Phe Asn Met Asp Arg
1 5 10 15

Val Asn Val Glu
20

<210> SEQ ID NO 144
<211> LENGTH: 16
<212> TYPE: PRT
<213> ORGANISM: Artificial Sequence
<220> FEATURE:
<223> OTHER INFORMATION: peptide B2

<400> SEQUENCE: 144

Glu Val Tyr Lys Gly Val Val Thr Glu Tyr His Asp Met Val Thr Glu
1 5 10 15

<210> SEQ ID NO 145
<211> LENGTH: 29
<212> TYPE: PRT
<213> ORGANISM: Artificial Sequence
<220> FEATURE:
<223> OTHER INFORMATION: peptide B3

<400> SEQUENCE: 145

Ala Ile Phe Gly Lys Thr Lys Ile Gln Asn Ala Val His Cys Thr Asp
1 5 10 15

Leu Pro Glu Asp Gly Leu Leu Glu Val Gln Tyr Phe Phe
20 25

<210> SEQ ID NO 146
<211> LENGTH: 1131
<212> TYPE: DNA
<213> ORGANISM: Artificial Sequence
<220> FEATURE:

<223> OTHER INFORMATION: Human NME7 a

<400> SEQUENCE: 146

```
atgaatcata gtgaaagatt cgttttcatt gcagagtggt atgatccaaa tgcttcactt     60
cttcgacgtt atgagctttt attttaccca ggggatggat ctgttgaaat gcatgatgta    120
aagaatcatc gcaccttttt aaagcggacc aaatatgata acctgcactt ggaagattta    180
tttataggca acaaagtgaa tgtcttttct cgacaactgg tattaattga ctatggggat    240
caatatacag ctcgccagct gggcagtagg aaagaaaaaa cgctagccct aattaaacca    300
gatgcaatat caaaggctgg agaaataatt gaaataataa acaaagctgg atttactata    360
accaaactca aaatgatgat gctttcaagg aaagaagcat tggattttca tgtagatcac    420
cagtcaagac cctttttcaa tgagctgatc cagtttatta caactggtcc tattattgcc    480
atggagattt taagagatga tgctatatgt gaatggaaaa gactgctggg acctgcaaac    540
tctggagtgg cacgcacaga tgcttctgaa agcattagag ccctctttgg aacagatggc    600
ataagaaatg cagcgcatgg ccctgattct tttgcttctg cggccagaga aatggagttg    660
ttttttcctt caagtggagg ttgtgggccg gcaaacactg ctaaatttac taattgtacc    720
tgttgcattg ttaaacccca tgctgtcagt gaaggactgt tgggaaagat cctgatggct    780
atccgagatg caggttttga aatctcagct atgcagatgt tcaatatgga tcgggttaat    840
gttgaggaat tctatgaagt ttataaagga gtagtgaccg aatatcatga catggtgaca    900
gaaatgtatt ctggcccttg tgtagcaatg gagattcaac agaataatgc tacaaagaca    960
tttcgagaat tttgtggacc tgctgatcct gaaattgccc ggcatttacg ccctggaact   1020
ctcagagcaa tctttggtaa aactaagatc cagaatgctg ttcactgtac tgatctgcca   1080
gaggatggcc tattagaggt tcaatacttc ttcaagatct tggataatta g            1131
```

<210> SEQ ID NO 147
<211> LENGTH: 376
<212> TYPE: PRT
<213> ORGANISM: Artificial Sequence
<220> FEATURE:
<223> OTHER INFORMATION: Human NME7 a

<400> SEQUENCE: 147

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140
```

-continued

```
Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Glu Phe Tyr Glu Val Tyr
        275                 280                 285

Lys Gly Val Val Thr Glu Tyr His Asp Met Val Thr Glu Met Tyr Ser
    290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn
    370                 375
```

<210> SEQ ID NO 148
<211> LENGTH: 1023
<212> TYPE: DNA
<213> ORGANISM: Artificial Sequence
<220> FEATURE:
<223> OTHER INFORMATION: Human NME7 b

<400> SEQUENCE: 148

```
atgcatgatg taaagaatca tcgcaccttt ttaaagcgga ccaaatatga taacctgcac     60

ttggaagatt tatttatagg caacaaagtg aatgtctttt ctcgacaact ggtattaatt    120

gactatgggg atcaatatac agctcgccag ctgggcagta ggaaagaaaa aacgctagcc    180

ctaattaaac cagatgcaat atcaaaggct ggagaaataa ttgaaataat aaacaaagct    240

ggatttacta taaccaaact caaaatgatg atgctttcaa ggaaagaagc attggatttt    300

catgtagatc accagtcaag acccttttc aatgagctga tccagtttat tacaactggt    360

cctattattg ccatggagat tttaagagat gatgctatat gtgaatggaa aagactgctg    420

ggacctgcaa actctggagt ggcacgcaca gatgcttctg aaagcattag agccctcttt    480

ggaacagatg gcataagaaa tgcagcgcat ggccctgatt cttttgcttc tgcggccaga    540

gaaatggagt tgttttttcc ttcaagtgga ggttgtgggc cggcaaacac tgctaaattt    600

actaattgta cctgttgcat tgttaaaccc catgctgtca gtgaaggact gttgggaaag    660

atcctgatgg ctatccgaga tgcaggtttt gaaatctcag ctatgcagat gttcaatatg    720
```

```
gatcgggtta atgttgagga attctatgaa gtttataaag gagtagtgac cgaatatcat    780

gacatggtga cagaaatgta ttctggccct tgtgtagcaa tggagattca acagaataat    840

gctacaaaga catttcgaga attttgtgga cctgctgatc ctgaaattgc ccggcattta    900

cgccctggaa ctctcagagc aatctttggt aaaactaaga tccagaatgc tgttcactgt    960

actgatctgc cagaggatgg cctattagag gttcaatact tcttcaagat cttggataat   1020

tag                                                                  1023


<210> SEQ ID NO 149
<211> LENGTH: 340
<212> TYPE: PRT
<213> ORGANISM: Artificial Sequence
<220> FEATURE:
<223> OTHER INFORMATION: Human NME7 b

<400> SEQUENCE: 149

Met His Asp Val Lys Asn His Arg Thr Phe Leu Lys Arg Thr Lys Tyr
1               5                   10                  15

Asp Asn Leu His Leu Glu Asp Leu Phe Ile Gly Asn Lys Val Asn Val
            20                  25                  30

Phe Ser Arg Gln Leu Val Leu Ile Asp Tyr Gly Asp Gln Tyr Thr Ala
        35                  40                  45

Arg Gln Leu Gly Ser Arg Lys Glu Lys Thr Leu Ala Leu Ile Lys Pro
    50                  55                  60

Asp Ala Ile Ser Lys Ala Gly Glu Ile Ile Glu Ile Ile Asn Lys Ala
65                  70                  75                  80

Gly Phe Thr Ile Thr Lys Leu Lys Met Met Met Leu Ser Arg Lys Glu
                85                  90                  95

Ala Leu Asp Phe His Val Asp His Gln Ser Arg Pro Phe Phe Asn Glu
            100                 105                 110

Leu Ile Gln Phe Ile Thr Thr Gly Pro Ile Ile Ala Met Glu Ile Leu
        115                 120                 125

Arg Asp Asp Ala Ile Cys Glu Trp Lys Arg Leu Leu Gly Pro Ala Asn
    130                 135                 140

Ser Gly Val Ala Arg Thr Asp Ala Ser Glu Ser Ile Arg Ala Leu Phe
145                 150                 155                 160

Gly Thr Asp Gly Ile Arg Asn Ala Ala His Gly Pro Asp Ser Phe Ala
                165                 170                 175

Ser Ala Ala Arg Glu Met Glu Leu Phe Phe Pro Ser Ser Gly Gly Cys
            180                 185                 190

Gly Pro Ala Asn Thr Ala Lys Phe Thr Asn Cys Thr Cys Cys Ile Val
        195                 200                 205

Lys Pro His Ala Val Ser Glu Gly Leu Leu Gly Lys Ile Leu Met Ala
    210                 215                 220

Ile Arg Asp Ala Gly Phe Glu Ile Ser Ala Met Gln Met Phe Asn Met
225                 230                 235                 240

Asp Arg Val Asn Val Glu Glu Phe Tyr Glu Val Tyr Lys Gly Val Val
                245                 250                 255

Thr Glu Tyr His Asp Met Val Thr Glu Met Tyr Ser Gly Pro Cys Val
            260                 265                 270

Ala Met Glu Ile Gln Gln Asn Asn Ala Thr Lys Thr Phe Arg Glu Phe
        275                 280                 285

Cys Gly Pro Ala Asp Pro Glu Ile Ala Arg His Leu Arg Pro Gly Thr
    290                 295                 300
```

```
Leu Arg Ala Ile Phe Gly Lys Thr Lys Ile Gln Asn Ala Val His Cys
305                 310                 315                 320

Thr Asp Leu Pro Glu Asp Gly Leu Leu Glu Val Gln Tyr Phe Phe Lys
                325                 330                 335

Ile Leu Asp Asn
            340


<210> SEQ ID NO 150
<211> LENGTH: 861
<212> TYPE: DNA
<213> ORGANISM: Artificial Sequence
<220> FEATURE:
<223> OTHER INFORMATION: Human NME7-AB

<400> SEQUENCE: 150

atggaaaaaa cgctagccct aattaaacca gatgcaatat caaaggctgg agaaataatt      60

gaaataataa acaaagctgg atttactata accaaactca aaatgatgat gctttcaagg     120

aaagaagcat tggattttca tgtagatcac cagtcaagac cctttttcaa tgagctgatc     180

cagtttatta caactggtcc tattattgcc atggagattt taagagatga tgctatatgt     240

gaatggaaaa gactgctggg acctgcaaac tctggagtgg cacgcacaga tgcttctgaa     300

agcattagag ccctctttgg aacagatggc ataagaaatg cagcgcatgg ccctgattct     360

tttgcttctg cggccagaga aatggagttg tttttttcctt caagtggagg ttgtgggccg     420

gcaaacactg ctaaatttac taattgtacc tgttgcattg ttaaacccca tgctgtcagt     480

gaaggactgt tgggaaagat cctgatggct atccgagatg caggttttga aatctcagct     540

atgcagatgt tcaatatgga tcgggttaat gttgaggaat tctatgaagt ttataaagga     600

gtagtgaccg aatatcatga catggtgaca gaaatgtatt ctggcccttg tgtagcaatg     660

gagattcaac agaataatgc tacaaagaca tttcgagaat tttgtggacc tgctgatcct     720

gaaattgccc ggcatttacg ccctggaact ctcagagcaa tctttggtaa aactaagatc     780

cagaatgctg ttcactgtac tgatctgcca gaggatggcc tattagaggt tcaatacttc     840

ttcaagatct tggataatta g                                               861


<210> SEQ ID NO 151
<211> LENGTH: 286
<212> TYPE: PRT
<213> ORGANISM: Artificial Sequence
<220> FEATURE:
<223> OTHER INFORMATION: Human NME7-AB

<400> SEQUENCE: 151

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110
```

```
Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe Lys Ile Leu Asp Asn
        275                 280                 285
```

<210> SEQ ID NO 152
<211> LENGTH: 759
<212> TYPE: DNA
<213> ORGANISM: Artificial Sequence
<220> FEATURE:
<223> OTHER INFORMATION: Human NME7 x1

<400> SEQUENCE: 152

```
atgatgatgc tttcaaggaa agaagcattg gattttcatg tagatcacca gtcaagaccc     60

tttttcaatg agctgatcca gtttattaca actggtccta ttattgccat ggagatttta    120

agagatgatg ctatatgtga atggaaaaga ctgctgggac ctgcaaactc tggagtggca    180

cgcacagatg cttctgaaag cattagagcc ctctttggaa cagatggcat aagaaatgca    240

gcgcatggcc ctgattcttt tgcttctgcg gccagagaaa tggagttgtt ttttccttca    300

agtggaggtt gtgggccggc aaacactgct aaatttacta attgtacctg ttgcattgtt    360

aaaccccatg ctgtcagtga aggactgttg ggaaagatcc tgatggctat ccgagatgca    420

ggttttgaaa tctcagctat gcagatgttc aatatggatc gggttaatgt tgaggaattc    480

tatgaagttt ataaaggagt agtgaccgaa tatcatgaca tggtgacaga aatgtattct    540

ggcccttgtg tagcaatgga gattcaacag aataatgcta caaagacatt tcgagaattt    600

tgtggacctg ctgatcctga aattgcccgg catttacgcc ctggaactct cagagcaatc    660

tttggtaaaa ctaagatcca gaatgctgtt cactgtactg atctgccaga ggatggccta    720

ttagaggttc aatacttctt caagatcttg gataattag                           759
```

<210> SEQ ID NO 153
<211> LENGTH: 252
<212> TYPE: PRT
<213> ORGANISM: Artificial Sequence
<220> FEATURE:
<223> OTHER INFORMATION: Human NME7 x1

<400> SEQUENCE: 153

```
Met Met Met Leu Ser Arg Lys Glu Ala Leu Asp Phe His Val Asp His
1               5                   10                  15

Gln Ser Arg Pro Phe Phe Asn Glu Leu Ile Gln Phe Ile Thr Thr Gly
            20                  25                  30

Pro Ile Ile Ala Met Glu Ile Leu Arg Asp Asp Ala Ile Cys Glu Trp
        35                  40                  45

Lys Arg Leu Leu Gly Pro Ala Asn Ser Gly Val Ala Arg Thr Asp Ala
    50                  55                  60

Ser Glu Ser Ile Arg Ala Leu Phe Gly Thr Asp Gly Ile Arg Asn Ala
65                  70                  75                  80

Ala His Gly Pro Asp Ser Phe Ala Ser Ala Ala Arg Glu Met Glu Leu
                85                  90                  95

Phe Phe Pro Ser Ser Gly Gly Cys Gly Pro Ala Asn Thr Ala Lys Phe
            100                 105                 110

Thr Asn Cys Thr Cys Cys Ile Val Lys Pro His Ala Val Ser Glu Gly
        115                 120                 125

Leu Leu Gly Lys Ile Leu Met Ala Ile Arg Asp Ala Gly Phe Glu Ile
    130                 135                 140

Ser Ala Met Gln Met Phe Asn Met Asp Arg Val Asn Val Glu Glu Phe
145                 150                 155                 160

Tyr Glu Val Tyr Lys Gly Val Val Thr Glu Tyr His Asp Met Val Thr
                165                 170                 175

Glu Met Tyr Ser Gly Pro Cys Val Ala Met Glu Ile Gln Gln Asn Asn
            180                 185                 190

Ala Thr Lys Thr Phe Arg Glu Phe Cys Gly Pro Ala Asp Pro Glu Ile
        195                 200                 205

Ala Arg His Leu Arg Pro Gly Thr Leu Arg Ala Ile Phe Gly Lys Thr
    210                 215                 220

Lys Ile Gln Asn Ala Val His Cys Thr Asp Leu Pro Glu Asp Gly Leu
225                 230                 235                 240

Leu Glu Val Gln Tyr Phe Phe Lys Ile Leu Asp Asn
                245                 250
```

<210> SEQ ID NO 154
<211> LENGTH: 1128
<212> TYPE: DNA
<213> ORGANISM: Artificial Sequence
<220> FEATURE:
<223> OTHER INFORMATION: Human NME7 a (optimized for E coli expression)

<400> SEQUENCE: 154

```
atgaatcact ccgaacgctt tgtttttatc gccgaatggt atgacccgaa tgcttccctg     60

ctgcgccgct acgaactgct gttttatccg ggcgatggta gcgtggaaat gcatgacgtt    120

aaaaatcacc gtacctttct gaaacgcacg aaatatgata atctgcatct ggaagacctg    180

tttattggca acaaagtcaa tgtgttctct cgtcagctgg tgctgatcga ttatggcgac    240

cagtacaccg cgcgtcaact gggtagtcgc aaagaaaaaa cgctggccct gattaaaccg    300

gatgcaatct ccaaagctgg cgaaattatc gaaattatca acaaagcggg tttcaccatc    360

acgaaactga aaatgatgat gctgagccgt aaagaagccc tggattttca tgtcgaccac    420

cagtctcgcc cgtttttcaa tgaactgatt caattcatca ccacgggtcc gattatcgca    480

atggaaattc tgcgtgatga cgctatctgc gaatggaaac gcctgctggg cccggcaaac    540

tcaggtgttg cgcgtaccga tgccagtgaa tccattcgcg ctctgtttgg caccgatggt    600
```

```
atccgtaatg cagcacatgg tccggactca ttcgcatcgg cagctcgtga aatggaactg    660

tttttcccga gctctggcgg ttgcggtccg gcaaacaccg ccaaatttac caattgtacg    720

tgctgtattg tcaaaccgca cgcagtgtca gaaggcctgc tgggtaaaat tctgatggca    780

atccgtgatg ctggctttga aatctcggcc atgcagatgt tcaacatgga ccgcgttaac    840

gtcgaagaat tctacgaagt ttacaaaggc gtggttaccg aatatcacga tatggttacg    900

gaaatgtact ccggtccgtg cgtcgcgatg gaaattcagc aaaacaatgc caccaaaacg    960

tttcgtgaat tctgtggtcc ggcagatccg gaaatcgcac gtcatctgcg tccgggtacc   1020

ctgcgcgcaa tttttggtaa aacgaaaatc cagaacgctg tgcactgtac cgatctgccg   1080

gaagacggtc tgctggaagt tcaatacttt ttcaaaattc tggataat                1128
```

```
<210> SEQ ID NO 155
<211> LENGTH: 378
<212> TYPE: PRT
<213> ORGANISM: Artificial Sequence
<220> FEATURE:
<223> OTHER INFORMATION: Human NME7 a (optimized for E coli expression)

<400> SEQUENCE: 155

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270
```

```
Met Phe Asn Met Asp Arg Val Asn Val Glu Glu Phe Tyr Glu Val Tyr
        275                 280                 285

Lys Gly Val Val Thr Glu Tyr His Asp Met Val Thr Glu Met Tyr Ser
    290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn Thr Gly
    370                 375


<210> SEQ ID NO 156
<211> LENGTH: 1020
<212> TYPE: DNA
<213> ORGANISM: Artificial Sequence
<220> FEATURE:
<223> OTHER INFORMATION: Human NME7 b (optimized for E coli expression)

<400> SEQUENCE: 156

atgcatgacg ttaaaaatca ccgtaccttt ctgaaacgca cgaaatatga taatctgcat     60

ctggaagacc tgtttattgg caacaaagtc aatgtgttct ctcgtcagct ggtgctgatc    120

gattatggcg accagtacac cgcgcgtcaa ctgggtagtc gcaaagaaaa aacgctggcc    180

ctgattaaac cggatgcaat ctccaaagct ggcgaaatta tcgaaattat caacaaagcg    240

ggtttcacca tcacgaaact gaaaatgatg atgctgagcc gtaaagaagc cctggatttt    300

catgtcgacc accagtctcg cccgtttttc aatgaactga ttcaattcat caccacgggt    360

ccgattatcg caatggaaat tctgcgtgat gacgctatct gcgaatggaa acgcctgctg    420

ggcccggcaa actcaggtgt tgcgcgtacc gatgccagtg aatccattcg cgctctgttt    480

ggcaccgatg gtatccgtaa tgcagcacat ggtccggact cattcgcatc ggcagctcgt    540

gaaatggaac tgtttttccc gagctctggc ggttgcggtc cggcaaacac cgccaaattt    600

accaattgta cgtgctgtat tgtcaaaccg cacgcagtgt cagaaggcct gctgggtaaa    660

attctgatgg caatccgtga tgctggcttt gaaatctcgg ccatgcagat gttcaacatg    720

gaccgcgtta acgtcgaaga attctacgaa gtttacaaag gcgtggttac cgaatatcac    780

gatatggtta cggaaatgta ctccggtccg tgcgtcgcga tggaaattca gcaaaacaat    840

gccaccaaaa cgtttcgtga attctgtggt ccggcagatc cggaaatcgc acgtcatctg    900

cgtccgggta ccctgcgcgc aatttttggt aaaacgaaaa tccagaacgc tgtgcactgt    960

accgatctgc cggaagacgg tctgctggaa gttcaatact tttcaaaat tctggataat    1020


<210> SEQ ID NO 157
<211> LENGTH: 342
<212> TYPE: PRT
<213> ORGANISM: Artificial Sequence
<220> FEATURE:
<223> OTHER INFORMATION: Human NME7 b (optimized for E coli expression)

<400> SEQUENCE: 157

Met His Asp Val Lys Asn His Arg Thr Phe Leu Lys Arg Thr Lys Tyr
1               5                   10                  15

Asp Asn Leu His Leu Glu Asp Leu Phe Ile Gly Asn Lys Val Asn Val
```

```
            20                  25                  30

Phe Ser Arg Gln Leu Val Leu Ile Asp Tyr Gly Asp Gln Tyr Thr Ala
        35                  40                  45

Arg Gln Leu Gly Ser Arg Lys Glu Lys Thr Leu Ala Leu Ile Lys Pro
    50                  55                  60

Asp Ala Ile Ser Lys Ala Gly Glu Ile Ile Glu Ile Ile Asn Lys Ala
65                  70                  75                  80

Gly Phe Thr Ile Thr Lys Leu Lys Met Met Met Leu Ser Arg Lys Glu
                85                  90                  95

Ala Leu Asp Phe His Val Asp His Gln Ser Arg Pro Phe Phe Asn Glu
            100                 105                 110

Leu Ile Gln Phe Ile Thr Thr Gly Pro Ile Ile Ala Met Glu Ile Leu
        115                 120                 125

Arg Asp Asp Ala Ile Cys Glu Trp Lys Arg Leu Leu Gly Pro Ala Asn
    130                 135                 140

Ser Gly Val Ala Arg Thr Asp Ala Ser Glu Ser Ile Arg Ala Leu Phe
145                 150                 155                 160

Gly Thr Asp Gly Ile Arg Asn Ala Ala His Gly Pro Asp Ser Phe Ala
                165                 170                 175

Ser Ala Ala Arg Glu Met Glu Leu Phe Phe Pro Ser Ser Gly Gly Cys
            180                 185                 190

Gly Pro Ala Asn Thr Ala Lys Phe Thr Asn Cys Thr Cys Cys Ile Val
        195                 200                 205

Lys Pro His Ala Val Ser Glu Gly Leu Leu Gly Lys Ile Leu Met Ala
    210                 215                 220

Ile Arg Asp Ala Gly Phe Glu Ile Ser Ala Met Gln Met Phe Asn Met
225                 230                 235                 240

Asp Arg Val Asn Val Glu Glu Phe Tyr Glu Val Tyr Lys Gly Val Val
                245                 250                 255

Thr Glu Tyr His Asp Met Val Thr Glu Met Tyr Ser Gly Pro Cys Val
            260                 265                 270

Ala Met Glu Ile Gln Gln Asn Asn Ala Thr Lys Thr Phe Arg Glu Phe
        275                 280                 285

Cys Gly Pro Ala Asp Pro Glu Ile Ala Arg His Leu Arg Pro Gly Thr
    290                 295                 300

Leu Arg Ala Ile Phe Gly Lys Thr Lys Ile Gln Asn Ala Val His Cys
305                 310                 315                 320

Thr Asp Leu Pro Glu Asp Gly Leu Leu Glu Val Gln Tyr Phe Phe Lys
                325                 330                 335

Ile Leu Asp Asn Thr Gly
            340
```

<210> SEQ ID NO 158
<211> LENGTH: 858
<212> TYPE: DNA
<213> ORGANISM: Artificial Sequence
<220> FEATURE:
<223> OTHER INFORMATION: Human NME7-AB (optimized for E coli expression)

<400> SEQUENCE: 158

```
atggaaaaaa cgctggccct gattaaaccg gatgcaatct ccaaagctgg cgaaattatc     60

gaaattatca acaaagcggg tttcaccatc acgaaactga aaatgatgat gctgagccgt    120

aaagaagccc tggattttca tgtcgaccac cagtctcgcc cgtttttcaa tgaactgatt    180

caattcatca ccacgggtcc gattatcgca atggaaattc tgcgtgatga cgctatctgc    240
```

```
gaatggaaac gcctgctggg cccggcaaac tcaggtgttg cgcgtaccga tgccagtgaa    300

tccattcgcg ctctgtttgg caccgatggt atccgtaatg cagcacatgg tccggactca    360

ttcgcatcgg cagctcgtga aatggaactg tttttcccga gctctggcgg ttgcggtccg    420

gcaaacaccg ccaaatttac caattgtacg tgctgtattg tcaaaccgca cgcagtgtca    480

gaaggcctgc tgggtaaaat tctgatggca atccgtgatg ctggctttga aatctcggcc    540

atgcagatgt tcaacatgga ccgcgttaac gtcgaagaat tctacgaagt ttacaaaggc    600

gtggttaccg aatatcacga tatggttacg gaaatgtact ccggtccgtg cgtcgcgatg    660

gaaattcagc aaaacaatgc caccaaaacg tttcgtgaat tctgtggtcc ggcagatccg    720

gaaatcgcac gtcatctgcg tccgggtacc ctgcgcgcaa tttttggtaa aacgaaaatc    780

cagaacgctg tgcactgtac cgatctgccg gaagacggtc tgctggaagt tcaatacttt    840

ttcaaaattc tggataat                                                 858
```

```
<210> SEQ ID NO 159
<211> LENGTH: 288
<212> TYPE: PRT
<213> ORGANISM: Artificial Sequence
<220> FEATURE:
<223> OTHER INFORMATION: Human NME7-AB (optimized for E coli expression)

<400> SEQUENCE: 159

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
```

```
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe Lys Ile Leu Asp Asn Thr Gly
        275                 280                 285


<210> SEQ ID NO 160
<211> LENGTH: 756
<212> TYPE: DNA
<213> ORGANISM: Artificial Sequence
<220> FEATURE:
<223> OTHER INFORMATION: Human NME7 X1 (optimized for E coli expression)

<400> SEQUENCE: 160

atgatgatgc tgagccgtaa agaagccctg gattttcatg tcgaccacca gtctcgcccg      60

tttttcaatg aactgattca attcatcacc acgggtccga ttatcgcaat ggaaattctg     120

cgtgatgacg ctatctgcga atggaaacgc ctgctgggcc cggcaaactc aggtgttgcg     180

cgtaccgatg ccagtgaatc cattcgcgct ctgtttggca ccgatggtat ccgtaatgca     240

gcacatggtc cggactcatt cgcatcggca gctcgtgaaa tggaactgtt tttcccgagc     300

tctggcggtt gcggtccggc aaacaccgcc aaatttacca attgtacgtg ctgtattgtc     360

aaaccgcacg cagtgtcaga aggcctgctg ggtaaaattc tgatggcaat ccgtgatgct     420

ggctttgaaa tctcggccat gcagatgttc aacatggacc gcgttaacgt cgaagaattc     480

tacgaagttt acaaaggcgt ggttaccgaa tatcacgata tggttacgga aatgtactcc     540

ggtccgtgcg tcgcgatgga aattcagcaa aacaatgcca ccaaaacgtt tcgtgaattc     600

tgtggtccgg cagatccgga aatcgcacgt catctgcgtc cgggtaccct gcgcgcaatt     660

tttggtaaaa cgaaaatcca gaacgctgtg cactgtaccg atctgccgga agacggtctg     720

ctggaagttc aatacttttt caaaattctg gataat                               756


<210> SEQ ID NO 161
<211> LENGTH: 254
<212> TYPE: PRT
<213> ORGANISM: Artificial Sequence
<220> FEATURE:
<223> OTHER INFORMATION: Human NME7 X1 (optimized for E coli expression)

<400> SEQUENCE: 161

Met Met Met Leu Ser Arg Lys Glu Ala Leu Asp Phe His Val Asp His
1               5                   10                  15

Gln Ser Arg Pro Phe Phe Asn Glu Leu Ile Gln Phe Ile Thr Thr Gly
            20                  25                  30

Pro Ile Ile Ala Met Glu Ile Leu Arg Asp Asp Ala Ile Cys Glu Trp
        35                  40                  45

Lys Arg Leu Leu Gly Pro Ala Asn Ser Gly Val Ala Arg Thr Asp Ala
    50                  55                  60

Ser Glu Ser Ile Arg Ala Leu Phe Gly Thr Asp Gly Ile Arg Asn Ala
65                  70                  75                  80

Ala His Gly Pro Asp Ser Phe Ala Ser Ala Ala Arg Glu Met Glu Leu
                85                  90                  95

Phe Phe Pro Ser Ser Gly Gly Cys Gly Pro Ala Asn Thr Ala Lys Phe
            100                 105                 110

Thr Asn Cys Thr Cys Cys Ile Val Lys Pro His Ala Val Ser Glu Gly
        115                 120                 125

Leu Leu Gly Lys Ile Leu Met Ala Ile Arg Asp Ala Gly Phe Glu Ile
```

-continued

```
    130                 135                 140

Ser Ala Met Gln Met Phe Asn Met Asp Arg Val Asn Val Glu Glu Phe
145                 150                 155                 160

Tyr Glu Val Tyr Lys Gly Val Val Thr Glu Tyr His Asp Met Val Thr
                165                 170                 175

Glu Met Tyr Ser Gly Pro Cys Val Ala Met Glu Ile Gln Gln Asn Asn
            180                 185                 190

Ala Thr Lys Thr Phe Arg Glu Phe Cys Gly Pro Ala Asp Pro Glu Ile
        195                 200                 205

Ala Arg His Leu Arg Pro Gly Thr Leu Arg Ala Ile Phe Gly Lys Thr
    210                 215                 220

Lys Ile Gln Asn Ala Val His Cys Thr Asp Leu Pro Glu Asp Gly Leu
225                 230                 235                 240

Leu Glu Val Gln Tyr Phe Phe Lys Ile Leu Asp Asn Thr Gly
                245                 250


<210> SEQ ID NO 162
<211> LENGTH: 91
<212> TYPE: PRT
<213> ORGANISM: Artificial Sequence
<220> FEATURE:
<223> OTHER INFORMATION: DM10 domain of NME7

<400> SEQUENCE: 162

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys
                85                  90
```

ANTI-CANCER PEPTIDE

RELATED APPLICATIONS

The present application is a continuation of and claims the benefit of priority to U.S. patent application Ser. No. 16/111,894 filed Aug. 24, 2018, now U.S. Pat. No. 11,702,483, which is a division of and claims the benefit of priority to U.S. patent application Ser. No. 15/302,461 filed Oct. 6, 2016, now abandoned, which is a National Stage Entry of International Patent Application No. PCT/US2015/024764 filed Apr. 7, 2015, which in turn claims the benefit of priority to U.S. Provisional Application Nos. 62/127,746 and 62/114,526 filed Mar. 3, 2015 and Feb. 10, 2015, respectively, and claims the benefit of priority to U.S. Provisional Application No. 61/976,390 filed Apr. 7, 2014, each of which is incorporated herein by reference it its entirety.

BACKGROUND OF THE INVENTION

The disclosure of each of the aforementioned patent applications is hereby incorporated by reference in the entirety for all purposes.

SEQUENCE LISTING

The instant application contains a Sequence Listing which has been submitted electronically in ASCII format and is hereby incorporated by reference in its entirety. Said ASCII copy, created on Apr. 1, 2022, is named 56699-730_302SL.txt and is 168,785 bytes in size.

Field of the Invention

The present application relates to NME proteins, peptides derived from NME proteins, and antibodies generated from the peptides thereof or antibody or antibody fragments selected by virtue of their ability to bind to said peptides. The present application also relates to treating or preventing diseases associated with the expression of NME in a patient.

General Background and State of the Art

NDPK (nucleoside diphosphate protein kinase) proteins are a family of proteins grouped together because they all contain an NDPK domain. The first NME proteins discovered, previously called NM23 proteins, were NM23-H1 and NM23-H2. For decades it was unclear whether they induced differentiation or prevented differentiation of hematopoietic cells. The inventors previously discovered that NM23-H1 prevents differentiation when it is a dimer, which binds to the MUC1* growth factor receptor, but at higher concentrations NM23-H1 becomes a hexamer, which does not bind to MUC1*, and it induces differentiation. NM23 used to be called a metastasis suppressor when it was found that it was under-expressed in some very aggressive cancers. The present inventors previously disclosed that NM23-H1 dimers bind to and dimerize the extracellular domain of the MUC1* growth factor receptor that is over expressed on the vast majority of cancers and such binding promotes the growth of cancer cells. Conversely, at higher concentrations, NM23 forms tetramers and hexamers that do not bind to MUC1* and do not promote tumorigenesis. Very recently more NME family proteins (NME 1-10) have been discovered although until now, their functions have not been elucidated. NME7 is a newly discovered NME family protein, but its NDPK domain has no enzymatic activity, unlike other NME family members. NME7 is either not expressed at all in adult tissues or is expressed at extremely low levels.

SUMMARY OF THE INVENTION

The present application is directed to a method of treating or preventing cancer in a subject, comprising administering to the subject an antibody made against a member of the NME family. The NME family may be NME7 family. The antibody may bind to NME7. The antibody may bind to NME7-AB or NME-AB-like protein. The antibody may bind to NME7-X1. The antibody may inhibit binding between NME7 and its cognate binding partner. The cognate binding partner may be MUC1*. The cognate binding partner may be PSMGFR portion of the MUC1* extracellular domain. In one aspect, the antibody may be generated or selected for its ability to bind to a peptide selected from those listed in FIGS. 16-19 (SEQ ID NOS:88 to 145). Preferably, the peptide may be selected from those listed in FIG. 19 (SEQ ID NOS:141 to 145).

The peptide may be highly homologous to, or to which is added or subtracted up to 7, up to 6, up to 5, up to 4, up to 3, up to 2, or up to 1 amino acid residues at the N-terminus or C-terminus, of the peptides listed in FIGS. 16-19 (SEQ ID NOS:88 to 145). In one aspect, the antibody may be selected for its ability to bind to NME7-AB or NME7-X1 but not to NME1. The antibody may be polyclonal, monoclonal, bivalent, monovalent, bispecific, an antibody fragment containing the variable region, or an antibody mimic. The antibody may be human or humanized. The antibody may be a single chain scFv.

In another aspect, the invention is directed to a method of treating or preventing cancer in a subject, comprising administering to the subject a peptide that is highly homologous or identical to regions of NME7-AB. The peptide may be at least 80% homologous to one or more of the peptides listed in FIG. 16. The peptide may be at least 80% homologous to one or more of the peptides listed in FIG. 17. The peptide may be at least 80% homologous to one or more of the peptides listed in FIG. 18. The peptide may be at least 80% homologous to one or more of the peptides listed in FIG. 19. The peptide may be selected from peptides listed in FIGS. 16-19 (SEQ ID NOS:88 to 145). The peptide may be selected from those listed in FIG. 19 (SEQ ID NOS:141 to 145). Or, the peptide may be highly homologous to, or to which is added or subtracted up to 7, up to 6, up to 5, up to 4, up to 3, up to 2, or up to 1 amino acid residues at the N-terminus or C-terminus, of the peptides listed in FIGS. 16-19 (SEQ ID NOS:88 to 145). The peptide may be connected to another peptide via a spacer or linker.

In another aspect, the invention is directed to a chimeric antigen receptor (CAR), for the treatment or prevention of cancer wherein the targeting extracellular portion of the CAR comprises at least a peptide fragment of a member of the NME family. NME family may be NME7 family. The member of the NME7 family may be NME7. Or, the member of the NME7 family may be NME7-AB or NME-AB-like protein. The member of the NME7 family may be also NME7-X1. The targeting extracellular portion of the CAR may include a peptide of the peptides listed in FIGS. 16-19 (SEQ ID NOS:88 to 145). The peptide may be selected from those listed in FIG. 19 (SEQ ID NOS:141 to 145). The peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIGS. 16-19 (SEQ ID NOS:88 to 145). The peptide may be connected to another peptide via a spacer or linker.

In yet another aspect, the invention is directed to a method of treating or preventing cancer or cancer metastasis, comprising engineering the chimeric antigen receptor according to claim 3, into an immune system cell and administering the cell to a subject in need thereof.

In another aspect, the invention is directed to a chimeric antigen receptor (CAR), for the treatment or prevention of cancer, wherein the targeting extracellular portion of the chimeric antigen receptor comprises a portion of an antibody that binds to NME7-AB, NME-AB-like protein or NME7-X1. The portion of the antibody may be a single chain scFv or may be human or humanized.

In yet another aspect, the invention is directed to a method of vaccinating a person against cancer or metastatic cancer comprising immunizing the person with a peptide fragment of a member of the NME family. The NME family may be NME7 family. The member of the NME7 family may be NME7 or NME7b. The member of the NME7 family may be NME7-AB or NME7-AB-like protein. The NME7 family may be NME7-X1. The immunizing peptide may be a peptide from the peptides listed in FIGS. 16-19 (SEQ ID NOS:88 to 145). Preferably, the peptide may be selected from those listed in FIG. 19 (SEQ ID NOS:141 to 145). The immunizing peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIGS. 16-19 (SEQ ID NOS:88 to 145). The immunizing peptide may be connected to another peptide via a spacer or linker.

In yet another aspect, the invention is directed to a method of treating or preventing cancer in a subject, comprising administering to the subject a nucleic acid that inhibits the expression of NME7, NME7b, NME7-AB-like protein or NME7-X1. The nucleic acid may be an anti-sense nucleic acid that suppresses expression of NME7, NME7-AB-like protein or NME7-X1. The nucleic acid may be an inhibitory RNA, siRNA, RNAi, or shRNA that inhibits expression of NME7, NME7-AB-like protein or NME7-X1.

In another aspect, the invention is directed to a method of treating or preventing cancer in a subject, comprising administering to the subject genetically edited nucleic acids that inhibit expression of NME7, NME7b, NME7-AB-like protein or NME7-X1. The genetically edited nucleic acids that inhibit expression of NME7, NME7b, NME7-AB-like protein or NME7-X1 may be inserted into cells that may be then administered to the patient. The genetically edited nucleic acids that inhibit expression of NME7, NME7b, NME7-AB-like protein or NME7-X1 may be inserted into cells using a viral vector. The viral vector may be a lentiviral system.

In another aspect, the invention is directed to a method of growing cancer cells comprising contacting the cells with NME7-AB, NME7b, NME7-AB-like protein or NME7-X1, 2i or 5i. The method may include culturing the cells in a medium that contains NME7-AB, NME7b, NME7-AB-like protein or NME7-X1, 2i or 5i, or growing cells in an animal that expresses human NME7-AB, NME7b, NME7-AB-like protein or NME7-X1, or to which NME7-AB, NME7b, NME7-AB-like protein or NME7-X1 is administered. The cancer cells may be breast, prostate, ovarian, colorectal, pancreatic, liver, melanoma or brain cancer cells. Drug candidates may be tested on the cells. Th efficacy of the drugs may be assessed by comparing cancer growth to a no drug control or comparing expression levels of metastatic markers or stem cell markers to a no drug control or comparing the ability of the resultant cells to form tumors in animals from low cell copy number compared to a no drug control and determining the efficacy of a candidate drug for the treatment of cancer or metastasis. The cells may be obtained from a patient being assessed for treatment for cancer and drugs that would be effective for that patient are selected based on results using methods described above. The cells may not be obtained from a patient being assessed for treatment for cancer but drugs that would be effective for that patient are selected based on results using the methods described above.

In another aspect, the invention is directed to a method of generating antibodies or antibody-like molecules from peptides or peptide mimics having a sequence derived from the sequence of NME. The NME may be NME7. The peptide may be used as an immunogen to generate antibodies or antibody-like molecules. The peptide may be administered to an animal to generate anti-NME7 antibodies. The peptide may be administered to a human to generate anti-NME7 antibodies. The peptide may have a sequence listed in FIGS. 16 to 19 (SEQ ID NOS:88 to 145). Preferably, the peptide may be selected from those listed in FIG. 19 (SEQ ID NOS:141 to 145). The peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIGS. 16-19 (SEQ ID NOS:88 to 145).

In another aspect, the invention is directed to a method of detecting presence of cancer or the progression of cancer, comprising the steps of:

1) obtaining a sample from a patient having cancer or at risk of developing a cancer;
2) subjecting that sample to an assay capable of detecting or measuring levels of a member of the NME7 family, or levels of nucleic acids encoding a member of the NME7 family;
3) comparing levels of the measured member of the NME7 family or the member of the NME7 family-encoding nucleic acids in the test sample to levels in control patients or control cells;
4) determining that the levels of the member of the NME7 family or nucleic acids encoding the member of the NME7 family are elevated compared to the controls; and
5) concluding that the donor of the test sample has cancer or has had a progression of cancer if the control to which the test was compared came from a donor previously diagnosed with a cancer. In this method, the detection of the member of the NME7 family in circulation or in a tissue may be an indicator of cancer in a patient. The member of the NME7 family may be NME7, NME7b, NME7-X1, or NME7-AB-like protein.

In yet another aspect, the invention is directed to a method comprising:

detecting presence of a member of the NME7 family or MUC1* in a patient; and administering anti-NME7 or anti-MUC1* antibody or antibodies to the patient exhibiting the member of the NME7 family or MUC1* expression. The member of the NME7 family may be NME7, NME7b, NME7-X1, or NME7-AB-like protein.

In yet another aspect, the invention is directed to a method for treating or preventing cancer comprising:

1) obtaining a sample from a patient suspected of having a cancer or at risk of developing a cancer or at risk of developing a metastatic cancer;
2) measuring an amount of the member of an NME7 family or a member of the NME7 family encoding nucleic acid, wherein the measured levels are significantly above those measured in a control sample;
3) determining that the patient has a cancer or has developed a more aggressive or a metastatic cancer;
4) administering to the patient an effective amount of a therapeutic agent that suppresses expression of the member of the NME7 family, inhibits cleavage of NME7 or inhibits NME7 binding to its targets. The target of the member of the NME7 family may be MUC1*. The target of the member of the NME7 family may be PSMGFR portion of the MUC1* extracellular domain. The member of the NME7 family may be NME7, NME7b, NME7-X1, or NME7-AB-like protein.

In any of the methods above regarding cancer, cancer may include breast, prostate, ovarian, colorectal, pancreatic, liver, melanoma or brain cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given herein below, and the accompanying drawings which are given by way of illustration only, and thus are not limitative of the present invention, and wherein;

FIGS. 3A-3C show panels of photos of Western blots of human embryonic stem (ES) cells (A) and induced pluripotent stem (iPS) cells (B, C) probed for the presence of NME7. Western blots show the presence of three forms of NME7 in the cell lysates. One with an apparent molecular weight of ~42 kDa (full length), ~33 kDa (NME7-AB domains devoid of the N-terminal DH domain) and a small ~25 kDa species. However, only the lower molecular weight species are in the conditioned media (B).

FIGS. 7A-7K show the 48 hour results of an experiment using an anti-NME7 antibody to inhibit cancer cell growth. Photos of the cells cultured in media alone (A), taxol (B), or anti-NME7 at the concentrations indicated (C-J); a graph of cell number obtained using a calcein AM assay is shown (K).

FIGS. 8A-8K show the 96 hour results of an experiment using an anti-NME7 antibody to inhibit cancer cell growth. Photos of the cells cultured in media alone (A), taxol (B), or anti-NME7 at the concentrations indicated (C-J); a graph of cell number obtained using a calcein AM assay is shown (K). The graph and the photos show anti-NME7 antibodies inhibit cancer cell growth at concentrations as low as in the nanomolar range.

FIG. 15 is a sequence alignment between human NME1 and human NME7-A or -B domain.

FIG. 16 lists immunogenic peptides from human NME7 with low sequence identity to NME1 and selected for their ability to generate therapeutic anti-NME7 antibodies for the treatment or prevention of cancers.

FIG. 17 lists immunogenic peptides from human NME7 that may be important for structural integrity or for binding to MUC1* selected for their ability to generate therapeutic anti-NME7 antibodies for the treatment or prevention of cancers.

FIG. 18 lists immunogenic peptides from human NME1 that may be important for structural integrity or for binding to MUC1* and selected for their ability to generate therapeutic anti-NME7 antibodies for the treatment or prevention of cancers.

FIG. 19 lists immunogenic peptides from human NME7 selected for their low sequence identity to NME1 and for their homology to bacterial NME1 proteins that have been implicated in cancers. These peptides are preferred for their ability to generate therapeutic anti-NME7 antibodies for the treatment or prevention of cancers. The peptides shown in this Figure include and added Cysteine covalently bound at the C-terminal end.

FIG. 20 shows photographs of two female athymice nu/nu mice out of 24 that were xenografted with only 50 human breast cancer cells that had first been grown for 7 days in NME7-AB and showed greatly increased expression of CXCR4, CHD1 and stem cell markers. In addition, half the mice were also injected daily with human recombinant NME7-AB. 82% of the mice that were also injected daily with NME7-AB developed remote metastases as well as tumors at the site of injection.

FIG. 21 shows a table of the results of the experiment in which mice were xenografted with cancer cells that were transformed to a more metastatic state by pre-culture in a medium containing human NME7-AB.

FIG. 30 shows a table of scientist observations when cancer cells were grown in either NME7-AB or 2i inhibitors, which both are able to transform cancer cells to a more metastatic state, and in the presence or absence of NME7 derived peptides A1, A2, B1, B2 and B3. The NME7-AB peptides inhibited the transition of adherent cancer cells to the floater cells, which RT-PCR measurements show have increased expression of metastatic markers, especially CXCR4.

FIGS. 31A-31C show a graph of RT-PCR measurements of CXCR4 expression in T47D breast cancer cells that were grown in either NME7-AB or 2i inhibitors, each of which transform cancer cells to a more metastatic state, and the inhibitory effect of anti-NME7 antibodies on the metastatic transformation (A). A graph of RT-PCR measurements of CXCR4, CHD1 and SOX2 expression in T47D breast cancer cells that were grown in 2i inhibitors for 72 hours or 144 hours, shows that the NME7-AB immunizing peptides are themselves inhibitory to the metastatic transformation. Peptides A1, A2 and B1 which were used in the inhibitory Combo 2 and 3 in part (A) are also inhibitory as peptides. Peptide B3 is the most inhibitory and is the immunizing peptide for antibody 61 which was the most inhibitory antibody tested in part (A). In part (C), the scale of the Y-axis of the graph of part (B) is reduced.

FIG. 32 shows a table of recorded RNA levels in samples that were used for RT-PCR measurement of CXCR4 in FIG. 31 as well as the threshold cycle number for CXCR4 expression as well as for the control housekeeping gene.

FIGS. 39A-39E show photographs of Western blots of a co-immunoprecipitation experiment. T47D breast cancer cell extracts were incubated with an antibody against the MUC1 cytoplasmic tail, Ab-5, or a control antibody, IgG, and co-immunoprecipitated. The gels were blotted with two different commercially available anti-NME7 antibodies B9 (A) and CF7 (B). Both gels show unique NME7 bands at ~33 kDa and ~30 kDa. The gels were stripped and re-probed with an antibody against the extracellular domain of MUC1*, anti-PSMGFR (C) and (D), which shows that the NME7 species and MUC1* interact. A recombinant NME7-AB and a recombinant NME7-X1 were mixed together and run on a gel, then probed with an anti-NME7 antibody, showing that the two unique NME7 species that are naturally occurring in breast cancer cells and that interact with MUC1* are an NME7-AB-like species and NME7-X1 (E).

DETAILED DESCRIPTION OF THE PREFERRED EMBODIMENTS

Definitions

Figures 1A, 1B, 1C, 1D:
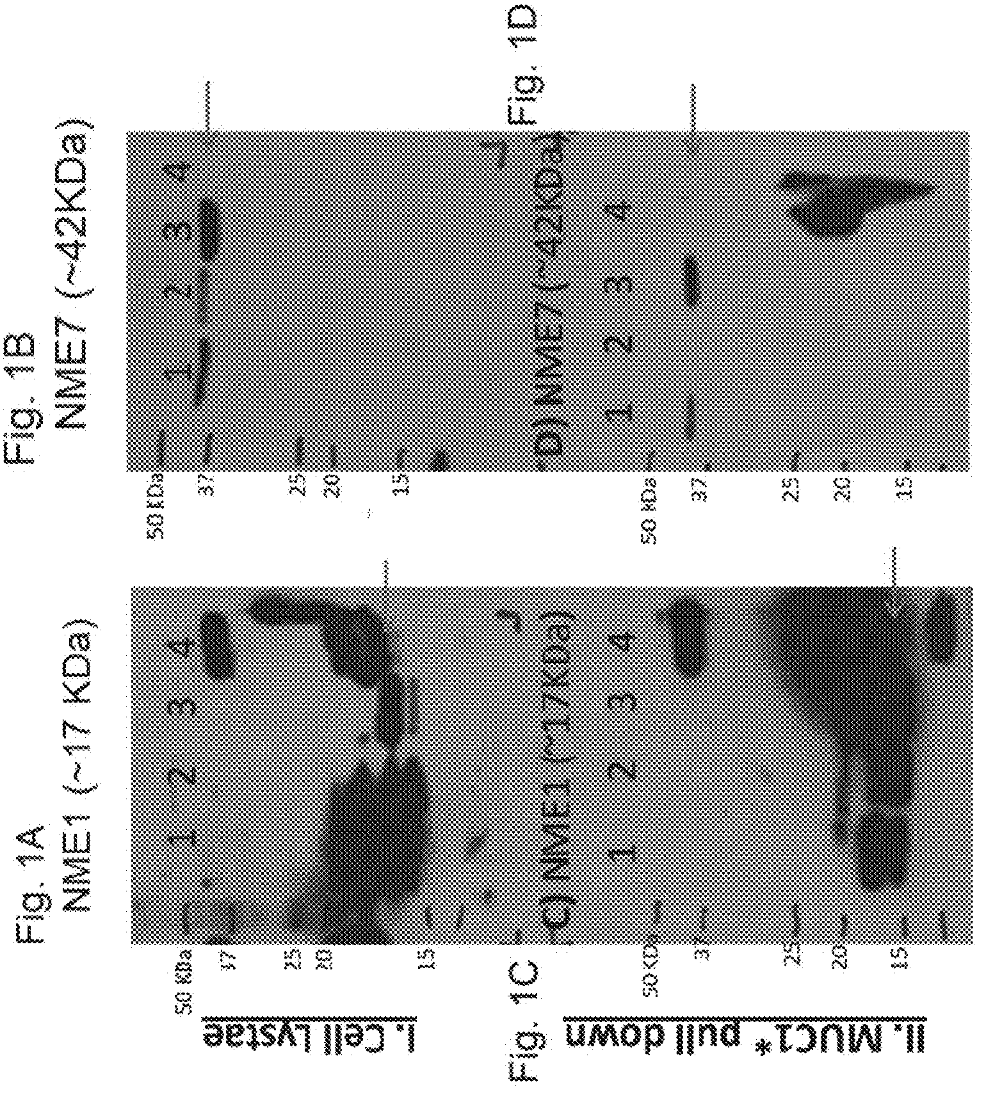
FIGS. 1A-1D. Photos of Western blot gels showing the expression of NME1 or NME7 in the cell lysate of: 1) BGO1V human embryonic stem cells cultured in NM23-H1 dimers over a surface coated with a MUC1* antibody surface (MN-C3 mab); 2) BGO1V human embryonic stem cells cultured according to standard protocol in bFGF over a layer of mouse feeder cells (MEFs); 3) T47D breast cancer cells cultured by standard method in RPMI media; and 4) recombinant human NM23-H1 wild type, "wt" (A, B). Bottom row (C, D) shows the results of a "pull-down" or an immuno-precipitation assay in which the cell lysates were separately incubated with beads to which was added an antibody to the MUC1 cytoplasmic tail, "Ab-5". Species captured by binding to the MUC1* peptide were separated by SDS-PAGE and blotted with antibodies against each respective NM23 protein. Same experiments were conducted with NME6 but data is not shown.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

As used herein, “fragments” or “functional derivatives” refers to biologically active amino acid sequence variants and fragments of the polypeptide of the present invention, as well as covalent modifications, including derivatives obtained by reaction with organic derivatizing agents, post-translational modifications, derivatives with nonproteinaceous polymers, and immunoadhesins.

As used herein, “carriers” include pharmaceutically acceptable carriers, excipients, or stabilizers which are nontoxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and PLURONICS®.

As used herein “pharmaceutically acceptable carrier and/or diluent” includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 μg to about 2000 mg. Expressed in proportions, the active compound is generally present in from about 0.5 μg/ml of carrier. In the case of compositions containing supplementary active ingredients, the dosages are determined by reference to the usual dose and manner of administration of the said ingredients.

As used herein, “vector”, “polynucleotide vector”, “construct” and “polynucleotide construct” are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-structures, such as polyamides.

As used herein, “host cell” includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change.

As used herein, “subject” is a vertebrate, preferably a mammal, more preferably a human.

As used herein, “mammal” for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, “treatment” is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. “Treatment” can also mean prolonging survival as compared to expected survival if not receiving treatment. “Treatment” refers to both therapeutic treatment and prophylactic or preventative measures. Those in need of treatment include those already with the disorder as well as those in which the disorder is to be prevented. “Palliating” a disease means that the extent and/or undesirable clinical manifestations of a disease state are lessened and/or the time course of the progression is slowed or lengthened, as compared to a situation without treatment.

As used herein, "A1" peptide, "A2" peptide, "B1" peptide, "B2" peptide and "B3" peptide refer to peptides that bind to human NME7-AB, but not (or significantly less) to human NME1. The peptides used to generate these antibodies are common to both NME7-AB and NME7-X1, and are set forth as below.

A1 is NME7A peptide 1 (A domain): MLSRKEALDFHVDHQS (SEQ ID NO:141)

A2 is NME7A peptide 2 (A domain): SGVARTDASES (SEQ ID NO:142)

B1 is NME7B peptide 1 (B domain): DAGFEISAMQMFNMDRVNVE (SEQ ID NO:143)

B2 is NME7B peptide 2 (B domain): EVYKGVVTEYHDMVTE (SEQ ID NO:144)

B3 is NME7B peptide 3 (B domain): AIFGKTKIQNAVHCTDLPEDGLLEVQYFF (SEQ ID NO:145)

Further, for the sake of clarity, NME7A (with capital letter "A") refers to the subunit A portion of NME7. NME7a (with small letter "a") refers to the full-length NME7 that is described elsewhere in this application. And, NME7B (with capital letter "B") refers to the subunit B portion of NME7. NME7b (with small letter "b") refers to a species of NME7 that is partially devoid of the DM10 region, which is described elsewhere in this application.

As used herein, the term "antibody-like" means a molecule that may be engineered such that it contains portions of antibodies but is not an antibody that would naturally occur in nature. Examples include but are not limited to CAR (chimeric antigen receptor) T cell technology and the Ylanthia® technology. The CAR technology uses an antibody epitope fused to a portion of a T cell so that the body's immune system is directed to attack a specific target protein or cell. The Ylanthia® technology consists of an "antibody-like" library that is a collection of synthetic human fabs that are then screened for binding to peptide epitopes from target proteins. The selected Fab regions can then be engineered into a scaffold or framework so that they resemble antibodies.

As used herein, an "effective amount of an agent to inhibit an NME family member protein" refers to the effective amount of the agent in hindering the activating interaction between the NME family member protein and its cognate receptor such as As used herein, "NME derived fragment" refers to a peptide sequence that is either a fragment of the NME or is highly homologous to the peptide sequence that is a fragment of the NME.

As used herein, the "MUC1*" extra cellular domain is defined primarily by the PSMGFR sequence (GTINVHDVETQFNQYKTEAASRYNLTISDVSVSDVPFPFSAQSGA (SEQ ID NO:6)). Because the exact site of MUC1 cleavage depends on the enzyme that clips it, and that the cleavage enzyme varies depending on cell type, tissue type or the time in the evolution of the cell, the exact sequence of the MUC1* extra cellular domain may vary at the N-terminus.

As used herein, the term "PSMGFR" is an acronym for Primary Sequence of MUC1 Growth Factor Receptor as set forth as GTINVHDVETQFNQYKTEAASRYNLTISDVSVSDVPFPFSAQSGA (SEQ ID NO:6). In this regard, the "N-number" as in "N-10 PSMGFR", "N-15 PSMGFR", or "N-20 PSMGFR" refers to the number of amino acid residues that have been deleted at the N-terminal end of PSMGFR. Likewise "C-number" as in "C-10 PSMGFR", "C-15 PSMGFR", or "C-20 PSMGFR" refers to the number of amino acid residues that have been deleted at the C-terminal end of PSMGFR.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein, "high homology" is considered to be at least 30%, 35%, 40%, 45%, 50%, 55%, 60%, 65%, 70%, 75%, 80%, 85%, 90%, 95%, or 97% identity in a designated overlapping region between any two polypeptides.

As used herein, "NME family proteins" or "NME family member proteins", numbered 1-10, are proteins grouped together because they all have at least one NDPK (nucleotide diphosphate kinase) domain. In some cases, the NDPK domain is not functional in terms of being able to catalyze the conversion of ATP to ADP. NME proteins were formerly known as NM23 proteins, numbered H1 and H2. Recently, as many as ten (10) NME family members have been identified. Herein, the terms NM23 and NME are interchangeable. Herein, terms NME1, NME2, LAMES, NME6, NME7, NME8 and NME9 are used to refer to the native protein as well as NME variants. In some cases these variants are more soluble, express better in *E. coli* or are more soluble than the native sequence protein. For example, NME7 as used in the specification can mean the native protein or a variant, such as NME7-AB that has superior commercial applicability because variations allow high yield expression of the soluble, properly folded protein in *E. coli*. NME7-AB consists primarily of the NME7 A and B domains but is devoid of most of the DM10 domain (SEQ ID NO:39), which is at the N-terminus of the native protein. "NME1" as referred to herein is interchangeable with "NM23-H1". It is also intended that the invention not be limited by the exact sequence of the NME proteins. The mutant NME1-5120G, also called NM23-5120G, are used interchangeably throughout the application. The 5120G mutants and the P96S mutant are preferred because of their preference for dimer formation, but may be referred to herein as NM23 dimers, NME1 dimers, or dimeric NME1, or dimeric NM23.

NME7 as referred to herein is intended to mean native NME7 having a molecular weight of about 42 kDa.

A "family of NME7" refers to full length NME7 as well as naturally occurring or artificially created cleaved form having a molecular weight about 30 kDa, 33 kDa, or a cleaved form having a molecular weight of about 25 kDa, a variant devoid or partially devoid of the DM10 leader sequence (SEQ ID NO:162), which is NME7 amino acids 1-91 of NME7 represented by SEQ ID NO:82 or 147, such as NME7b, NME7-X1, NME7-AB or a recombinant NME7 protein, or variants thereof whose sequence may be altered to allow for efficient expression or that increase yield, solubility or other characteristics that make the NME7 more effective or commercially more viable. The "family of NME7" may also include "NME7-AB-like" protein, which is a protein in the range of 30 to 33 kDa that is expressed in cancer cells.

As used herein, an "an agent that maintains stem cells in the naïve state or reverts primed stem cells to the naïve state" refers to a protein, small molecule or nucleic acid that alone or in combination maintains stem cells in the naïve state, resembling cells of the inner cell mass of an embryo. Examples include but are not limited to human NME1 dimers, bacterial, fungal, yeast, viral or parasitic NME proteins that have high sequence identity to human NME proteins, especially NME1, NME7, NME7-X1, NME7-AB, NME6, 2i (Silva J et al, 2008; Hanna et al, 2010), 5i (Theunissen T W et al, 2014), nucleic acids such as siRNA that suppress expression of MBD3, CHD4 (Rais Y1 et al, 2013), BRD4, or JMJD6 (Liu W et al 2013).

As used herein, an "an agent that promotes pluripotency" or "reverts somatic cells to a stem-like or cancer-like state" refers to a protein, small molecule or nucleic acid that alone or in combination induces expression of or suppresses expression of certain genes such that the genetic signature shifts to one that more closely resembles stem cells or cancer cells. Examples include but are not limited to NME1 dimers, NME7, NME7-X1, NME7-AB, 2i, 5i, nucleic acids such as siRNA that suppress expression of MBD3, CHD4, BRD4, or JMJD6, microbial NME proteins that have high sequence homology to human NME1, NME2, NME5, NME6, NME7, NME8, or NME9, preferably with the regions that house NDPK domains.

As used herein, in reference to an agent being referred to as a "small molecule", it may be a synthetic chemical or chemically based molecule having a molecular weight between 50 Da and 2000 Da, more preferably between 150 Da and 1000 Da, still more preferably between 200 Da and 750 Da.

As used herein, in reference to an agent being referred to as a "natural product", it may be chemical molecule or a biological molecule, so long as the molecule exists in nature.

As used herein, FGF, FGF-2 or bFGF refer to fibroblast growth factor (Xu R H et al, 2005; Xu C et al, 2005).

As used herein, "Rho associated kinase inhibitors" may be small molecules, peptides or proteins (Rath N, et al, 2012). Rho kinase inhibitors are abbreviated here and elsewhere as ROCi or ROCKi, or Ri. The use of specific rho kinase inhibitors are meant to be exemplary and can be substituted for any other rho kinase inhibitor.

As used herein, the term "cancer stem cells" or "tumor initiating cells" refers to cancer cells that express levels of genes that have been linked to a more metastatic state or more aggressive cancers. The terms "cancer stem cells" or "tumor initiating cells" can also refer to cancer cells for which far fewer cells are required to give rise to a tumor when transplanted into an animal. Cancer stem cells and tumor initiating cells are often resistant to chemotherapy drugs.

As used herein, the terms "stem/cancer", "cancer-like", "stem-like" refers to a state in which cells acquire characteristics of stem cells or cancer cells, share important elements of the gene expression profile of stem cells, cancer cells or cancer stem cells. Stem-like cells may be somatic cells undergoing induction to a less mature state, such as increasing expression of pluripotency genes. Stem-like cells also refers to cells that have undergone some de-differentiation or are in a meta-stable state from which they can alter their terminal differentiation. Cancer like cells may be cancer cells that have not yet been fully characterized but display morphology and characteristics of cancer cells, such as being able to grow anchorage-independently or being able to give rise to a tumor in an animal.

As used herein, "spacers" or "linkers" of different lengths can be incorporated anywhere in the peptide. Spacer attachment is usually through an amide linkage but other functionalities are possible.

NME, NME7 and Protein Family of NME7

The present inventors discovered that NME7 is highly expressed in early human stem cells and also in most cancer cells (FIGS. 1, 2, 3, 35, 36, 38, 39 and 40 and Examples 2, 3, and 4). Further, we demonstrated that like NM23-H1, NME7 binds to and dimerizes the MUC1* growth factor receptor on both stem cells and cancer cells. FIG. 15 shows a sequence alignment of NME1 and NME7 A and B domains.

Figure 9:
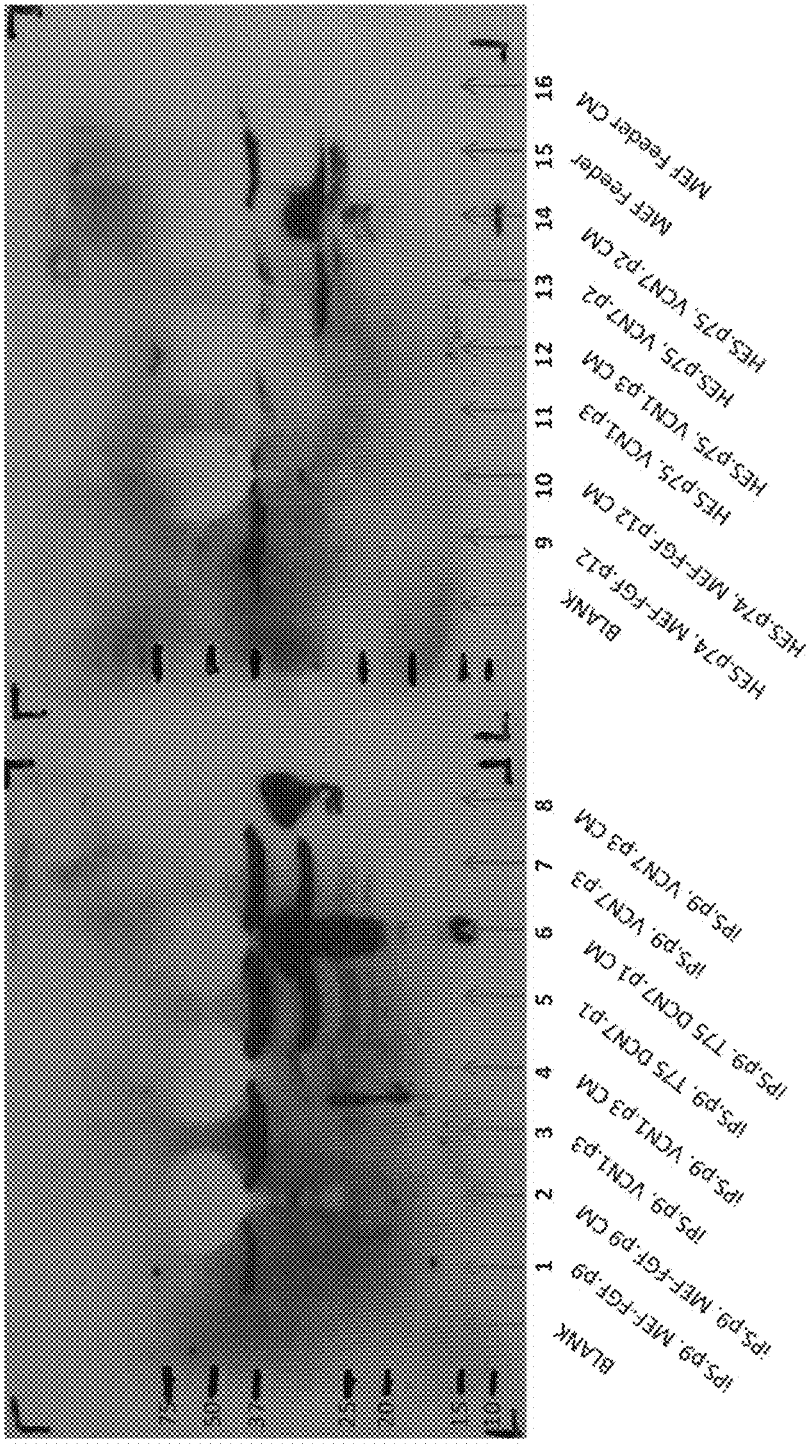
FIG. 9 is a photo of a Western blot wherein stem cell lysates (odd numbered lanes) or cell-conditioned media (even numbered lanes) were probed for the presence of NME7. iPS (induced pluripotent stem) cells were cultured in FGF over MEFs (lanes 1,2), NM23-H1 dimers over an anti-MUC1* antibody (C3) surface (lanes 3,4) or NME7 over an anti-MUC1* antibody (C3) surface (lanes 5-8). HES-3 (human embryonic stem) cells were cultured in FGF over MEFs (lanes 9,10), NM23-H1 dimers over an anti-MUC1* antibody (C3) surface (lanes 11,12) or NME7 over an anti-MUC1* antibody (C3) surface (lanes 13,14). Mouse embryonic fibroblast (MEFs) cells were also probed (lanes 15,16). The Western blot shows that the cell lysates contain an NME7 species with molecular weight of ~42 kDa, which corresponds to the full-length protein. However, the secreted species runs with an apparent MW of ~33 kDa, which corresponds to an NME7 species that is devoid of the N-terminal leader sequence.
Figure 10B:
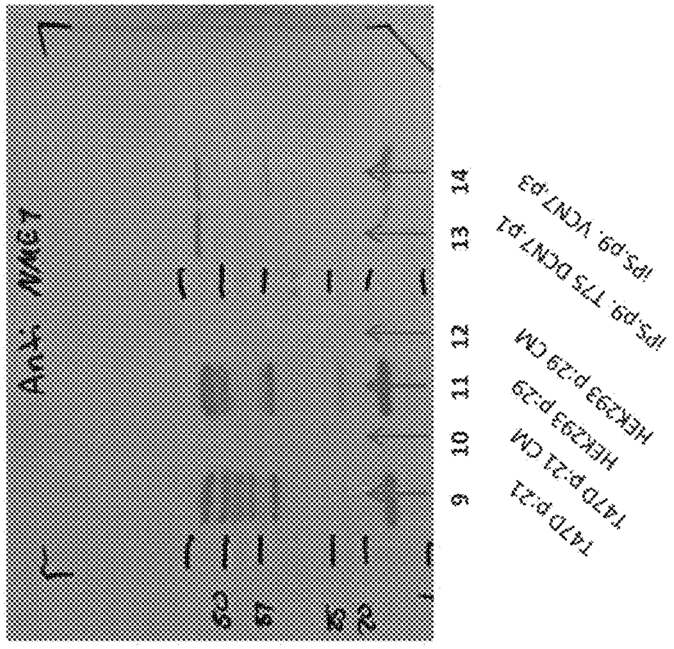
FIGS. 10A-10B show photos of Western blots of various cell lysates and corresponding conditioned media probed for the presence of NME7 using a mouse monoclonal antibody (A) or another monoclonal antibody that only recognizes the N-terminal DM10 sequence (B). The lack of binding of the DM10 specific antibody to the ~33 kDa NME7 species in the samples from the conditioned media of the cells indicates that the secreted form of NME7 is devoid of most if not all of the N-terminal DM10 leader sequence.
Figure 10A:
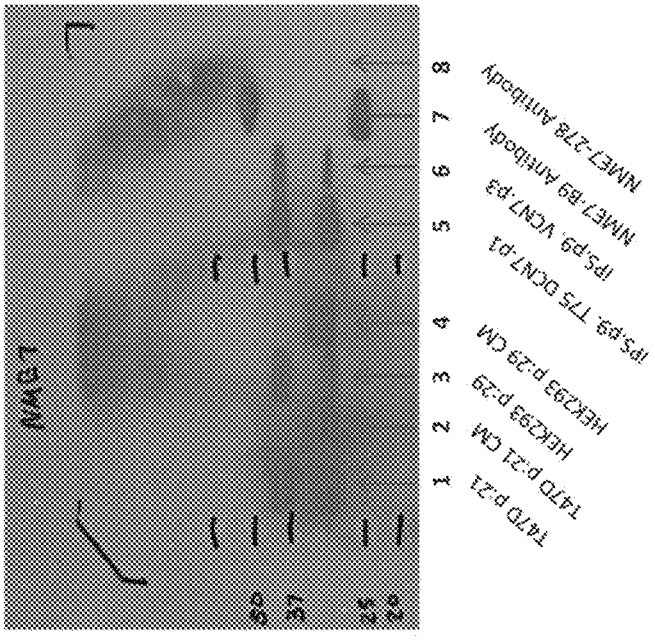

The inventors recently discovered that NME7 is a primitive form of NME1 (NM23-H1) that is expressed in very early embryonic stem cells. NME7 is either not expressed at all, or is expressed at extremely low levels, in adult tissues. However, the inventors discovered that NME7 is expressed at high levels in cancerous cells and tissues and at even higher levels in metastatic cancer cells and tissues. A cleaved form of NME7 may be a secreted form allowing it to bind to and activate extracellular receptors. We detect full-length NME7, MW 42 kDa, as well as NME7 species that are approximately 33 kDa and 30 kDa. The 33 kDa and 30 kDa species are secreted from cancer cells. Western blots detect full-length NME7 in cell lysates, but smaller 30-33 kDa NME7 species in their condition media (FIGS. 9 and 10). Western blots probed with either an antibody that recognizes NME7 or an antibody that only recognizes the DM10 domain show that the lower molecular weight NME7 species that are secreted into the conditioned media are devoid of the DM10 domain (FIG. 10). These data are consistent with the idea that naturally occurring NME7 species are comparable to the recombinant NME7-AB we generated as they have nearly the same molecular weight, both are secreted and are both devoid of the 91 amino acids of the DM10 domain which may keep the protein retained within the cell.

Figure 33:
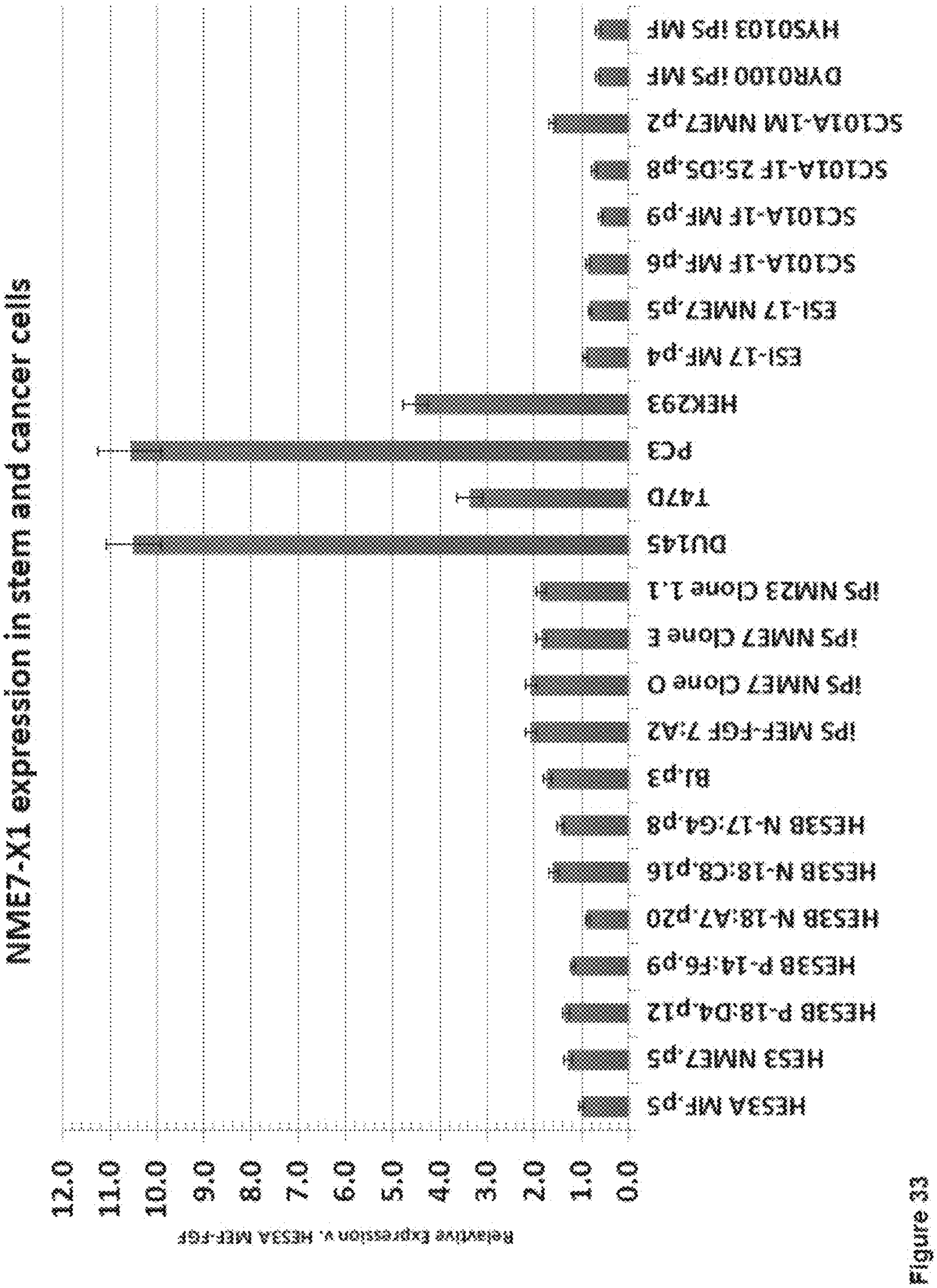
FIG. 33 shows a graph of RT-PCR measurement of the expression of NME7-X1 in a panel of human stem cells and cancer cells.
Figure 34:
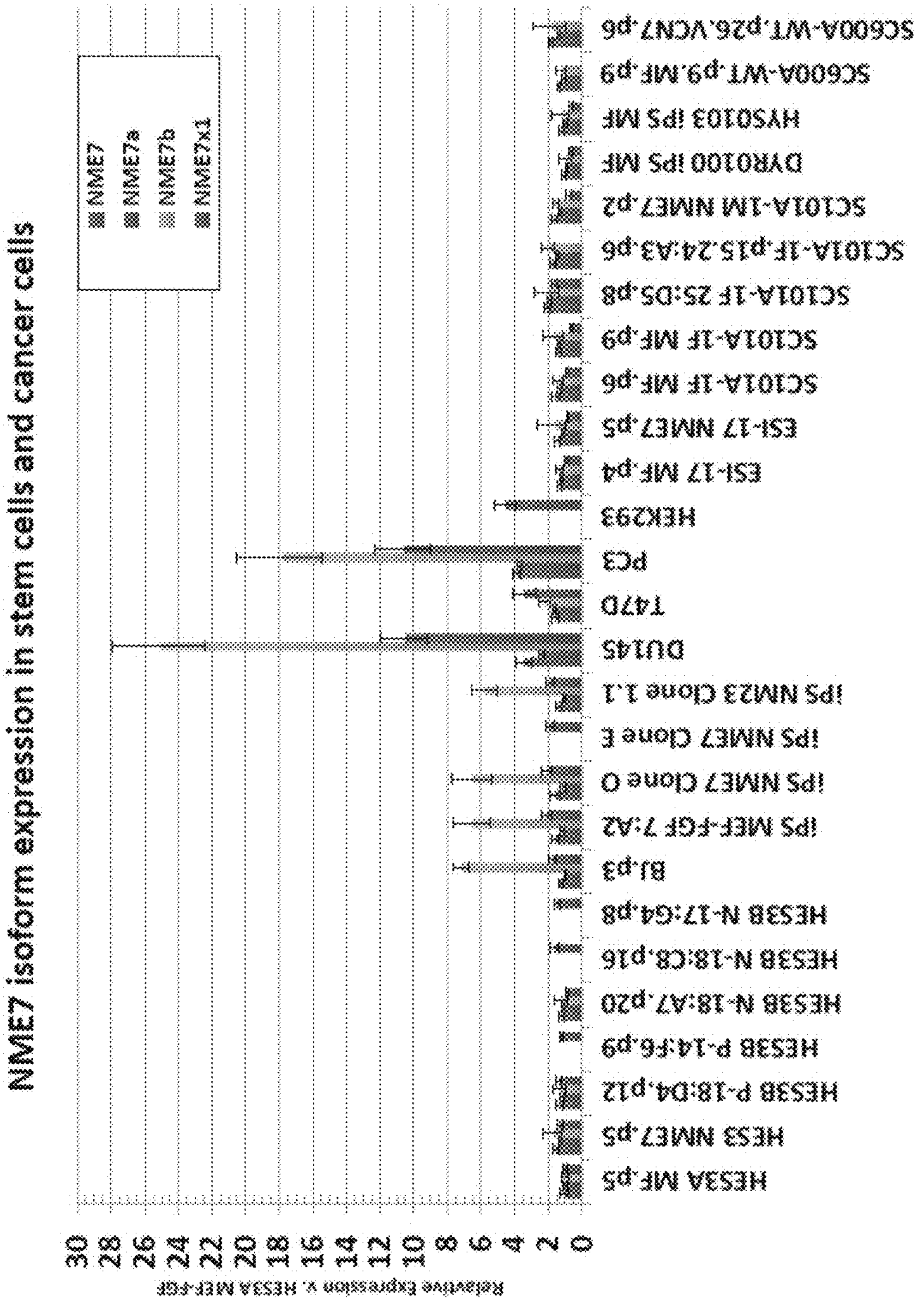
FIG. 34 shows a graph of RT-PCR measurement of the expression of NME7, NME7a, NME7b and NME7-X1 in a panel of human stem cells and cancer cells. NME7a is full-length NME7, NME7b is missing a small portion of the DM10 domain, NME7-X1 is missing all of the DM10 domain and a small portion of the N-terminus of the first NDPK A domain. The bar labeled NME7 means that primers were used that detected both NME7a and NME7b.

We discovered a new NME7 isoform, NME7-X1, and also discovered that it is over-expressed in cancers and is particularly over-expressed in prostate cancers (FIG. 33, 34). NME7-X1, molecular weight ~30 kDa, comprises NME7 amino acids 125-376, whereas the recombinant NME7-AB, molecular weight ~33 kDa, that we generated spans amino acids 92-376, so includes 33 more N-terminal amino acids. NME7b spans amino acids 37-376 and is devoid of only 37 amino acids of the DM10 domain is also overexpressed in prostate cancers (FIG. 34). We generated a human recombinant NME7-X1 and show that it is the secreted 30 kDa NME7 species in cancer cells that runs just lower than a naturally occurring ~33 kDa NME7 species that appears to be a naturally occurring "NME7-AB-like" protein that is a cleavage product or alternative isoform.

We tested a panel of cancer cell lines and found that they express high levels of NME7 and lower molecular weight species that may be truncations similar to NME7-AB, such as NME7-AB-like protein, or alternate isoforms such as NME7-X1.

Figure 4A:
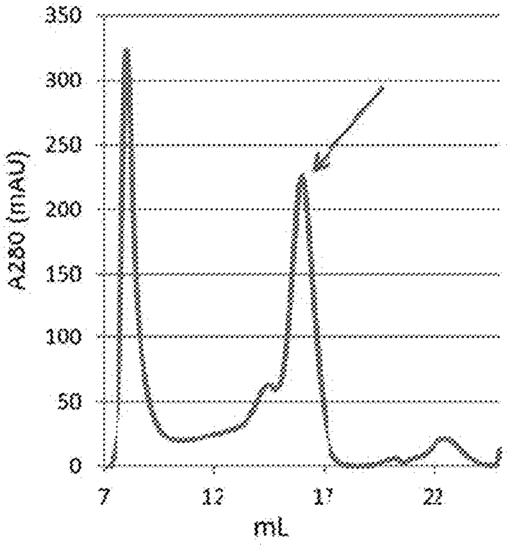
FIGS. 4A-4C. (A) is an elution profile of size exclusion chromatography purification of NME7-AB; (B) is non-reducing SDS-PAGE gel from NME7-AB peak fractions; (C) is the elution profile of size exclusion chromatography of the purified NME7-AB.
Figure 4B:
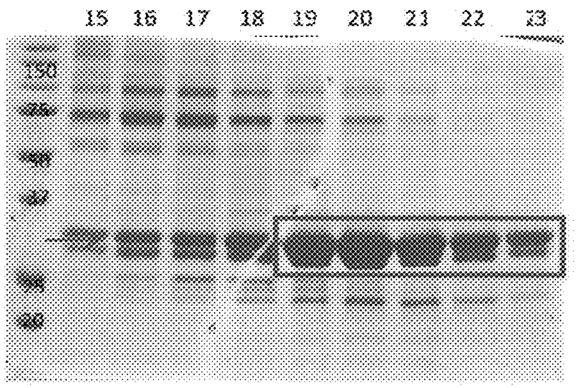
Figure 4C:
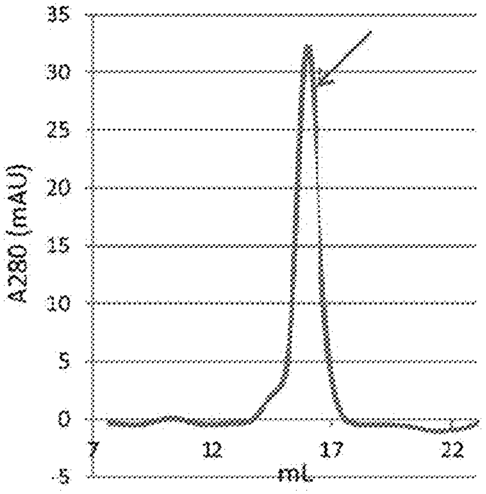
Figure 5A:
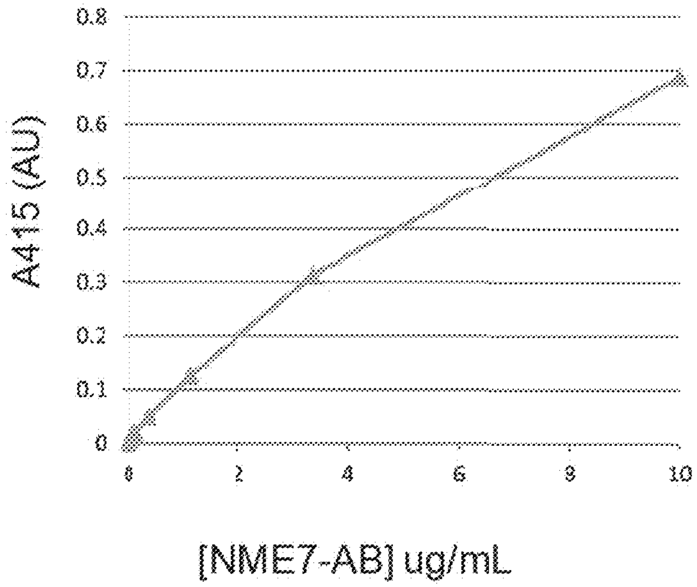
FIGS. 5A-5B show graphs of HRP signal from ELISA sandwich assay showing NME7-AB dimerizes MUC1* extra cellular domain peptide.
Figure 5B:
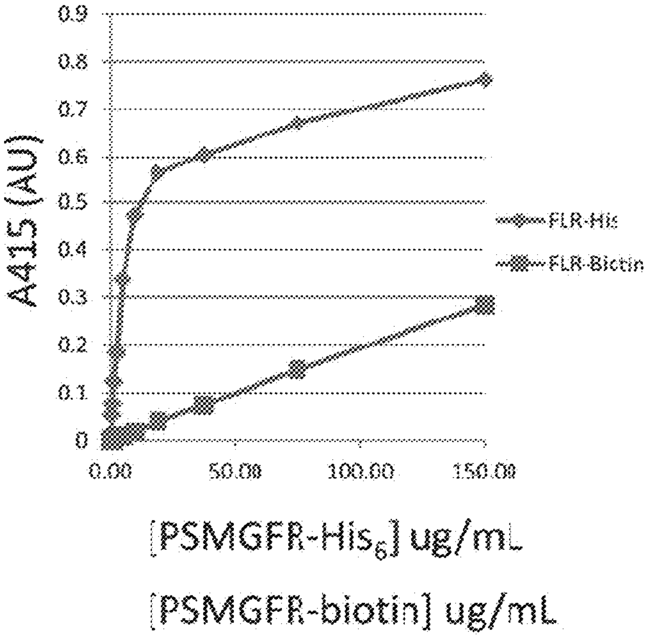
Figure 6A:
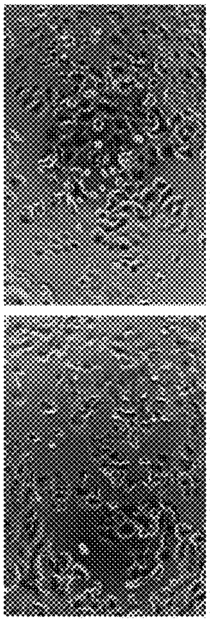
FIGS. 6A-6G show photos of MUC1*-positive cancer cells treated with nothing (Row A), Taxol (Row B) or an anti-NME7 antibody (Rows C-E); a graph showing cell count in response to treatment at 48 hours (F), and a dot-blot used to estimate antibody concentration used in the cancer cell inhibition experiment (G).
Figure 6B:
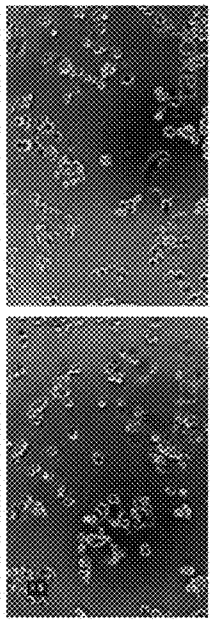
Figure 6C:
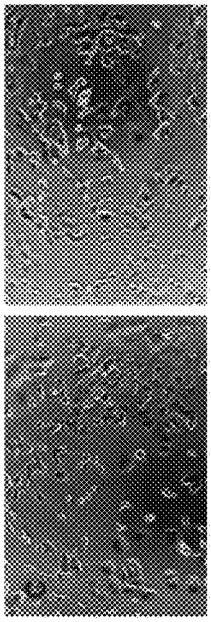
Figure 6D:
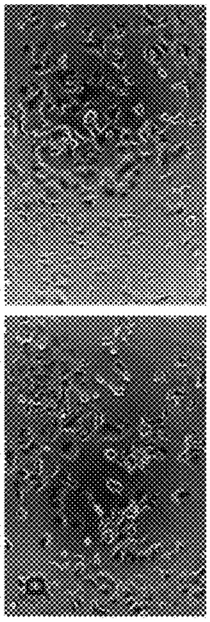
Figure 6E:
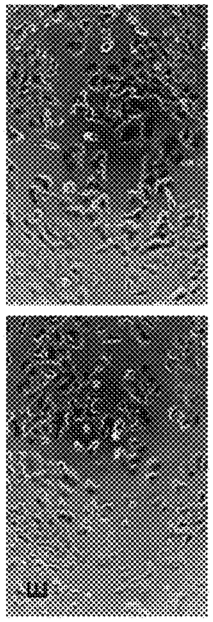
Figure 6F:
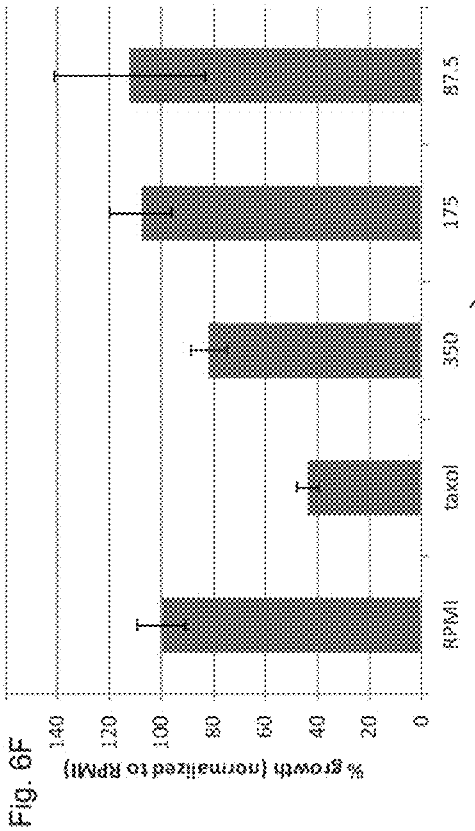
Figure 6G:
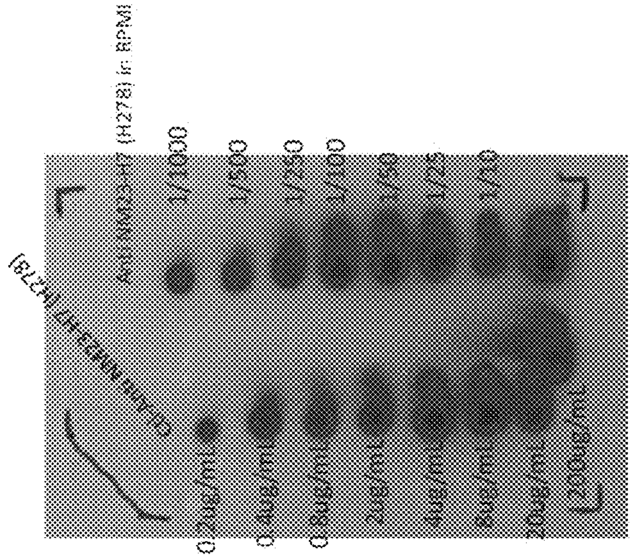

Whereas NM23-H1 (aka NME1) has to be a dimer, NME7 is a monomer with two binding sites for MUC1* extracellular domain. We generated a recombinant human NME7 that is devoid of the DM10 domain, which we call NME7-AB. FIGS. 4A-4C show the elution profile of size exclusion chromatography purification of NME7-AB, a non-reducing SDS-PAGE gel from NME7-AB peak fractions and the elution profile of size exclusion chromatography of the purified NME7-AB. A sandwich ELISA binding assay that shows that a recombinant NME7, NME7-AB simultaneously binds to two PSMGFR peptides wherein the extracellular domain of MUC1* is comprised of most or all of the PSMGFR sequence (FIG. 5, Example 6). In a nanoparticle binding assay, NME7 was also shown to be able to bind to and dimerize the PSMGFR portion of the MUC1* extracellular domain.

Agents that disable NME7, block its interaction with its binding partners or suppress its expression are potent anti-cancer therapeutics. Such agents may be antibodies, small molecules or nucleic acids. They may act on NME7 directly, on molecules that regulate NME7 expression, or on enzymes that cleave NME7 to cancer-promoting forms.

We discovered that like NM23-H1 dimers, a recombinant NME7-AB monomer was fully able to support pluripotent human stem cell growth in the absence of any other growth factor, cytokine or serum. Competitively inhibiting the interaction between NME7 and MUC1* extracellular domain, comprised essentially of the PSMGFR sequence, induced differentiation of stem cells, showing that it is the interaction of NME7 and MUC1* that promotes stem cell growth and inhibits differentiation.

Next, we showed that NME7-AB alone is also able to fully support human cancer cell growth. NME7-AB, when added to regular cancer cell growth media, stimulated cancer cell growth and in particular the growth of MUC1-positive and MUC1*-positive cancer cells. Inhibiting the interaction of NME7 with MUC1* inhibited cancer cell growth. Blocking the MUC1* growth factor receptor with an anti-MUC1* Fab potently inhibited cancer cell growth. Similarly, antibodies that bind to NME7 inhibit cancer cell growth. One example of inhibition of cancer growth by anti-NME7 antibody is shown in FIGS. 6-8 and Example 10. In this case, the polyclonal antibody was generated from immunizing an animal with the portion of NME7 that spans amino acids 100-376. However, we found that antibodies generated from immunizing with shorter peptides from NME7-AB or from NME7-X1 also inhibit cancer growth. In particular, they inhibit the growth of MUC1 and MUC1*-positive cancers.

NME7 Causes Cancer Metastasis

The inventors further discovered that culturing cancer cells in a minimal media containing NME7-AB induced a wide variety of cancer cells to become transformed to a more metastatic state. Evidence of this induced metastatic state include a change from adherent cell growth to no-adherent cell growth, aka, "floater" cells and accompanying up-regulation of specific metastatic markers that were especially upregulated in the floating cells. These metastatic markers that are upregulated after culture in NME7-AB include but are not limited to CXCR4, CHD1 aka E-cadherin, CD44, and pluripotent stem cell markers such as OCT4, SOX2, NANOG and KLF2/4. Cancer cells cultured in NME7-AB had dramatically higher engraftment rates when xenografted into test animals, which were over 90%. In addition, very low numbers of implanted cancer cells formed tumors in the test animals, which is evidence that NME7-AB had transformed them into cancer stem cells also known as metastatic cancer cells. Because cancer cells make either an NME7 cleavage product or alternative isoform that is essentially equivalent to NME7-AB, the methods described here are not limited to using NME7-AB; other NME7 species could work as well. For example, we discovered another NME7 isoform, NME7-X1, is expressed by cancer cells. It is identical to our recombinant NME7-AB with the exception that the X1 isoform is missing 33 amino acids from the N-terminus. NME7-X1 is expected to function like NME7-AB. "NME7-AB-like" protein has also been detected in cancer cells as being about 33 Da species.

We note that the inventors' previous work showed that NME7-AB alone is able to revert human stem cells to an earlier naïve state. We discovered that culturing cancer cells in the presence of other reagents that make stem cells revert to a more naïve state, makes the cancer cells transform to a more metastatic state. We demonstrated that NME7-AB (FIGS. 11 and 12), "2i" inhibitors (FIG. 14A), human NME1 dimers or bacterial NME1 dimers with high sequence homology to human NME1 or human NME7 (FIG. 14B) are each able to transform regular cancer cells into metastatic cancer cells, which are also called cancer stem cells "CSCs" or tumor initiating cells "TICs" (FIGS. 11-14).

2i is the name given to two biochemical inhibitors that researchers found made human stem cells revert to a more naïve state. 2i are MEK and GSK3-beta inhibitors PD0325901 and CHIR99021, which are added to culture medium to final concentrations of about 1 mM and 3 mM, respectively. NME7-AB and NME7-X1 are at a final concentration of about 4 nM when added to separate batches of minimal medium to make cancer cells transform to metastatic cells, although lower and higher concentrations also work well in the range of about 1 nM to 16 nM. Human or bacterial NME1 dimers are used at a final concentration of 4 nM to 32 nM, with 16 nM typically used in these experiments, wherein the human NME bears the S120G mutation. Lower concentrations may be required if using wild type. It is not intended that these exact concentrations are important. It is important that the NME1 proteins are dimers and the range of concentrations over which this happens is in the low nanomolar range although certain mutations allow higher concentrations to remain as dimers. Similarly, the concentrations of NME7 proteins can vary. NME7-AB and NME7-X1 are monomers and concentrations used to transform cancer cells to metastatic cells should allow the proteins to remain as monomers.

In addition to NME7, NME7-AB, NME7-X1, and the 2i inhibitors MEKi and GSK3i, other reagents and inhibitors have been shown by others to cause stem cells to revert to a more naïve state. These inhibitors, "i's" include JNKi, p38i, PKCi, ROCKi, BMPi, BRAFi, SRCi as well as growth factors activing and LIF (Gafni et al 2013, Chan et al 2013, Valamehr et al 2014, Ware et al 2014, Theunissen et al 2014). These reagents can also be used to make cancer cells progress to a more metastatic state. Cells that have been induced to transform to a more metastatic state using any single factor or combination of the inhibitors or growth factors, that make stem cells revert to a more naïve state, can then be used as discovery tools to identify or test drugs to treat or prevent cancer metastasis.

Various molecular markers have been proposed as being indicators of metastatic cancer cells. Different cancer types may have different molecules that are up-regulated. For example, the receptor CXCR4 is up-regulated in metastatic breast cancers while E-cadherin, also known as CHD1, is up-regulated more in metastatic prostate cancers. In addition to these specific metastasis markers, typical markers of pluripotency such as OCT4, SOX2, NANOG, and KLF4 are up-regulated as cancers become metastatic. The starting cancer cells and the later metastatic cancer cells are assayed by PCR to measure expression levels of these genes. We demonstrated that these cancer cells, cultured in agents such as NME7-AB that cause them to be transformed to a more metastatic state, as evidenced by increased expression of metastatic markers and pluripotent stem cell markers, function as metastatic cancer cells.

A functional test of whether or not a population of cancer cells is metastatic is to implant very low numbers, e.g. 200, of the cells in immuno-compromised mice and see if they develop into a tumor. Typically 5-6 million cancer cells are required to form a tumor in an immuno-compromised mouse. We showed that as few as 50 of the NME-induced metastatic cancer cells formed tumors in mice. In addition, mice that were injected throughout the test period with human NME7-AB, NME1, or NME7-X1 developed remote metastases.

In one particular experiment, T47D human breast cancer cells were cultured in standard RPMI media for 14 days with media changes every 48 hours and passed by trypsinization when approximately 75% confluent. The cells were then plated into 6-well plates and cultured in minimal stem cell media (see Example 1) that was supplemented with 4 nM NME7-AB. Media was changed every 48 hours. By about Day 4, some cells become detached from the surface and float. Media is carefully changed so as to retain the "floaters" as these are the cells that have the highest metastatic potential as evidence by RT-PCR measurement of metastatic markers. On Day 7 or 8, the floaters are harvested and counted. Samples are retained for RT-PCR measurement. The key marker measured is CXCR4, which is up-regulated by 40-200-times after being briefly cultured in NME7-AB.

The freshly harvested floater metastatic cells were xenografted into the flank of female nu/nu athymic mice that have been implanted with 90-day slow release estrogen pellets. Floater cells were xenografted with 10,000, 1,000, 100 or 50 cells each. Half of the mice in each group of 6 were also injected daily with 32 nM NME7-AB near the original implantation site. The parent T47D cells that were cultured in RPMI media without NME7-AB were also implanted into mice at 6 million, 10,000 or 100 as controls. Mice implanted with the NME7-induced floater cells developed tumors even when as few as 50 cells were implanted. Mice that were implanted with the floater cells and that received daily injections of NME7-AB also developed remote tumors or remote metastases in various organs (FIG. 20-25). 11 out of the 12 mice, or 92%, that were injected with human NME7-AB after implantation of the NME7-AB cultured cancer cells developed tumors at the injection site. Only 7 out of the 12 mice, or 58%, that were not injected with human NME7-AB after implantation developed tumors. 9 out of the 11 mice, or 82%, that exhibited tumors and were injected with human NME7-AB developed multiple tumors remote from the injection site. None of the mice that were not injected with NME7-AB developed multiple, visible tumors.

After sacrifice, RT-PCR and Western blots showed that the remote bumps on the mice injected with NME7-AB were indeed human breast tumors. Similar analysis of their organs showed that in addition to remote bumps, mice had randomly metastasized to the liver and lung with human breast cancer characteristic of the human breast cancer cells that were implanted. As expected, only the mice implanted with 6 million cells grew tumors.

Figure 11:
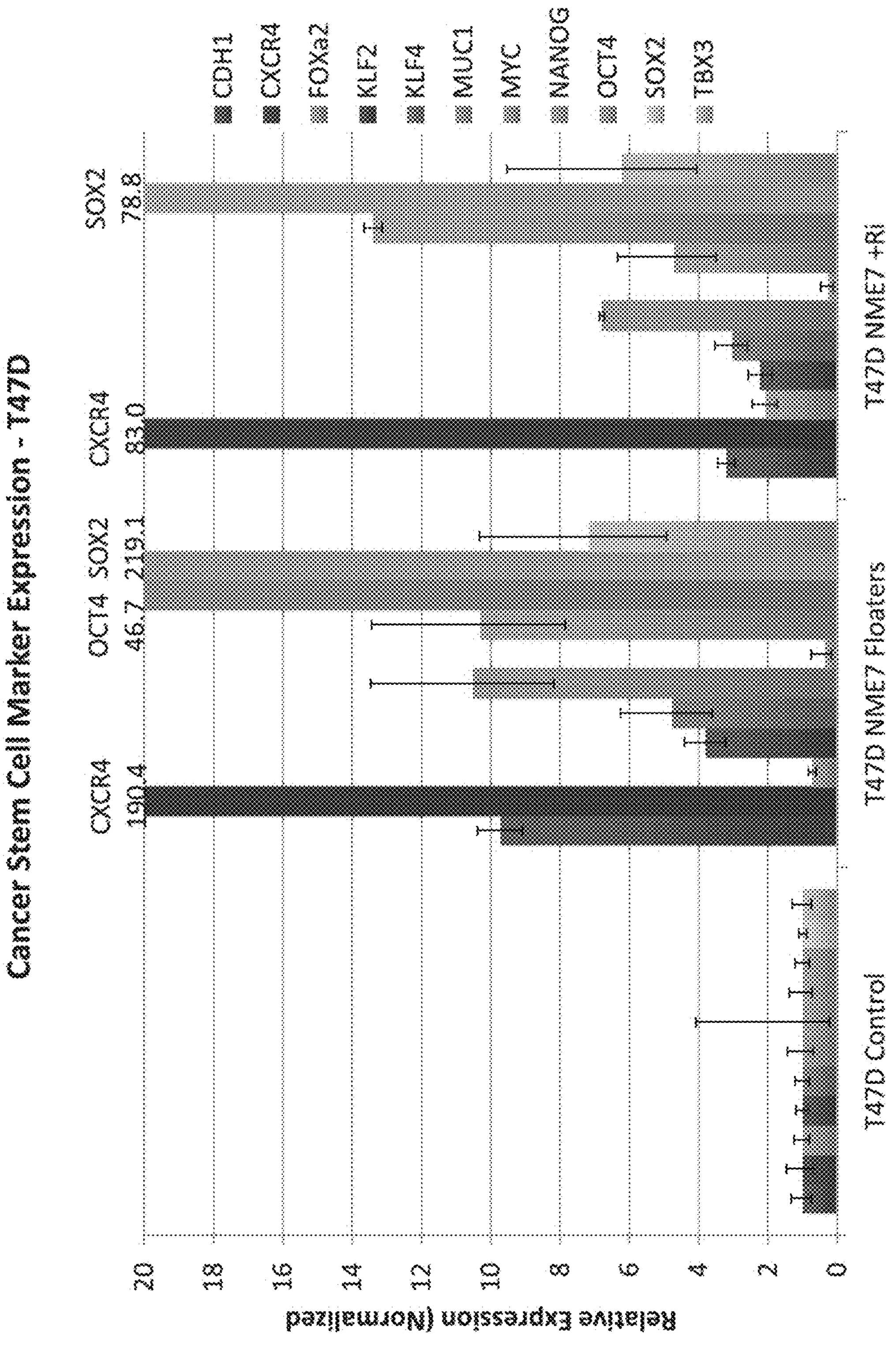
FIG. 11 is a graph of RT-PCR measurements of gene expression for stem cell markers and cancer stem cell markers for T47D cancer cells after being cultured in traditional media or a media containing NME7, wherein cells that became non-adherent (floaters) were analyzed separate from those that remained adherent.
Figure 12:
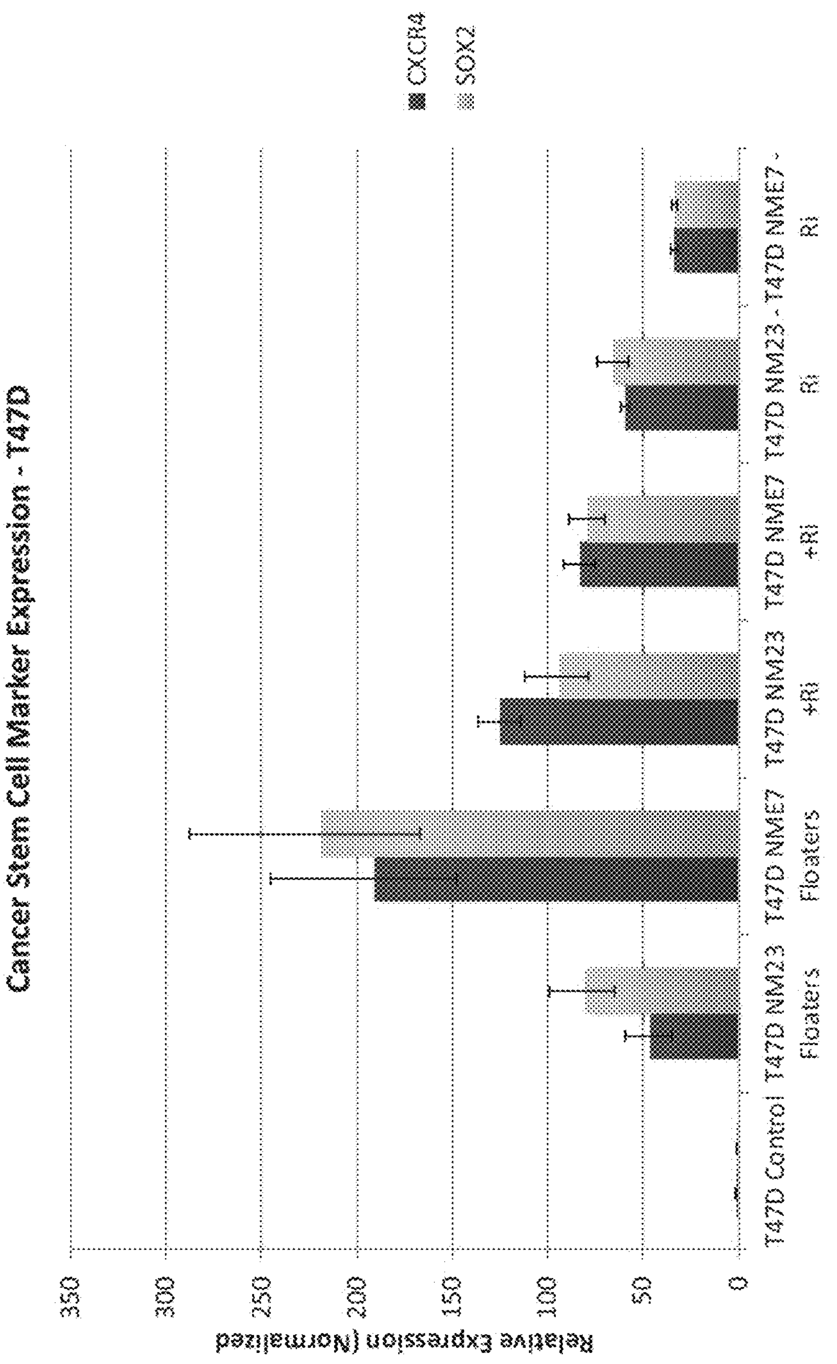
FIG. 12 is a graph of RT-PCR measurements of gene expression for stem cell marker SOX2 and cancer stem cell marker CXCR4 for T47D cancer cells. Cells were cultured either in traditional media or a media containing NME1 dimers or NME7 (NME7-AB). Cell types that were separately analyzed were floating cells, cells plus Rho kinase inhibitor (+Ri), which made all cells adhere, or cells that remained adherent after floaters were removed which was in the absence of rho kinase inhibitor (−Ri).

We have demonstrated that human recombinant NME7-AB is comparable in size and sequence to NME7-X1 and to a 30-33 kDa NME7 cleavage product. We have shown that NME7-AB promotes cancerous growth and causes cancer cells to accelerate to the highly metastatic cancer stem cell (CSC) state also called tumor initiating cells (TIC). Therefore, we conclude that NME7-X1 and an NME7 cleavage product that removes the DM10 domain also promote cancerous growth and causes cancer cells to accelerate to the highly metastatic cancer stem cell (CSC) state also called tumor initiating cells (TIC). In one example, NME7-AB was added to cancer cells in a serum-free media and in the absence of any other growth factors or cytokines. Within 7-10 days, the cancer cells had reverted to the highly metastatic CSCs/TICs as evidenced by more than 100-fold increase in the expression of molecular markers such as CXCR4, which are indicators of metastatic cancer cells. In one example, T47D breast cancer cells were cultured in either standard RPMI media or in a Minimal Stem Cell Media (Example 1) to which was added recombinant NME7-AB to a final concentration of 16 nM. After 10 days cells were collected and analyzed by RT-PCR for expression of molecular markers of CSCs which were elevated by 10-200-times (FIGS. 11, 12). This is a specific, detailed example of how we transformed one cancer cell type to a more metastatic state. It is not intended that the invention be limited by these details as there are a range of cancer cells that are transformed in this way, a range of reagents that revert stem cells to a more naïve state that also progress cancer cells to a more metastatic state and a range of concentrations over which the added reagents transform the cancer cells. Other types of cancer cells have required longer periods of culture in NME7-AB for dramatic upregulation of metastatic markers and ability to form tumors from very low numbers of cancer cells implanted. For example, prostate cancer cells cultured in NME7-AB, 2i, human NME1 or bacterial NME1 that has high homology to human NME1 or human NME7 showed dramatic increase in metastatic markers after 2-3 passages.

Metastasis marker CXCR4 is particularly elevated in metastatic breast cancer cells, while CHD1 is particularly elevated in metastatic prostate cancer. Here we show that pluripotent stem cell markers such as OCT4, SOX2, NANOG, KLF2/4 and TBX3 are also up-regulated when cancer cells transform to more metastatic cells.

Figure 13:
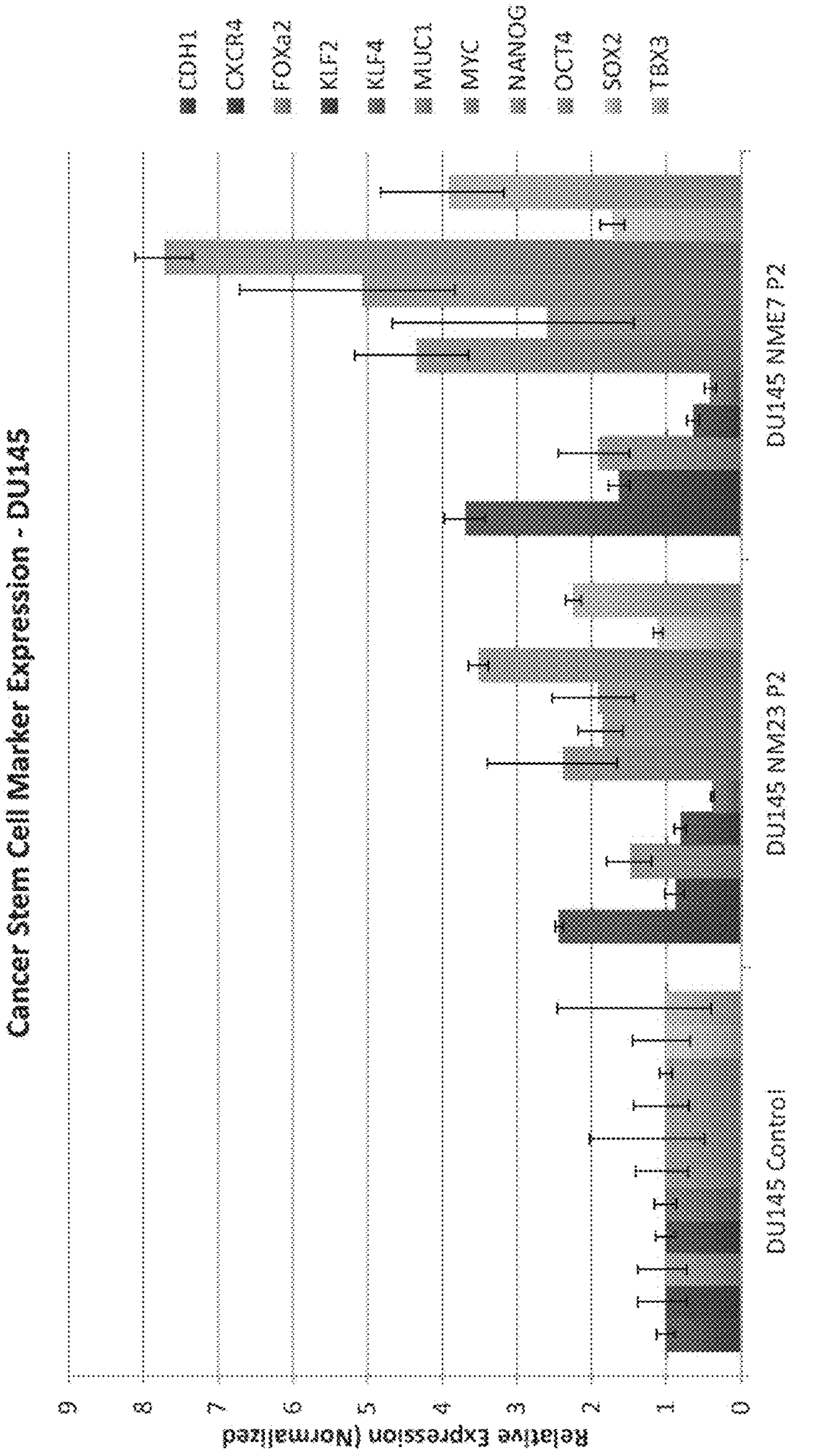
FIG. 13 is a graph of RT-PCR measurements of gene expression for a variety of stem and putative cancer stem cell markers for DU145 prostate cancer cells. Cells were cultured either in traditional media or a media containing NME1 dimers ("NM23") or NME7 (NME7-AB). Rho kinase inhibitor was not used because by passage 2, cells remained adherent.
Figure 37A:
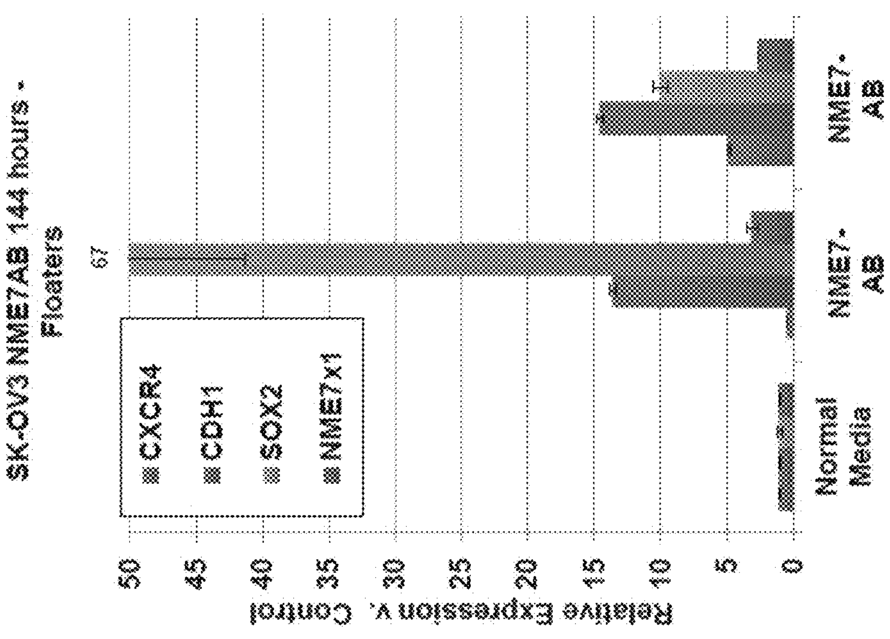
FIGS. 37A-37C show graphs of RT-PCR measurements of metastatic markers in cancer cells after being cultured in a serum-free media containing NME7-AB compared to the standard media. A) SK-OV3, a MUC1-positive ovarian cancer cell line increased expression of metastatic markers CXCR4, CDH1 aka E-cadherin, SOX2 and NME7-X1; B) OV-90 a MUC1-negative ovarian cancer cell line increased expression of metastatic markers CXCR4 and NME7-X1; C) MDA-MB a breast cancer cell line that expresses minimal levels of MUC1 increased expression of metastatic markers CDH1 aka E-cadherin and SOX2.
Figure 37B:
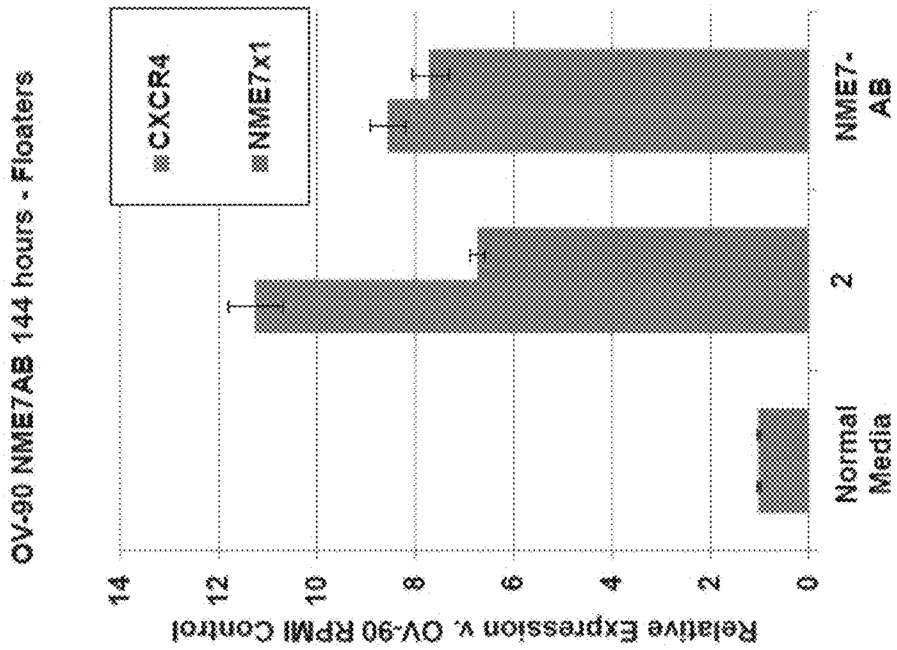
Figure 37C:
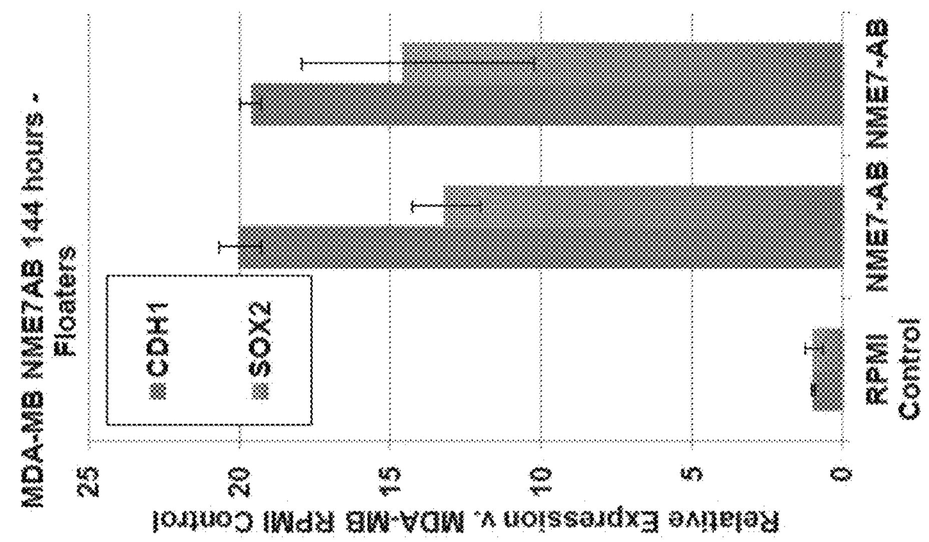

DU145 prostate cancer cells were cultured similarly and those cells cultured in NME7-AB also showed dramatic increases in expression of CSC markers (FIG. 13). In prostate cancer cells, CHD1 (aka E-cadherin) and CXCR4 were up-regulated compared to the control cancer cells, which were not grown in NME7-AB, along with other pluripotent stem cell markers. Ovarian cancer cells, pancreatic cancer cells and melanoma cells were also cultured in NME7-AB and were transformed to a more metastatic state after as few as 3 days in culture. FIGS. 37A-C shows that ovarian cancer cell lines SK-OV3, OV-90 and breast cancer cell line MDA-MB all transitioned from adherent to non-adherent floater cells and increased expression of metastatic markers after 72 or 144 hours in culture with NME7-AB.

Figures 40A, 40B, 40C:
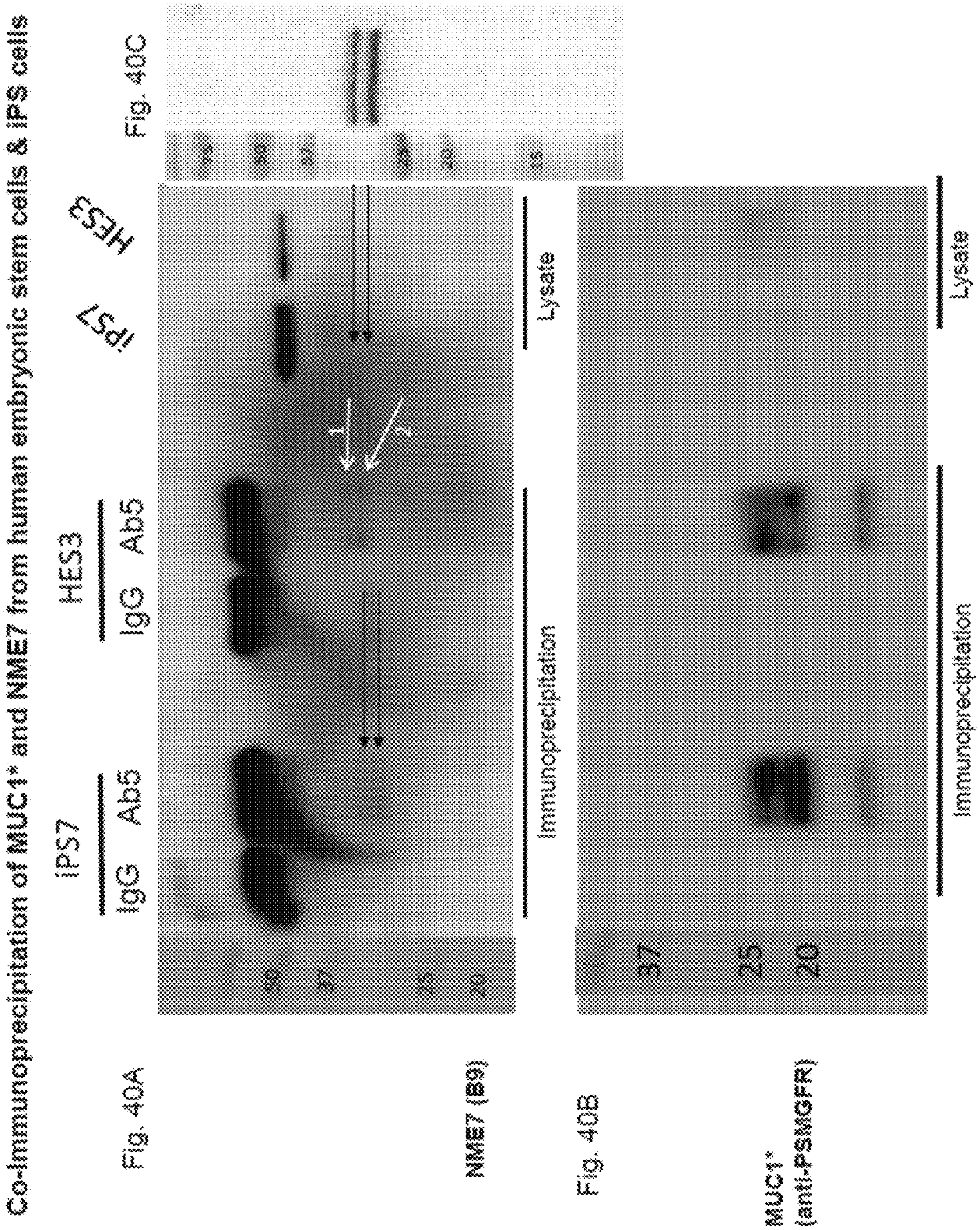
FIGS. 40A-40C show photographs of Western blots of a co-immunoprecipitation experiment. Human induced pluripotent stem, iPS7, or embryonic stem, HES3, cell extracts were incubated with an antibody against the MUC1 cytoplasmic tail, Ab-5, or a control antibody, IgG, and co-immunoprecipitated. The gel was blotted with a commercially available anti-NME7 antibody B9 (A). Both cell types show unique NME7 bands at ~33 kDa and ~30 kDa. The gel was stripped and re-probed with an antibody against the extracellular domain of MUC1*, anti-PSMGFR (B), which shows that the NME7 species and MUC1* interact. A recombinant NME7-AB and a recombinant NME7-X1 were mixed together and run on a gel, then probed with an anti-NME7 antibody, showing that the two unique NME7 species that are naturally occurring in breast cancer cells and that interact with MUC1* are an NME7-AB-like species and NME7-X1 (C).

Here we have shown that NME7-AB transforms a wide range of cancer cells to a more metastatic state. We have also shown that cancer cells express a naturally occurring species that is approximately the same molecular weight as recombinant NME7-AB 33 kDa (FIGS. 33-36 and FIG. 38) and is also devoid of the DM10 domain (FIG. 10) like NME7-AB and also express an alternative isoform NME7-X1 30 kDa which is the same sequence as NME7-AB except is missing 33 amino acids from the N-terminus. A co-immunoprecipitation experiment was performed on T47D breast cancer cells, wherein the cell extracts were incubated with an antibody against the MUC1 cytoplasmic tail, Ab-5, or a control antibody, IgG, and co-immunoprecipitated. The immunoprecipitated species were separated by gel electrophoresis. The gels were blotted with two different commercially available anti-NME7 antibodies. Both gels show unique NME7 bands at ~33 kDa and ~30 kDa (FIG. 39A,B). The gels were stripped and re-probed with an antibody against the extracellular domain of MUC1*, anti-PSMGFR (FIG. 39 C,D), which shows that the NME7 species and MUC1* interact. A recombinant NME7-AB and a recombinant NME7-X1 that we made were mixed together and run on a gel, then probed with an anti-NME7 antibody, showing that the two unique NME7 species that are naturally occurring in breast cancer cells and that interact with MUC1* are an NME7-AB-like species and NME7-X1 (FIG. 39E). A similar experiment was carried out in human stem cells. FIGS. 40A-C show photographs of Western blots of a co-immunoprecipitation experiment. Human induced pluripotent stem, iPS7, or embryonic stem, HES3, cell extracts were incubated with an antibody against the MUC1 cytoplasmic tail, Ab-5, or a control antibody, IgG, and co-immunoprecipitated. The gel was blotted with a commercially available anti-NME7 antibody B9 (A). Both cell types show unique NME7 bands at ~33 kDa and ~30 kDa. The gel was stripped and re-probed with an antibody against the extracellular domain of MUC1*, anti-PSMGFR (B), which shows that the NME7 species and MUC1* interact. A recombinant NME7-AB and a recombinant NME7-X1 that we made were mixed together and run on a gel, then probed with an anti-NME7 antibody, showing that the two unique NME7 species that are naturally occurring in breast cancer cells and that interact with MUC1* are an NME7-AB-like species and NME7-X1 (C). Because NME7-AB is a recombinant protein, we do not know if the naturally occurring species may contain an extra 1-15 additional amino acids or devoid of 1-15 additional amino acids than the recombinant NME7-AB, yet run with the same apparent molecular weight. By "NME7-AB-like", we mean an NME7 species that runs with an apparent molecular weight of approximately 33 kDa that is able to function the way the recombinant NME7-AB does, in that it is able to stimulate cancer cell growth, induce transition of cancer cells to a more metastatic state and is able to fully support pluripotent growth of human stem cells.

Figures 38A, 38B, 38C:
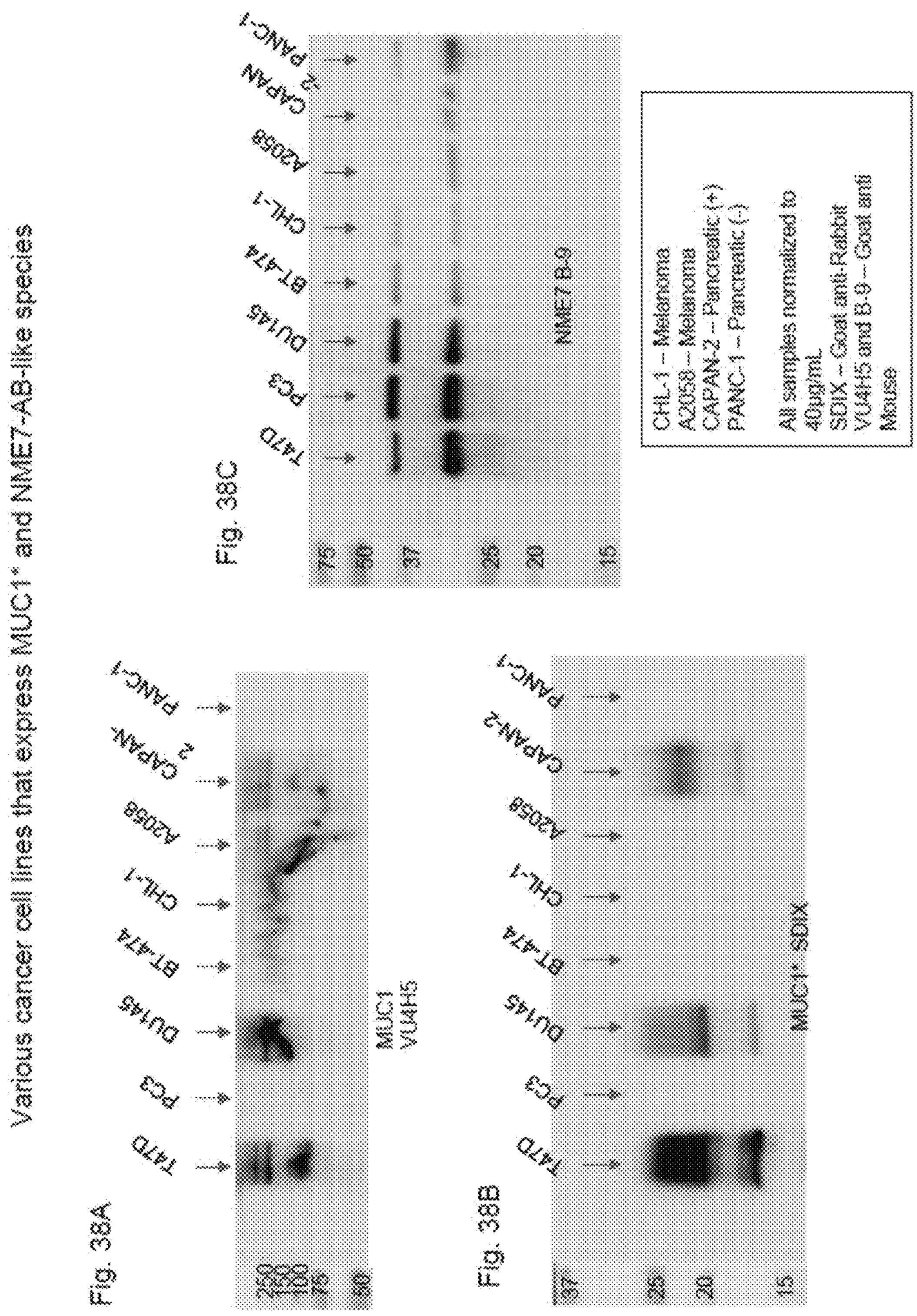
FIGS. 38A-38F show photographs of Western blots and cancer growth graphs. A) various cancer cell lines are probed for the expression of full-length MUC1 using an anti-tandem repeat antibody VU4H5. B) various cancer cell lines are probed for the expression of cleaved form MUC1* using anti-PSMGFR antibody. C) various cancer cell lines are probed for the expression of NME7 species using a commercially available anti-NME7 antibody B9, showing full-length NME7 as well as a 33 kDa and 30 kDa species, consistent with a naturally occurring NME7-AB-like species as well as NME7-X1. D) HER2 positive BT-474 breast cancer cells express little to no MUC1 or MUC1* until they acquire resistance to chemotherapy drugs and metastasize. Parent cells were made resistant to Herceptin, Taxol, Doxorubicin and cyclophosphamide by culturing the cells in sub-lethal levels of the drug. Part (D) shows that the expression level of HER2 has not changed but expression of MUC1* has dramatically increased. E) shows a graph of the growth of the parent BT-474 cells compared to the drug resistant metastatic cells in response to treatment with Herceptin in the presence or absence of an anti-MUC1* Fab. F) shows a graph of the growth of the parent BT-474 cells compared to the drug resistant metastatic cells in response to treatment with Taxol in the presence or absence of an anti-MUC1* Fab.
Figure 38D:
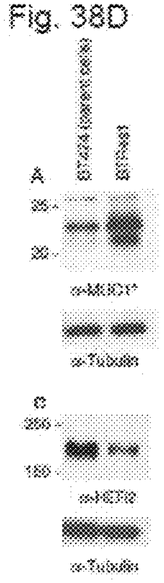
Figure 38E:
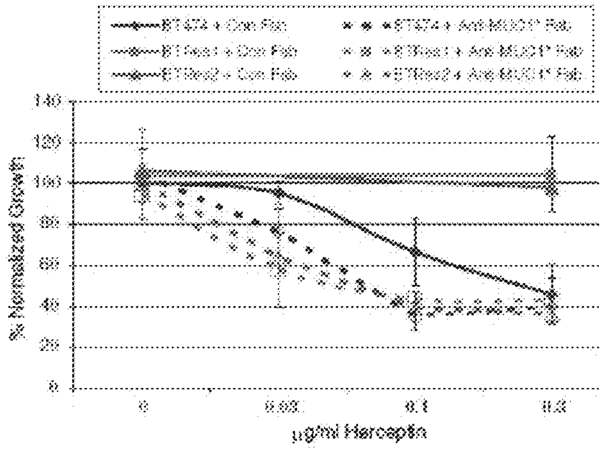
Figure 38F:
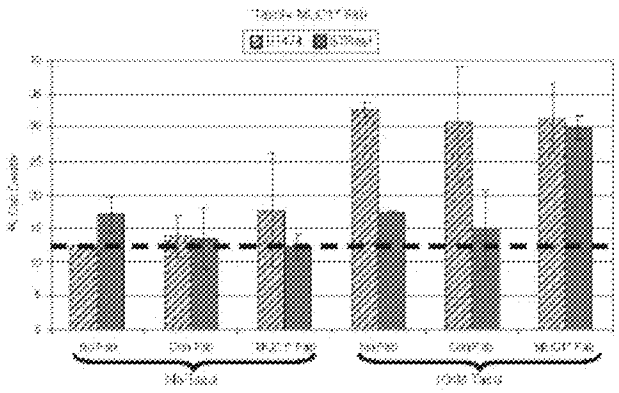

We conclude that cancer cell lines and cancer cell populations that express NME7 and lower molecular weight NME7 species contain some cancer cells that are CSCs or metastatic cancer cells. These cancers can be made more metastatic or increase the population of cells that are metastatic by culturing the cells in NME7-AB, NME7-X1 or lower molecular weight NME7 species. FIG. 35 shows a Western blot of a panel of cancer cells all expressing NME7 as well as lower molecular weight species NME7-AB-like at 33 kDa and NME7-X1 at 30 kDa. FIG. 38 shows that cancer cell lines T47D breast cancer, PC3 and DU145 prostate cancer, BT-474 breast cancer, CHL-1 and A2058 both melanoma cell lines and CAPAN-2 and PANC-1 both pancreatic cell lines all express MUC1, MUC1* and NME7-AB-like species and NME7-X1. In FIG. 38A, BT0474 cells appear not to express MUC1 or MUC1* however, we previously showed (Fessler et al 2009) that when these HER2 positive breast cancer cells become resistant to chemotherapy drugs, i.e. metastatic, they do so by increasing expression of MUC1* (FIG. 38 D). Blocking the MUC1* receptor with an anti-MUC1* Fab reversed their resistance to Herceptin (FIG. 38E), Taxol (FIG. 38F) as well as other chemo agents. These cancer types and other cancer types that express NME7 and lower molecular weight NME7 species such as 33 kDa, 30 kDa can be made more metastatic or increase the population of cells that are metastatic by culturing the cells in NME7-AB, NME7-X1 or lower molecular weight NME7 species.

Conversely, the metastatic potential of these and other cancer types that express NME7 and lower molecular weight NME7 species such as 33 kDa or 30 kDa can be reversed by treating the cells with anti-NME7 antibodies. Anti-NME7 antibodies or antibodies that bind to NME7-AB or NME7-X1 are administered to a patient for the treatment or prevention of cancers including breast, prostate, ovarian, pancreatic and liver cancers. Because we have shown that NME7-AB exerts its tumorigenic effects by binding to and activating the MUC1* growth factor receptor, anti-NME7 antibodies will be effective against any MUC1*-positive cancers, which include but are not limited to breast, lung, liver, pancreatic, gastric colorectal, prostate, brain, melanoma, kidney and others. Anti-NME7, anti-NME7-AB or anti-NME7-X1 antibodies are administered to patients for the treatment or prevention of cancers that are NME7-AB, NME7-AB-like, or NME7-X1 positive or a MUC1* positive.

Testing Patient Cancer Cells for Effective Therapies

NME7-AB, NME7-X1 as well as 2i and other reagents that revert stem cells to a more naïve state also induce cancer cells to transform to a more metastatic state. After treatment with any one or combination of these reagents, cancer cells have a higher engraftment rate and require up to 100,000-times less cells to cause a tumor to form in a test animal. Therefore, methods described in this disclosure can be used to enable xenografting of a patient's primary tumor cells into a test animal.

Candidate therapeutic agents can then be tested on the recipient animal. Effective therapeutic agents identified in this way can be used to treat the donor patient or other patients with similar cancers. In one embodiment, a method of identifying effective therapeutics for a particular patient or a particular type of cancer comprises the steps of: 1) cancer cells are obtained from a cell line, a patient or a patient to whom the therapeutic being tested will be administered; 2) cancer cells are cultured in NME7-AB, NME7-X1, human NME1, bacterial NME1 that has high homology to human NME1 or NME7, 2i, or other reagents shown to revert stem cells to a more naïve state; 3) resultant cancer cells are implanted into a test animal to which human NME7-AB, NME7-X, human NME1, bacterial NME1 that has high homology to human NME1 or NME7, 2i, or other reagents shown to revert stem cells to a more naïve state may also be administered or animal is transgenic for human NME7-AB or NME7-X1; 4) candidate anti-cancer therapeutic agents are administered to the animal; 5) efficacy of the therapeutic agents are assessed; and 6) effective therapeutic agent is administered to the donor patient or to another patient with similar cancer.

Anti-NME7 Antibodies

Anti-NME7 antibodies are potent anti-cancer agents. NME7 is a growth factor that promotes the growth of cancer cells and also promotes their progression to a more metastatic state or a more aggressive state. NME7 and a truncated form of NME7 that is ~33 kDa or 30 kDa have been shown to fully support cancer growth even in serum-free media devoid of any other growth factors or cytokines. In pull-down assays, ELISAs and nanoparticle binding experiments, we have shown that the growth factor receptor MUC1* is a binding partner of NME7 and NME7-AB. Promotion of this interaction by eliminating all other growth factors or cytokines increased expression of cancer stem cell markers. Blocking this interaction even in the presence of serum, using a polyclonal antibody that specifically binds to NME7 actively killed the cancer cells. Thus, anti-NME7 or anti-NME7-AB antibodies are potent anti-cancer agents that can be administered to a patient for the treatment or prevention of cancers. More than 75% of all cancers are MUC1* positive. MUC1* is the transmembrane cleavage product of MUC1 wherein most of the extracellular domain has been shed, leaving a portion of the extracellular domain that contains most of the PSMGFR sequence and may contain 9-20 additional amino acids N-terminal to the boundary of the of the PSMGFR sequence.

One aspect of the invention is a method of treating or preventing cancer in a subject, comprising administering to the subject an effective amount of an anti-NME7 antibody. In one instance, the anti-NME7 antibody is able to bind to NME7-AB. In another instance, the anti-NME7 antibody is able to bind to NME7-X1. In yet another instance, the anti-NME7 antibody that is administered to a patient inhibits or prevents its binding to its target in the promotion of cancers. In one case, the target is the extracellular domain of a cleaved MUC1. More specifically, the NME7 target that promotes cancer is the PSMGFR region of the MUC1* extracellular domain. In one aspect, an effective therapeutic agent is one that disrupts or prevents the interaction between an NME7 species and MUC1* extracellular domain, consisting primarily of the PSMGFR portion of MUC1* or the PSMGFR peptide. Agents for the treatment or prevention of cancers are those agents that directly or indirectly inhibit the expression or function of NME7, an NME7-AB-like cleavage product or alternative isoform, including NME7-X1. In one case an effective anti-cancer therapeutic agent is one that binds to the NME7 species or disables its tumorigenic activity. An effective therapeutic agent for the treatment or prevention of cancers is an agent that binds to or disables NME7, an NME7-AB-like cleavage product or alternative isoform, or NME7-X1. In one aspect, the therapeutic agents that binds to the NME7 species is an antibody. The antibody may be polyclonal, monoclonal, bispecific, bivalent, monovalent, single chain, scFv, or an antibody mimic that may be animal in origin, human-animal chimera, humanized or human. The antibody can be generated by inoculation or immunization with an NME7 species or fragment thereof or selected, for example from a library or a pool of antibodies, for their ability to bind to an NME7 species, including NME7, an NME7-AB-like cleavage product or alternative isoform, including NME7-X1.

Generation of Anti-NME7 Antibodies

Anti-NME7 antibodies can be generated outside of the patient such as in a host animal or in a patient. Antibodies can be generated by immunization of NME7 or NME7 fragments or selected from a library or pool of antibodies that may be natural, synthetic, whole or antibody fragments based on their ability to bind to desired NME7 species such as NME7-AB or NME7-X1. In one aspect, the antibody is generated from immunization with, or selected for its ability to bind to, a peptide selected from those listed in FIGS. 16-19. In another aspect, the antibody is generated from peptides whose sequences are not identical to those of human NME1 or the antibodies are selected for their ability to bind to NME7 species and their inability to bind to human NME1.

One method used to identify NME7 or NME7-X1 derived peptides that give rise to antibodies that inhibit cancer growth and inhibit transition to metastasis or peptides that are themselves inhibitory is as follows: 1) protein sequences of human NME1, human NME7, human NME7-X1 and several bacterial or fungal NME proteins that have high sequence homology to either human NME1 or human NME7 are aligned; 2) regions of high sequence homology among all the NMEs are identified; 3) peptide sequences that are unique to NME7 or NME7-X1 but are flanking the regions of high sequence homology are identified. The peptides are then synthesized and used to generate antibodies in a human or host animal. The resultant antibodies are tested for their ability to inhibit cancer growth or inhibit the transition to metastatic cancer cells.

Use of Anti-NME7 Antibody for Treatment of Cancer

Figure 26:
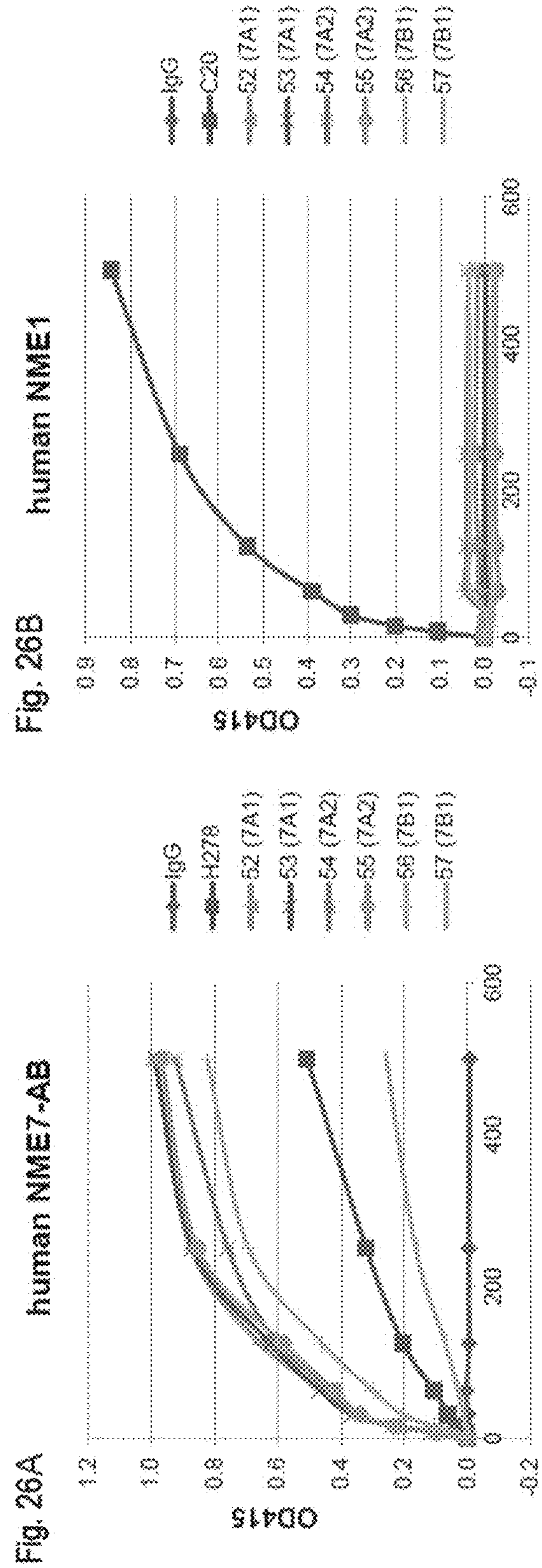
FIGS. 26A-26B show graphs of ELISA assays in which either NME7-AB (A) or NME1 (B) is adsorbed to the plate and anti-NME7 antibodies generated by NME7 peptides A1, A2, B1, B2 and B3 are tested for their ability to bind to NME7 but not to NME1. C20 is an anti-NME1 antibody.
Figure 27:
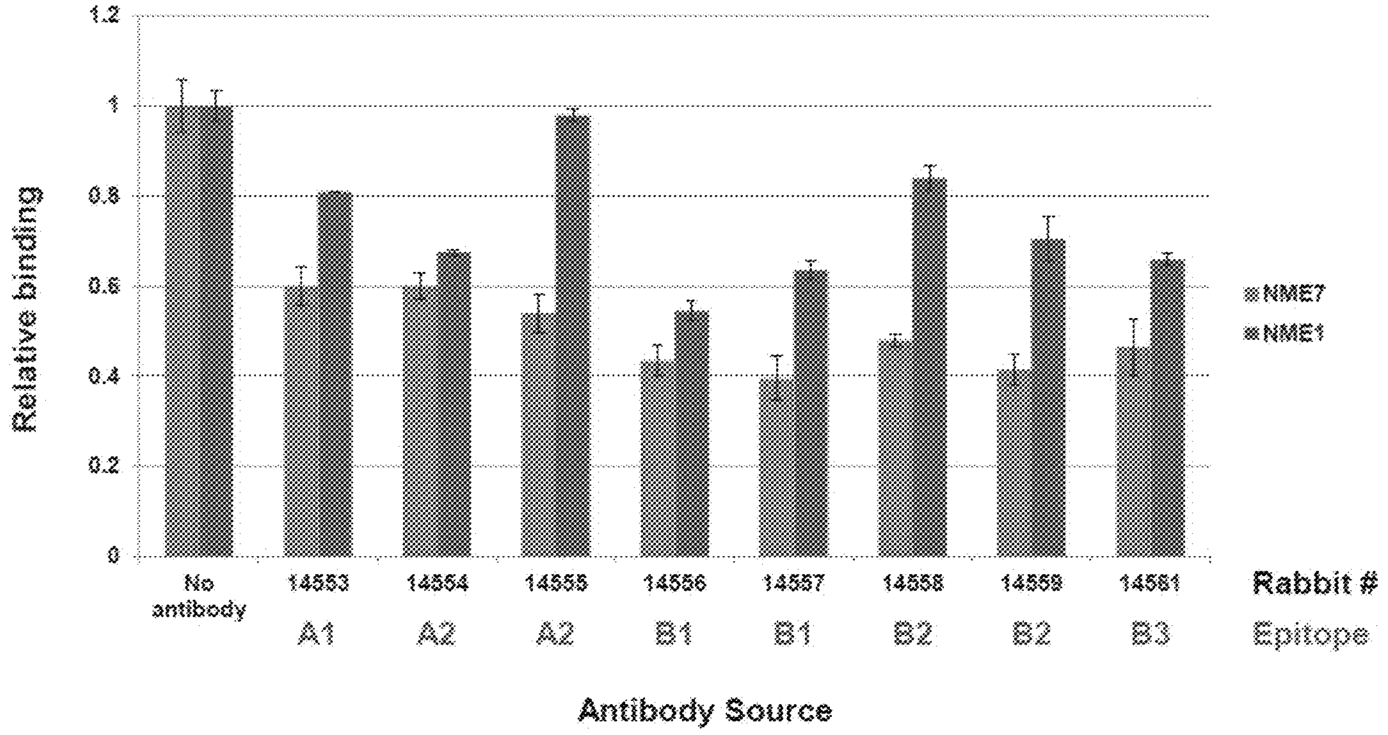
FIG. 27 shows graphs of ELISA assays in which anti-NME7 antibodies generated are tested for their ability to inhibit binding of NME7-AB to a surface immobilized MUC1* peptide but not inhibit binding of NME1.

Those antibodies that inhibit cancer growth or transition to a more metastatic state are selected for use as anti-cancer therapeutics and may be administered to a patient for the treatment or prevention of cancers. Selected antibodies may be further optimized for example by engineering or making human chimera antibodies or fully human antibodies. To demonstrate the efficacy of this approach, we selected NME7 peptides from regions of NME7 suspected to be critical to its cancerous function. We then generated antibodies using these peptides and then tested both the resultant antibodies as well as the immunizing peptides for their ability to: a) inhibit cancerous growth; and b) inhibit the induced transition from cancer cells to metastatic cancer cells. NME7 peptides were selected as immunizing agents for antibody production and as inhibitory agents themselves (FIG. 19 and Example 11). Peptides A1 (SEQ ID NO:141), A2 (SEQ ID NO:142), B1 (SEQ ID NO:143), B2 (SEQ ID NO:144) and B3 (SEQ ID NO:145), wherein A refers to the domain from which the peptide is derived, i.e. the NDPK A domain and the B denotes that the peptide is derived from the NDPK B domain (FIG. 15). Each peptide was used as an immunogen and injected into 2 rabbits each for production of polyclonal antibodies. The antibodies that were harvested from the blood of the immunized rabbits were purified over a column derivatized with the immunizing peptide. The purified antibodies were then tested for their ability to bind to human NME7. All of the resultant antibodies bound to human NME7 but not human NME1 as desired (FIG. 26A-B, Example 12). These results show that by choosing peptides whose sequence is found in NME7 but not exactly identical in NME1, antibodies are generated that specifically bind to NME7 but not NME1. Because NME1 has healthy function, it is in most cases desirable to generate antibodies that do not interfere with NME1. The antibodies were also tested for their ability to inhibit the binding of NME7 to a MUC1* extracellular domain peptide. The ELISA experiment shown in FIG. 27 shows that the antibodies inhibited the binding of NME7-AB to a MUC1* extracellular domain peptide much more than they inhibited binding of NME1.

This is but one example of selecting peptides that generate antibodies that inhibit the cancerous function of NME7 and NME7 species. Sequence alignment among human NME1, human NME7, human NME7-X1 and bacterial NME proteins that had high sequence homology to human NME1 or NME7 identified five regions of homology. The fact that peptides A1, A2, B1, B2 and B3 all generated antibodies that inhibited cancer growth or their transition to a metastatic state means that the five regions from which these peptides were derived are regions of NME7 that are important for its function in the promotion of cancer. Other peptides from these regions will also give rise to anti-NME7 antibodies that will inhibit cancer growth and metastasis and are therefore potent anti-cancer therapeutics. Antibodies generated from peptides A1, A2, B1, B2 and B3 were shown to inhibit cancer growth and inhibited the transition to a more metastatic state. Monoclonal antibodies generated by immunization with the same or similar peptides and subsequent testing of the monoclonals will identify antibodies that, after humanizing or other engineering known to those skilled in the art, would be administered to a patient for the treatment or prevention of cancers.

In a particular experiment, the antibodies generated by immunization with peptides A1, A2, B1, B2 and B3, as well as the immunizing peptides themselves, were added to cancer cells in culture to see if the addition of the antibodies or the immunizing peptides would inhibit cancer cell growth. At low concentrations and added separately, the antibodies as well as the immunizing peptides inhibited cancer cells growth (see FIG. 28 for one example). However, when added at higher concentrations or combined, the antibodies as well as the immunizing peptides robustly inhibited cancer cell growth (FIG. 29). The corresponding human NME7 amino acid numbers of immunizing peptides A1, A2, B1, B2 and B3 are 127-142, 181-191, 263-282, 287-301, 343-371, respectively, from human full-length NME7 having SEQ ID NO:82 or 147.

To clarify, when residue numbers of NME7 are discussed, they refer to the residue numbers of NME7 as set forth in SEQ ID NO:82 or 147.

Figure 28:
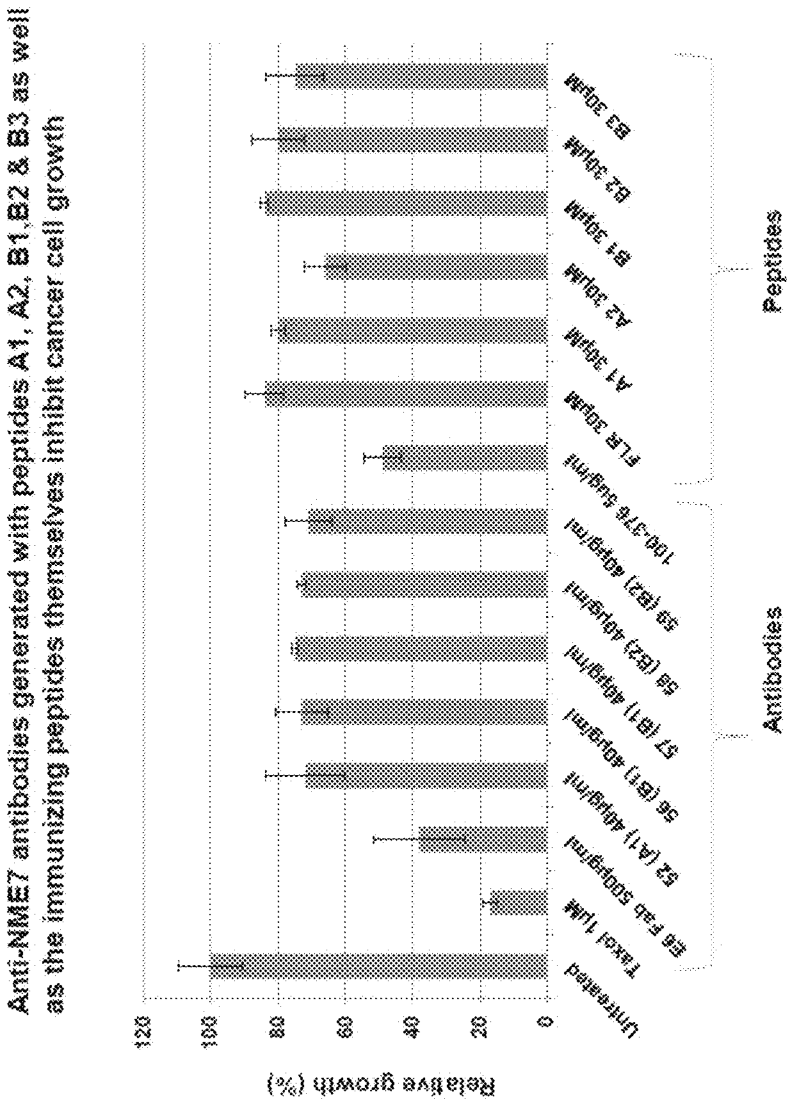
FIG. 28 shows a graph of a cancer cell growth experiment in which breast cancer cells were grown in the presence or absence of NME7 antibodies or short peptides derived from NME7, which were used to generate or select the antibodies. In addition, an antibody generated by immunization with nearly the entire NME7-AB peptide, amino acids 100-376, was shown to inhibit cancer cell growth.
Figure 29:
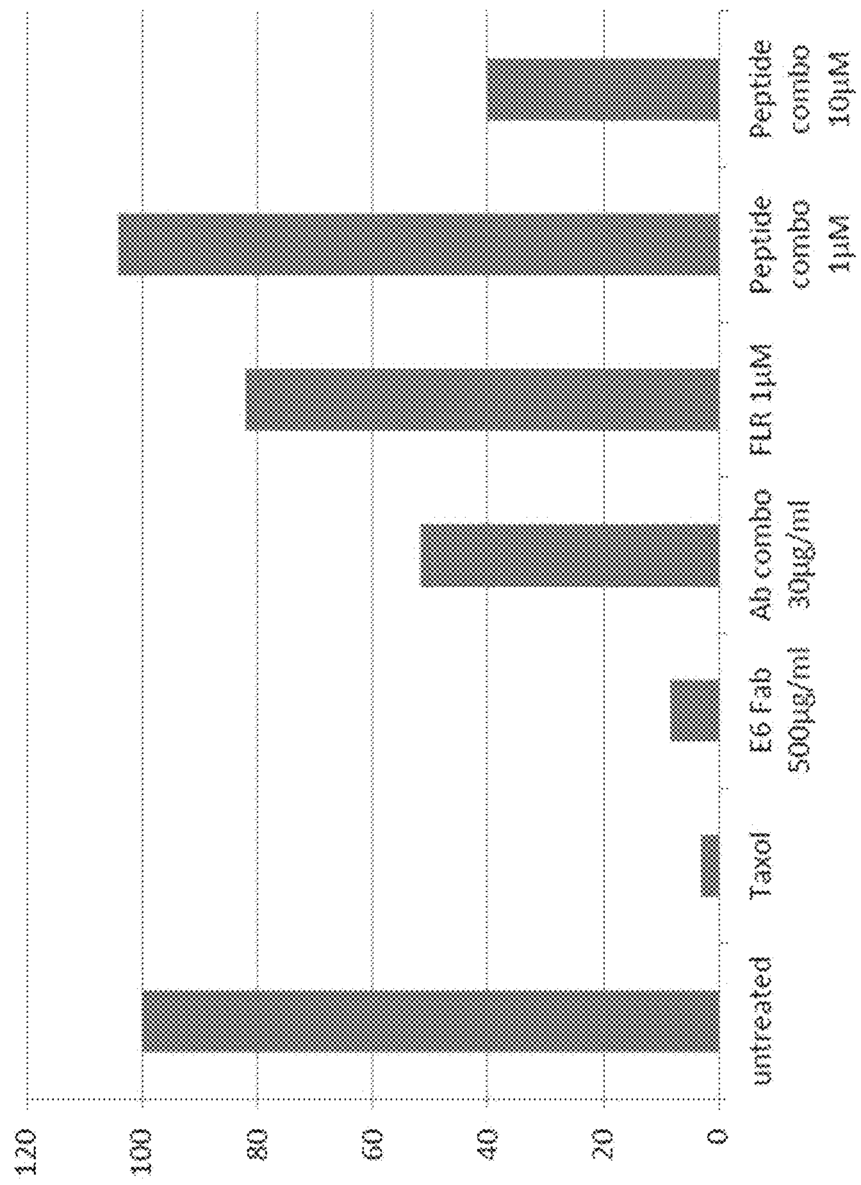
FIG. 29 shows a graph of a cancer cell growth experiment in which breast cancer cells were grown in the presence or absence of combinations of NME7 antibodies or combinations of the short peptides derived from NME7, which were used to generate or select the antibodies. Both antibodies as well as their immunizing NME7-AB peptides inhibited growth of cancer cells.

The antibody used in the cancer growth inhibition experiments shown in FIGS. 6-8 and one of the antibodies shown in FIG. 28 was generated by immunizing with NME7 peptide corresponding to amino acids 100-376 of NME7 (SEQ ID NO:82 or 147). To generate higher affinity and specific anti-NME7 antibodies, the following steps are followed: immunize animal with a peptide containing human NME7 amino acids 100-376, then: 1) de-select those antibodies that bind to human NME1; 2) select those antibodies that inhibit NME7-AB, 2i, or other NME induced transition of cancer cells to a more metastatic state; 3) select those antibodies that inhibit the growth of cancer cells; 4) select those antibodies that inhibit the growth of MUC1* positive cancer cells; 5) select those antibodies that inhibit binding of NME7-AB or NME7-X1 to MUC1* extracellular domain, essentially inhibit binding to the PSMGFR peptide; and/or 6) select those antibodies that bind to one or more of the peptides listed in FIG. 19—A1, A2, B1, B2 or B3 peptides.

Higher affinity monoclonal antibodies or monoclonal antibodies generated from longer peptides may be more effective antibody therapeutics. Alternatively, combinations of anti-NME7, anti-NME7-AB or anti-NME7-X1 antibodies are administered to a patient to increase efficacy.

Anti-NME7 antibodies inhibit the transition of cancer cells to metastatic cancer cells.

Anti-NME7 antibodies inhibit transition of cancer cells to metastatic cancer cells also called cancer stem cells (CSCs) or tumor initiating cells (TICs). Recall that we have demonstrated that culturing a wide variety of cancer cells in the presence of NME7-AB causes them to transition from regular cancer cells to the metastatic CSCs or TICs. Thus, antibodies that bind to NME7, NME7-AB or NME7-X1 will inhibit the progression of cancer cells to a more metastatic state.

Cancer cells transform to a more metastatic state when cultured in the presence of agents that revert stem cells to a more naïve state. We have demonstrated that culturing cancer cells in NME7-AB, human NME1 dimers, bacterial NME1 dimers or MEK and GSK3-beta inhibitors, called "2i", causes the cells to become more metastatic. As the cells transition to a more metastatic state, they become non-adherent or less adherent and float off of the culture plate. These floating cells, "floaters" were collected separately from those that were adherent and were shown to: a) express much higher levels of metastatic genes; and b) generated tumors when xenografted into mice at very low copy number. RT-PCR measurement of specific metastatic markers such as CXCR4 for breast cancers, CHD1 for prostate cancer, and other pluripotent stem cell markers such as OCT4, SOX2, NANOG, KLF4 and others were dramatically over-expressed in cancer cells that were cultured in NME7-AB and most over-expressed in the cells that became non-adherent, called "floaters" here and in figures.

In one example, NME7-AB specific antibodies, generated by immunization with NME7-derived peptides A1, A2, B1, B2 and B3, as well as the immunizing peptides themselves, were added into the media along with either NME7-AB or 2i to determine if they inhibited the transformation of regular cancer cells to metastatic cancer stem cells. Antibodies and peptides were separately added along with the agent that causes metastatic transformation; in this case NME7-AB or the 2i inhibitors PD0325901 and CHIR99021. NME7-AB and 2i were separately used to induce the cancer cells to be transformed to a more aggressive metastatic state. 2i was used so that it could not be argued that the antibodies that were added to the media simply sopped up all of the NME7-AB so that the causative agent effectively was not there (Example 14).

Figure 31B:
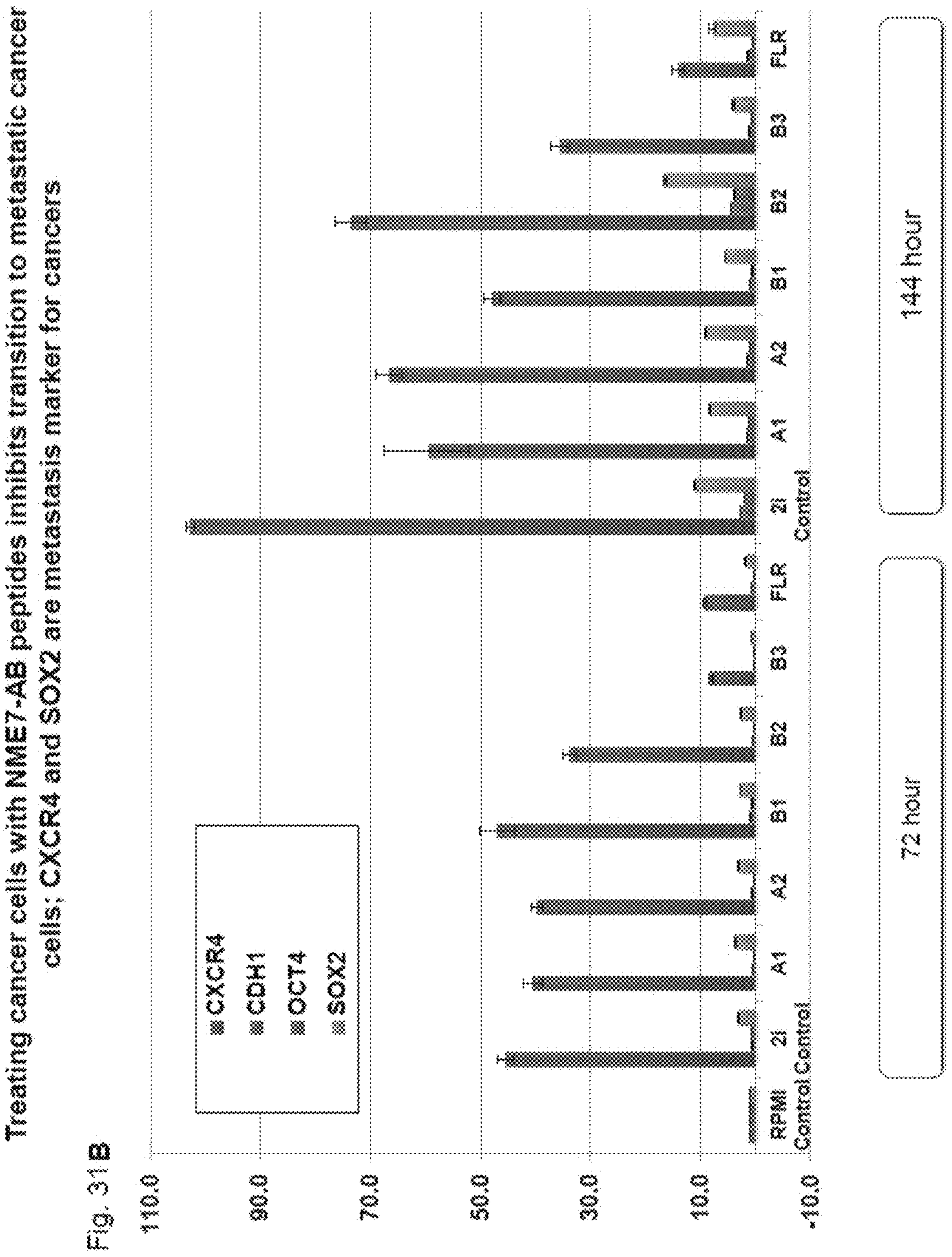
Figure 31C:
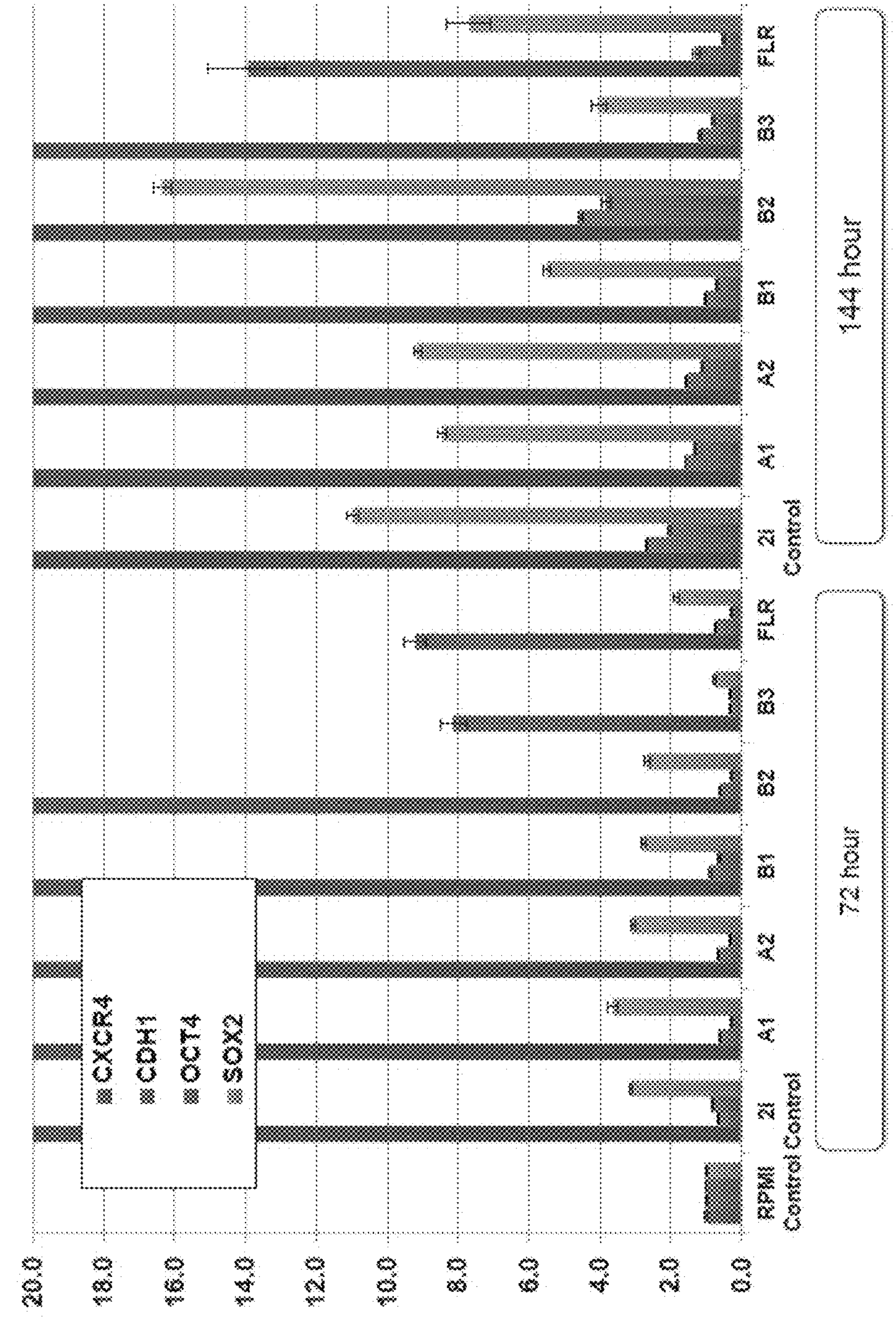

Visual observation was independently recorded by two scientists as the experiment progressed (FIG. 30). The most striking observation was that the antibodies and the peptides dramatically reduced the number of floater cells, which was the first indication that the antibodies and peptides inhibit the transformation to metastatic cancer cells. In particular, cells to which the antibody generated from immunization with the B3 peptide barely generated any floater cells. mRNA was extracted from both the floater cells, the adherent cells and the control cancer cells. The amount of mRNA, which indicates cell viability and growth, was measured. Cells that were treated with antibody had much less mRNA, indicating less live dividing cells (FIG. 32), which confirms that anti-NME7-AB antibodies inhibit cancer cell growth as well as their transition to a more metastatic state. RT-PCR was used to measure expression levels of metastatic markers, including CXCR4. Treatment with the anti-NME7 antibodies greatly reduced the amount of metastatic markers, such as CXCR4, indicating that the anti-NME7 antibodies or peptides inhibit the transition to metastatic cancer (FIG. 31A-C). These results show that antibodies that bind to NME7-AB can be administered to a patient for the treatment or prevention of metastatic cancers.

Peptides derived from NME7-AB or NME7-X1 competitively inhibit the binding of intact NME7-AB and NME7-X1 and are anti-cancer agents.

In another aspect of the invention, therapeutic agents for the treatment or prevention of cancers are peptides derived from the NME7 sequence, which are administered to a patient for the treatment or prevention of cancers. In one aspect, the NME7-derived peptides are administered to a patient so that the peptides, which should be shorter than the entire NME7 and unable to confer the oncogenic activity of NME7, bind to the targets of NME7 and competitively inhibit the interaction of intact NME7 with its targets, wherein such interactions promote cancer. Since NME7-AB is fully able to confer oncogenic activity, the sequence of NME7-AB is preferred as the source for the shorter peptide(s), wherein it must be confirmed that the peptides themselves are not able to promote cancerous growth or other tumorigenic or oncogenic activity. In a preferred embodiment, one or more peptides having the sequence of a portion of NME7-AB and being preferably about 12-56 amino acids in length are administered to a patient. To increase half-life, the peptides may be peptide mimics, such as peptides with unnatural backbone or D-form amino acids for L. In yet another case, the anti-cancer therapeutic agent is a peptide or peptide mimic wherein the peptide has a sequence highly homologous to at least a portion of NME7, NME7-AB, or NME7-X1 or its target the MUC1* extracellular domain, comprising the PSMGFR peptide, also called "FLR" in some cases herein.

FIGS. 16-19 provide a listing of preferred amino acid sequences that are predicted to inhibit NME7 binding to its cognate target. In a still more preferred embodiment, the peptides that are chosen for administration to a patient suffering from cancer or at risk of developing cancer are chosen because they bind to an NME7 binding partner and they do not themselves confer tumorigenic activity. In a yet more preferred embodiment, the NME7 binding partner is the extracellular domain of MUC1*. In a still more preferred embodiment, the NME7 binding partner is the PSMGFR peptide.

By the term "conferring tumorigenic activity or oncogenic activity", it is meant that the peptides themselves cannot support or promote the growth of cancers. Another way of testing whether or not a peptide or peptides derived from NME7 can promote tumorigenesis is to test whether or not the peptides can support pluripotent growth of human stem cells. NME proteins and peptides that support pluripotent human stem cell growth also support cancer growth. In yet another method, peptides are de-selected if they can cause somatic cells to revert to a less mature state.

Fragments of NME7-AB inhibit cancer cell growth and the transition of cancer cells to a more metastatic state. As a demonstration, NME7 peptides A1, A2, B1, B2 and B3 added separately (FIG. 28) or in combinations (FIG. 29) inhibit the growth of cancer cells. In addition, NME7 peptides A1, A2, B1, B2 and B3 inhibited the transition of cancer cell to a more metastatic state (FIG. 31 B-C).

Thus, antibodies generated by immunizing with peptides specific to NME7, and specific to NME7-AB or NME7-X1 will block the cancerous action of NME7 species and will be potent anti-cancer agents. Similarly, these results show that the peptides specific to NME7, and specific to NME7-AB or NME7-X1 will block the cancerous action of NME7 species. In one aspect of the invention, the peptides are chosen from the list shown in FIG. 16. In one aspect of the invention the peptides are chosen from the list shown in FIG. 17. In one aspect of the invention the peptides are chosen from the list shown in FIG. 18. In yet another aspect of the invention the peptides are chosen from the list shown in FIG. 19.

Anti-NME7 antibodies for use in the treatment or prevention of cancers can be generated by standard methods known to those skilled in the art wherein those methods are used to generate antibodies or antibody-like molecules that recognize NME7, NME7-AB or a shorter form of NME7-AB wherein an additional 10-25 amino acids form the N-terminus are not present.

In another aspect of the invention, small molecules are anti-cancer agents that are selected for their ability to inhibit the tumorigenic effects of NME7, NME7-AB or NME7-X1. For example, a high throughput screen identifies small molecules that will treat cancer. In a multi-well plate, small molecules are separately added to wells in which cancer cells are cultured in a medium containing NME7-AB. If the small molecule diminishes the amount of cells that become floaters and/or reduces the expression of metastatic markers such as CXCR4, CHD1 or pluripotent stem cell markers, then that small molecule is an anti-cancer drug candidate. Another method of identifying small molecules that are anti-cancer agents is to select those small molecules that bind to NME7, NME7-AB or NME7-X1 or suppresses expression of the NME7 species. Yet another high throughput screen is to select for small molecules that inhibit the binding of NME7-AB to the PSMGFR peptide of the MUC1* extracellular domain and those small molecules will be anti-cancer agents.

The sequences of NME7-AB and NME7-X1 differ only in that NME7-X1 is missing some of the N-terminal sequence that NME7-AB has. Experiments show that there is a naturally occurring NME7 species that is nearly identical to NME7-AB, which we call NME-AB-like species. Antibodies that bind to NME7-X1 may also bind to the naturally occurring species that mimics NME7-AB, unless there are conformational differences that an antibody can differentiate. Therefore, if it is desired to inhibit NME7-X1 but not NME7-AB-like species, or vice versa, siRNA, anti-sense nucleic acids, or genetic editing techniques can be used to inhibit expression of one but not the other.

In one case, the anti-cancer therapeutic agent is a nucleic acid that directly or indirectly suppresses specific expression of NME7, NME7-X1 or NME7-AB-like species. Such nucleic acids can be siRNA, RNAi, anti-sense nucleic acids and the like that directly suppress the NME7 species. In another aspect of the invention, the nucleic acid can indirectly suppress the NME7 species for example by altering the expression of a molecule that regulates it. For example, the super enhancer BRD4 suppresses expression of NME7. Therefore, an effective therapeutic for the treatment or prevention of cancer is an agent that increases expression of BRD4. An effective therapeutic may be an agent that increases expression of BRD4's co-factor, JMJD6.

Peptides derived from NME7-AB or NME7-X1, or the entire protein, are used to generate anti-NME7 or anti-NME7-X1 antibodies in animals that we have demonstrated inhibit cancer growth and inhibit transition of cancer cells to metastatic cancer cells. Similarly, NME7 derived peptides can be administered to a human such that they generate antibodies that treat or prevent cancer or inhibit transition of cancer cells to metastatic cancer cells. NME7 peptides or proteins are administered to a person as a type of vaccine to stimulate the production of anti-NME7, anti-NME7-AB or anti-NME7-X1 antibodies in the recipient. The results shown in FIGS. 28 and 29 indicate that immunizing a person with a collection of peptides derived from NME7, especially in the NME7-X1 or NME7-AB sequences may be a more effective vaccine than immunizing with a single peptide. Said peptides or proteins may further be conjugated to a carrier protein or other adjuvant, known to those skilled in the art to aid in the stimulation of an immune response.

NME7 peptides that lie outside of the DM10 domain are preferred to generate antibodies for the treatment or prevention of cancer. Peptides that can be administered to a patient for the prevention of cancer or metastasis contain sequences of the peptides listed in FIGS. 16-19. A1, A2, B1, B2 and B3 are examples of peptides that generate antibodies that bind to NME7-AB and NME7-X1 and are administered to a patient for the treatment or prevention of cancer. The invention is not limited to peptides of the exact sequence as is naturally occurring in NME7 or NME7-X1. As is known to those skilled in the art, substitution of several amino acids of a peptide sequence can still give rise to antibodies that specifically recognize the natural protein sequence. It is not intended that the invention be limited to the peptides demonstrated herein to inhibit cancer growth or inhibit the transition of regular cancer cells to metastatic cancer cells. The methods used here to identify peptides A1, A2, B1, B2 and B3 can also be used to identify other peptide sequences that could be equally or more effective than the peptides demonstrated here.

Chimeric antigen receptor molecules comprising portions of human NME7-AB or NME7-X1 or comprising an antibody fragment that binds to NME7-AB or NME7-X1 are anti-cancer therapeutics and are administered to a patient for the treatment or prevention of cancers.

In one instance, the recognition units or variable regions of anti-NME7 antibodies are fused to molecules of T cells using the technology known as CAR (chimeric antigen receptor) technology or CAR T technology. The salient feature of antibodies or fragments thereof that can be used therapeutically to treat or prevent cancers is the identification of antibody-like variable regions that recognize NME7 and prevent its interaction with targets that promote cancers. In one case, the target is the PSMGFR region of MUC1*.

Antibodies, antibody fragments or single chain antibodies can be engineered into chimeric molecules, including chimeric antigen receptors, also known as CARs, which molecules are then transfected or transduced into an immune system cell, such as a T cell, and administered to a patient. The humanized antibodies or antibody fragments, typically an scFv comprises much of the extracellular domain of a CAR. The antibody fragment is biochemically fused to immune system signaling molecules, such as CD8 as the transmembrane domain and cytoplasmic signaling motifs such as T cell receptor signaling molecules also called activation domains, or co-stimulatory domains including but not limited to CD3-zeta, CD28, 41bb, OX40. CARs can be transfected into T cells or other cells, preferably immune system cells and administered to a patient. Here we describe CARs in which the extracellular portion contains an anti-NME7, anti-NME7-AB or anti-NME7-X1 antibody, antibody fragment or single chain, scFv antibody fragment. In a preferred embodiment, the antibody or antibody fragment is human or humanized.

Effective anti-NME7 or anti-NME7-X1 antibodies or fragments will have the ability to bind to native NME7, NME7-AB or NME7-X1. In practice, the parent antibody, from which the extracellular domain of the CAR is engineered, is generated by immunizing an animal with an NME7, NME7-AB or NME7-X1 derived peptide. In one aspect of the invention, the immunizing peptide is comprised of NME7 amino acids 1-376. In one aspect of the invention, the immunizing peptide is comprised of NME7 amino acids 92-376. In another aspect of the invention, the immunizing peptide is comprised of NME7 amino acids 125-376. In yet another aspect of the invention, the immunizing peptide is made up of sequences listed in FIGS. 16-18. In another aspect of the invention, the immunizing peptide is made up of sequences listed in FIG. 19. Alternatively, the parent antibody or the antibody fragment is selected from a library or pool of antibodies, which may be natural, synthetic or fragments of either, wherein they are selected for their ability to bind to NME7, NME7-AB or NME7-X1, peptides listed in FIGS. 16-18, or peptides listed in FIG. 19.

The targeting portion of a CAR need not be an antibody or antibody fragment. Here we describe a CAR wherein the extracellular domain contains an NME7 fragment. NME7-derived peptide(s) are engineered into a different sort of CAR wherein the targeting portion of the extracellular domain is a protein fragment or peptide rather than an antibody or antibody fragment. The peptide CARs are transfected or transduced into an immune system cell, typically a T cell. The NME7 fragments or NME7 derived peptides are selected for their ability to bind to their cognate binding partners but should not be able to function as intact NME7, NME7-AB or NME7-X1 and confer tumorigenic activity. NME7 fragments or NME7 derived peptides are biochemically fused to immune system signaling molecules, such as CD8 as the transmembrane domain and cytoplasmic signaling motifs such as T cell receptor signaling molecules also called activation domains, or co-stimulatory domains including but not limited to CD3-zeta, CD28, 41bb, OX40.

In one aspect of the invention, the NME7 fragment is most or all of the NME7 NDPK B domain. In another aspect of the invention, the NME7 fragment is an NME7 peptide that contains one or more of the peptide sequences listed in FIGS. 16-19. Experiments indicate that, for strategies that use NME7 or fragments of NME7, NME7-AB, or NME7-X1 as the targeting portion of a chimeric antigen receptor (CAR) for engineered immune cell therapeutics, fairly large fragments of NME7-AB or NME7-X1 would be more effective than shorter peptides, for example peptides less than 15 amino acids in length. Alternatively, a collection of CARs, each bearing a different NME7-AB derived peptide can collectively be transfected or transduced into an immune system cell and administered to a patient for the treatment or prevention of cancers. Experiments shown in FIGS. 28 and 29 support the validity of this approach.

CARs that contain an NME7 fragment in its extracellular domain are transfected or transduced into an immune system cell, typically a T cell, and administered to a patient for the treatment or prevention of cancers. In one aspect, the cancer is a MUC1*-positive cancer. In another aspect, the cancer is a metastatic cancer.

Agents that inhibit an enzyme that cleaves NME7 can be used to treat or prevent cancers. Some forms of NME7 are sequestered within the cell and therefore are not secreted from the cell whereupon they can act as growth factors to promote cancers. Full-length NME7 is 42 kDa. However, we found that a ~33 kDa NME7 species that is devoid of the DM10 domain and appears to be essentially identical to the recombinant NME7-AB that we generated, is secreted from cancer cells and stem cells. This ~33 kDa NME7 species and another ~25 kDa NME7 species may be cleavage products that would be eliminated by an agent that inhibited cleavage of NME7.

The detection of elevated levels of NME7, or an ~33 kDa NME7 species, which we call NME7-AB-like species, or NME7-X1 in a patient sample is diagnostic of the presence of cancer or its progression to a more aggressive or metastatic state. The inventors have discovered that both early stage, naïve stem cells and cancer cells, especially MUC1*-positive cancer cells, express high levels of a ~33 kDa NME7 that is devoid of the DM10 domain and NME7-X1.

NME7-X1 was recently listed in a protein database as being a theoretical alternative isoform of NME7, however, it had never been detected in tissues or cells. We designed primers that differentiate NME7-X1 from NME7 by PCR. The expression levels of human NME7, NME7a, NME7b and NME7-X1 were measured by PCR in a panel of cells that included fibroblast cells, human embryonic stem cells, human iPS cells, T47D human breast cancer cells, DU145 human prostate cancer cells, PC3 human prostate cancer cells, HEK295 human fetal liver cells, and other human stem cell lines. NME7 is expressed at higher levels in cancer cells than in stem cells. Particularly, NME7-X1 is expressed 10-fold higher in prostate cancer cells and 3-fold higher in breast cancer cells, than it is in fibroblast cells or stem cells. NME7-X1 is expressed ~5-fold higher in HEK293 fetal liver cells than it is in fibroblast cells or stem cells and therefore predicts that NME7-X1 is elevated in liver cancers. NME7b is expressed 17-25-times higher in prostate cancer cells than in stem cells.

Detection of elevated levels of NME7 species in a patient sample will be indicators that the patient has a cancer or is at risk of developing a cancer. Levels of NME7 species levels can be measured or assessed by PCR, hybridization schemes, cycling probe technologies, FISH, immunocytochemistry, IHC, Western blot, immunoprecipitation, sandwich assays, ELISA assays and the like. The patient sample may be a fluid sample, a blood sample, milk, urine, cells, liquid biopsy, biopsy and the like. In a patient diagnosed with cancer, elevated levels of NME7 species are indicators of increased metastatic potential. Elevated levels of NME7-X1 are indicators of prostate cancer. Antibodies of the invention are used to detect and distinguish NME7 species and are used as a diagnostic tool.

Because adult cells and tissues do not express significant levels of NME7 or secrete NME7, an effective way to diagnose cancer or to diagnose a more aggressive or metastatic form, or a shift to a more aggressive form, is to measure levels of NME7 in a sample from a patient, from a collection of cells or tissues or from cultured cells, compared to NME7 levels in a healthy sample or compared to levels of NME7 known to exist in healthy adult cells or tissues. Increased levels of NME7 indicate the presence of cancer, the presence of a metastatic cancer or the onset of metastasis. Increased levels of NME7 is also indicative of a MUC1*-positive cancer. The sample assayed for the presence of NME7 may be a collection of cells that may be cultured cell lines or cells from a patient, a bodily fluid, a blood sample, a tissue specimen, or a biopsy specimen. Therefore, a diagnostic assay that will detect the presence of cancer or the progression of cancer, comprises the steps of: 1) obtaining a sample from a patient having cancer or at risk of developing a cancer; 2) subjecting that sample to an assay capable of detecting or measuring levels of NME7, or levels of nucleic acids encoding NME7; 3) comparing levels of the measured NME7 protein or NME7-encoding nucleic acids in the test sample to levels in control patients or control cells; 4) determining that the levels of NME7 or nucleic acids encoding NME7 are elevated compared to the controls; and 5) concluding that the donor of the test sample has cancer or has had a progression of cancer if the control to which the test was compared came from a donor previously diagnosed with a cancer.

In this assay, the control sample to which the test sample is compared can be non-cancerous cells, cultured cells, a sample from a healthy donor, a non-cancerous sample from the donor, or a sample from the donor of the test sample wherein the control sample was taken from the donor at a previous point in time. The source of such samples may be any specimen taken from the patient being tested for the presence or progression of cancer, including bodily fluids, cerebrospinal fluid, bone marrow samples, blood, tissues, cells, biopsy tissues or cells, cultured cells derived from a patient's cells and the like. The source of the sample to which the test sample is compared can be bodily fluids, cerebrospinal fluid, bone marrow samples, blood, tissues, cells, biopsy tissues or cells, or cultured cells that may be derived from a healthy donor or the test patient wherein the samples were taken at a previous point in time. The measured levels to which the test sample is compared may be from previously recorded data and compiled into lists for comparison to test samples.

Theranostics

Patients diagnosed with elevated levels of NME7 protein or nucleic acids encoding NME7 are then treated with therapeutic agents that suppress expression of NME7, inhibit cleavage of NME7 or inhibit NME7 binding to its targets, wherein such interaction promotes cancers. An important target of NME7 or a cleavage product of NME7, is MUC1*. NME7 binds to and dimerizes the extracellular domain of MUC1*. Therefore, patients diagnosed with elevated levels of NME7 will benefit from treatment with therapeutic agents that inhibit NME7 and/or therapeutic agents that inhibit the dimerization of a cleaved form of MUC1, whose extracellular domain is comprised of some or all of the PSMGFR sequence. Thus assessing suitability of cancer treatments and administration of an effective amount of a therapeutic for the treatment or prevention of cancers would consists of the steps of: 1) obtaining a sample from a patient suspected of having a cancer or at risk of developing a cancer or at risk of developing a metastatic cancer; 2) measuring an amount of NME7 or a cleavage product thereof or an NME7 encoding nucleic acid wherein the measured levels are significantly above those measured in a control sample; 3) determining that the patient has a cancer or has developed a more aggressive or a metastatic cancer; 4) administering to the patient an effective amount of a therapeutic agent that suppresses expression of NME7, inhibits cleavage of NME7 or inhibits NME7 binding to its targets and/or administering to the patient an effective amount of a therapeutic agent that suppresses expression of MUC1, inhibits cleavage of MUC1 to MUC1* or inhibits MUC1* binding to its targets. In a preferred embodiment, the therapeutic agent that inhibits NME7 binding to its targets, inhibits its interaction with MUC1*. In a more preferred embodiments, it inhibits its interaction with the extracellular domain of MUC1* comprised essentially of the PSMGFR sequence. In a preferred embodiment, the therapeutic agent that inhibits MUC1* binding to its targets, inhibits the interaction between MUC1* and NME7. In a more preferred embodiment, the therapeutic agent that inhibits the interaction between MUC1* and NME7 inhibits the binding of MUC1* to the portion of NME7 that is comprised essentially of the sequence of NME7-AB.

Chemically Modified Peptides

Polypeptide or antibody therapeutics may suffer from short circulating half-life, and proteolytic degradation and low solubility. To improve the pharmacokinetics and pharmacodynamics properties of the inventive biopharmaceuticals, methods such as manipulation of the amino acid sequence may be made to decrease or increase immunogenicity and decrease proteolytic cleavage; fusion or conjugation of the peptides to immunoglobulins and serum proteins, such as albumin may be made; incorporation into drug delivery vehicles for the biopharmaceuticals such as the inventive peptides and antibodies for protection and slow release may also be made; and conjugating to natural or synthetic polymers are also contemplated. In particular, for synthetic polymer conjugation, pegylation or acylation, such as N-acylation, S-acylation and so forth are also contemplated.

Nucleic Acid Constructs

Also provided is an expression vector comprising a nucleic acid molecule of the invention as described herein, wherein the nucleic acid molecule is operatively linked to an expression control sequence. Also provided is a host-vector system for the production of a polypeptide which comprises the expression vector of the invention which has been introduced into a host cell suitable for expression of the polypeptide. The suitable host cell may be a bacterial cell such as *E. coli*, a yeast cell, such as *Pichia pastoris*, an insect cell, such as *Spodoptera frugiperda*, or a mammalian cell, such as a COS, HEK or CHO cell.

The present invention also provides for methods of producing the polypeptides of the invention by growing cells of the host-vector system described herein, under conditions permitting production of the polypeptide and recovering the polypeptide so produced. The polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, polypeptide includes functionally equivalent molecules in which amino acid residues are substituted for residues within the sequence resulting in a silent or conservative change. For example, one or more amino acid residues within the sequence can be substituted by another amino acid of a similar polarity, which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. The potential glycosylation amino acids include serine, threonine, and asparagine. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Any of the methods known to one skilled in the art for the insertion of DNA fragments into a vector may be used to construct expression vectors encoding the polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the polypeptides of the invention may be regulated by a second nucleic acid sequence so that the polypeptide is expressed in a host transformed with the recombinant DNA molecule. For example, expression of the polypeptides described herein may be controlled by any promoter/enhancer element known in the art. Promoters which may be used to control expression of the polypeptide include, but are not limited to the long terminal repeat as described in Squinto et al., (1991, Cell 65:1-20); the SV40 early promoter region (Bernoist and Chambon, 1981, Nature 290:304-310), the CMV promoter, the M-MuLV 5' terminal repeat the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), Sendai virus, lenti virus, albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a polypeptide as described herein, are used to transfect the host and thereby direct expression of such nucleic acid to produce polypeptides which may then be recovered in biologically active form. As used herein, a biologically active form includes a form capable of binding to the relevant receptor and causing a differentiated function and/or influencing the phenotype of the cell expressing the receptor.

Expression vectors containing the nucleic acid inserts can be identified by without limitation, at least three general approaches: (a) DNA-DNA hybridization, (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The polypeptide, in particular modified of the present invention, may be expressed in the host cells transiently, constitutively or permanently.

Effective doses useful for treating the diseases or disorders indicated in the present application may be determined using methods known to one skilled in the art (see, for example, Fingl, et al., The Pharmacological Basis of Therapeutics, Goodman and Gilman, eds. Macmillan Publishing Co, New York, pp. 1-46 (1975). Pharmaceutical compositions for use according to the invention include the polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions, which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

Gene Therapy

Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, NY (1990).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Lentiviral vectors, such as retroviral vectors, and other vectors such as adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

The formulation of therapeutic compounds is generally known in the art and reference can conveniently be made to Remington's Pharmaceutical Sciences, 17th ed., Mack Publishing Co., Easton, Pa., USA. For example, from about 0.05 ng to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intra ocular, intradermal or suppository routes or implanting (eg using slow release molecules by the intraperitoneal route or by using cells e.g. monocytes or dendrite cells sensitized in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, intra ocular, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

(SEQ ID NO: 1)

```
MTPGTQSPFF LLLLLTVLTV VTGSGHASST PGGEKETSAT QRSSVPSSTE

KNAVSMTSSV LSSHSPGSGS STTQGQDVTL APATEPASGS AATWGQDVTS

VPVTRPALGS TTPPAHDVTS APDNKPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS

APDTRPAPGS TAPPAHGVTS APDTRPAPGS TAPPAHGVTS APDTRPAPGS

TAPPAHGVTS APDTRPAPGS TAPPAHGVTS APDTRPAPGS TAPPAHGVTS
```

-continued

APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDTRPAPGS
TAPPAHGVTS APDTRPAPGS TAPPAHGVTS APDTRPAPGS TAPPAHGVTS
APDTRPAPGS TAPPAHGVTS APDTRPAPGS TAPPAHGVTS APDNRPALGS
TAPPVHNVTS ASGSASGSAS TLVHNGTSAR ATTTPASKST PFSIPSHEISD
TPTTLASHST KTDASSTHHS SVPPLTSSNH STSPQLSTGV SFFFLSFHIS NLQFNSSLED
PSTDYYQELQ RDISEMFLQI YKQGGFLGLS NIKFRPGSVV VQLTLAFREG
TINVHDVETQ FNQYKTEAAS RYNLTISDVS VSDVPFPFSA QSGAGVPGWG
IALLVLVCVL VALAIVYLIA LAVCQCRRKN YGQLDIFPAR DTYHPMSEYP
TYHTHGRYVP PSSTDRSPYE KVSAGNGGSS LSYTNPAVAA
ASANL describes full-length MUC1 Receptor (Mucin 1 precursor, Genbank Accession number: P15941).

(SEQ ID NO: 2)
MTPGTQSPFFLLLLLTVLT (SEQ ID NO: 3)
MTPGTQSPFFLLLLLTVLT VVTA (SEQ ID NO: 4)
MTPGTQSPFFLLLLLTVLT VVTG

SEQ ID NOS:2, 3 and 4 describe N-terminal MUC-1 signaling sequence for directing MUC1 receptor and truncated isoforms to cell membrane surface. Up to 3 amino acid residues may be absent at C-terminal end as indicated by variants in SEQ ID NOS:2, 3 and 4.

GTINVHDVETQFNQYKTEAAS-RYNLTISDVSVSDVPFPFSAQSGAGVPGWGI ALL-VLVCVLVALAIVYLIALA-VCQCRRKNYGQLDIFPARDTYHPMSEYPTYHTHGR YVP PSSTDRSPYEKVSAGNGGSSLSYTN-PAVAAASANL (SEQ ID NO:5) describes a truncated MUC1 receptor isoform having nat-PSMGFR at its N-terminus and including the transmembrane and cytoplasmic sequences of a full-length MUC1 receptor.

GTINVHDVETQFNQYKTEAAS-RYNLTISDVSVSDVPFPFSAQSGA (SEQ ID NO:6) describes the extracellular domain of Native Primary Sequence of the MUC1 Growth Factor Receptor (nat-PSMGFR—an example of "PSMGFR"):

TINVHDVETQFNQYKTEAAS-RYNLTISDVSVSDVPFPFSAQSGA (SEQ ID NO:7) describes the extracellular domain of Native Primary Sequence of the MUC1 Growth Factor Receptor (nat-PSMGFR—An example of "PSMGFR"), having a single amino acid deletion at the N-terminus of SEQ ID NO:6).

GTINVHDVETQFNQYK-TEAASPYNLTISDVSVSDVPFPFSAQSGA (SEQ ID NO:8) describes the extracellular domain of "SPY" functional variant of the native Primary Sequence of the MUC1 Growth Factor Receptor having enhanced stability (var-PSMGFR—An example of "PSMGFR").

TINVHDVETQFNQYK-TEAASPYNLTISDVSVSDVPFPFSAQSGA (SEQ ID NO:9) describes the extracellular domain of "SPY" functional variant of the native Primary Sequence of the MUC1 Growth Factor Receptor having enhanced stability (var-PSMGFR—An example of "PSMGFR"), having a single amino acid deletion at the C-terminus of SEQ ID NO:8).

(SEQ ID NO: 10)
tgtcagtgccgccgaaagaactacgggcagctggacatctttccagcccgggatacctaccatcctatgagcgagtaccc
cacctaccacacccatgggcgctatgtgccccctagcagtaccgatcgtagcccctatgagaaggtttctgcaggtaacggtggcagcagc
ctctcttacacaaacccagcagtggcagccgcttctgccaacttg describes MUC1 cytoplasmic domain nucleotide sequence.

(SEQ ID NO: 11)
CQCRRKNYGQLDIFPARDTYHPMSEYPTYHTHGRYVPPSSTDRSPYEKVSAG
NGGSSLSYTNPAVAAASANL describes MUC1 cytoplasmic domain amino acid sequence.

-continued (SEQ ID NO: 12)

gagatcctgagacaatgaatcatagtgaaagattcgttttcattgcagagtggtatgatccaaatgcttcacttcttcgacgtta tgagatttattttacccaggggatggatctgttgaaatgcatgatgtaaagaatcatcgcacctttttaaagcggaccaaatatgataacctgca cttggaagatttatttataggcaacaaagtgaatgtattttctcgacaactggtattaattgactatggggatcaatatacagctcgccagctggg cagtaggaaagaaaaaacgctagccctaattaaaccagatgcaatatcaaaggctggagaaataattgaaataataaacaaagctggatttta ctataaccaaactcaaaatgatgatgattcaaggaaagaagcattggattttcatgtagatcaccagtcaagacccttttttcaatgagctgatc cagtttattacaactggtcctattattgccatggagattttaagagatgatgctatatgtgaatggaaaagactgctgggacctgcaaactctgg agtggcacgcacagatgatctgaaagcattagagccctattggaacagatggcataagaaatgcagcgcatggccctgattcttttgcttct gcggccagagaaatggagttgttttttccttcaagtggaggttgtgggccggcaaacactgctaaatttactaattgtacctgttgcattgttaaa ccccatgctgtcagtgaaggtatgttgaatacactatattcagtacattttgttaataggagagcaatgtttattttcttgatgtactttatgtatagaa aataa describes NME7 nucleotide sequence (NME7: GENBANK ACCESSION AB209049).

(SEQ ID NO: 13)

DPETMNHSERFVFIAEWYDPNASLLRRYELLFYPGDGSVEMHDVKNHRTFL

KRTKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDDAI

CEWKRLLGPANSGVARTDASESIRALFGTDGIRNAAHGPDSFASAAREMELFFPSSGGC

GPANTAKFTNCTCCIVKPHAVSEGMLNTLYSVHFVNRRAMFIFLMYFMYRK describes NME7 amino acid sequence (NME7: GENBANK ACCESSION AB209049).

(SEQ ID NO: 14)

atggtgctactgtctactttagggatcgtctttcaaggcgaggggcctcctatctcaagctgtgatacaggaaccatggccaa ctgtgagcgtaccttcattgcgatcaaaccagatggggtccagcggggtcttgtgggagagattatcaagcgttttgagcagaaaggattcc gccttgttggtctgaaattcatgcaagatccgaagatcttctcaaggaacactacgttgacctgaaggaccgtccattctttgccggcctggtg aaatacatgcactcagggccggtagttgccatggtctgggaggggctgaatgtggtgaagacgggccgagtcatgctcggggagaccaa ccctgcagactccaagcctgggaccatccgtggagacttctgcatacaagttggcaggaacattatacatggcagtgattctgtggagagtg cagagaaggagatcggcttgtggtttcaccctgaggaactggtagattacacgagctgtgctcagaactggatctatgaatga describes NM23-H1 nucleotide sequence (NM23-H1: GENBANK ACCESSION AF487339).

(SEQ ID NO: 15)

MVLLSTLGIVFQGEGPPISSCDTGTMANCERTFIAIKPDGVQRGLVGEIIKRFE

QKGFRLVGLKFMQASEDLLKEHYVDLKDRPFFAGLVKYMHSGPVVAMVWEGLNVVK

TGRVMLGETNPADSKPGTIRGDFCIQVGRNIIHGSDSVESAEKEIGLWFHPEELVDYTSC

AQNWIYE NM23-H1 describes amino acid sequence (NM23-H1: GENBANK ACCESSION AF487339).

(SEQ ID NO: 16)

atggtgctactgtctactttagggatcgtctttcaaggcgaggggcctcctatctcaagctgtgatacaggaaccatggccaa ctgtgagcgtaccttcattgcgatcaaaccagatggggtccagcggggtatgtgggagagattatcaagcgttttgagcagaaaggattcc gccttgttggtctgaaattcatgcaagatccgaagatcttctcaaggaacactacgttgacctgaaggaccgtccattctttgccggcctggtg aaatacatgcactcagggccggtagttgccatggtctgggaggggctgaatgtggtgaagacgggccgagtcatgctcggggagaccaa ccctgcagactccaagcctgggaccatccgtggagacttctgcatacaagttggcaggaacattatacatggcggtgattctgtggagagtg cagagaaggagatcggcttgtggtttcaccctgaggaactggtagattacacgagctgtgctcagaactggatctatgaatga describes NM23-H1 S120G mutant nucleotide sequence (NM23-H1: GENBANK ACCESSION AF487339).

-continued (SEQ ID NO: 17)

MVLLSTLGIVFQGEGPPISSCDTGTMANCERTFIAIKPDGVQRGLVGEIIKRFE

QKGFRLVGLKFMQASEDLLKEHYVDLKDRPFFAGLVKYMHSGPVVAMVWEGLNVVK

TGRVMLGETNPADSKPGTIRGDFCIQVGRNIIHGGDSVESAEKEIGLWFHPEELVDYTSC

AQNWIYE describes NM23-H1 S120G mutant amino acid sequence (NM23-H1: GENBANK ACCESSION AF487339).

(SEQ ID NO: 18)

atggccaacctggagcgcaccttcatcgccatcaagccggacggcgtgcagcgcggcctggtgggcgagatcatcaag cgcttcgagcagaagggattccgcctcgtggccatgaagttcctccgggcctctgaagaacacctgaagcagcactacattgacctgaaag accgaccattcttccctgggctggtgaagtacatgaactcagggccggttgtggccatggtctgggaggggctgaacgtggtgaagacag gccgagtgatgcttggggagaccaatccagcagattcaaagccaggcaccattcgtggggacttctgcattcaggttggcaggaacatcat tcatggcagtgattcagtaaaaagtgctgaaaaagaaatcagcctatggtttaagcctgaagaactggttgactacaagtcttgtgctcatgac tgggtctatgaataa describes NM23-H2 nucleotide sequence (NM23-H2: GENBANK ACCESSION AK313448).

(SEQ ID NO: 19)

MANLERTFIAIKPDGVQRGLVGEIIKRFEQKGFRLVAMKFLRASEEHLKQHYI

DLKDRPFFPGLVKYMNSGPVVAMVWEGLNVVKTGRVMLGETNPADSKPGTIRGDFCIQ

VGRNIIHGSDSVKSAEKEISLWFKPEELVDYKSCAHDWVYE describes NM23-H2 amino acid sequence (NM23-H2: GENBANK ACCESSION AK313448).

Human NM23-H7-2 Sequence Optimized for *E. coli* Expression:

(DNA)

(SEQ ID NO: 20)

atgcatgacgttaaaaatcaccgtacctttctgaaacgcacgaaatatg ataatctgcatctggaagacctgtttattggcaacaaagtcaatgtgtt ctctcgtcagctggtgctgatcgattatggcgaccagtacaccgcgcgt caactgggtagtcgcaaagaaaaaacgctggccctgattaaaccggatg caatctccaaagctggcgaaattatcgaaattatcaacaaagcgggttt caccatcacgaaactgaaaatgatgatgctgagccgtaaagaagccctg gattttcatgtcgaccaccagtctcgcccgtttttcaatgaactgattc aattcatcaccacgggtccgattatcgcaatggaaattctgcgtgatga cgctatctgcgaatggaaacgcctgctgggcccggcaaactcaggtgtt gcgcgtaccgatgccagtgaatccattcgcgctctgtttggcaccgatg gtatccgtaatgcagcacatggtccggactcattcgcatcggcagctcg tgaaatggaactgtttttcccgagctctggcggttgcggtccggcaaac accgccaaatttaccaattgtacgtgctgtattgtcaaaccgcacgcag tgtcagaaggcctgctgggtaaaattctgatggcaatccgtgatgctgg ctttgaaatctcggccatgcagatgttcaacatggaccgcgttaacgtc gaagaattctacgaagtttacaaaggcgtggttaccgaatatcacgata tggttacggaaatgtactccggtccgtgcgtcgcgatggaaattcagca aaacaatgccaccaaaacgtttcgtgaattctgtggtccggcagatccg gaaatcgcacgtcatctgcgtccgggtaccctgcgcgcaatttttggta -continued aaacgaaaatccagaacgctgtgcactgtaccgatctgccggaagacgg tctgctggaagttcaatactttttcaaaattctggataattga (amino acids)

(SEQ ID NO: 21)

MHDVKNHRTFLKRTKYDNLHLEDLFIGNKVNVFSRQLVLIDYGDQYTAR

QLGSRKEKTLALIKPDAISKAGEIIEIINKAGFTITKLKMMMLSRKEAL

DFHVDHQSRPFFNELIQFITTGPIIAMEILRDDAICEWKRLLGPANSGV

ARTDASESIRALFGTDGIRNAAHGPDSFASAAREMELFFPSSGGCGPAN

TAKFTNCTCCIVKPHAVSEGLLGKILMAIRDAGFEISAMQMFNMDRVNV

EEFYEVYKGVVTEYHDMVTEMYSGPCVAMEIQQNNATKTFREFCGPADP

EIARHLRPGTLRAIFGKTKIQNAVHCTDLPEDGLLEVQYFFKILDN-

Human NME7-A:

(DNA)

(SEQ ID NO: 22)

atggaaaaaacgctagccctaattaaaccagatgcaatatcaaaggctg gagaaataattgaaataataaacaaagctggatttactataaccaaact caaaatgatgatgctttcaaggaaagaagcattggattttcatgtagat caccagtcaagacccttttttcaatgagctgatccagtttattacaactg gtcctattattgccatggagattttaagagatgatgctatatgtgaatg gaaaagactgctgggacctgcaaactctggagtggcacgcacagatgat ctgaaagcattagagccctattggaacagatggcataagaaatgcagcg catggccctgattcttttgcttctgcggccagagaaatggagttgtttt
tttga (amino acids)
(SEQ ID NO: 23)
MEKTLALIKPDAISKAGEIIEIINKAGFTITKLKMMMLSRKEALDFHVD
HQSRPFFNELIQFITTGPIIAMEILRDDAICEWKRLLGPANSGVARTDA
SESIRALFGTDGIRNAAHGPDSFASAAREMELFF- Human NME7-A1:

(DNA)
(SEQ ID NO: 24)
atggaaaaaacgctagccctaattaaaccagatgcaatatcaaaggctg
gagaaataattgaaataataaacaaagctggatttactataaccaaact
caaaatgatgatgctttcaaggaaagaagcattggattttcatgtagat
caccagtcaagaccctttttcaatgagctgatccagtttattacaactg
gtcctattattgccatggagattttaagagatgatgctatatgtgaatg
gaaaagactgctgggacctgcaaactctggagtggcacgcacagatgat
ctgaaagcattagagccctattggaacagatggcataagaaatgcagcg
catggccctgattatttgcttctgcggccagagaaatggagttgttttt
tccttcaagtggaggttgtgggccggcaaacactgctaaatttacttga (amino acids)
(SEQ ID NO: 25)
MEKTLALIKPDAISKAGEIIHINKAGFTITKLKMMMLSRKEALDFHVDH
QSRPFFNELIQFITTGPIIAMEILRDDAICEWKRLLGPANSGVARTDAS
ESIRALFGTDGIRNAAHGPDSFASAAREMELFFPSSGGCGPANTAKFT- Human NME7-A2:

(DNA)
(SEQ ID NO: 26)
atgaatcatagtgaaagattcgttttcattgcagagtggtatgatccaa
atgatcacttcttcgacgttatgagatttattttacccaggggatggat
ctgttgaaatgcatgatgtaaagaatcatcgcaccttttttaaagcggac
caaatatgataacctgcacttggaagatttatttataggcaacaaagtg
aatgtatttctcgacaactggtattaattgactatggggatcaatatac
agctcgccagctgggcagtaggaaagaaaaaacgctagccctaattaaa
ccagatgcaatatcaaaggctggagaaataattgaaataataaacaaag
ctggatttactataaccaaactcaaaatgatgatgctttcaaggaaaga
agcattggattttcatgtagatcaccagtcaagacccttttttcaatgag
ctgatccagtttattacaactggtcctattattgccatggagattttaa
gagatgatgctatatgtgaatggaaaagactgctgggacctgcaaactc
tggagtggcacgcacagatgcttctgaaagcattagagccctattggaa
cagatggcataagaaatgcagcgcatggccctgattcttttgcttctgc
ggccagagaaatggagttgtttttttga (amino acids)
(SEQ ID NO: 27)
MNHSERFVFIAEWYDPNASLLRRYELLFYPGDGSVEMHDVKNHRTFLKR TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFF- Human NME7-A3:

(DNA)
(SEQ ID NO: 28)
atgaatcatagtgaaagattcgttttcattgcagagtggtatgatccaa
atgcttcacttcttcgacgttatgagatttattttacccaggggatgga
tctgttgaaatgcatgatgtaaagaatcatcgcacctttttaaagcgga
ccaaatatgataacctgcacttggaagatttatttataggcaacaaagt
gaatgtatttctcgacaactggtattaattgactatggggatcaatata
cagctcgccagctgggcagtaggaaagaaaaaacgctagccctaattaa
accagatgcaatatcaaaggctggagaaataattgaaataataaacaaa
gctggatttactataaccaaactcaaaatgatgatgattcaaggaaaga
agcattggattttcatgtagatcaccagtcaagaccattttcaatgagc
tgatccagtttattacaactggtcctattattgccatggagattttaag
agatgatgctatatgtgaatggaaaagactgctgggacctgcaaactct
ggagtggcacgcacagatgatctgaaagcattagagccctattggaaca
gatggcataagaaatgcagcgcatggccctgattcttttgcttctgcgg
ccagagaaatggagttgtttttttccttcaagtggaggttgtgggccggc
aaacactgctaaatttacttga (amino acids)
(SEQ ID NO: 29)
MNHSERFVFIAEWYDPNASLLRRYELLFYPGDGSVEMHDVKNHRTFLKR
TKYDNLHLEDLFIGNKVNVFSRQLVLIDYGDQYTARQLGSRKEKTLALI
KPDAISKAGEIIEIINKAGFTITKLKMMMLSRKEALDFHVDHQSRPFFN
ELIQFITTGPIIAMEILRDDAICEWKRLLGPANSGVARTDASESIRALF
GTDGIRNAAHGPDSFASAAREMELFFPSSGGCGPANTAKFT- Human NME7-B:

(DNA)
(SEQ ID NO: 30)
atgaattgtacctgttgcattgttaaaccccatgctgtcagtgaaggac
tgttgggaaagatcctgatggctatccgagatgcaggttttgaaatctc
agctatgcagatgttcaatatggatcgggttaatgttgaggaattctat
gaagtttataaaggagtagtgaccgaatatcatgacatggtgacagaaa
tgtattctggccccttgtgtagcaatggagattcaacagaataatgctac
aaagacatttcgagaattttgtggacctgctgatcctgaaattgcccgg
catttacgccctggaactctcagagcaatctttggtaaaactaagatcc
agaatgctgttcactgtactgatctgccagaggatggcctattagaggt
tcaatacttcttctga -continued (amino acids)

(SEQ ID NO: 31)

MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIAR

HLRPGTLRAIFGKTKIQNAVHCTDLPEDGLLEVQYFF-

Human NME7-B1:

(DNA)

(SEQ ID NO: 32)

atgaattgtacctgttgcattgttaaaccccatgctgtcagtgaaggac tgttgggaaagatcctgatggctatccgagatgcaggttttgaaatctc agctatgcagatgttcaatatggatcgggttaatgttgaggaattctat gaagtttataaaggagtagtgaccgaatatcatgacatggtgacagaaa tgtattctggcccttgtgtagcaatggagattcaacagaataatgctac aaagacatttcgagaattttgtggacctgctgatcctgaaattgcccgg catttacgccctggaactctcagagcaatctttggtaaaactaagatcc agaatgctgttcactgtactgatctgccagaggatggcctattagaggt tcaatacttcttcaagatcttggataattagtga (amino acids)

(SEQ ID NO: 33)

MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIAR

HLRPGTLRAIFGKTKIQNAVHCTDLPEDGLLEVQYFFKILDN-

Human NME7-B2:

(DNA)

(SEQ ID NO: 34)

atgccttcaagtggaggttgtgggccggcaaacactgctaaatttacta attgtacctgttgcattgttaaaccccatgctgtcagtgaaggactgtt gggaaagatcctgatggctatccgagatgcaggttttgaaatctcagct atgcagatgttcaatatggatcgggttaatgttgaggaattctatgaag tttataaaggagtagtgaccgaatatcatgacatggtgacagaaatgta ttctggcccttgtgtagcaatggagattcaacagaataatgctacaaag acatttcgagaattttgtggacctgctgatcctgaaattgcccggcatt tacgccctggaactctcagagcaatctttggtaaaactaagatccagaa tgctgttcactgtactgatctgccagaggatggcctattagaggttcaa tacttcttctga (amino acids)

(SEQ ID NO: 35)

MPSSGGCGPANTAKFTNCTCCIVKPHAVSEGLLGKILMAIRDAGFEISA

MQMFNMDRVNVEEFYEVYKGVVTEYHDMVTEMYSGPCVAMEIQQNNATK

TFREFCGPADPEIARHLRPGTLRAIFGKTKIQNAVHCTDLPEDGLLEVQ

YFF-

Human NME7-B3:

(DNA)

(SEQ ID NO: 36)

atgccttcaagtggaggttgtgggccggcaaacactgctaaatttacta attgtacctgttgcattgttaaaccccatgctgtcagtgaaggactgtt gggaaagatcctgatggctatccgagatgcaggttttgaaatctcagct atgcagatgttcaatatggatcgggttaatgttgaggaattctatgaag tttataaaggagtagtgaccgaatatcatgacatggtgacagaaatgta ttctggcccttgtgtagcaatggagattcaacagaataatgctacaaag acatttcgagaattttgtggacctgctgatcctgaaattgcccggcatt tacgccctggaactctcagagcaatctttggtaaaactaagatccagaa tgctgttcactgtactgatctgccagaggatggcctattagaggttcaa tacttcttcaagatcttggataattagtga (amino acids)

(SEQ ID NO: 37)

MPSSGGCGPANTAKFTNCTCCIVKPHAVSEGLLGKILMAIRDAGFEISA

MQMFNMDRVNVEEFYEVYKGVVTEYHDMVTEMYSGPCVAMEIQQNNATK

TFREFCGPADPEIARHLRPGTLRAIFGKTKIQNAVHCTDLPEDGLLEVQ

YFFKILDN--

Human NME7-AB:

(DNA)

(SEQ ID NO: 38)

atggaaaaaacgctagccctaattaaaccagatgcaatatcaaaggctg gagaaataattgaaataataaacaaagctggatttactataaccaaact caaaatgatgatgctttcaaggaaagaagcattggattttcatgtagat caccagtcaagaccctttttcaatgagctgatccagtttattacaactg gtcctattattgccatggagattttaagagatgatgctatatgtgaatg gaaaagactgctgggacctgcaaactctggagtggcacgcacagatgct tctgaaagcattagagccctctttggaacagatggcataagaaatgcag cgcatggccctgattcttttgcttctgcggccagagaaatggagttgtt ttttccttcaagtggaggttgtgggccggcaaacactgctaaatttact aattgtacctgttgcattgttaaaccccatgctgtcagtgaaggactgt tgggaaagatcctgatggctatccgagatgcaggttttgaaatctcagc tatgcagatgttcaatatggatcgggttaatgttgaggaattctatgaa gtttataaaggagtagtgaccgaatatcatgacatggtgacagaaatgt attctggcccttgtgtagcaatggagattcaacagaataatgctacaaa gacatttcgagaattttgtggacctgctgatcctgaaattgcccggcat ttacgccctggaactctcagagcaatctttggtaaaactaagatccaga atgctgttcactgtactgatctgccagaggatggcctattagaggttca atacttcttcaagatcttggataattagtga (amino acids)

(SEQ ID NO: 39)

MEKTLALIKPDAISKAGEIIEIINKAGFTITKLKMMMLSRKEALDFHVD

HQSRPFFNELIQFITTGPIIAMEILRDDAICEWKRLLGPANSGVARTDA

-continued

SESIRALFGTDGIRNAAHGPDSFASAAREMELFFPSSGGCGPANTAKFT

NCTCCIVKPHAVSEGLLGKILMAIRDAGFEISAMQMFNMDRVNVEEFYE

VYKGVVTEYHDMVTEMYSGPCVAMEIQQNNATKTFREFCGPADPEIARH

LRPGTLRAIFGKTKIQNAVHCTDLPEDGLLEVQYFFKILDN--

Human NME7-AB1:

(DNA)

(SEQ ID NO: 40)

atggaaaaaacgctagccctaattaaaccagatgcaatatcaaaggctg gagaaataattgaaataataaacaaagctggatttactataaccaaact caaaatgatgatgctttcaaggaaagaagcattggattttcatgtagat caccagtcaagacccttttttcaatgagctgatccagtttattacaactg gtcctattattgccatggagattttaagagatgatgctatatgtgaatg gaaaagactgctgggacctgcaaactctggagtggcacgcacagatgat ctgaaagcattagagccctattggaacagatggcataagaaatgcagcg catggccctgattcttttgcttctgcggccagagaaatggagttgtttt ttccttcaagtggaggttgtgggccggcaaacactgctaaatttactaa ttgtacctgttgcattgttaaaccccatgctgtcagtgaaggactgttg ggaaagatcctgatggctatccgagatgcaggttttgaaatctcagcta tgcagatgttcaatatggatcgggttaatgttgaggaattctatgaagt ttataaaggagtagtgaccgaatatcatgacatggtgacagaaatgtat tctggcccttgtgtagcaatggagattcaacagaataatgctacaaaga catttcgagaattttgtggacctgctgatcctgaaattgcccggcattt acgccctggaactctcagagcaatctttggtaaaactaagatccagaat gctgttcactgtactgatctgccagaggatggcctattagaggttcaat acttcttctga (amino acids)

(SEQ ID NO: 41)

MEKTLALIKPDAISKAGEIIEIINKAGFTITKLKMMMLSRKEALDFHVD

HQSRPFFNELIQFITTGPIIAMEILRDDAICEWKRLLGPANSGVARTDA

SESIRALFGTDGIRNAAHGPDSFASAAREMELFFPSSGGCGPANTAKFT

NCTCCIVKPHAVSEGLLGKILMAIRDAGFEISAMQMFNMDRVNVEEFYE

VYKGVVTEYHDMVTEMYSGPCVAMEIQQNNATKTFREFCGPADPEIARH

LRPGTLRAIFGKTKIQNAVHCTDLPEDGLLEVQYFF-

Human NME7-A Sequence Optimized for *E. coli* Expression:

(DNA)

(SEQ ID NO: 42)

atggaaaaaacgctggccctgattaaaccggatgcaatctccaaagctg gcgaaattatcgaaattatcaacaaagcgggtttcaccatcacgaaact gaaaatgatgatgctgagccgtaaagaagccctggattttcatgtcgac caccagtctcgcccgtttttcaatgaactgattcaattcatcaccacgg gtccgattatcgcaatggaaattctgcgtgatgacgctatctgcgaatg -continued gaaacgcctgctgggcccggcaaactcaggtgttgcgcgtaccgatgcc agtgaatccattcgcgctctgtttggcaccgatggtatccgtaatgcag cacatggtccggactcattcgcatcggcagctcgtgaaatggaactgtt tttctga (amino acids)

(SEQ ID NO: 43)

MEKTLALIKPDAISKAGEIIHINKAGFTITKLKMMMLSRKEALDFHVDH

QSRPFFNELIQFITTGPIIAMEILRDDAICEWKRLLGPANSGVARTDAS

ESIRALFGTDGIRNAAHGPDSFASAAREMELFF-

Human NME7-A1 Sequence Optimized for *E. coli* Expression:

(DNA)

(SEQ ID NO: 44)

atggaaaaaacgctggccctgattaaaccggatgcaatctccaaagctgg cgaaattatcgaaattatcaacaaagcgggtttcaccatcacgaaactga aaatgatgatgctgagccgtaaagaagccctggattttcatgtcgaccac cagtctcgcccgtttttcaatgaactgattcaattcatcaccacgggtcc gattatcgcaatggaaattctgcgtgatgacgctatctgcgaatggaaac gcctgctgggcccggcaaactcaggtgttgcgcgtaccgatgccagtgaa tccattcgcgctctgtttggcaccgatggtatccgtaatgcagcacatgg tccggactcattcgcatcggcagctcgtgaaatggaactgtttttcccga gctctggcggttgcggtccggcaaacaccgccaaatttacctga (amino acids)

(SEQ ID NO: 45)

MEKTLALIKPDAISKAGEHEIINKAGFTITKLKMMMLSRKEALDFHVDHQ

SRPFFNELIQFITTGPIIAMEILRDDAICEWKRLLGPANSGVARTDASES

IRALFGTDGIRNAAHGPDSFASAAREMELFFPSSGGCGPANTAKFT-

Human NME7-A2 Sequence Optimized for *E. coli* Expression:

(DNA)

(SEQ ID NO: 46)

atgaatcactccgaacgctttgtttttatcgccgaatggtatgacccgaa tgatccctgctgcgccgctacgaactgctgttttatccgggcgatggtag cgtggaaatgcatgacgttaaaaatcaccgtacctttctgaaacgcacga aatatgataatctgcatctggaagacctgtttattggcaacaaagtcaat gtgttctctcgtcagctggtgctgatcgattatggcgaccagtacaccgc gcgtcaactgggtagtcgcaaagaaaaaacgctggccctgattaaaccgg atgcaatctccaaagctggcgaaattatcgaaattatcaacaaagcgggt ttcaccatcacgaaactgaaaatgatgatgctgagccgtaaagaagccct ggattttcatgtcgaccaccagtctcgcccgtttttcaatgaactgattc aattcatcaccacgggtccgattatcgcaatggaaattctgcgtgatgac gctatctgcgaatggaaacgcctgctgggcccggcaaactcaggtgttgc gcgtaccgatgccagtgaatccattcgcgctctgtttggcaccgatggta -continued tccgtaatgcagcacatggtccggactcattcgcatcggcagctcgtgaa atggaactgtttttctga (amino acids)

(SEQ ID NO: 47)

MNHSERFVFIAEWYDPNASLLRRYELLFYPGDGSVEMHDVKNHRTFLKRT

KYDNLHLEDLFIGNKVNVFSRQLVLIDYGDQYTARQLGSRKEKTLALIKP

DAISKAGEIIEIINKAGFTITKLKMMMLSRKEALDFHVDHQSRPFFNELI

QFITTGPIIAMEILRDDAICEWKRLLGPANSGVARTDASESIRALFGTDG

IRNAAHGPDSFASAAREMELFF-

Human NME7-A3 Sequence Optimized for *E. coli* Expression:

(DNA)

(SEQ ID NO: 48)

atgaatcactccgaacgctttgtttttatcgccgaatggtatgacccga atgatccctgctgcgccgctacgaactgctgttttatccgggcgatggt agcgtggaaatgcatgacgttaaaaatcaccgtacctttctgaaacgca cgaaatatgataatctgcatctggaagacctgtttattggcaacaaagt caatgtgttctctcgtcagctggtgctgatcgattatggcgaccagtac accgcgcgtcaactgggtagtcgcaaagaaaaaacgctggccctgatta aaccggatgcaatctccaaagctggcgaaattatcgaaattatcaacaa agcgggtttcaccatcacgaaactgaaaatgatgatgctgagccgtaaa gaagccctggattttcatgtcgaccaccagtctcgcccgtttttcaatg aactgattcaattcatcaccacgggtccgattatcgcaatggaaattct gcgtgatgacgctatctgcgaatggaaacgcctgctgggcccggcaaac tcaggtgttgcgcgtaccgatgccagtgaatccattcgcgctctgtttg gcaccgatggtatccgtaatgcagcacatggtccggactcattcgcatc ggcagctcgtgaaatggaactgtttttcccgagctctggcggttgcggt ccggcaaacaccgccaaatttacctga (amino acids)

(SEQ ID NO: 49)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALI

KPDAISKAGEIIEIINKAGFTITKLKMMMLSRKEALDFHVDHQSRPFFN

ELIQFITTGPIIAMEILRDDAICEWKRLLGPANSGVARTDASESIRALF

GTDGIRNAAHGPDSFASAAREMELFFPSSGGCGPANTAKFT-

Human NME7-B Sequence Optimized for *E. coli* Expression:

(DNA)

(SEQ ID NO: 50)

atgaattgtacgtgctgtattgtcaaaccgcacgcagtgtcagaaggcc tgctgggtaaaattctgatggcaatccgtgatgctggattgaaatctcg gccatgcagatgttcaacatggaccgcgttaacgtcgaagaattctacg aagtttacaaaggcgtggttaccgaatatcacgatatggttacggaaat -continued gtactccggtccgtgcgtcgcgatggaaattcagcaaaacaatgccacc aaaacgtttcgtgaattctgtggtccggcagatccggaaatcgcacgtc atctgcgtccgggtaccctgcgcgcaatttttggtaaaacgaaaatcca gaacgctgtgcactgtaccgatctgccggaagacggtctgctggaagtt caatactttttctga (amino acids)

(SEQ ID NO: 51)

MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIAR

HLRPGTLRAIFGKTKIQNAVHCTDLPEDGLLEVQYFF-

Human NME7-B1 Sequence Optimized for *E. coli* Expression:

(DNA)

(SEQ ID NO: 52)

atgaattgtacgtgctgtattgtcaaaccgcacgcagtgtcagaaggcc tgctgggtaaaattctgatggcaatccgtgatgctggctttgaaatctc ggccatgcagatgttcaacatggaccgcgttaacgtcgaagaattctac gaagtttacaaaggcgtggttaccgaatatcacgatatggttacggaaa tgtactccggtccgtgcgtcgcgatggaaattcagcaaaacaatgccac caaaacgtttcgtgaattctgtggtccggcagatccggaaatcgcacgt catctgcgtccgggtaccctgcgcgcaatttttggtaaaacgaaaatcc agaacgctgtgcactgtaccgatctgccggaagacggtctgctggaagt tcaatactttttcaaaattctggataattga (amino acids)

(SEQ ID NO: 53)

MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIAR

HLRPGTLRAIFGKTKIQNAVHCTDLPEDGLLEVQYFFKILDN-

Human NME7-B2 Sequence Optimized for *E. coli* Expression:

(DNA)

(SEQ ID NO: 54)

atgccgagctctggcggttgcggtccggcaaacaccgccaaatttacca attgtacgtgctgtattgtcaaaccgcacgcagtgtcagaaggcctgct gggtaaaattctgatggcaatccgtgatgctggctttgaaatctcggcc atgcagatgttcaacatggaccgcgttaacgtcgaagaattctacgaag tttacaaaggcgtggttaccgaatatcacgatatggttacggaaatgta ctccggtccgtgcgtcgcgatggaaattcagcaaaacaatgccaccaaa acgtttcgtgaattctgtggtccggcagatccggaaatcgcacgtcatc tgcgtccgggtaccctgcgcgcaatttttggtaaaacgaaaatccagaa cgctgtgcactgtaccgatctgccggaagacggtctgctggaagttcaa tactttttctga (amino acids)

(SEQ ID NO: 55)

MPSSGGCGPANTAKFTNCTCCIVKPHAVSEGLLGKILMAIRDAGFEISA

-continued

MQMFNMDRVNVEEFYEVYKGVVTEYHDMVTEMYSGPCVAMEIQQNNATK

TFREFCGPADPEIARHLRPGTLRAIFGKTKIQNAVHCTDLPEDGLLEVQ

YFF-

Human NME7-B3 Sequence Optimized for *E. coli* Expression:

(DNA)

(SEQ ID NO: 56)

atgccgagctctggcggttgcggtccggcaaacaccgccaaatttacca attgtacgtgctgtattgtcaaaccgcacgcagtgtcagaaggcctgct gggtaaaattctgatggcaatccgtgatgctggctttgaaatctcggcc atgcagatgttcaacatggaccgcgttaacgtcgaagaattctacgaag tttacaaaggcgtggttaccgaatatcacgatatggttacggaaatgta ctccggtccgtgcgtcgcgatggaaattcagcaaaacaatgccaccaaa acgtttcgtgaattctgtggtccggcagatccggaaatcgcacgtcatc tgcgtccgggtaccctgcgcgcaatttttggtaaaacgaaaatccagaa cgctgtgcactgtaccgatctgccggaagacggtctgctggaagttcaa tactttttcaaaattctggataattga (amino acids)

(SEQ ID NO: 57)

MPSSGGCGPANTAKFTNCTCCIVKPHAVSEGLLGKILMAIRDAGFEISA

MQMFNMDRVNVEEFYEVYKGVVTEYHDMVTEMYSGPCVAMEIQQNNATK

TFREFCGPADPEIARHLRPGTLRAIFGKTKIQNAVHCTDLPEDGLLEVQ

YFFKILDN-

Human NME7-AB Sequence Optimized for *E. coli* Expression:

(DNA)

(SEQ ID NO: 58)

atggaaaaaacgctggccctgattaaaccggatgcaatctccaaagctg gcgaaattatcgaaattatcaacaaagcgggtttcaccatcacgaaact gaaaatgatgatgctgagccgtaaagaagccctggattttcatgtcgac caccagtctcgcccgtttttcaatgaactgattcaattcatcaccacgg gtccgattatcgcaatggaaattctgcgtgatgacgctatctgcgaatg gaaacgcctgctgggcccggcaaactcaggtgttgcgcgtaccgatgcc agtgaatccattcgcgctctgtttggcaccgatggtatccgtaatgcag cacatggtccggactcattcgcatcggcagctcgtgaaatggaactgtt tttcccgagctctggcggttgcggtccggcaaacaccgccaaatttacc aattgtacgtgctgtattgtcaaaccgcacgcagtgtcagaaggcctgc tgggtaaaattctgatggcaatccgtgatgctggctttgaaatctcggc catgcagatgttcaacatggaccgcgttaacgtcgaagaattctacgaa gtttacaaaggcgtggttaccgaatatcacgatatggttacggaaatgt actccggtccgtgcgtcgcgatggaaattcagcaaaacaatgccaccaa aacgtttcgtgaattctgtggtccggcagatccggaaatcgcacgtcat -continued ctgcgtccgggtaccctgcgcgcaatttttggtaaaacgaaaatccaga acgctgtgcactgtaccgatctgccggaagacggtctgctggaagttca atactttttcaaaattctggataattga (amino acids)

(SEQ ID NO: 59)

MEKTLALIKPDAISKAGEIIEIINKAGFTITKLKMMMLSRKEALDFHVD

HQSRPFFNELIQFITTGPIIAMEILRDDAICEWKRLLGPANSGVARTDA

SESIRALFGTDGIRNAAHGPDSFASAAREMELFFPSSGGCGPANTAKFT

NCTCCIVKPHAVSEGLLGKILMAIRDAGFEISAMQMFNMDRVNVEEFYE

VYKGVVTEYHDMVTEMYSGPCVAMEIQQNNATKTFREFCGPADPEIARH

LRPGTLRAIFGKTKIQNAVHCTDLPEDGLLEVQYFFKILDN-

Human NME7-AB1 Sequence Optimized for *E. coli* Expression:

(DNA)

(SEQ ID NO: 60)

Atggaaaaaacgctggccctgattaaaccggatgcaatctccaaagctg gcgaaattatcgaaattatcaacaaagcgggtttcaccatcacgaaact gaaaatgatgatgctgagccgtaaagaagccctggattttcatgtcgac caccagtctcgcccgtttttcaatgaactgattcaattcatcaccacgg gtccgattatcgcaatggaaattctgcgtgatgacgctatctgcgaatg gaaacgcctgctgggcccggcaaactcaggtgttgcgcgtaccgatgcc agtgaatccattcgcgctctgtttggcaccgatggtatccgtaatgcag cacatggtccggactcattcgcatcggcagctcgtgaaatggaactgtt tttcccgagctctggcggttgcggtccggcaaacaccgccaaatttacc aattgtacgtgctgtattgtcaaaccgcacgcagtgtcagaaggcctgc tgggtaaaattctgatggcaatccgtgatgctggctttgaaatctcggc catgcagatgttcaacatggaccgcgttaacgtcgaagaattctacgaa gtttacaaaggcgtggttaccgaatatcacgatatggttacggaaatgt actccggtccgtgcgtcgcgatggaaattcagcaaaacaatgccaccaa aacgtttcgtgaattctgtggtccggcagatccggaaatcgcacgtcat ctgcgtccgggtaccctgcgcgcaatttttggtaaaacgaaaatccaga acgctgtgcactgtaccgatctgccggaagacggtctgctggaagttca atactttttctga (amino acids)

(SEQ ID NO: 61)

MEKTLALIKPDAISKAGEIIEIINKAGFTITKLKMMMLSRKEALDFHVD

HQSRPFFNELIQFITTGPIIAMEILRDDAICEWKRLLGPANSGVARTDA

SESIRALFGTDGIRNAAHGPDSFASAAREMELFFPSSGGCGPANTAKFT

NCTCCIVKPHAVSEGLLGKILMAIRDAGFEISAMQMFNMDRVNVEEFYE

VYKGVVTEYHDMVTEMYSGPCVAMEIQQNNATKTFREFCGPADPEIARH

LRPGTLRAIFGKTKIQNAVHCTDLPEDGLLEVQYFF-

Mouse NME6

(DNA)

(SEQ ID NO: 62)

Atgacctccatcttgcgaagtccccaagctcttcagctcacactagccc

-continued tgatcaagcctgatgcagttgcccacccactgatcctggaggctgttca
tcagcagattctgagcaacaagttcctcattgtacgaacgagggaactg
cagtggaagctggaggactgccggaggttttaccgagagcatgaagggc
gtttttttctatcagcggctggtggagttcatgacaagtgggccaatccg
agcctatatccttgcccacaaagatgccatccaactttggaggacactg
atgggacccaccagagtatttcgagcacgctatatagccccagattcaa
ttcgtggaagtttgggcctcactgacacccgaaatactacccatggctc
agactccgtggtttccgccagcagagagattgcagccttcttccctgac
ttcagtgaacagcgctggtatgaggaggaggaaccccagctgcggtgtg
gtcctgtgcactacagtccagaggaaggtatccactgtgcagctgaaac
aggaggccacaaacaacctaacaaaacctag (amino acids)
(SEQ ID NO: 63)
MTSILRSPQALQLTLALIKPDAVAHPLILEAVHQQILSNKFLIVRTREL
QWKLEDCRRFYREHEGRFFYQRLVEFMTSGPIRAYILAHKDAIQLWRTL
MGPTRVFRARYIAPDSIRGSLGLTDTRNTTHGSDSVVSASREIAAFFPD
FSEQRWYEEEEPQLRCGPVHYSPEEGIHCAAETGGHKQPNKT- Human NME6:

(DNA)
(SEQ ID NO: 64)
Atgacccagaatctggggagtgagatggcctcaatcttgcgaagccctc
aggctctccagctcactctagccctgatcaagcctgacgcagtcgccca
tccactgattctggaggctgttcatcagcagattctaagcaacaagttc
ctgattgtacgaatgagagaactactgtggagaaaggaagattgccaga
ggttttaccgagagcatgaagggcgtttttttctatcagaggctggtgga
gttcatggccagcgggccaatccgagcctacatccttgcccacaaggat
gccatccagctctggaggacgctcatgggacccaccagagtgttccgag
cacgccatgtggccccagattctatccgtgggagtttcggcctcactga
cacccgcaacaccacccatggttcggactctgtggtttcagccagcaga
gagattgcagccttcttccctgacttcagtgaacagcgctggtatgagg
aggaagagccccagttgcgctgtggccctgtgtgctatagcccagaggg
aggtgtccactatgtagctggaacaggaggcctaggaccagcctga (amino acids)
(SEQ ID NO: 65)
MTQNLGSEMASILRSPQALQLTLALIKPDAVAHPLILEAVHQQILSNKF
LIVRMRELLWRKEDCQRFYREHEGRFFYQRLVEFMASGPIRAYILAHKD
AIQLWRTLMGPTRVFRARHVAPDSIRGSFGLTDTRNTTHGSDSVVSASR
EIAAFFPDFSEQRWYEEEEPQLRCGPVCYSPEGGVHYVAGTGGLGPA- Human NME6 1:

(DNA)
(SEQ ID NO: 66)
Atgacccagaatctggggagtgagatggcctcaatcttgcgaagccctc
aggctctccagctcactctagccctgatcaagcctgacgcagtcgccca
tccactgattctggaggctgttcatcagcagattctaagcaacaagttc
ctgattgtacgaatgagagaactactgtggagaaaggaagattgccaga
ggttttaccgagagcatgaagggcgtttttttctatcagaggctggtgga
gttcatggccagcgggccaatccgagcctacatccttgcccacaaggat
gccatccagctctggaggacgctcatgggacccaccagagtgttccgag
cacgccatgtggccccagattctatccgtgggagtttcggcctcactga
cacccgcaacaccacccatggttcggactctgtggtttcagccagcaga
gagattgcagccttcttccctgacttcagtgaacagcgctggtatgagg
aggaagagccccagttgcgctgtggccctgtgtga (amino acids)
(SEQ ID NO: 67)
MTQNLGSEMASILRSPQALQLTLALIKPDAVAHPLILEAVHQQILSNKF
LIVRMRELLWRKEDCQRFYREHEGRFFYQRLVEFMASGPIRAYILAHKD
AIQLWRTLMGPTRVFRARHVAPDSIRGSFGLTDTRNTTHGSDSVVSASR
EIAAFFPDFSEQRWYEEEEPQLRCGPV- Human NME6 2:

(DNA)
(SEQ ID NO: 68)
Atgctcactctagccctgatcaagcctgacgcagtcgcccatccactga
ttctggaggctgttcatcagcagattctaagcaacaagttcctgattgt
acgaatgagagaactactgtggagaaaggaagattgccagaggttttac
cgagagcatgaagggcgtttttttctatcagaggctggtggagttcatgg
ccagcgggccaatccgagcctacatccttgcccacaaggatgccatcca
gctctggaggacgctcatgggacccaccagagtgttccgagcacgccat
gtggccccagattctatccgtgggagtttcggcctcactgacacccgca
acaccacccatggttcggactctgtggtttcagccagcagagagattgc
agccttcttccctgacttcagtgaacagcgctggtatgaggaggaagag
ccccagttgcgctgtggccctgtgtga (amino acids)
(SEQ ID NO: 69)
MLTLALIKPDAVAHPLILEAVHQQILSNKFLIVRMRELLWRKEDCQRFY
REHEGRFFYQRLVEFMASGPIRAYILAHKDAIQLWRTLMGPTRVFRARH
VAPDSIRGSFGLTDTRNTTHGSDSVVSASREIAAFFPDFSEQRWYEEEE
PQLRCGPV- Human NME6 3:

(DNA)
(SEQ ID NO: 70)
Atgctcactctagccctgatcaagcctgacgcagtcgcccatccactga
ttctggaggctgttcatcagcagattctaagcaacaagttcctgattgt
acgaatgagagaactactgtggagaaaggaagattgccagaggttttac
cgagagcatgaagggcgtttttttctatcagaggctggtggagttcatgg
ccagcgggccaatccgagcctacatccttgcccacaaggatgccatcca
gctctggaggacgctcatgggacccaccagagtgttccgagcacgccat gtggccccagattctatccgtgggagtttcggcctcactgacacccgca acaccacccatggttcggactctgtggtttcagccagcagagagattgc agccttcttccctgacttcagtgaacagcgctggtatgaggaggaagag ccccagttgcgctgtggccctgtgtgctatagcccagagggaggtgtcc actatgtagctggaacaggaggcctaggaccagcctga (amino acids)

(SEQ ID NO: 71)

MLTLALIKPDAVAHPLILEAVHQQILSNKFLIVRMRELLWRKEDCQRFY

REHEGRFFYQRLVEFMASGPIRAYILAHKDAIQLWRTLMGPTRVFRARH

VAPDSIRGSFGLTDTRNTTHGSDSVVSASREIAAFFPDFSEQRWYEEEE

PQLRCGPVCYSPEGGVHYVAGTGGLGPA-

Human NME6 Sequence Optimized for *E. coli* Expression:

(DNA)

(SEQ ID NO: 72)

Atgacgcaaaatctgggctcggaaatggcaagtatcctgcgctccccgc aagcactgcaactgaccctggctctgatcaaaccggacgctgttgctca tccgctgattctggaagcggtccaccagcaaattctgagcaacaaattt ctgatcgtgcgtatgcgcgaactgctgtggcgtaaagaagattgccagc gtttttatcgcgaacatgaaggccgtttcttttatcaacgcctggttga attcatggcctctggtccgattcgcgcatatatcctggctcacaaagat gcgattcagctgtggcgtaccctgatgggtccgacgcgcgtctttcgtg cacgtcatgtggcaccggactcaatccgtggctcgttcggtctgaccga tacgcgcaataccacgcacggtagcgactctgttgttagtgcgtcccgt gaaatcgcggcctttttcccggacttctccgaacagcgttggtacgaag aagaagaaccgcaactgcgctgtggcccggtctgttattctccggaagg tggtgtccattatgtggcgggcacgggtggtctgggtccggcatga (amino acids)

(SEQ ID NO: 73)

MTQNLGSEMASILRSPQALQLTLALIKPDAVAHPLILEAVHQQILSNKF

LIVRMRELLWRKEDCQRFYREHEGRFFYQRLVEFMASGPIRAYILAHKD

AIQLWRTLMGPTRVFRARHVAPDSIRGSFGLTDTRNTTHGSDSVVSASR

EIAAFFPDFSEQRWYEEEEPQLRCGPVCYSPEGGVHYVAGTGGLGPA-

Human NME6 1 Sequence Optimized for *E. coli* Expression:

(DNA)

(SEQ ID NO: 74)

Atgacgcaaaatctgggctcggaaatggcaagtatcctgcgctccccgc aagcactgcaactgaccctggctctgatcaaaccggacgctgttgctca tccgctgattctggaagcggtccaccagcaaattctgagcaacaaattt ctgatcgtgcgtatgcgcgaactgctgtggcgtaaagaagattgccagc gtttttatcgcgaacatgaaggccgtttcttttatcaacgcctggttga attcatggcctctggtccgattcgcgcatatatcctggctcacaaagat gcgattcagctgtggcgtaccctgatgggtccgacgcgcgtctttcgtg cacgtcatgtggcaccggactcaatccgtggctcgttcggtctgaccga tacgcgcaataccacgcacggtagcgactctgttgttagtgcgtcccgt gaaatcgcggcctttttcccggacttctccgaacagcgttggtacgaag aagaagaaccgcaactgcgctgtggcccggtctga (amino acids)

(SEQ ID NO: 75)

MTQNLGSEMASILRSPQALQLTLALIKPDAVAHPLILEAVHQQILSNKF

LIVRMRELLWRKEDCQRFYREHEGRFFYQRLVEFMASGPIRAYILAHKD

AIQLWRTLMGPTRVFRARHVAPDSIRGSFGLTDTRNTTHGSDSVVSASR

EIAAFFPDFSEQRWYEEEEPQLRCGPV-

Human NME6 2 Sequence Optimized for *E. coli* Expression:

(DNA)

(SEQ ID NO: 76)

Atgctgaccctggctctgatcaaaccggacgctgttgctcatccgctga ttctggaagcggtccaccagcaaattctgagcaacaaatttctgatcgt gcgtatgcgcgaactgctgtggcgtaaagaagattgccagcgtttttat cgcgaacatgaaggccgtttcttttatcaacgcctggttgaattcatgg cctctggtccgattcgcgcatatatcctggctcacaaagatgcgattca gctgtggcgtaccctgatgggtccgacgcgcgtctttcgtgcacgtcat gtggcaccggactcaatccgtggctcgttcggtctgaccgatacgcgca ataccacgcacggtagcgactctgttgttagtgcgtcccgtgaaatcgc ggcctttttcccggacttctccgaacagcgttggtacgaagaagaagaa ccgcaactgcgctgtggcccggtctga (amino acids)

(SEQ ID NO: 77)

MLTLALIKPDAVAHPLILEAVHQQILSNKFLIVRMRELLWRKEDCQRFY

REHEGRFFYQRLVEFMASGPIRAYILAHKDAIQLWRTLMGPTRVFRARH

VAPDSIRGSFGLTDTRNTTHGSDSVVSASREIAAFFPDFSEQRWYEEEE

PQLRCGPV-

Human NME6 3 Sequence Optimized for *E. coli* Expression:

(DNA)

(SEQ ID NO: 78)

Atgctgaccctggctctgatcaaaccggacgctgttgctcatccgctgattctggaagcggtccaccagcaaattctgagc aacaaatttctgatcgtgcgtatgcgcgaactgctgtggcgtaaagaagattgccagcgtttttatcgcgaacatgaaggccgtttcttttatca acgcctggttgaattcatggcctctggtccgattcgcgcatatatcctggctcacaaagatgcgattcagctgtggcgtaccctgatgggtcc -continued gacgcgcgtctttcgtgcacgtcatgtggcaccggactcaatccgtggctcgttcggtctgaccgatacgcgcaataccacgcacggtagc gactctgttgttagtgcgtcccgtgaaatcgcggcctttttcccggacttctccgaacagcgttggtacgaagaagaagaaccgcaactgcg ctgtggcccggtctgttattctccggaaggtggtgtccattatgtggcgggcacgggtggtctgggtccggcatga (amino acids)

(SEQ ID NO: 79)

MLTLALIKPDAVAHPLILEAVHQQILSNKFLIVRMRELLWRKEDCQRFYREHE

GRFFYQRLVEFMASGPIRAYILAHKDAIQLWRTLMGPTRVFRARHVAPDSIRGSFGLTDT

RNTTHGSDSVVSASREIAAFFPDFSEQRWYEEEEPQLRCGPVCYSPEGGVHYVAGTGGL

GPA-

OriGene-NME7-1 full length
(DNA)

(SEQ ID NO: 80)

gacgttgtatacgactcctatagggcggccgggaattcgtcgactggatccggtaccgaggagatctgccgccgcgatcg ccatgaatcatagtgaaagattcgttttcattgcagagtggtatgatccaaatgcttcacttcttcgacgttatgagcttttattttacccaggggat ggatctgttgaaatgcatgatgtaaagaatcatcgcacctttttaaagcggaccaaatatgataacctgcacttggaagatttatttataggcaa caaagtgaatgtcttctctcgacaactggtattaattgactatggggatcaatatacagctcgccagctgggcagtaggaaagaaaaaacgct agccctaattaaaccagatgcaatatcaaaggctggagaaataattgaaataataaacaaagctggatttactataaccaaactcaaaatgat gatgctttcaaggaaagaagcattggattttcatgtagatcaccagtcaagacccttttttcaatgagctgatccagtttattacaactggtcctatt attgccatggagattttaagagatgatgctatatgtgaatggaaaagactgctgggacctgcaaactctggagtggcacgcacagatgcttct gaaagcattagagccctctttggaacagatggcataagaaatgcagcgcatggccctgattcttttgcttctgcggccagagaaatggagttg tttttccttcaagtggaggttgtgggccggcaaacactgctaaatttactaattgtacctgttgcattgttaaaccccatgctgtcagtgaaggac tgttgggaaagatcctgatggctatccgagatgcaggttttgaaatctcagctatgcagatgttcaatatggatcgggttaatgttgaggaattct atgaagtttataaaggagtagtgaccgaatatcatgacatggtgacagaaatgtattctggcccttgtgtagcaatggagattcaacagaataa tgctacaaagacatttcgagaattttgtggacctgctgatcctgaaattgcccggcatttacgccctggaactctcagagcaatctttggtaaaa ctaagatccagaatgctgttcactgtactgatctgccagaggatggcctattagaggttcaatacttatcaagatcttggataatacgcgtacg cggccgctcgagcagaaactcatctcagaagaggatctggcagcaaatgatatcctggattacaaggatgacgacgataaggtttaa (amino acids)

(SEQ ID NO: 81)

MNHSERFVFIAEWYDPNASLLRRYELLFYPGDGSVEMHDVKNHRTFLKRTK

YDNLHLEDLFIGNKVNVFSRQLVLIDYGDQYTARQLGSRKEKTLALIKPDAISKAGEIIEII

NKAGFTITKLKMMMLSRKEALDFHVDHQSRPFFNELIQFITTGPIIAMEILRDDAICEWK

RLLGPANSGVARTDASESIRALFGTDGIRNAAHGPDSFASAAREMELFFPSSGGCGPANT

AKFTNCTCCIVKPHAVSEGLLGKILMAIRDAGFEISAMQMFNMDRVNVEEFYEVYKGV

VTEYHDMVTEMYSGPCVAMEIQQNNATKTFREFCGPADPEIARHLRPGTLRAIFGKTKI

QNAVHCTDLPEDGLLEVQYFFKILDNTRTRRLEQKLISEEDLAANDILDYKDDDDKV

Abnova NME7-1 Full length
(amino acids)

(SEQ ID NO: 82)

MNHSERFVFIAEWYDPNASLLRRYELLFYPGDGSVEMHDVKNHRTFLKRTK

YDNLHLEDLFIGNKVNVFSRQLVLIDYGDQYTARQLGSRKEKTLALIKPDAISKAGEIIEII

NKAGFTITKLKMMMLSRKEALDFHVDHQSRPFFNELIQFITTGPIIAMEILRDDAICEWK

RLLGPANSGVARTDASESIRALFGTDGIRNAAHGPDSFASAAREMELFFPSSGGCGPANT

AKFTNCTCCIVKPHAVSEGLLGKILMAIRDAGFEISAMQMFNMDRVNVEEFYEVYKGV

VTEYHDMVTEMYSGPCVAMEIQQNNATKTFREFCGPADPEIARHLRPGTLRAIFGKTKI

QNAVHCTDLPEDGLLEVQYFFKILDN

Abnova Partial NME7-B

-continued (amino acids)

(SEQ ID NO: 83)

DRVNVEEFYEVYKGVVTEYHDMVTEMYSGPCVAMEIQQNNATKTFREFCG

PADPEIARHLRPGTLRAIFGKTKIQNAVHCTDLPEDGLLEVQYFFKIL

Histidine Tag (SEQ ID NO: 84)

(ctcgag)caccaccaccaccaccactga

Strept II Tag (SEQ ID NO: 85)

(accggt)tggagccatcctcagttcgaaaagtaatga

N-10 peptide:

(SEQ ID NO: 86)

QFNQYKTEAASRYNLTISDVSVSDVPFPFSAQSGA

C-10 peptide (SEQ ID NO: 87)

GTINVHDVETQFNQYKTEAASRYNLTISDVSVSDV (SEQ ID NO: 88)

LALIKPDA (SEQ ID NO: 89)

MMMLSRKEALDFHVDHQS (SEQ ID NO: 90)

ALDFHVDHQS (SEQ ID NO: 91)

EILRDDAICEWKRL (SEQ ID NO: 92)

FNELIQFITTGP (SEQ ID NO: 93)

RDDAICEW (SEQ ID NO: 94)

SGVARTDASESIRALFGTDGIRNAA (SEQ ID NO: 95)

ELFFPSSGG (SEQ ID NO: 96)

KFTNCTCCIVKPHAVSEGLLGKILMA (SEQ ID NO: 97)

LMAIRDAGFEISAMQMFNMDRVNVEEFYEVYKGVVT (SEQ ID NO: 98)

EFYEVYKGVVTEYHD (SEQ ID NO: 99)

EIQQNNATKTFREFCGPADPEIARHLRPGTLRAIFGKTKIQNA (SEQ ID NO: 100)

YSGPCVAM (SEQ ID NO: 101)

FREFCGP (SEQ ID NO: 102)

VHCTDLPEDGLLEVQYFFKILDN (SEQ ID NO: 103)

IQNAVHCTD (SEQ ID NO: 104)

TDLPEDGLLEVQYFFKILDN (SEQ ID NO: 105)

PEDGLLEVQYFFK (SEQ ID NO: 106)

EIINKAGFTITK (SEQ ID NO: 107)

MLSRKEALDFHVDHQS

-continued (SEQ ID NO: 108)
NELIQFITT (SEQ ID NO: 109)
EILRDDAICEWKRL (SEQ ID NO: 110)
SGVARTDASESIRALFGTDGI (SEQ ID NO: 111)
SGVARTDASES (SEQ ID NO: 112)
ALFGTDGI (SEQ ID NO: 113)
NCTCCIVKPHAVSE (SEQ ID NO: 114)
LGKILMAIRDA (SEQ ID NO: 115)
EISAMQMFNMDRVNVE (SEQ ID NO: 116)
EVYKGVVT (SEQ ID NO: 117)
EYHDMVTE (SEQ ID NO: 118)
EFCGPADPEIARHLR (SEQ ID NO: 119)
AIFGKTKIQNAV (SEQ ID NO: 120)
LPEDGLLEVQYFFKILDN (SEQ ID NO: 121)
GPDSFASAAREMELFFP Immunizing peptides derived from human NME7

(SEQ ID NO: 122)
ICEWKRL (SEQ ID NO: 123)
LGKILMAIRDA (SEQ ID NO: 124)
HAVSEGLLGK (SEQ ID NO: 125)
VTEMYSGP (SEQ ID NO: 126)
NATKTFREF (SEQ ID NO: 127)
AIRDAGFEI (SEQ ID NO: 128)
AICEWKRLLGPAN (SEQ ID NO: 129)
DHQSRPFF (SEQ ID NO: 130)
AICEWKRLLGPAN (SEQ ID NO: 131)
VDHQSRPF (SEQ ID NO: 132)
PDSFAS (SEQ ID NO: 133)
KAGEIIEIINKAGFTITK

Immunizing peptides derived from human NME1

-continued (SEQ ID NO: 134)
MANCERTFIAIKPDGVQRGLVGEIIKRFE (SEQ ID NO: 135)
VDLKDRPF (SEQ ID NO: 136)
HGSDSVESAEKEIGLWF (SEQ ID NO: 137)
ERTFIAIKPDGVQRGLVGEIIKRFE (SEQ ID NO: 138)
VDLKDRPFFAGLVKYMHSGPVVAMVWEGLN (SEQ ID NO: 139)
NIIHGSDSVESAEKEIGLWFHPEELV (SEQ ID NO: 140)
KPDGVQRGLVGEII Immunizing peptide derived from human NME7, but which does not bind NME1

(SEQ ID NO: 141)
MLSRKEALDFHVDHQS peptide A1

(SEQ ID NO: 142)
SGVARTDASES peptide A2

(SEQ ID NO: 143)
DAGFEISAMQMFNMDRVNVE peptide B1

(SEQ ID NO: 144)
EVYKGVVTEYHDMVTE peptide B2

(SEQ ID NO: 145)
AIFGKTKIQNAVHCTDLPEDGLLEVQYFF peptide B3

Human NME7 a
(DNA)

(SEQ ID NO: 146)
atgaatcatagtgaaagattcgttttcattgcagagtggtatgatccaaatgatcacttcttcgacgttatgagatttattttacc caggggatggatctgttgaaatgcatgatgtaaagaatcatcgcacctttttaaagcggaccaaatatgataacctgcacttggaagatttattt ataggcaacaaagtgaatgtatttctcgacaactggtattaattgactatggggatcaatatacagctcgccagctgggcagtaggaaagaa aaaacgctagccctaattaaaccagatgcaatatcaaaggctggagaaataattgaaataataaacaaagctggatttactataaccaaactc aaaatgatgatgctttcaaggaaagaagcattggattttcatgtagatcaccagtcaagaccctttttcaatgagctgatccagtttattacaact ggtcctattattgccatggagattttaagagatgatgctatatgtgaatggaaaagactgctgggacctgcaaactctggagtggcacgcaca gatgcttctgaaagcattagagccctattggaacagatggcataagaaatgcagcgcatggccctgattcttttgcttctgcggccagagaa atggagttgtttttttccttcaagtggaggttgtgggccggcaaacactgctaaatttactaattgtacctgttgcattgttaaaccccatgctgtca gtgaaggactgttgggaaagatcctgatggctatccgagatgcaggttttgaaatctcagctatgcagatgttcaatatggatcgggttaatgtt gaggaattctatgaagtttataaaggagtagtgaccgaatatcatgacatggtgacagaaatgtattctggcccttgtgtagcaatggagattc aacagaataatgctacaaagacatttcgagaattttgtggacctgctgatcctgaaattgcccggcatttacgccctggaactctcagagcaat ctttggtaaaactaagatccagaatgctgttcactgtactgatctgccagaggatggcctattagaggttcaatacttcttcaagatcttggataa ttag (amino acids)

(SEQ ID NO: 147)
MNHSERFVFIAEWYDPNASLLRRYELLFYPGDGSVEMHDVKNHRTFLKRTK

YDNLHLEDLFIGNKVNVFSRQLVLIDYGDQYTARQLGSRKEKTLALIKPDAISKAGEIIEII

NKAGFTITKLKMMMLSRKEALDFHVDHQSRPFFNELIQFITTGPIIAMEILRDDAICEWK

RLLGPANSGVARTDASESIRALFGTDGIRNAAHGPDSFASAAREMELFFPSSGGCGPANT

AKFTNCTCCIVKPHAVSEGLLGKILMAIRDAGFEISAMQMFNMDRVNVEEFYEVYKGV

VTEYHDMVTEMYSGPCVAMEIQQNNATKTFREFCGPADPEIARHLRPGTLRAIFGKTKI

QNAVHCTDLPEDGLLEVQYFFKILDN

-continued

Human NME7 b
(DNA)

(SEQ ID NO: 148)

atgcatgatgtaaagaatcatcgcaccttttttaaagcggaccaaatatgataacctgcacttggaagatttatttataggcaac aaagtgaatgtatttctcgacaactggtattaattgactatggggatcaatatacagctcgccagctgggcagtaggaaagaaaaaacgcta gccctaattaaaccagatgcaatatcaaaggctggagaaataattgaaataataaacaaagctggatttactataaccaaactcaaaatgatg atgctttcaaggaaagaagcattggattttcatgtagatcaccagtcaagacccttttttcaatgagctgatccagtttattacaactggtcctattat tgccatggagattttaagagatgatgctatatgtgaatggaaaagactgctgggacctgcaaactctggagtggcacgcacagatgcttctga aagcattagagccctctttggaacagatggcataagaaatgcagcgcatggccctgattcttttgcttctgcggccagagaaatggagttgttt tttccttcaagtggaggttgtgggccggcaaacactgctaaatttactaattgtacctgttgcattgttaaaccccatgctgtcagtgaaggactg ttgggaaagatcctgatggctatccgagatgcaggttttgaaatctcagctatgcagatgttcaatatggatcgggttaatgttgaggaattctat gaagtttataaaggagtagtgaccgaatatcatgacatggtgacagaaatgtattctggcccttgtgtagcaatggagattcaacagaataatg ctacaaagacatttcgagaattttgtggacctgctgatcctgaaattgcccggcatttacgccctggaactctcagagcaatctttggtaaaact aagatccagaatgctgttcactgtactgatctgccagaggatggcctattagaggttcaatacttcttcaagatcttggataattag (amino acids)

(SEQ ID NO: 149)

MHDVKNHRTFLKRTKYDNLHLEDLFIGNKVNVFSRQLVLIDYGDQYTARQL

GSRKEKTLALIKPDAISKAGEHEIINKAGFTITKLKMMMLSRKEALDFHVDHQSRPFFNE

LIQFITTGPIIAMEILRDDAICEWKRLLGPANSGVARTDASESIRALFGTDGIRNAAHGPDS

FASAAREMELFFPSSGGCGPANTAKFTNCTCCIVKPHAVSEGLLGKILMAIRDAGFEISA

MQMFNMDRVNVEEFYEVYKGVVTEYHDMVTEMYSGPCVAMEIQQNNATKTFREFCG

PADPEIARHLRPGTLRAIFGKTKIQNAVHCTDLPEDGLLEVQYFFKILDN

Human NME7-AB
(DNA)

(SEQ ID NO: 150)

atggaaaaaacgctagccctaattaaaccagatgcaatatcaaaggctggagaaataattgaaataataaacaaagctgga tttactataaccaaactcaaaatgatgatgctttcaaggaaagaagcattggattttcatgtagatcaccagtcaagacccttttttcaatgagctg atccagtttattacaactggtcctattattgccatggagattttaagagatgatgctatatgtgaatggaaaagactgctgggacctgcaaactct ggagtggcacgcacagatgatctgaaagcattagagccctattggaacagatggcataagaaatgcagcgcatggccctgattcttttgct tctgcggccagagaaatggagttgttttttccttcaagtggaggttgtgggccggcaaacactgctaaatttactaattgtacctgttgcattgtta aaccccatgctgtcagtgaaggactgttgggaaagatcctgatggctatccgagatgcaggttttgaaatctcagctatgcagatgttcaatat ggatcgggttaatgttgaggaattctatgaagtttataaaggagtagtgaccgaatatcatgacatggtgacagaaatgtattctggcccttgtg tagcaatggagattcaacagaataatgctacaaagacatttcgagaattttgtggacctgctgatcctgaaattgcccggcatttacgccctgg aactctcagagcaatctttggtaaaactaagatccagaatgctgttcactgtactgatctgccagaggatggcctattagaggttcaatacttctt caagatcttggataattag (amino acids)

(SEQ ID NO: 151)

MEKTLALIKPDAISKAGEHEIINKAGFTITKLKMMMLSRKEALDFHVDHQSRP

FFNELIQFITTGPIIAMEILRDDAICEWKRLLGPANSGVARTDASESIRALFGTDGIRNAAH

GPDSFASAAREMELFFPSSGGCGPANTAKFTNCTCCIVKPHAVSEGLLGKILMAIRDAGF

EISAMQMFNMDRVNVEEFYEVYKGVVTEYHDMVTEMYSGPCVAMEIQQNNATKTFRE

FCGPADPEIARHLRPGTLRAIEGKTKIQNAVHCTDLPEDGLLEVQYFFKILDN

Human NME7-X1
(DNA)

(SEQ ID NO: 152)

atgatgatgctttcaaggaaagaagcattggattttcatgtagatcaccagtcaagacccttttttcaatgagctgatccagtttat tacaactggtcctattattgccatggagattttaagagatgatgctatatgtgaatggaaaagactgctgggacctgcaaactctggagtggca -continued cgcacagatgcttctgaaagcattagagccctctttggaacagatggcataagaaatgcagcgcatggccctgattcttttgcttctgcggcc agagaaatggagttgtttttccttcaagtggaggttgtgggccggcaaacactgctaaatttactaattgtacctgttgcattgttaaaccccat gctgtcagtgaaggactgttgggaaagatcctgatggctatccgagatgcaggttttgaaatctcagctatgcagatgttcaatatggatcgg gttaatgttgaggaattctatgaagtttataaaggagtagtgaccgaatatcatgacatggtgacagaaatgtattctggcccttgtgtagcaat ggagattcaacagaataatgctacaaagacatttcgagaattttgtggacctgctgatcctgaaattgcccggcatttacgccctggaactctc agagcaatctttggtaaaactaagatccagaatgctgttcactgtactgatctgccagaggatggcctattagaggttcaatacttcttcaagat cttggataattag (amino acids)

(SEQ ID NO: 153)

MMMLSRKEALDFHVDHQSRPFFNELIQFITTGPIIAMEILRDDAICEWKRLLGP

ANSGVARTDASESIRALFGTDGIRNAAHGPDSFASAAREMELFFPSSGGCGPANTAKFTN

CTCCIVKPHAVSEGLLGKILMAIRDAGFEISAMQ1VIENMDRVNVEEFYEVYKGVVTEYH

DMVTEMYSGPCVAMEIQQNNATKTFREFCGPADPEIARHLRPGTLRAIFGKTKIQNAVH

CTDLPEDGLLEVQYFFKILDN*

Human NME7 a (optimized for *E coli* expression)
(DNA)

(SEQ ID NO: 154)

atgaatcactccgaacgctttgtttttatcgccgaatggtatgacccgaatgcttccctgctgcgccgctacgaactgctgtttt atccgggcgatggtagcgtggaaatgcatgacgttaaaaatcaccgtacctttctgaaacgcacgaaatatgataatctgcatctggaagac ctgtttattggcaacaaagtcaatgtgttctctcgtcagctggtgctgatcgattatggcgaccagtacaccgcgcgtcaactgggtagtcgca aagaaaaaacgctggccctgattaaaccggatgcaatctccaaagctggcgaaattatcgaaattatcaacaaagcgggtttcaccatcacg aaactgaaaatgatgatgctgagccgtaaagaagccctggattttcatgtcgaccaccagtctcgcccgtttttcaatgaactgattcaattcat caccacgggtccgattatcgcaatggaaattctgcgtgatgacgctatctgcgaatggaaacgcctgctgggcccggcaaactcaggtgtt gcgcgtaccgatgccagtgaatccattcgcgctctgtttggcaccgatggtatccgtaatgcagcacatggtccggactcattcgcatcggc agctcgtgaaatggaactgtttttcccgagctctggcggttgcggtccggcaaacaccgccaaatttaccaattgtacgtgctgtattgtcaaa ccgcacgcagtgtcagaaggcctgctgggtaaaattctgatggcaatccgtgatgctggctttgaaatctcggccatgcagatgttcaacatg gaccgcgttaacgtcgaagaattctacgaagtttacaaaggcgtggttaccgaatatcacgatatggttacggaaatgtactccggtccgtgc gtcgcgatggaaattcagcaaaacaatgccaccaaaacgtttcgtgaattctgtggtccggcagatccggaaatcgcacgtcatctgcgtcc gggtaccctgcgcgcaatttttggtaaaacgaaaatccagaacgctgtgcactgtaccgatctgccggaagacggtctgctggaagttcaat actttttcaaaattctggataat (amino acids)

(SEQ ID NO: 155)

MNHSERFVFIAEWYDPNASLLRRYELLFYPGDGSVEMHDVKNHRTFLKRTK

YDNLHLEDLFIGNKVNVFSRQLVLIDYGDQYTARQLGSRKEKTLALIKPDAISKAGEIIEII

NKAGFTITKLKMMMLSRKEALDFHVDHQSRPFFNELIQFITTGPIIAMEILRDDAICEWK

RLLGPANSGVARTDASESIRALFGTDGIRNAAHGPDSFASAAREMELFFPSSGGCGPANT

AKFTNCTCCIVKPHAVSEGLLGKILMAIRDAGFEISAMQMFNMDRVNVEEFYEVYKGV

VTEYHDMVTEMYSGPCVAMEIQQNNATKTFREFCGPADPEIARHLRPGTLRAIFGKTKI

QNAVHCTDLPEDGLLEVQYFFKILDNTG

Human NME7 b (optimized for *E coli* expression)
(DNA)

(SEQ ID NO: 156)

atgcatgacgttaaaaatcaccgtacctttctgaaacgcacgaaatatgataatctgcatctggaagacctgtttattggcaac aaagtcaatgtgttctctcgtcagctggtgctgatcgattatggcgaccagtacaccgcgcgtcaactgggtagtcgcaaagaaaaaacgct ggccctgattaaaccggatgcaatctccaaagctggcgaaattatcgaaattatcaacaaagcgggtttcaccatcacgaaactgaaaatgat -continued gatgctgagccgtaaagaagccctggattttcatgtcgaccaccagtctcgcccgtttttcaatgaactgattcaattcatcaccacgggtccg attatcgcaatggaaattctgcgtgatgacgctatctgcgaatggaaacgcctgctgggcccggcaaactcaggtgttgcgcgtaccgatgc cagtgaatccattcgcgctctgtttggcaccgatggtatccgtaatgcagcacatggtccggactcattcgcatcggcagctcgtgaaatgga actgtttttcccgagctctggcggttgcggtccggcaaacaccgccaaatttaccaattgtacgtgctgtattgtcaaaccgcacgcagtgtca gaaggcctgctgggtaaaattctgatggcaatccgtgatgctggctttgaaatctcggccatgcagatgttcaacatggaccgcgttaacgtc gaagaattctacgaagtttacaaaggcgtggttaccgaatatcacgatatggttacggaaatgtactccggtccgtgcgtcgcgatggaaatt cagcaaaacaatgccaccaaaacgtttcgtgaattctgtggtccggcagatccggaaatcgcacgtcatctgcgtccgggtaccctgcgcg caatttttggtaaaacgaaaatccagaacgctgtgcactgtaccgatctgccggaagacggtctgctggaagttcaatactttttcaaaattctg gataat (amino acids)

(SEQ ID NO: 157)

MHDVKNHRTFLKRTKYDNLHLEDLFIGNKVNVFSRQLVLIDYGDQYTARQL

GSRKEKTLALIKPDAISKAGEIIEIINKAGFTITKLKMMMLSRKEALDFHVDHQSRPFFNE

LIQFITTGPIIAMEILRDDAICEWKRLLGPANSGVARTDASESIRALFGTDGIRNAAHGPDS

FASAAREMELFFPSSGGCGPANTAKFTNCTCCIVKPHAVSEGLLGKILMAIRDAGFEISA

MQMFNMDRVNVEEFYEVYKGVVTEYHDMVTEMYSGPCVAMEIQQNNATKTFREFCG

PADPEIARHLRPGTLRAIEGKTKIQNAVHCTDLPEDGLLEVQYFFKILDNTG

Human NME7-AB (optimized for *E coli* expression)
(DNA)

(SEQ ID NO: 158)

atggaaaaaacgctggccctgattaaaccggatgcaatctccaaagctggcgaaattatcgaaattatcaacaaagcgggt ttcaccatcacgaaactgaaaatgatgatgctgagccgtaaagaagccctggattttcatgtcgaccaccagtctcgcccgtttttcaatgaac tgattcaattcatcaccacgggtccgattatcgcaatggaaattctgcgtgatgacgctatctgcgaatggaaacgcctgctgggcccggcaa actcaggtgttgcgcgtaccgatgccagtgaatccattcgcgctctgtttggcaccgatggtatccgtaatgcagcacatggtccggactcatt cgcatcggcagctcgtgaaatggaactgtttttcccgagctctggcggttgcggtccggcaaacaccgccaaatttaccaattgtacgtgctg tattgtcaaaccgcacgcagtgtcagaaggcctgctgggtaaaattctgatggcaatccgtgatgctggctttgaaatctcggccatgcagat gttcaacatggaccgcgttaacgtcgaagaattctacgaagtttacaaaggcgtggttaccgaatatcacgatatggttacggaaatgtactcc ggtccgtgcgtcgcgatggaaattcagcaaaacaatgccaccaaaacgtttcgtgaattctgtggtccggcagatccggaaatcgcacgtc atctgcgtccgggtaccctgcgcgcaatttttggtaaaacgaaaatccagaacgctgtgcactgtaccgatctgccggaagacggtctgctg gaagttcaatactttttcaaaattctggataat (amino acids)

(SEQ ID NO: 159)

MEKTLALIKPDAISKAGEHEIINKAGFTITKLKMMMLSRKEALDFHVDHQSRP

FFNELIQFITTGPIIAMEILRDDAICEWKRLLGPANSGVARTDASESIRALFGTDGIRNAAH

GPDSFASAAREMELFFPSSGGCGPANTAKFTNCTCCIVKPHAVSEGLLGKILMAIRDAGF

EISAMQMFNMDRVNVEEFYEVYKGVVTEYHDMVTEMYSGPCVAMEIQQNNATKTFRE

FCGPADPEIARHLRPGTLRAIFGKTKIQNAVHCTDLPEDGLLEVQYFFKILDNTG

Human NME7-X1 (optimized for *E coli* expression)
(DNA)

(SEQ ID NO: 160)

atgatgatgctgagccgtaaagaagccctggattttcatgtcgaccaccagtctcgcccgtttttcaatgaactgattcaattc atcaccacgggtccgattatcgcaatggaaattctgcgtgatgacgctatctgcgaatggaaacgcctgctgggcccggcaaactcaggtgt tgcgcgtaccgatgccagtgaatccattcgcgctctgtttggcaccgatggtatccgtaatgcagcacatggtccggactcattcgcatcggc agctcgtgaaatggaactgtttttcccgagctctggcggttgcggtccggcaaacaccgccaaatttaccaattgtacgtgctgtattgtcaaa ccgcacgcagtgtcagaaggcctgctgggtaaaattctgatggcaatccgtgatgctggctttgaaatctcggccatgcagatgttcaacatg gaccgcgttaacgtcgaagaattctacgaagtttacaaaggcgtggttaccgaatatcacgatatggttacggaaatgtactccggtccgtgc -continued

```
gtcgcgatggaaattcagcaaaacaatgccaccaaaacgtttcgtgaattctgtggtccggcagatccggaaatcgcacgtcatctgcgtcc

gggtaccctgcgcgcaatttttggtaaaacgaaaatccagaacgctgtgcactgtaccgatctgccggaagacggtctgctggaagttcaat

actttttcaaaattctggataat

(amino acids)
                                                                        (SEQ ID NO: 161)
MMMLSRKEALDFHVDHQSRPFFNELIQFITTGPIIAMEILRDDAICEWKRLLGP

ANSGVARTDASESIRALFGTDGIRNAAHGPDSFASAAREMELFFPSSGGCGPANTAKFTN

CTCCIVKPHAVSEGLLGKILMAIRDAGFEISAMQMENMDRVNVEEFYEVYKGVVTEYH

DMVTEMYSGPCVAMEIQQNNATKTFREFCGPADPEIARHLRPGTLRAIFGKTKIQNAVH

CTDLPEDGLLEVQYFFKILDNTG

DM10 domain of NME7
(amino acids)
                                                                        (SEQ ID NO: 162)
MNHSERFVFIAEWYDPNASLLRRYELLFYPGDGSVEMHDVKNHRTFLKRTK

YDNLHLEDLFIGNKVNVFSRQLVLIDYGDQYTARQLGSRK
```

EXAMPLES

Example 1—Components of Minimal Serum-Free Base ("MM") (500 mls)

400 ml DME/F12/GlutaMAX I (Invitrogen #10565-018)

100 ml Knockout Serum Replacement (KO-SR, Invitrogen #10828-028)

5 ml 100×MEM Non-essential Amino Acid Solution (Invitrogen #11140-050)

0.9 ml (0.1 mM) β-mercaptoethanol (55 mM stock, Invitrogen #21985-023)

Example 2—Probing Cancer and Stem Cells for the Presence of NME1, NME6 and NME7

In this series of experiments, we probed the expression of NME6 and NME7 in stem cells and cancer cells. In addition, we identified MUC1* as the target of NME7. We first performed Western blot assays on cell lysates to determine the presence or absence of NME1, NME6 and NME7. In FIG. 1A, lysates from BGO1v human embryonic stem cells that had been cultured in NME1 dimers over a surface coated with anti-MUC1* antibodies (Lane 1), or cultured in bFGF over MEFs (Lane 2) or T47D human breast cancer cell lysates (Lane 3) or NME1-wt as a positive control, were separated by SDS-PAGE then probed with an anti-NME1 specific antibody. The results show that NME1 is strongly expressed in human ES cells whether cultured in NME1 dimers or bFGF, and in T47D cancer cells. The same cell lysates are separated by SDS-PAGE and then probed with an anti-NME6 specific antibody (anti-NME6 from Abnova). No NME6 was detected (data not shown), however it was detected later in a more concentrated sample (see FIG. 2).

In FIG. 1B, the same cell lysates are separated by SDS-PAGE and then probed with an anti-NME7 specific antibody (nm23-H7 B9 from Santa Cruz Biotechnology, Inc). The results show that NME7 is strongly expressed in human ES cells cultured in NME1 dimers over an anti-MUC1* antibody surface (Lane 1), weakly expressed in the same ES cells that were cultured in bFGF over MEFs (Lane 2), and strongly expressed in breast cancer cells (Lane 3). Lane 4 in which NME1 was added is blank indicating that the NME7 antibody does not cross react with NME1. The fact that NME7 is expressed to a greater degree in stem cells cultured in NME1 dimers, which we have shown express markers indicating that they are in a more naïve state than cells cultured in bFGF, means that NME7 is expressed at a higher level in naïve cells, compared to its expression in primed cells.

To determine whether NME7 also functions as a growth factor with MUC1* as its target receptor, we performed pull-down assays. In these experiments, a synthetic MUC1* extra cellular domain peptide (His-tagged PSMGFR sequence) was immobilized on NTA-Ni magnetic beads. These beads were incubated with the cell lysates of BGO1v human embryonic stem cells that had been cultured in NME1 dimers over a surface coated with anti-MUC1* antibodies (Lane 1), or cultured in bFGF over MEFs (Lane 2) or T47D human breast cancer cell lysates (Lane 3). Beads were rinsed and captured proteins were released by addition of imidazole. Proteins were separated by SDS-PAGE and then probed with either an anti-NME1 antibody (FIG. 1C) or an NME7 antibody (FIG. 1D). The results show that NME7 binds to the MUC1* extra cellular domain peptide. This means that in stem cells and cancer cells, NME7 via its portions of its two NDPK domains, activates pluripotency pathways by dimerizing the MUC1* extra cellular domain.

Figures 2A, 2B, 2C, 2D, 2E:
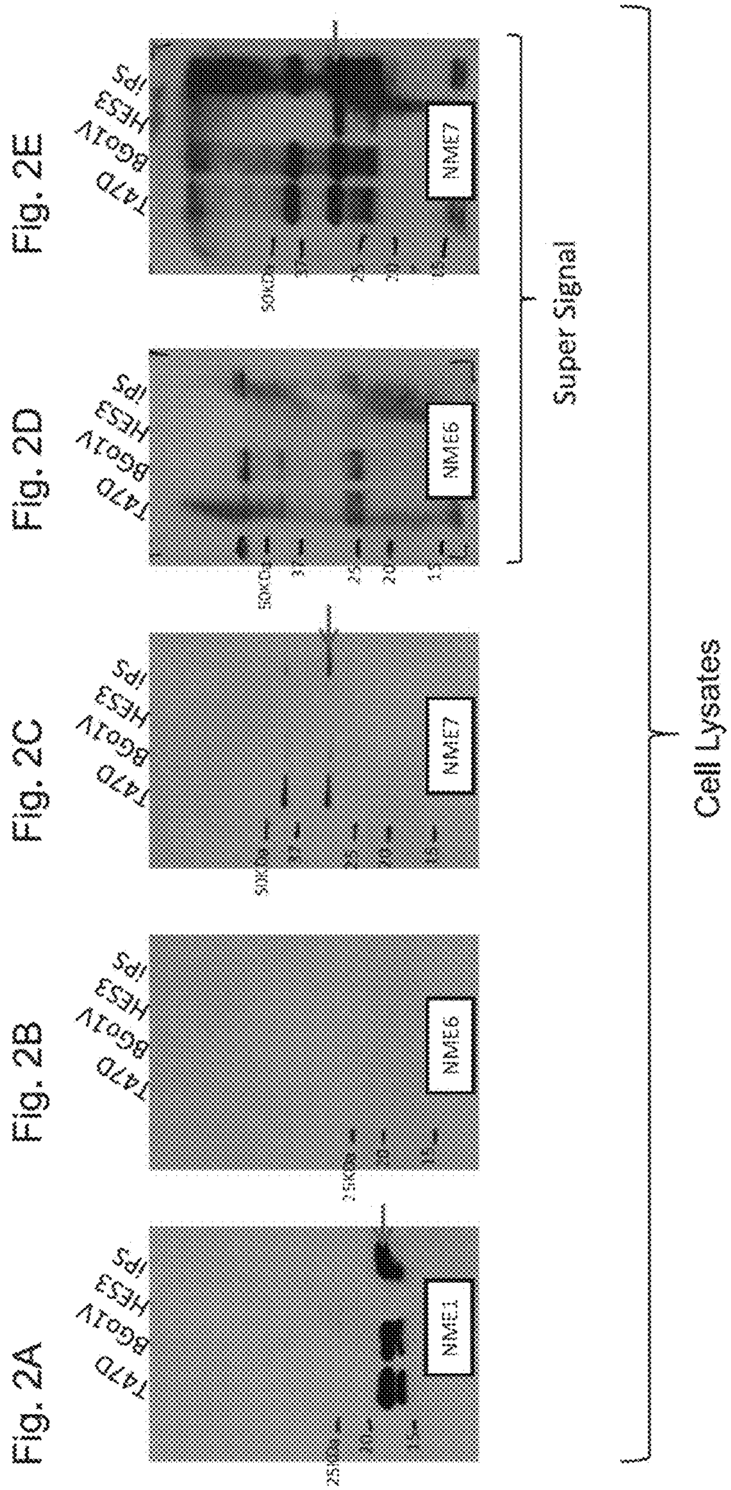
FIGS. 2A-2E show photos of Western blots in which cell lysates from T47D breast cancer cells, BGO1V and HES-3 human ES cells and human SC101-A1 iPS cells were probed for the presence of NME1, NME6 or NME7. NME1 in all cell lines ran with an apparent molecular weight of ~17 kDa (A). In all cell lines, NME7 ~33 kDa species and the 42 kDa species (C, E) could be detected in all but the HES-3 cell line (cultured in FGF). Species that reacted with an NME6-specific antibody were detected in all cell lines except the HES-3 cell line, when visualization was enhanced using Super Signal.

Example 3—a MUC1 Pull Down Assay Shows that NME1, NME6 and NME7 Bind to a MUC1 Species Protein A pull down assay using an antibody to the MUC1* cytoplasmic tail (Ab-5) was performed on a panel of cells. Results are shown in FIGS. 2A-2F. The proteins pulled down by the MUC1 antibody were separated by SDS-PAGE then probed with antibodies specific for NME1, NME6 and NME7, using Western blot technique. MUC1*-positive breast cancer cell line T47D cells (ATCC), human embryonic stem cell line BGO1v (LifeTechnologies), human ES cells (HES-3, BioTime Inc.), human iPS cells (SC101A-1, System Biosciences Inc.) and T47D cancer cells were grown according to ATCC protocol in RPMI-1640 (ATCC) plus 10% FBS (VWR). All stem cells were cultured in minimal stem cell media "MM" with 8 nM NM23-RS (recombinant NME1 S120G dimers). Stem cells were grown on plasticware coated with 12.5 ug/mL anti-MUC1* C3 mab. Cells were lysed with 200 uL RIPA buffer for 10 min on ice. After removal of cell debris by centrifugation, the supernatant was used in a co-immunoprecipitation assay. MUC1* was pulled down using the Ab-5 antibody (anti-MUC-1 Ab-5, Thermo Scientific), which recognizes the MUC1 cytoplasmic tail, coupled to Dynabeads protein G (Life Technologies). The beads were washed twice with RIPA buffer and resuspended in reducing buffer. A sample of the supernatant was subjected to a reducing SDS-PAGE followed by transfer of the protein to a PVDF membrane. In FIG. 2, the membrane was then probed with: A) an anti-NM23-H1 (NME1) Antibody (C-20, Santa Cruz Biotechnology); B) anti-NME6 (Abnova); or C) anti-NM23-H7 Antibody (B-9, Santa Cruz Biotechnology); D) the staining of NME6 was enhanced using Supersignal (Pierce); and E) the staining of NME7 was enhanced using Supersignal.

After incubation with their respective secondary antibody coupled to HRP, the proteins were detected by chemiluminescence. The photos show that native NME1, NME6 and NME7 are present in MUC1*-positive breast cancer cells, in human ES cells and in human iPS cells and that they bind to MUC1*. Note that the number of cells present in the HES-3 pellet was less than the number present in the other samples.

Example 4—Detection of NME7 in Embryonic Stem Cells and iPS Cells

Results are shown in FIG. 3. Human ES cells (BGO1v and HES-3) were cultured in NME-based media wherein cells were plated over a layer of anti-MUC1* antibody. To identify NME7 species, cells were harvested and lysed with RIPA buffer (Pierce), supplemented with protease inhibitor (Pierce). Cell lysates (20 uL) were separated by electrophoresis on a 12% SDS-PAGE reducing gel and transferred to a PVDF membrane (GE Healthcare). The blot was blocked with PBS-T containing 3% milk and then incubated with primary antibody (anti NM23-H7 clone B-9, Santa Cruz Biotechnology) at 4° C. overnight. After washing with PBS-T, the membrane was incubated with horseradish peroxidase (HRP)-conjugated secondary antibody (goat anti mouse, Pierce) for 1 hr at room temperature. Signals were detected with Immun-Star Chemiluminescence kit (Bio-Rad). FIG. 3A shows that the lysates from human stem cells contain three NME7 species: full-length at 42 kDa and two lower molecular weight NME7 species at ~33 kDa and ~30 kDa. FIGS. 3B and C shows the difference between NME7 species that are secreted (B), and those that are retained within the cell (C). FIG. 3B shows that only the 30-33 kDa NME7 species are secreted from the cells. FIG. 3C shows that the lysates of those same cells have both the full-length form and a lower molecular weight species that may be a cleavage product or alternate isoform of both. For part (B), iPS Conditioned media (20 uL) was separated by electrophoresis on either a 12% SDS-PAGE reducing gel and transferred to a PVDF membrane (GE Healthcare). The blot was blocked with PBS-T containing 3% milk and then incubated with primary antibody (anti NM23-H7 clone B-9, Santa Cruz Biotechnology) at 4° C. overnight. After washing with PBS-T, the membrane was incubated with horseradish peroxidase (HRP)-conjugated secondary antibody (goat anti mouse, Pierce) for 1 hr at room temperature. Signals were detected with Immun-Star Chemiluminescence kit (Bio-Rad). For part (C) experiment was similarly performed except that the cell lysate was used instead of the conditioned media.

Example 5—Generation of Protein Constructs

For generating recombinant NME7, first, constructs were made to make a recombinant NME7 that could be expressed efficiently and in soluble form. The first approach was to make a construct that would encode the native NME7 (a) or an alternative splice variant NME7 (b), which has an N-terminal deletion. In some cases, the constructs carried a histidine tag or a strep tag to aid in purification. NME7-a, full-length NME7 expressed poorly in *E. coli* and NME7-b did not express at all in *E. coli*. However, a novel construct was made in which the DM10 sequence was deleted and the NME7 comprised essentially the NDPK A and B domains having a calculated molecular weight of 33 kDa.

This novel NME7-AB expressed very well in *E. coli* and existed as the soluble protein. NME7-AB was first purified over an NTA-Ni column and then further purified by size exclusion chromatography (FPLC) over a Sephadex 200 column (FIG. 4A). Fractions were collected and tested by SDS-PAGE to identify fractions with the highest and purest expression of NME7-AB (FIG. 4B). FIG. 4C shows the FPLC trace for the combined fractions that were the most pure. The purified NME7-AB protein was then tested and shown to fully support the growth of human stem cells and further reverts them to the most naïve, pre-X-inactivation state. The purified NME7-AB was also shown to accelerate the growth of cancer cells.

Example 6—ELISA Assay Showing NME7-AB Simultaneously Binds to Two MUC1* Extra Cellular Domain Peptides Results are shown in FIG. 5. The PSMGFR peptide bearing a C-terminal Cysteine (PSMGFR-Cys) was covalently coupled to BSA using Imject Maleimide activated BSA kit (Thermo Fisher). PSMGFR-Cys coupled BSA was diluted to 10 ug/mL in 0.1M carbonate/bicarbonate buffer pH 9.6 and 50 uL was added to each well of a 96 well plate. After overnight incubation at 4° C., the plate was washed twice with PBS-T and a 3% BSA solution was added to block remaining binding site on the well. After 1 h at RT the plate was washed twice with PBS-T and NME7, diluted in PBS-T+1% BSA, was added at different concentrations. After 1 h at RT the plate was washed 3× with PBS-T and anti-NM23-H7 (B-9, Santa Cruz Biotechnology), diluted in PBS-T+1% BSA, was added at 1/500 dilution. After 1 h at RT the plate was washed 3× with PBS-T and goat anti mouse-HRP, diluted in PBS-T+1% BSA, was added at 1/3333 dilution. After 1 h at RT the plate was washed 3× with PBS-T and binding of NME7 was measured at 415 nm using ABTS solution (Pierce).

ELISA MUC1* dimerization: The protocol for NME7 binding was used, and NME7 was used at 11.6 ug/mL.

After 1 h at RT the plate was washed 3× with PBS-T and HisTagged PSMGFR peptide (PSMGFR-His) or biotinylated PSMGFR peptide (PSMGFR-biotin), diluted in PBS-T+1% BSA, was added at different concentration. After 1 h at RT the plate was washed 3× with PBS-T and anti-Histag-HRP (Abcam) or streptavidin-HRP (Pierce), diluted in PBS-T+1% BSA, was added at a concentration of 1/5000. After 1 h at RT the plate was washed 3× with PBS-T and binding of PSMGFR peptide to NME7 already bound to another PSMGFR peptide (which could not signal by anti-His antibody or by streptavidin) coupled BSA was measured at 415 nm using a ABTS solution (Pierce).

Example 7—Functional Testing of Human Recombinant NME7-AB

For testing recombinant NME7-AB for ability to maintain pluripotency and inhibit differentiation, a soluble variant of NME7, NME7-AB, was generated and purified. Human stem cells (iPS cat #SC101a-1, System Biosciences) were grown per the manufacturer's directions in 4 ng/ml bFGF over a layer of mouse fibroblast feeder cells for four passages. These source stem cells were then plated into 6-well cell culture plates (Vita™, Thermo Fisher) that had been coated with 12.5 ug/well of a monoclonal anti-MUC1* antibody, MN-C3. Cells were plated at a density of 300,000 cells per well. The base media was Minimal Stem Cell Media consisting of: 400 ml DME/F12/GlutaMAX I (Invitrogen #10565-018), 100 ml Knockout Serum Replacement (KO-SR, Invitrogen #10828-028), 5 ml 100×MEM Non-essential Amino Acid Solution (Invitrogen #11140-050) and 0.9 ml (0.1 mM) β-mercaptoethanol (55 mM stock, Invitrogen #21985-023). The base media can be any media. In a preferred embodiment, the base media is free of other growth factors and cytokines. To the base media was added either 8 nM of NME7-AB or 8 nM NM23-H1 refolded and purified as stable dimers. Media was changed every 48 hours and due to accelerated growth, had to be harvested and passaged at Day 3 post-plating. Comparable pluripotent stem cell growth was achieved when stem cells were grown in NM23-H1 dimers or in NME7 monomers.

NME7 and NM23-H1 (NME1) dimers both grew pluripotently and had no differentiation even when 100% confluent. As can be seen in the photos, NME7 cells grew faster than the cells grown in NM23-H1 dimers. Cell counts at the first harvest verified that culture in NME7 produced 1.4-times more cells than culture in NM23-H1 dimers. ICC staining for the typical pluripotent markers confirmed that NME7-AB fully supported human stem cell growth, pluripotency, and resisted differentiation.

The NME7 species of ~30-33 kDa may be an alternative splice isoform or a post translational modification such as cleavage, which may enable secretion from the cell.

Example 8~Inducing Transition of Cancer Cells to Metastatic Cancer Cells by Culturing Cells Under Conditions that Revert Stem Cells to a More Naïve State Cancer cells are normally cultured in a serum-containing media such as RPMI. We discovered that culturing cancer cells in the presence of reagents that make stem cells revert to a more naïve state, makes the cancer cells transform to a more metastatic state.

We demonstrated that NME7-AB, human NME1 dimers, bacterial NME1 dimers, NME7-X1 and "2i" inhibitors were each able to transform regular cancer cells into metastatic cancer cells, which are also called cancer stem cells "CSCs" or tumor initiating cells "TICs". 2i is the name given to two biochemical inhibitors that researchers found made human stem cells revert to a more naïve state. 2i are MEK and GSK3-beta inhibitors PD0325901 and CHIR99021, which are added to culture medium to final concentrations of about 1 mM and 3 mM, respectively.

NME7-AB and NME7-X1 are at a final concentration of about 4 nM when added to separate batches of minimal medium to make cancer cells transform to metastatic cells, although lower and higher concentrations also work well in the range of about 1 nM to 16 nM. Human or bacterial NME1 dimers are used at a final concentration of 4 nM to 32 nM, with 16 nM typically used in these experiments, wherein the human NME bears the S120G mutation. Lower concentrations may be required if using wild type. It is not intended that these exact concentrations are important. It is important that the NME1 proteins are dimers and the range of concentrations over which this happens is in the low nanomolar range although certain mutations allow higher concentrations to remain as dimers.

Similarly, the concentrations of NME7 proteins can vary. NME7-AB and NME7-X1 are monomers and concentrations used to transform cancer cells to metastatic cells should allow the proteins to remain as monomers. Various molecular markers have been proposed as being indicators of metastatic cancer cells. Different cancer types may have different molecules that are up-regulated. For example, the receptor CXCR4 is up-regulated in metastatic breast cancers while E-cadherin, also known as CHD1, is up-regulated more in metastatic prostate cancers.

In addition to these specific metastasis markers, typical markers of pluripotency such as OCT4, SOX2, NANOG, and KLF4 are up-regulated as cancers become metastatic. The starting cancer cells and the later metastatic cancer cells can be assayed by PCR to measure expression levels of these genes.

FIG. 11 shows a graph of RT-PCR measurements of T47D breast cancer cells that were cultured in a media that contained NME7-AB. A rho I kinase inhibitor, ROCi, ROCKi or Ri, was added to prevent the transformed cells from floating off the plate. Expression levels of various metastatic markers as well as pluripotent stem cell markers were measured for the parent cells and for the NME7-AB cultured cells. The results show that the floater cells express higher amounts of metastatic and pluripotency markers compared to the cells that received ROCi. We reasoned it was because those measurements were the average of cells that did not transform and those that did but the ROCi made them remain adherent. This can clearly be seen in FIG. 12 wherein "—Ri" means adherent cells that did not receive ROCi and so were not mixed with the highly metastatic cells that float.

Prostate cancer cells also transitioned to a more metastatic state when cultured in media containing NM23, aka NME1, or NME7-AB. Here we show that for every cell line tested so far, culture in NME7-AB, human NME1 dimers, or bacterial NMEs that have high sequence homology to human, induces transition to a more metastatic state.

Figure 14A:
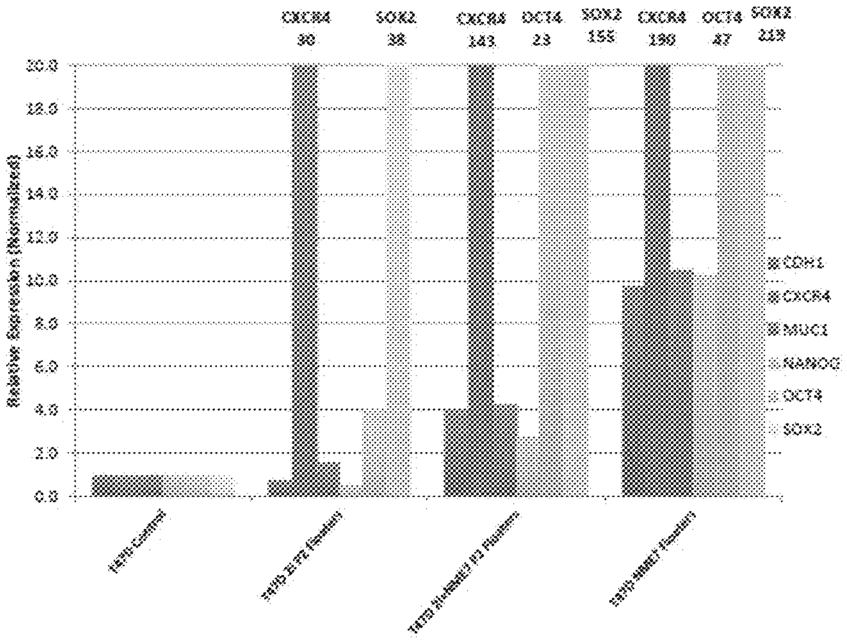
FIGS. 14A-14B are a graphs of RT-PCR measurement of the metastatic markers and pluripotent stem cell markers showing that the 2i inhibitors (GSK3-beta and MEK inhibitors) (A) that were previously shown to revert stem cells to a more naïve state or bacterial NMEs (B) that have high sequence homology to human NME1 or human NME7, also transform cancer cells to a more metastatic state.
Figure 14B:
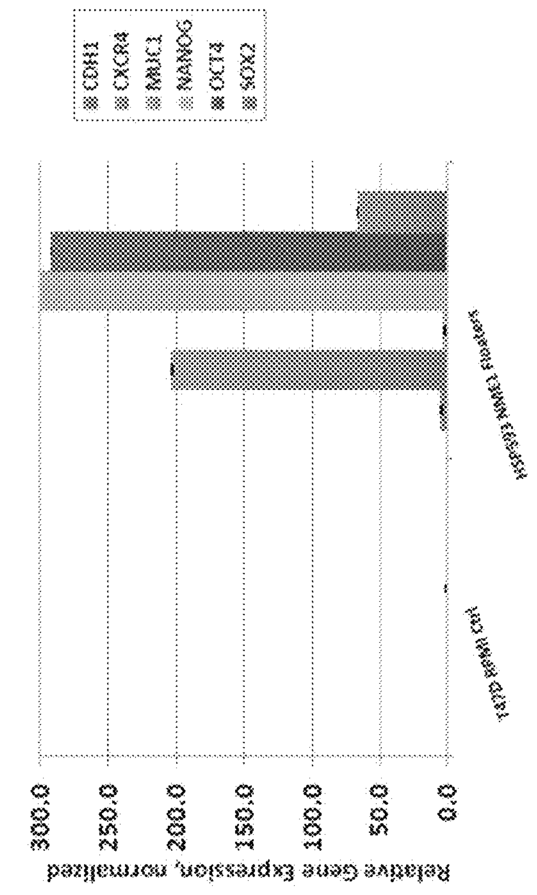
Figure 22A:
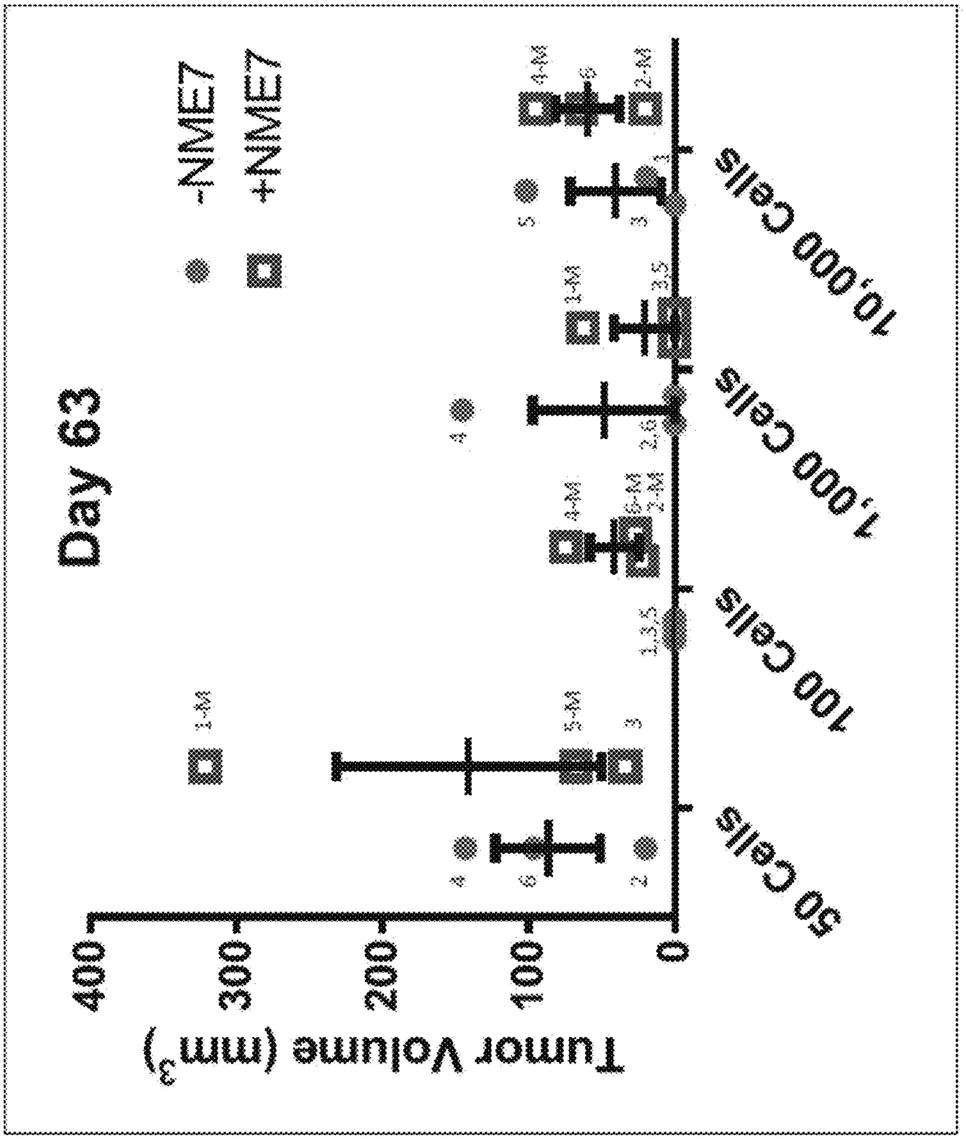
FIG. 22A shows a graph of tumor volume measurements for four (4) groups of immune-compromised nu/nu female mice implanted with either 50, 100, 1,000 or 10,000 cells subcutaneously in the flank wherein the cells that were implanted were human MUC1-positive breast cancer cells that were cultured for seven (7) days in recombinant human NME7-AB wherein the 'floaters' were collected and verified to overexpress metastasis receptor CXCR4 by more than 100-fold. Half the mice in each group were injected daily with human recombinant NME7-AB. Numbers within the graph refer to the mouse tracking number. 'M' denotes a mouse with multiple tumors.
Figure 22B:
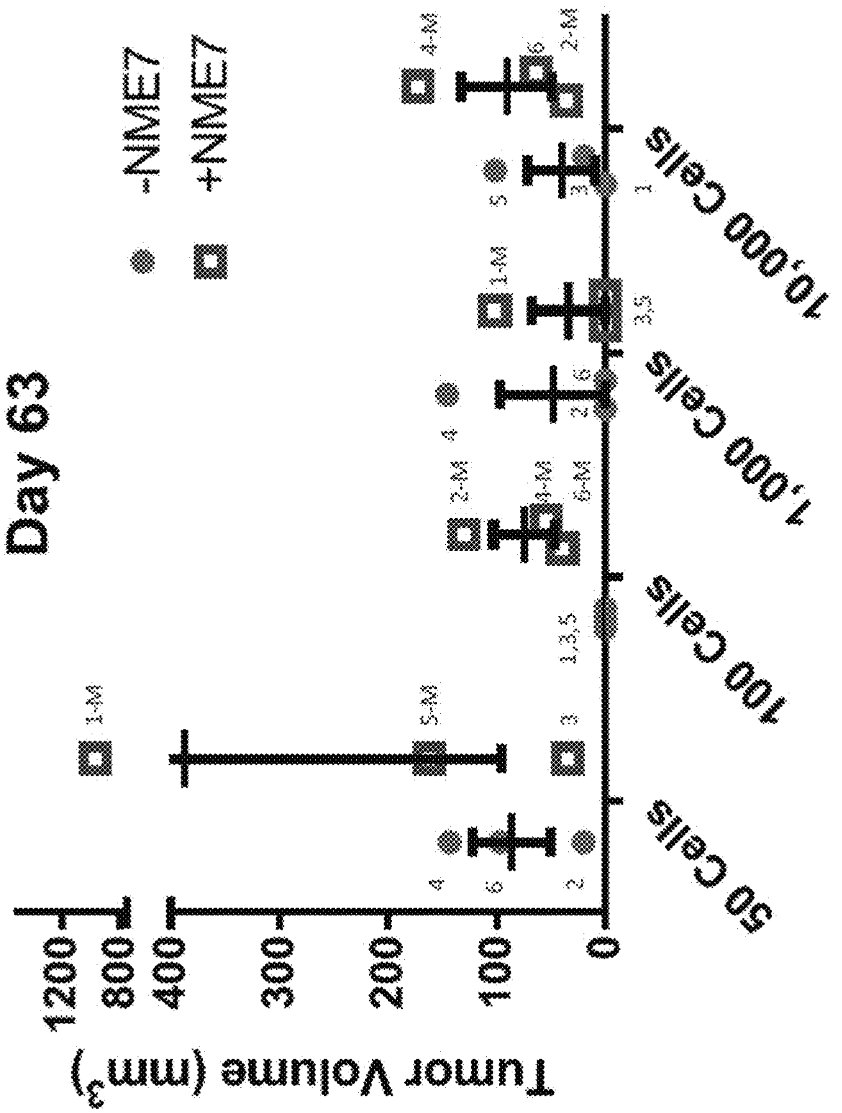
FIG. 22B shows a graph of tumor volume measurements for four (4) groups of immune-compromised nu/nu female mice implanted with either 50, 100, 1,000 or 10,000 cells subcutaneously in the flank wherein the cells that were implanted were human MUC1-positive breast cancer cells that were cultured for seven (7) days in recombinant human NME7-AB wherein the 'floaters' were collected and verified to overexpress metastasis receptor CXCR4 by more than 100-fold. Half the mice in each group were injected daily with human recombinant NME7-AB. Of the mice that received daily injections of NME7-AB, 80% developed multiple tumors. This graph shows the combined volumes of multiple tumors in the same mouse. Numbers within the graph refer to the mouse tracking number. 'M' denotes a mouse with multiple tumors.
Figure 23:
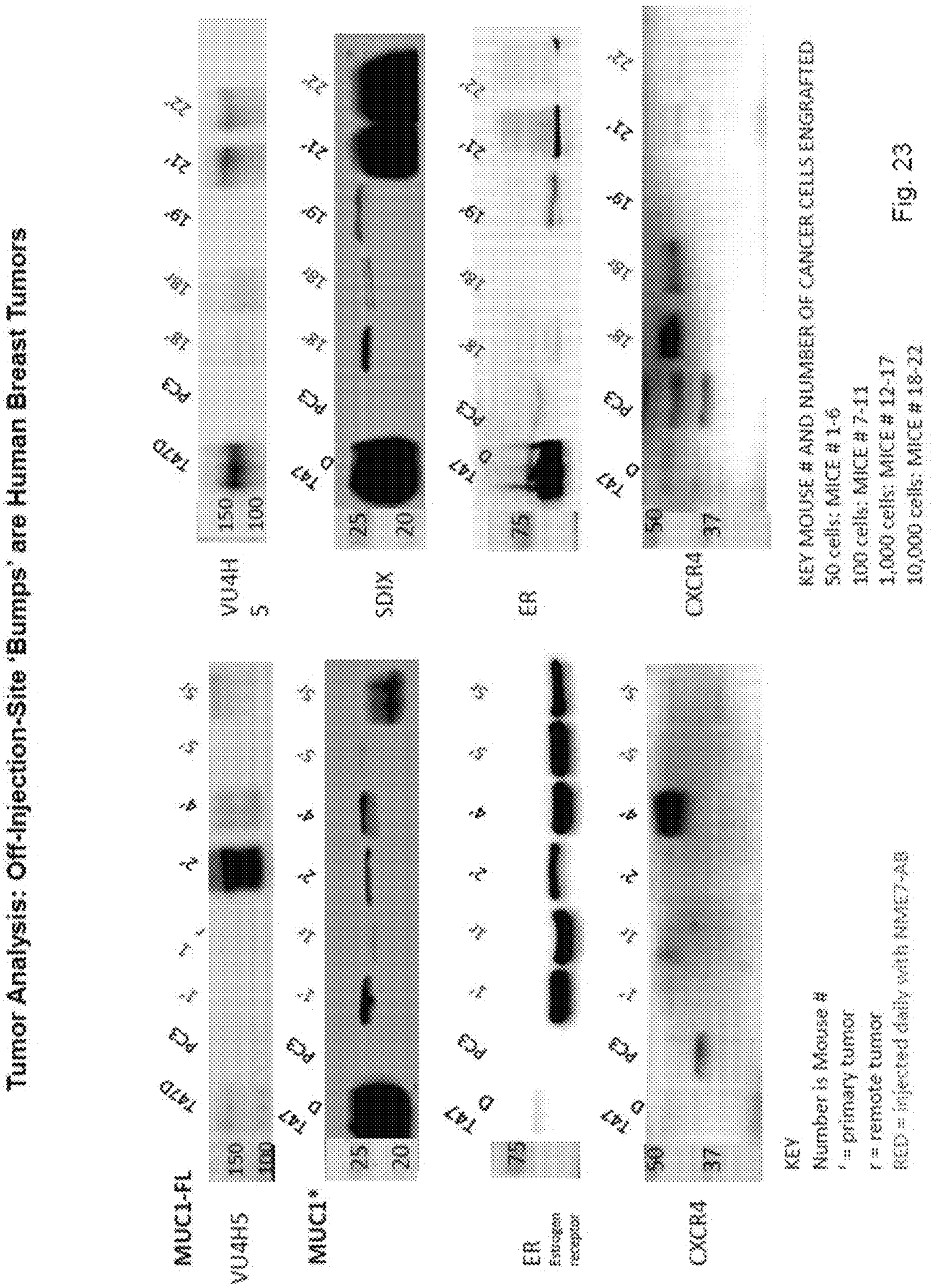
FIG. 23 shows Western blots of primary tumors as well as the remote bumps on mice xenografted with human breast cancer cells that were transformed to a more metastatic state by pre-culture in a medium containing human NME7-AB. Westerns show that the remote bumps were human breast tumors as VU4H5 antibody only stains human MUC1, not murine.
Figure 24:
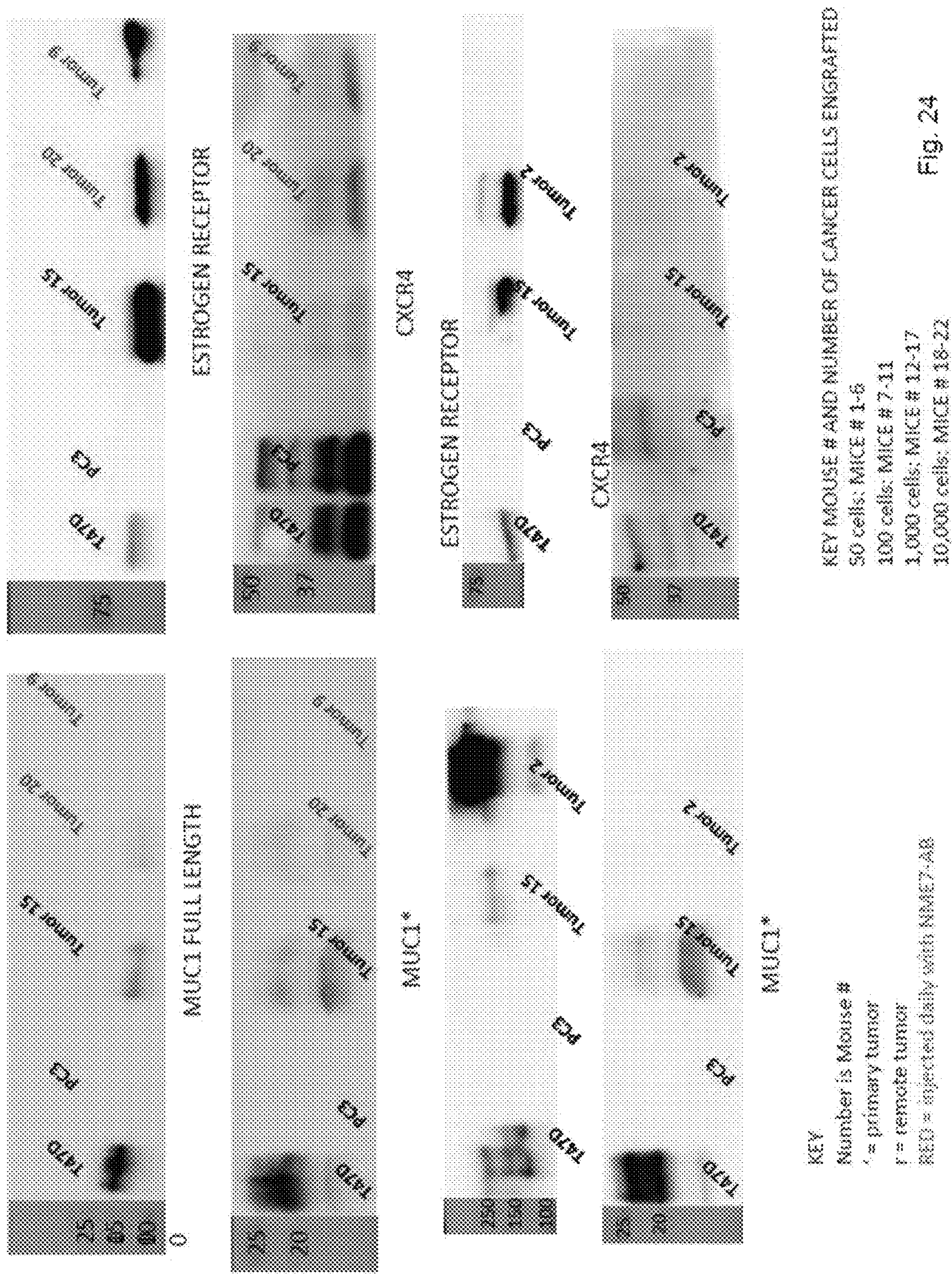
FIG. 24 shows Western blots of primary tumors on mice xenografted with human breast cancer cells that were transformed to a more metastatic state by pre-culture in a medium containing human NME7-AB. Westerns show that the visible bumps are human breast tumors as VU4H5 antibody only stains human MUC1, not murine.
Figure 25:
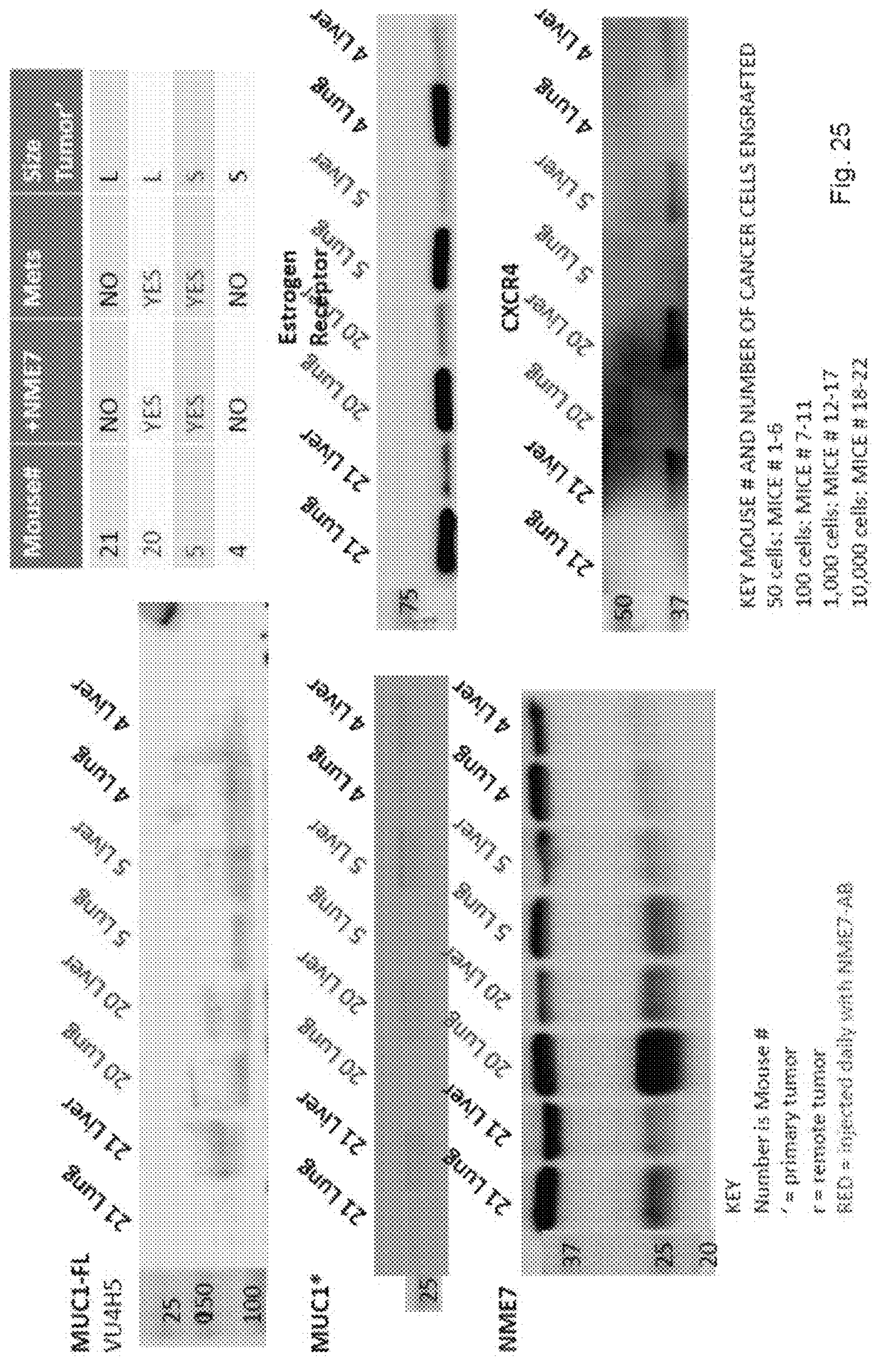
FIG. 25 shows Western blots of organs harvested from mice xenografted with human breast cancer cells that were transformed to a more metastatic state by pre-culture in a medium containing human NME7-AB. Westerns show that some mice that did not appear to have remote tumors, have human MUC1-positive cancer in some of their organs.

FIG. 14A shows a graph of RT-PCR measurements of expression levels of metastatic and pluripotency markers for breast cancer cells that are cultured in media containing either 2i inhibitors, NME7-AB or both. As can be seen, 2i inhibitors are also able to induce the transition of cancer cells to a more metastatic state. FIG. 14B shows a graph of RT-PCR measurements of expression levels of metastatic and pluripotency markers for breast cancer cells that were cultured in media containing an NME1 from bacteria HSP593, whose sequence is highly homologous to human NME1 and NME7-AB, showing that bacterial NMEs with high sequence homology can mimic the effect of human NME1 and NME7-AB in that they induce transition to a more metastatic state. Ovarian cancer cell lines SK-OV3, OV-90, pancreatic cancer cell lines CAPAN-2 and PANC-1, breast cancer cell line MDA-MB all displayed the morphological transition of going from adherent to non-adherent when cultured in NME7-AB and or 2i inhibitors.

FIG. 37 shows graphs of RT-PCR measurement of metastatic or pluripotency markers for various cancer cell lines cultured for 72 or 144 hours in NME7-AB. FIG. 37A shows that SK-OV3 cells increase expression of metastatic markers CHD1, SOX2 and NME7-X1 when cultured in NME7-AB. FIG. 37B shows that OV-90 cells increase expression of metastatic markers CXCR4 and NME7-X1 after culture in NME7-AB.

Example 9—Demonstration that Cancer Cells Cultured in NME7 Become Metastatic

A functional test of whether or not a population of cancer cells is metastatic is to implant very low numbers, e.g. 200, of the cells in immuno-compromised mice and see if they develop into a tumor. Typically 5-6 million cancer cells are required to form a tumor in an immuno-compromised mouse. We showed that as few as 50 of the NME-induced metastatic cancer cells formed tumors in mice. In addition, mice that were injected throughout the test period with human NME7-AB, NME1, or NME7-X1 developed remote metastases.

T47D human breast cancer cells were cultured in standard RPMI media for 14 days with media changes every 48 hours and passed by trypsinization when approximately 75% confluent. The cells were then plated into 6-well plates and cultured in minimal stem cell media (see Example 1) that was supplemented with 4 nM NME7-AB. Media was changed every 48 hours. By about Day 4, some cells become detached from the surface and float. Media is carefully changed so as to retain the "floaters" as these are the cells that have the highest metastatic potential as evidenced by RT-PCR measurement of metastatic markers. On Day 7 or 8, the floaters are harvested and counted. Samples are retained for RT-PCR measurement. The key marker measured is CXCR4 which is up-regulated by 40-200 times after being briefly cultured in NME7-AB.

The freshly harvested floater metastatic cells are xenografted into the flank of female nu/nu athymic mice that have been implanted with 90-day slow release estrogen pellets. Floater cells were xenografted as 10,000, 1,000, 100 or 50 cells each. Half of the mice in each group of 6 were also injected daily with 32 nM NME7-AB near the original implantation site. The parent T47D cells that were cultured in RPMI media without NME7-AB were also implanted into mice as 6 million, 10,000 or 100 as controls. Mice implanted with the NME7-induced floater cells developed tumors even when as few as 50 cells were implanted. Mice that were implanted with the floater cells and that received daily injections of NME7-AB also developed remote tumors or remote metastases in various organs (FIG. 20-25). 11 out of the 12 mice, or 92%, that were injected with human NME7-AB after implantation of the NME7-AB cultured cancer cells, developed tumors at the injection site. Only 7 out of the 12 mice, or 58%, that were not injected with human NME7-AB after implantation developed tumors. 9 out of the 11 mice, or 82%, that got tumors and were injected with human NME7-AB developed multiple tumors remote from the injection site. None of the mice that were not injected with NME7-AB developed multiple, visible tumors.

After sacrifice, RT-PCR and Western blots showed that the remote bumps on the mice injected with NME7-AB were indeed human breast tumors. Similar analysis of their organs showed that in addition to remote bumps, mice had randomly metastasized to the liver and lung with human breast cancer characteristic of the human breast cancer cells that were implanted. As expected, only the mice implanted with 6 million cells grew tumors.

Several experiments like the one described above were performed with essentially the same results. In each experiment, there were either 24 or 52 mice, including all proper controls.

Example 10—Anti-NME7 Antibodies Inhibit Cancer Cell Growth

T47D breast cancer cells and DU145 prostate cancer cells were cultured according to recommended protocols by ATCC. Cells were grown to ~30% confluency. An anti-NME7 polyclonal rabbit antibody was raised against a fragment of NME7 that encompasses nearly the entire protein: amino acids 100 to 376. This polyclonal antibody was added to the cancer cells at concentrations between 2.7 to 375 ng/mL. Taxol was used as the positive control. Cells were photographed and counted at 48 hours (FIGS. 6 and 7) and after 96 hours (FIG. 8). The photos and cell counts show that the antibody potently inhibited the growth of breast and prostate cancer cells. However, because there was no attempt to select immunizing peptides that were unique to NME7, this antibody could be exerting cytotoxic effects by binding to and inhibiting both NME7-AB-like species and NME1.

Example 11—Peptides Selected Because their Sequence is Unique to NME7, A1, A2, B1, B2 and B3, Inhibit the Binding of NME7 Species to MUC1* Extracellular Domain Peptide NME7 peptides were selected as immunizing agents for antibody production. NME7 peptides A1, A2, B1, B2 and B3 (FIG. 19) were chosen using a process of sequence alignment among human NME1, human NME7 and several bacterial NMEs that were homologous to human NME1 or human NME7. Five regions that had high sequence homology among all were identified. However, to prevent selecting peptides that would give rise to antibodies that would inhibit human NME1 as well as human NME7, we chose NME7 sequences that were adjacent to the homologous regions wherein those peptides had sequences that were different from human NME1. We did ELISA assays to see if the peptides on their own could bind to a synthetic MUC1* peptide on the surface and inhibit the binding of human NME7 or human NME1 to the immobilized peptide (FIG. 27). FIG. 27 shows that the peptides inhibited the binding of NME7 and NME1 to the immobilized peptide. This showed that those regions from which the peptides were derived were the regions that interacted with MUC1* and would give rise to antibodies that would bind to those regions of NME7 and inhibit its binding to MUC1* receptor.

In another experiment, the free peptides A1, A2, B1, B2 and B3 were added to cancer cells in culture that were undergoing transition to a more metastatic state by culturing in either NME7-AB or 2i. FIG. 30 shows a table of scientist observations when cancer cells are grown in either NME7-AB or 2i inhibitors, and shows that the free peptides inhibited the morphological change from adherent cells to floaters, which for breast cancer cells is directly correlated to increased expression of metastatic markers, especially CXCR4. RT-PCR measurements confirm that the NME7-AB peptides inhibited the increase in expression of metastasis marker CXCR4.

FIG. 31 shows a graph of RT-PCR measurements of CXCR4 expression in T47D breast cancer cells that were grown in either NME7-AB or 2i inhibitors, each of which transform cancer cells to a more metastatic state, and the inhibitory effect of NME7-derived peptides, A1, A2, B1, B2 and B3, on the metastatic transformation. FIG. 32 shows a table of recorded RNA levels in samples that were used for RT-PCR measurement of CXCR4 in FIG. 31 as well as the threshold cycle number for CXCR4 expression as well as for the control housekeeping gene.

Example 12—Anti-NME7 Antibodies Specifically Bind to Human NME7 but not to Human NME1

A standard ELISA assay was performed to determine whether or not the NME7 antibodies we generated by immunization with NME7-AB peptides A1, A2, B1, B2, and B3 would bind specifically to NME7-AB, but not to human NME1 as it has healthy functions and it may be detrimental to a human to block it with an antibody. The ELISA of FIG. 26 shows that all of the NME7 antibodies we generated from peptides A1, A2, B1, B2, and B3 bind to human NME7-AB (A) but not to human NME1 (B). The peptides used to generate these antibodies are common to both NME7-AB and NME7-X1. This assays show that the antibodies generated from peptides A1, A2, B1, B2, and B3 specifically bind to NME7-AB and by extension will bind to NME7-X1.

```
NME7A peptide 1 (A domain):
                                        (SEQ ID NO: 141)
MLSRKEALDFHVDHQS

NME7A peptide 2 (A domain):
                                        (SEQ ID NO: 142)
SGVARTDASES

NME7B peptide 1 (B domain):
                                        (SEQ ID NO: 143)
DAGFEISAMQMFNMDRVNVE

NME7B peptide 2 (B domain):
                                        (SEQ ID NO: 144)
EVYKGVVTEYHDMVTE

NME7B peptide 3 (B domain):
                                        (SEQ ID NO: 145)
AIFGKTKIQNAVHCTDLPEDGLLEVQYFF
```

Example 13—Anti-NME7 Specific Antibodies and the Peptides that Generated them Inhibit Cancer Cell Growth Rabbits were immunized with NME7 peptides A1, A2, B1, B2, and B3 and antibodies were generated, collected and purified over a column to which the immunizing peptide had been conjugated. T47D breast cancer cells were plated and cultured according to ATCC protocols in RPMI media supplemented with serum. Antibodies generated from immunization with peptides A1, A2, B1, B2, and B3 were added at the concentrations indicated in FIG. 28. Immunizing peptides A1, A2, B1, B2, and B3, and the PSMGFR extracellular domain peptide of MUC1*, "FLR" here, were also added separately to growing T47D breast cancer cells. Taxol and the E6 anti-MUC1* Fab were added as controls. The graph of FIG. 28 shows that the antibodies generated, as well as the free peptides, potently inhibited the growth of the cancer cells. Note the comparison to inhibition using Taxol, which is a chemotherapy agent that kills healthy and cancer cells alike. Also, for comparison, a polyclonal antibody generated using a large stretch of NME7 from amino acid 100 to 376 is shown. Although this antibody is a potent inhibitor of cancer growth it could have non-specific effects since it can bind to NME1 as well as to NME7.

In a similar experiment, combinations of the antibodies generated from immunization with peptides A1, A2, B1, B2, and B3 as well as the peptides themselves were added to growing cancer cells at the concentrations indicated. The graphs of cell growth shown in FIG. 29 show that the combinations of antibodies and peptides potently inhibited the growth of cancer cells. In these two experiments, the cells were MUC1* positive breast cancer cells.

Example 14—Anti-NME7 Antibodies Inhibit the Transition of Cancer Cells to Metastatic Cancer Cells Cancer cells transform to a more metastatic state when cultured in the presence of agents that revert stem cells to a more naïve state. We have demonstrated that culturing cancer cells in NME7-AB, human NME1 dimers, bacterial NME1 dimers or MEK and GSK3-beta inhibitors, called "2i", causes the cells to become more metastatic. As the cells transition to a more metastatic state, they become non-adherent and float off of the culture plate. These floating cells, "floaters" were collected separately from those that were adherent and were shown to: a) express much higher levels of metastatic genes; and b) when xenografted into mice, the floater cells were able to generate tumors when implanted at very low numbers. RT-PCR measurement of specific metastatic markers such as CXCR4 in breast cancers, CHD1 in prostate cancer, and other pluripotent stem cell markers such as OCT4, SOX2, NANOG, KLF4, c-Myc and others were dramatically over-expressed in cancer cells that were cultured in NME7-AB and most over-expressed in the cells that became non-adherent, called "floaters" here and in figures.

Here we show that the NME7-specific antibodies, generated by immunization with NME7-derived peptides A1, A2, B1, B2 and B3, as well as the peptides themselves, inhibit the transition from cancer cell to metastatic cancer cells. In the first of these experiments, the antibodies generated by immunization with A1, A2, B1, B2 and B3 were tested for their ability to inhibit the metastatic transition induced by culture of T47D breast cancer cells in NME7-AB or in 2i inhibitors. The most striking observation was that the antibodies and the peptides dramatically reduced the number of floater cells, which was the first indication that the antibodies and peptides had inhibited the transformation to metastatic cancer cells. In particular, cells to which the antibody generated from immunization with the B3 peptide barely generated any floater cells.

FIG. 30 shows the recorded observations of the percentage of floater cells visible for each antibody relative to the control wells that did not receive any antibody treatment. mRNA was extracted from both the floater cells and the adherent cells. RT-PCR was used to measure expression levels of metastatic markers, including CXCR4. Treatment with the anti-NME7 antibodies greatly reduced the amount of metastatic markers, such as CXCR4, indicating the antibodies inhibited the transition to metastatic cancer. (See FIG. 31). Notably, the antibody generated by immunization with peptide B3, aka antibody #61, essentially completely inhibited the transition to a more metastatic state. FIG. 31B shows that breast cancer cells that were treated with the NME7-AB peptides, A1, A2, B1, B2 and B3, alone were able to potently inhibit the transition to a more metastatic state induced by culturing the cells in a media containing the 2i inhibitors. Peptide B3 was especially effective as was antibody #61 that it generated. FIG. 31C shows the same graph but with the Y-axis expanded to show the peptide inhibition of metastatic markers. The amount of mRNA, which indicates cell viability and growth, was measured. Cells that were treated with antibody had much less mRNA, indicating that in addition to inhibiting the transition to a more metastatic state, the anti-NME7-AB antibodies inhibited the growth of the cancer cells. FIG. 32 shows a table of the amounts of RNA recovered for the inhibition experiment shown in FIG. 31A.

Figure 36A:
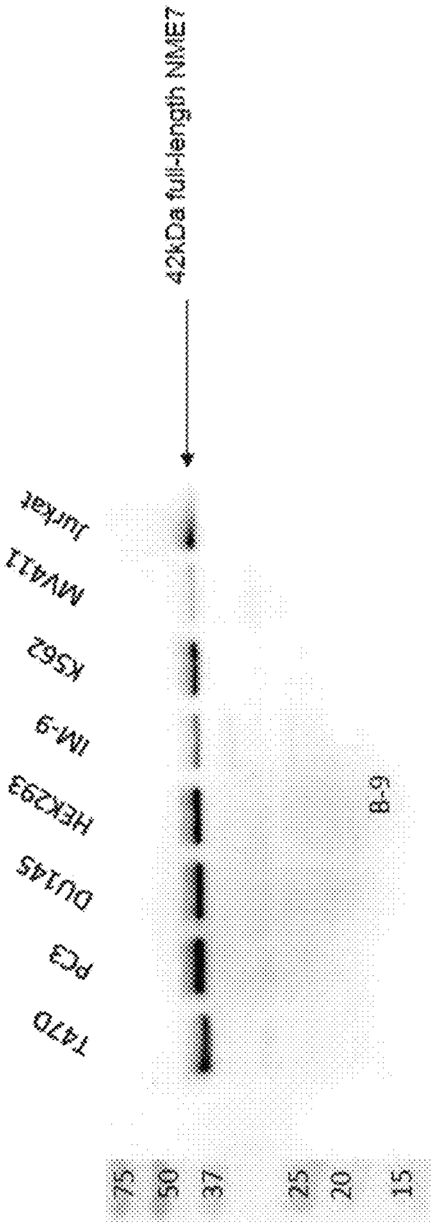
FIGS. 36A-36B show photographs of Western blots in which various cancer cell lines are probed for expression of NME7 species using commercially available antibodies.
Figure 36B:
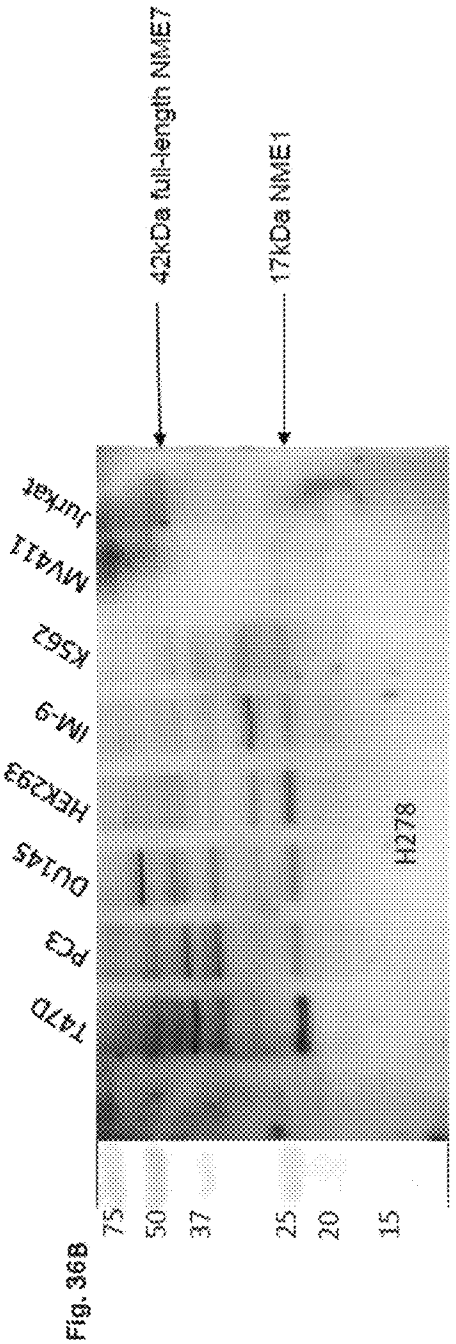

Example 15—Anti-NME7 Antibodies Generated with NME7-Derived Peptides A1, A2, B1, B2 and B3 Identify Novel NME7 Species not Detectable Using any Commercially Available Antibodies As is known to those skilled in the art, some antibodies recognize a linear portion of the target protein and can be used in Western blot assays while other antibodies recognize a non-linear conformational motif and can be used in pull-down or immunoprecipitation assays. Previous to this application, cleaved NME7 or isoform NME7-X1 was not known to exist. Using antibodies that were commercially available at the time of filing shows that existing antibodies could not specifically detect these important NME7 species. B9 (Santa Cruz Biotechnology) is a monoclonal antibody raised against NME7 amino acids 100-376. FIG. 36A shows that it only detects full-length 42 kDa NME7. Another commercially available antibody, H278, is a rabbit polyclonal raised against NME7 amino acids 100-376, which includes amino acid sequences that are not unique to NME7. FIG. 36B shows that this antibody also stains NME1, which is 17 kDa as well as full-length NME7 and other bands that do not appear to be specific to NME7-AB.

Figure 35A:
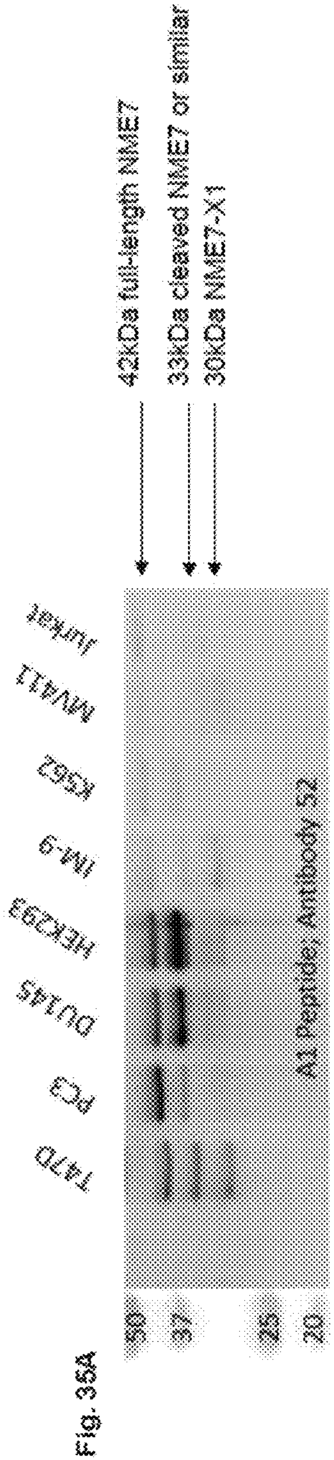
FIGS. 35A-35C show photographs of Western blots in which various cancer cell lines are probed for expression of NME7 species using antibodies generated by immunization with NME7 derived short peptides.
Figure 35B:
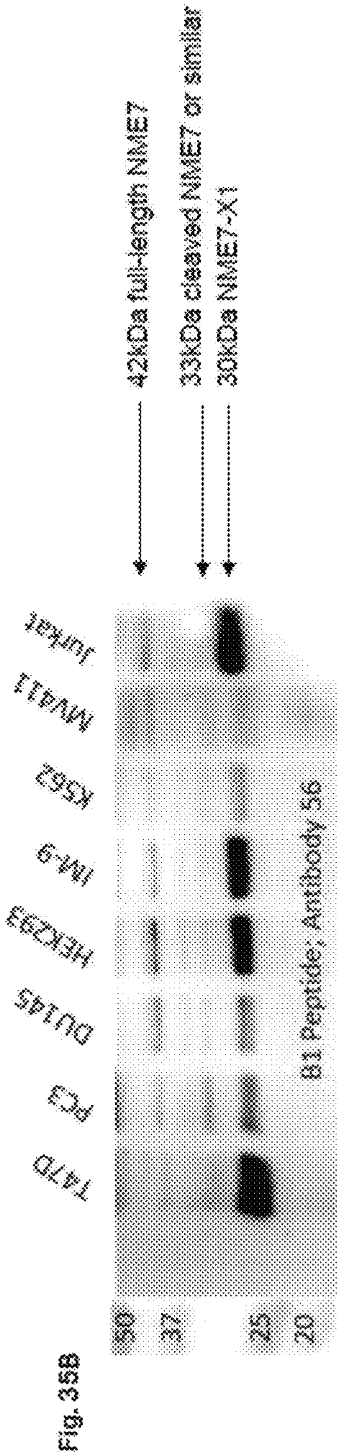
Figure 35C:
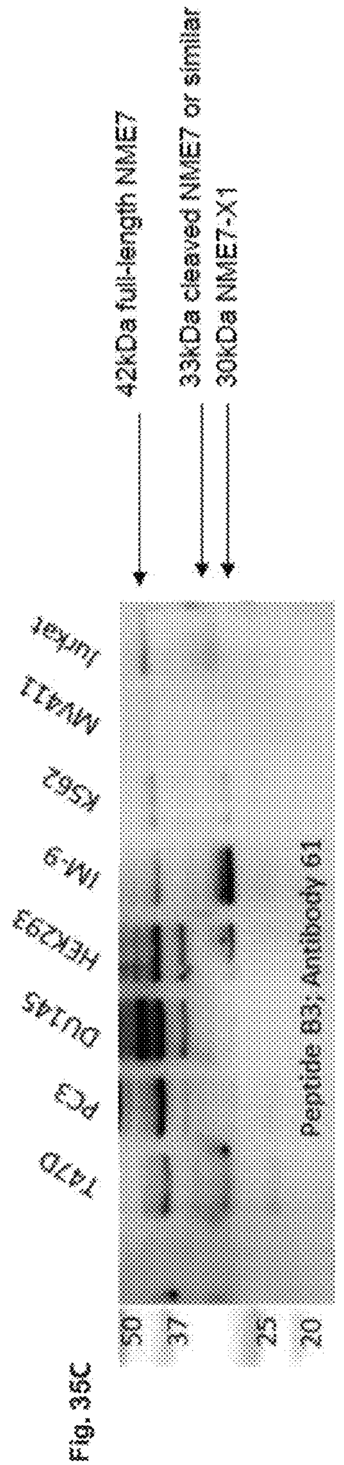

NME7 antibodies generated by immunization with NME7-AB peptides A1, A2, B1, B2 or B3 identify new NME7 species including the full-length 42 kDa protein, a ~33 kDa NME7 species that may be a cleavage product or alternative isoform, a ~30 kDa NME7 species that may be a cleavage product or alternative isoform, wherein the ~30 kDa species appears to be NME7-X1. FIG. 35A-C shows that antibodies generated by peptides A1, B1 and B3 identify the secreted forms of NME7, NME7-AB and NME7-X1 in a wide range of cancer cell lines, including T47D breast cancer cells, PC3 and DU145 prostate cancer cells, HEK293 fetal liver cells, and leukemia cells IM-9, K562, and MV411.

All of the references cited herein are incorporated by reference in their entirety.

CITED REFERENCES LIST

Clarke M F, Dick J E, Dirks P B, Eaves C J, Jamieson C H, Jones D L, Visvader J, Weissman I L, Wahl G M. (2006) *Cancer stem cells—perspectives on current status and future directions: AACR Workshop on cancer stem cell*. Cancer Res. October 1; 66(19):9339-44. Epub 2006 Sep. 21.

Chen K, Huang Y H, Chen J L. (2013) Understanding and targeting cancer stem cells: therapeutic implications and challenges. Acta Pharmacologica Sinica 34: 732-740; Review Darash-Yahana M, Pikarsky E, Abramovitch R, Zeira E, Pal B, Karplus R, Beider K, Avniel S, Kasem S, Galun E, Peled A (2004) Role of high expression levels of CXCR4 in tumor growth, vascularization, and metastasis. FASEB J 18(11): 1240-1242

Mahanta S, Fessler S, Park J, Bamdad C. A Minimal Fragment of MUC1 Mediates Growth of Cancer Cells, 2008 PLoS ONE 3:e2054-2065.

Hikita S, Clegg O, Kosik K, Bamdad C. MUC1* Mediates the Growth of Human Pluripotent Stem Cells, 2008 PLoS ONE 3:e3312-3325.

Kumar S M, Liu S, Lu H, Zhang H, Zhang P J, Gimotty P A, Guerra M, Guo W, Xu X. (2012) Acquired cancer stem cell phenotypes through Oct4-mediated dedifferentiation. Oncogene. November 22; 31(47):4898-911.

Liu K, Lin B, Zhao M, Yang X, Chen M, Gao A, Liu F, Que J, Lan X. (2013) The multiple roles for Sox2 in stem cell maintenance and tumorigenesis. Cellular Signaling May; 25(5):1264-71. Review Wang M L, Chiou S H, Wu C W. (2013) Targeting cancer stem cells: emerging role of Nanog transcription factor. Onco targets and Therapy. September 4; 6:1207-20. Review.

Xu C, Rosler E, Jiang J, Lebkowski J S, Gold J D, et al. (2005) Basic Fibroblast Growth Factor Supports Undifferentiated Human Embryonic Stem Cell Growth Without Conditioned Medium. STEM CELLS 23: 315-323.

Fessler S, Wotkowicz M, Mahanta S, Bamdad C (2009) MUC1* is a determinant of trastuzumab (Herceptin) resistance in breast cancer cells, Breast Cancer Res Treat 118:113-124 DOI 10.1007/s10549-009-0412-3

Miki J, Furusato B, Li H, Gu Y, Takahashi H, Egawa S, Sesterhenn I A, McLeod D G, Srivastava S, Rhim J S. Identification of putative stem cell markers, CD133 and CXCR4, in hTERT-immortalized primary nonmalignant and malignant tumor-derived human prostate epithelial cell lines and in prostate cancer specimens. Cancer Res. 2007 Apr. 1; 67(7):3153-61.

Jeter C R, Liu B, Liu X, Chen X, Liu C, Calhoun-Davis T, Repass J, Zaehres H, Shen J J, Tang D G. NANOG promotes cancer stem cell characteristics and prostate cancer resistance to androgen deprivation. Oncogene. 2011 Sep. 8; 30(36):3833-45. PMCID:

Faber A, Goessler U R, Hoermann K, Schultz J D, Umbreit C, Stern-Straeter J. SDF-1-CXCR4 axis: cell trafficking in the cancer stem cell niche of head and neck squamous cell carcinoma. Oncol. Rep. 2013 June; 29(6):2325-31.

Mukherjee D, Zhao J. The Role of chemokine receptor CXCR4 in breast cancer metastasis. Am J Cancer Res. 2013; 3(1):46-57. PMCID: PMC3555200

Herreros-Villanueva M, Zhang J-S, Koenig A, Abel E V, Smyrk T C, Bamlet W R, de Narvajas A A-M, Gomez T S, Simeone D M, Bujanda L, Billadeau D D. SOX2 promotes dedifferentiation and imparts stem cell-like features to pancreatic cancer cells. Oncogenesis. 2013; 2:e61. PMCID: PMC3759123

Hanna J, Cheng A W, Saha K, Kim J, Lengner C J, et al. (2010) Human embryonic stem cells with biological and epigenetic characteristics similar to those of mouse ESCs. Proc Natl Acad Sci USA 107: 9222-9227.

Smagghe, B. J. Stewart A. K., Carter M. G., Shelton L. S., Bernier K. J., Hartman E. J., Calhoun A. K., Hatziioannou V. M., Lillacci G., Kirk B. A., DiNardo B. A., Kosik K. S., Bamdad C. (2013) MUC1* Ligand, NM23-H1, Is a Novel Growth Factor That Maintains Human Stem Cells in a More Naïve State. PLoS ONE 8(3): e58601

Theunissen T W, Powell B E, Wang H, Mitalipova M, Faddah D A, Reddy J, Fan Z P, Maetzel D, Ganz K, Shi L, Lungjangwa T, Imsoonthornruksa S, Stelzer Y, Rangarajan S, D'Alessio A, Zhang J, Gao Q, Dawlaty M M, Young R A, Gray N S, Jaenisch R. (2014) Systematic Identification of Culture Conditions for Induction and Maintenance of Naïve Human Pluripotency. Cell Stem Cell. 2014 Jul. 24, S1934-5909(14)00298-7.

Rais Y1, Zviran A, Geula S, Gafni O, Chomsky E, Viukov S, Mansour A A, Caspi I, Krupalnik V, Zerbib M, Maza I, Mor N, Baran D, Weinberger L, Jaitin D A, Lara-Astiaso D, Blecher-Gonen R, Shipony Z, Mukamel Z, Hagai T, Gilad S, Amann-Zalcenstein D, Tanay A, Amit I, Novershtern N, Hanna J H (2013). Deterministic direct reprogramming of somatic cells to pluripotency., 502(7469): 65-70.

Xu R H, Peck R M, Li D S, Feng X, Ludwig T, et al. (2005) Basic FGF and suppression of BMP signaling sustain undifferentiated proliferation of human ES cells. Nat Methods 2: 185-190.

Liu W, Ma Q, Wong K, Li W, Ohgi K, Zhang J, Aggarwal A K, Rosenfeld M G. Brd4 and JMJD6-Associated Anti- Pause Enhancers in Regulation of Transcriptional Pause Release. Cell. 2013 Dec. 19; 155(7):1581-95. PMCID: PMC3886918.

Silva J, Barrandon O, Nichols J, Kawaguchi J, Theunissen T W, Smith A. Promotion of reprogramming to ground state pluripotency by signal inhibition. PLoS Biol. 2008 Oct. 21; 6(10):e253. PMCID: PMC2570424

Takahashi K and Yamanaka S (2006) Induction of pluripotent stem cells from mouse embryonic and adult fibroblast cultures by defined factors. Cell 126(4):663-676.

Porter D et al. (2011) Chimeric antigen receptor-modified T cells in chronic lymphoid leukemia. N Engl J Med 365: 725-733 DOI: 10.1056/NEJMoa1103849

Tiller T et al. (2013) A fully synthetic human Fab antibody library based on fixed VH/VL framework pairings with favorable biophysical properties. MABs 9:5(3) PMID: 23571156

Webb P A, Perisic O, Mendola C E, Backer J M and Williams R L. The crystal structure of a human nucleoside diphosphate kinase, NM23-H2. J Mol Biol. 1995, 251: 574-587.

Min K, Song H K, Chang C, Kim S Y, Lee K J and Suh S W. Crystal structure of human nucleoside diphosphate kinase A, a metastasis suppressor. Proteins. 2002, 46:340-342.

Okabe-Kado et al., "A new function of Nm23/NDP kinase as a differentiation inhibitory factor, which does not require it's kinase activity", FEBS Letters 363: 311-315, 1995

Lombardi et al., "nm23: Unraveling Its Biological Function in Cell Differentiation" JOURNAL OF CELLULAR PHYSIOLOGY 182:144-149 (2000)

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method for vaccinating a subject in need thereof against a MUC1*-positive cancer or metastatic cancer associated with an aberrant expression of nucleoside diphosphate protein kinase 7 (NME7), the method comprising immunizing the subject with a composition that comprises:

(i) a synthetic peptide which is at least 90% identical to the entire length of one of the following:

a) a peptide fragment of SEQ ID NO: 39, wherein the peptide fragment is SEQ ID NO: 141 with up to 7 amino acids added or subtracted from either end, wherein the amino acids added are contiguous to SEQ ID NO: 141 within SEQ ID NO: 39;

b) a peptide fragment of SEQ ID NO: 39, wherein the peptide fragment is SEQ ID NO: 142 with up to 7 amino acids added or subtracted from either end, wherein the amino acids added are contiguous to SEQ ID NO: 142 within SEQ ID NO: 39;

c) a peptide fragment of SEQ ID NO: 39, wherein the peptide fragment is SEQ ID NO: 143 with up to 7 amino acids added or subtracted from either end, wherein the amino acids added are contiguous to SEQ ID NO: 143 within SEQ ID NO: 39;

d) a peptide fragment of SEQ ID NO: 39, wherein the peptide fragment is SEQ ID NO: 144 with up to 7 amino acids added or subtracted from either end, wherein the amino acids added are contiguous to SEQ ID NO: 144 within SEQ ID NO: 39; or e) a peptide fragment of SEQ ID NO: 39, wherein the peptide fragment is SEQ ID NO: 145 with up to 7 amino acids added to or subtracted from either end, except up to only 5 amino acids can be added to the C-terminus, wherein the amino acids added are contiguous to SEQ ID NO: 145 within SEQ ID NO: 39; or (ii) a synthetic nucleic acid encoding the peptide of (i), thereby vaccinating the subject against the cancer or metastatic cancer.

2. The method according to claim 1, wherein the synthetic peptide is at least 90% identical to the entire length of a peptide fragment of SEQ ID NO: 39, wherein the peptide fragment is SEQ ID NO: 145 with up to 7 amino acids added or subtracted from either end, except up to only 5 amino acids can be added to the C-terminus, wherein the amino acids added are contiguous to SEQ ID NO: 145 within SEQ ID NO: 39.

3. The method according to claim 1, wherein the synthetic peptide is any one of SEQ ID NOS: 141-145.

4. The method according to claim 1, wherein the nucleic acid is operatively linked to an expression control sequence.

5. The method according to claim 1, wherein the synthetic peptide is connected to another peptide via a spacer or linker.

6. The method according to claim 1, wherein the composition comprises a pharmaceutically acceptable carrier.

7. The method according to claim 1, wherein the composition comprises an adjuvant.

8. The method according to claim 1, wherein the composition is formulated in a dosage unit form.

9. The method according to claim 1, wherein the composition is formulated for systemic administration.

10. The method according to claim 1, wherein the composition is formulated for local administration.

11. An anti-cancer vaccine composition against a MUC1*-positive cancer associated with an aberrant expression of nucleoside diphosphate protein kinase 7 (NME7), the composition comprising:

(i) a synthetic peptide which is at least 90% identical to the entire length of one of the following:

a) a peptide fragment of SEQ ID NO: 39, wherein the peptide fragment is SEQ ID NO: 141 with up to 7 amino acids added or subtracted from either end, wherein the amino acids added are contiguous to SEQ ID NO: 141 within SEQ ID NO: 39;

b) a peptide fragment of SEQ ID NO: 39, wherein the peptide fragment is SEQ ID NO: 142 with up to 7 amino acids added or subtracted from either end, wherein the amino acids added are contiguous to SEQ ID NO: 142 within SEQ ID NO: 39;

c) a peptide fragment of SEQ ID NO: 39, wherein the peptide fragment is SEQ ID NO: 143 with up to 7 amino acids added or subtracted from either end, wherein the amino acids added are contiguous to SEQ ID NO: 143 within SEQ ID NO: 39;

d) a peptide fragment of SEQ ID NO: 39, wherein the peptide fragment is SEQ ID NO: 144 with up to 7 amino acids added or subtracted from either end, wherein the amino acids added are contiguous to SEQ ID NO: 144 within SEQ ID NO: 39; or e) a peptide fragment of SEQ ID NO: 39, wherein the peptide fragment is SEQ ID NO: 145 with up to 7 amino acids added to or subtracted from either end, except up to only 5 amino acids can be added to the C-terminus, wherein the amino acids added are contiguous to SEQ ID NO: 145 within SEQ ID NO: 39; or (ii) a synthetic nucleic acid encoding the peptide of (i).

12. The anti-cancer vaccine composition according to claim 11, wherein the synthetic peptide is at least 90% identical to the entire length of a peptide fragment of SEQ ID NO: 39, wherein the peptide fragment is SEQ ID NO: 145 with up to 7 amino acids added to or subtracted from either end, except up to only 5 amino acids can be added to the C-terminus, wherein the amino acids added are contiguous to SEQ ID NO: 145 within SEQ ID NO: 39.

13. The anti-cancer vaccine composition according to claim 11, wherein the synthetic peptide is any one of SEQ ID NOS: 141-145.

14. The anti-cancer vaccine composition according to claim 11, wherein the synthetic nucleic acid is operatively linked to an expression control sequence.

15. The anti-cancer vaccine composition according to claim 11, wherein the synthetic peptide is connected to another peptide sequence via a spacer or linker.

16. The anti-cancer vaccine composition according to claim 11, further comprising a pharmaceutically acceptable carrier.

17. The anti-cancer vaccine composition according to claim 11, further comprising an adjuvant.

18. The anti-cancer vaccine composition according to claim 11, wherein the anti-cancer vaccine composition is formulated in a dosage unit form.

19. The anti-cancer vaccine composition according to claim 11, wherein the anti-cancer vaccine composition is formulated for systemic administration.

20. The anti-cancer vaccine composition according to claim 11, wherein the anti-cancer vaccine composition is formulated for local administration.

* * * * *